United States Patent
Carreras et al.

(10) Patent No.: US 10,272,079 B2
(45) Date of Patent: Apr. 30, 2019

(54) NHE3-BINDING COMPOUNDS AND METHODS FOR INHIBITING PHOSPHATE TRANSPORT

(71) Applicant: ARDELYX, INC., Fremont, CA (US)

(72) Inventors: Christopher Carreras, Fremont, CA (US); Dominique Charmot, Fremont, CA (US); Jeffrey W Jacobs, Fremont, CA (US); Eric Labonte, Fremont, CA (US); Jason G. Lewis, Fremont, CA (US)

(73) Assignee: ARDELYX, INC., Fremont, CA (US)

( * ) Notice: Subject to any disclaimer, the term of this patent is extended or adjusted under 35 U.S.C. 154(b) by 0 days.

(21) Appl. No.: 14/783,983

(22) PCT Filed: Apr. 10, 2014

(86) PCT No.: PCT/US2014/033603
§ 371 (c)(1),
(2) Date: Oct. 12, 2015

(87) PCT Pub. No.: WO2014/169094
PCT Pub. Date: Oct. 16, 2014

(65) Prior Publication Data
US 2016/0067242 A1 Mar. 10, 2016

Related U.S. Application Data

(60) Provisional application No. 61/811,613, filed on Apr. 12, 2013, provisional application No. 61/888,879, filed on Oct. 9, 2013.

(51) Int. Cl.
| | |
|---|---|
| *A61K 31/4725* | (2006.01) |
| *A61K 31/472* | (2006.01) |
| *A61K 31/4545* | (2006.01) |
| *A61K 47/48* | (2006.01) |

(52) U.S. Cl.
CPC ...... *A61K 31/4725* (2013.01); *A61K 31/4545* (2013.01); *A61K 31/472* (2013.01); *A61K 47/481* (2013.01)

(58) Field of Classification Search
None
See application file for complete search history.

(56) References Cited

U.S. PATENT DOCUMENTS

| | | |
|---|---|---|
| 3,926,891 A | 12/1975 | Gross |
| 3,935,099 A | 1/1976 | Weaver |
| 3,997,484 A | 12/1976 | Weaver |
| 4,076,663 A | 2/1978 | Masuda |
| 4,090,013 A | 5/1978 | Ganslaw |
| 4,093,776 A | 6/1978 | Aoki |
| 4,190,562 A | 2/1980 | Westerman |
| 4,286,082 A | 8/1981 | Tsubakimoto |
| 4,340,706 A | 7/1982 | Obayashi |
| 4,446,261 A | 5/1984 | Yamasaki |
| 4,459,396 A | 7/1984 | Yamasaki |
| 4,470,975 A | 9/1984 | Berger |
| 4,683,274 A | 7/1987 | Nakamura |
| 4,708,997 A | 11/1987 | Stanley, Jr. |
| 4,766,004 A | 8/1988 | Moskowitz |
| 4,806,532 A | 2/1989 | Dousa |
| 4,857,610 A | 8/1989 | Chmelir |
| 4,985,518 A | 1/1991 | Alexander |
| 4,999,200 A | 3/1991 | Casillan |
| 5,126,150 A | 6/1992 | Piatt |
| 5,130,474 A | 7/1992 | Makovec |
| 5,140,102 A | 8/1992 | Currie |
| 5,145,906 A | 9/1992 | Chambers |
| 5,273,983 A | 12/1993 | Christinaki |
| 5,364,842 A | 11/1994 | Justice |
| 5,445,831 A | 8/1995 | Leis, Jr. |
| 5,489,670 A | 2/1996 | Currie |
| 5,510,353 A | 4/1996 | Giger |
| 5,587,454 A | 12/1996 | Justice |
| 5,629,377 A | 5/1997 | Burgert |
| 5,650,222 A | 7/1997 | DesMarais |
| 5,763,499 A | 6/1998 | DesMarais |
| 5,795,864 A | 8/1998 | Amstutz |
| 5,824,645 A | 10/1998 | Justice |
| 5,824,691 A | 10/1998 | Kuno |
| 5,859,186 A | 1/1999 | Justice |
| 5,866,610 A | 2/1999 | Lang |
| 5,891,849 A | 4/1999 | Amstutz |
| 5,900,436 A | 5/1999 | Ramakrishna |

(Continued)

FOREIGN PATENT DOCUMENTS

| | | |
|---|---|---|
| CA | 2177007 | 11/1996 |
| CA | 2241531 | 7/1997 |

(Continued)

OTHER PUBLICATIONS

Silva, A., Mini-Reviews in Medicinal Chemistry, 2005, vol. 5, pp. 893-914, at p. 893.*
Katopodis, K. Renal Failure 2011 vol. 33 pp. 562-567.*
Miyamoto, K-I. J. Pharm Sci. 2011 vol. 100, pp. 3719-30.*
Molony, D. et al., Adv. Chron. Kidney Disease 2011 abstract.*
Barreto, F. et al Exp Op Pharmacother. 2011 vol. 12 pp. 2627-2640.*
STN Medline AN 2011625687.*
Achinger et al. "Left Ventricular Hypertrophy: Is Hyperphosphatemia among Dialysis Patients a Risk Factor?", J. Am Soc Nephrol. 17(12 Suppl 3):S255-61, 2006.

(Continued)

*Primary Examiner* — Heidi Reese
(74) *Attorney, Agent, or Firm* — Viksnins Harris Padys Malen LLP

(57) ABSTRACT

Provided are NHE3-binding and/or NHE3-modulating agents having activity as phosphate transport inhibitors, including inhibitors of phosphate transport in the gastrointestinal tract and the kidneys, and methods for their use as therapeutic or prophylactic agent.

15 Claims, 16 Drawing Sheets

(56) References Cited

U.S. PATENT DOCUMENTS

| | | |
|---|---|---|
| 5,969,097 A | 10/1999 | Wiegard |
| 5,994,305 A | 11/1999 | Justice |
| 6,005,010 A | 12/1999 | Schwark |
| 6,054,429 A | 4/2000 | Bowersox |
| 6,087,091 A | 7/2000 | Justice |
| 6,107,356 A | 8/2000 | DesMarais |
| 6,136,786 A | 10/2000 | Justice |
| 6,166,002 A | 12/2000 | Weichert |
| 6,277,862 B1 | 8/2001 | Giardina |
| 6,287,609 B1 | 9/2001 | Marlett |
| 6,319,518 B1 | 11/2001 | Lee |
| 6,333,354 B1 | 12/2001 | Schudt |
| 6,355,823 B1 | 3/2002 | Peerce |
| 6,399,824 B1 | 6/2002 | Hofmeister |
| 6,413,494 B1 | 7/2002 | Lee |
| 6,414,016 B1 | 7/2002 | Ueno |
| 6,451,781 B1 | 9/2002 | Kleemann et al. |
| 6,504,057 B2 | 1/2003 | Schwark et al. |
| 6,624,150 B2 | 9/2003 | Yerxa |
| 6,703,405 B2 | 3/2004 | Hofmeister |
| 6,734,188 B1 | 5/2004 | Rhodes |
| 6,736,705 B2 | 5/2004 | Benning |
| 6,737,423 B2 | 5/2004 | Heinelt |
| 6,787,528 B2 | 9/2004 | Peerce |
| 6,887,870 B1 | 5/2005 | Ahmad |
| 6,908,609 B2 | 6/2005 | Simon |
| 6,911,453 B2 | 6/2005 | Hofmeister et al. |
| 7,014,862 B2 | 3/2006 | Myatt |
| 7,026,303 B2 | 4/2006 | Cimiluca |
| 7,041,786 B2 | 5/2006 | Shailubhai |
| 7,109,184 B2 | 9/2006 | Jozefiak |
| 7,119,120 B2 | 10/2006 | Jozefiak |
| 7,241,775 B2 | 7/2007 | Hofmeister et al. |
| 7,309,690 B2 | 12/2007 | Dardenne |
| 7,326,705 B2 | 2/2008 | Ahmad |
| 7,666,898 B2 | 2/2010 | Chang |
| 7,772,262 B2 | 8/2010 | Kleemann |
| 7,790,742 B2 | 9/2010 | Lang et al. |
| 8,134,015 B2 | 3/2012 | Eto |
| 9,408,840 B2 | 8/2016 | Bell et al. |
| 2001/0006972 A1 | 7/2001 | Williams |
| 2003/0109417 A1 | 6/2003 | Nimmo |
| 2003/0171580 A1 | 9/2003 | Hofmeister et al. |
| 2003/0216449 A1 | 11/2003 | Weinstock |
| 2004/0039001 A1 | 2/2004 | Gericke |
| 2004/0044211 A1 | 3/2004 | Hofmeister et al. |
| 2004/0113396 A1 | 6/2004 | Tsai |
| 2004/0224965 A1 | 11/2004 | Gericke |
| 2005/0009863 A1 | 1/2005 | Hofmeister et al. |
| 2005/0020612 A1 | 1/2005 | Gericke |
| 2005/0054705 A1 | 3/2005 | Heinelt |
| 2005/0113396 A1 | 5/2005 | Gericke et al. |
| 2005/0176746 A1 | 8/2005 | Weber |
| 2005/0244367 A1 | 11/2005 | Hui |
| 2007/0135383 A1 | 6/2007 | Chang |
| 2007/0135385 A1 | 6/2007 | Chang et al. |
| 2007/0225323 A1 | 9/2007 | Lang |
| 2007/0270414 A1 | 11/2007 | Kleemann |
| 2008/0058328 A1 | 3/2008 | Heinelt et al. |
| 2008/0194621 A1 | 8/2008 | Lang |
| 2008/0227685 A1 | 9/2008 | Currie |
| 2008/0234317 A1 | 9/2008 | Kleemann et al. |
| 2012/0040025 A9 | 2/2012 | Currie et al. |
| 2012/0263670 A1 | 10/2012 | Charmot |
| 2013/0274285 A1 | 10/2013 | Bell et al. |

FOREIGN PATENT DOCUMENTS

| | | | |
|---|---|---|---|
| CA | 2387529 | 3/2001 | |
| EP | 505322 B1 | 9/1992 | |
| EP | 507672 B1 | 10/1992 | |
| EP | 625162 B1 | 11/1994 | |
| EP | 0744397 | 11/1996 | |
| EP | 835126 B1 | 4/1998 | |
| EP | 873753 A1 | 10/1998 | |
| EP | 876347 A1 | 11/1998 | |
| EP | 1321142 A1 | 6/2003 | |
| EP | 1336409 A1 | 8/2003 | |
| EP | 1485391 | 8/2006 | |
| EP | 1465638 | 5/2007 | |
| EP | 1196396 B1 | 3/2008 | |
| JP | 2007131532 | 5/2007 | |
| WO | WO 93/13128 A1 | 7/1993 | |
| WO | WO 95/28418 | 10/1995 | |
| WO | WO 97/01351 A1 | 1/1997 | |
| WO | WO 97/19927 | 6/1997 | |
| WO | WO 97/21680 A1 | 6/1997 | |
| WO | WO 97/24113 | 7/1997 | |
| WO | WO 98/11090 | 3/1998 | |
| WO | WO 01/05398 | 1/2001 | |
| WO | WO 01/17954 | 3/2001 | |
| WO | WO 01/19849 | 3/2001 | |
| WO | WO 01/21582 | 3/2001 | |
| WO | WO 01/52844 A1 | 7/2001 | |
| WO | WO 01/64212 A1 | 9/2001 | |
| WO | WO 01/72742 | 10/2001 | |
| WO | WO 01/82924 | 11/2001 | |
| WO | WO 01/87294 | 11/2001 | |
| WO | WO 02/28353 | 4/2002 | |
| WO | WO 02/094187 A2 | 11/2002 | |
| WO | WO 03/048129 A1 | 6/2003 | |
| WO | WO 03/048134 | 6/2003 | |
| WO | WO 03/053432 | 7/2003 | |
| WO | WO 03/057225 | 7/2003 | |
| WO | WO 03/080630 | 10/2003 | |
| WO | WO 2004/085382 | 10/2004 | |
| WO | WO 2004/085404 A1 | 10/2004 | |
| WO | WO 2004/085448 | 10/2004 | |
| WO | WO 2006/001931 A2 | 1/2006 | |
| WO | WO 2006/032372 A1 | 6/2006 | |
| WO | WO 2008/002971 A2 | 1/2008 | |
| WO | WO 2008/106429 A2 | 9/2008 | |
| WO | WO 2008/137318 A1 | 11/2008 | |
| WO | WO 2010/025856 | 3/2010 | |
| WO | WO 2010/078449 | 7/2010 | |
| WO | WO-2010078449 A2 * | 7/2010 | ............. A61K 31/18 |
| WO | WO 2012/006473 | 1/2012 | |
| WO | WO 2012/006475 | 1/2012 | |
| WO | WO 2012/006477 | 1/2012 | |
| WO | WO2012/054110 | 4/2012 | |
| WO | WO 2014/029983 A1 | 2/2014 | |
| WO | WO 2014/029984 A1 | 2/2014 | |

OTHER PUBLICATIONS

Ahmad, S. et al., Aminoimidazoles as Bioisosteres of Acylguanidines: Novel, Potent, Selective and Orally Bioavailable Inhibitors of the Sodium Hydrogen Exchanger Isoform-1, Boorganic & Med. Chem. Lett., pp. 177-180 (2004).

Bundgard, H., "Design of Prodrugs: Bioreversible derivatives for various functional groups and chemical entites", Design of Prodrugs (1985), pp. 7 9, 21 24 (Elsevier, Amsterdam).

Chou et al., "Obstructive Sleep Apnea: a stand-alone risk for chronic kidney dieases", Nephrol. Dial. Transplant. 0:1-6, 2011.

Di Marco et al., "High phosphate directly affects endothelial function by downregulating annexin II" Kidney International. 83:213-222, 2013.

Ertl et al., "Fast Calculation of Molecular Polar Surface Area as Sun of Fragment-Based Contributions and Its Application to the Prediction of Drug Transport Properties", Journal of Medicinal Chemistry, 43, 3714-3717 (2000).

Giachelli, "The emerging role of phosphate in vascular calcification" Kidney Int. 75:890-897, 2009.

Guerin et al.,"Impact of Aortic Stiffness Attenuation of Survival of Patients in End-Stage Renal Failure" Circulation. 103:987-992, 2001.

Kirkpantur et al., "Serum fibroblast growth factor-23 (FGF-23) levels are independently associated with left ventricular mass and myocardial performance index in maintenance haemodialysus patents" *Nephrol Dial Transplant.* 26:1346-54, 2011.

Lang, H. J., "*Chemistry of NHE Inhibitors*" in The Sodium-Hydrogen Exchanger, Harmazyn, M., Avkiran, M. and Fliegel, L.,

(56) References Cited

OTHER PUBLICATIONS

Eds., Kluwer Academic Publishers 2003. See also B. Masereel et al., An Overview of Inhibitors of Na+ / H+ Exchanger, *European J. of Med. Chem.*, 38, pp. 547-554 (2003).
Lewis et al., "Stool Form Scale as a Useful Guide to Intestinal Transit Time", Scand. J. Gastroenterol. 32:920-4, 1997.
Linz et al., "Antihypertensive and Laxative Effects by Pharmacological Inhibition of Sodium-Proton-Exchanger Subtype 3-Mediated Sodium Absorption in the Gut", *Hypertension.* 60:1560-7, 2012.
Lipinski et al., "Experimental and Computational approaches to estimate solubility and permeability in druf discovery and development settings" Advanced Drug Delivery Reviews, 46:3-26, 2001.
Lipinski, "Drug-like Properties and the Causes of Poor Solubility and Poor Permeability", J. Pharm. & Toxicol. Methods, 44:235-249 (2000).
Lopez et al., "Calcimimetic R-568 Decreases Extraosseous Calcifications in Uremic Rats Treated with Calcitriol" *J. Am. Soc. Nephrol.* 17:795-804, 2006.
Luks et al., "Chronic Kidney Disease at High Altitude" *J Am Soc Nephrol.* 19:2262-2271, 2008.
Masereel et al., An Overview of Inhibitors of Na+ / H+ Exchanger, *European J. of Med. Chem.*, 38, pp. 547-554 (2003).
Mohrmann et al. "Sodium-dependent transport of $P_i$ by an established intential epithelial cell line (CaCo-2)" *Am. J. Phys.* 250(3 pt 1):G323-30, 1986.
Ohnishi et al. "Dietary and genetic evidence for phosphate toxicity accelerating mammalian aging" and Razzaque, *FASEB J.* 24:3562-71, 2010.
Paradiso, et al., "Na'-H' exchange in gastric glands as measured with a cytoplasmic-trapped, fluorescent pH indicator" PNAS USA. 81(23): 7436-7440 (1984).
Rao et al., "Evaluation of gastrointestinal transit in clinical practice: position paper of the American and European Neurogastroenterology and Motility Societies" Neurogastroenterol Motil. 23:8-23, 2011.
Sarkar et al., "Interdialytic Weight Gain: Implications in Hemodialysis Patients" *Semin Dial.* 19:429-33, 2006.
Selvaraj et al., "Tool development for Prediction of pIC50 values from the IC50 values—A pIC50 value calculator" Current Trends in Biotechnology and Pharmacy. 5:1104-1109, 2011.
(Shuto et al., "Dietary Phosphorus Acutely Impairs Endothelial Function" 2009b, J.Am.Soc.Nephrol., v. 20, No. 7, p. 1504-1512).
Van et al., "Dietary Phosphorus Acutely Impairs Endothelial Function" *J Clin Biochem Nutr.* 51:27-32, 2012.
Vigne et al., "The Amiloride-sensitive Na+/H' Exchange System in SkeleMtalu scle Cells in Culture*" *J. Biol. Chem.* 1982, 257, 9394.
Wiley et al. "Peptidomimetics Derived from Natural Products" Medical Research Reviews 1993, 13(3), 327-384).
Wohnsland et al., "High-Throughput Permeability pH Profile and High-Throughput Alkane/Water log P with Artificial Membranes" J. Med. Chem. 44:923-930, 2001.
Ahmed et al., "A propensity-matched study of the effects of chronic diuretic therapy on mortality and hospitalization in older adults with heart failure", *Int J Cardiol.* Apr. 10, 2008; 125(2): 246-253.
Akbar, A. et al. "Review article: visceral hypersensitivity in irritable bowel syndrome: molecular mechanisms and therapeutic agents", *Aliment. Pharmaco. Ther.*, 2009, 30, 423-435.
Altun, B., and M. Arici, 2006, "Salt and blood pressure: time to challenge", Cardiology, v. 105, No. 1, p. 9-16 (2006).
Basit, A. W., Advances in Colonic Drug Delivery, *Drugs* 2005, 65 (14), 1991-2007.
Beubler, E. et al. "5-HT receptor antagonists and heat-stable *Escherichia coli* enterotoxin-induced effects in the rat", *Eur. J. Pharm.*, 219:445, 1992.
Bleakman, D., and R. J. Naftalin, "Hypertonic fluid absorption from rabbit descending colon in vitro", 1990, *Am J Physiol*, v. 258, No. 3 Pt 1, p. G377-G390.

Bouras EP, et al., "Prucalopride Accelerates Gastrointestinal and Colonic Transit in Patients With Constipation Without a Rectal Evacuation Disorder", *Gastroenterology*, 2001; 120:354-360.
Brandt et al., "An Evidence-Based Approach to the Management of Chronic Constipation in North America", 2005, *Am. J. Gastroenterol.* 100(Suppl.1):S1-S21.
Bueno et al., "Serotonergic and non-serotonergic targets in the pharmacotherapy of visceral hypersensitivity", *Neurogastroenterol Motility* (2007) 19 (suppl.1), 89-119.
Burton DD, et al., "Colonic Transit Scintigraphy Labeled Activated Charcoal Compared with Ion Exchange Pellets", *J. Nucl. Med.*, 1997;38:1807-1810.
Camilleri M, et al., "Effect of Renzapride on Transit in Constipation-Predominant Irritable Bowel Syndrome", *Clin. Gastroenterol. Hepatol.*, 2004;2:895-904.
Camilleri M, Zinsmeister AR, "Towards a Relatively Inexpensive, Noninvasive, Accurate Test for Colonic Motility Disorders", *Gastroenterology*, 1992; 103:36-42.
Campbell, R. K. "Type 2 diabetes: where we are today: an overview of disease burden, current treatments, and treatment strategies" *Journal of the American Pharmacists Association* 2009, 49(5), S3-S9.
Campbell C.A. et al., "Characterisation of SB-221420-A—a neuronal Ca2+ and Na+ channel antagonist in experimental models of stroke", *European Journal of Pharmacology*, vol. 401, (Jan. 1, 2000), pp. 419-428.
Chen, J. et al. "Synthesis and characterization of superporous hydrogel Composites", *Journal of Controlled Release*, 65, pp. 73-82 (2000).
Chang et al., "Current Gut-Directed Therapies for Irritable Bowel Syndrome", 2006, *Curr. Teat. Options Gastroenterol.* 9(4):314-323.
Cheng et al., "Macroporous poly(N-isopropylacrylamide) hydrogels with fast response rates and improved protein release properties",Journal of Biomedical Materials Research—Part A, vol. 67, Issue 1, Oct. 1, 2003, pp. 96-103.
Chiba, Shunsuke et al. "A Pd(II)-Catalyzed Ring-Expansion Reaction of Cyclic 2—Azidoalcohol Derivatives: Synthesis of Azaheterocycles", J. Am. Chem. Soc. 2009, 131, (36), 12886-12887.
Chourasia, M. K. et al., "Polysaccharides for Colon-Targeted Drug Delivery", *Drug Deliv.* 2004, 11 (2), 129-148.
Chourasia, M. K.et al., "*Pharmaceutical Approaches to Colon Targeted Drug Delivery Systems,"* J. Pharm. Sci. 2003, 6 (1), 33-66.
Colin et al., "Characterisation of SB-221420-A—a neuronal Ca2+ and Na+ channel antagonist in experimental models of stroke", *European Journal of Pharmacology*, vol. 401, Jan. 1, 2000, pp. 419-428.
Coulie B, et al., "Recombinant Human Neurotrophic Factors Accelerate Colonic Transit and Relieve Constipation in Humans", *Gastroenterology*, 2000; 119:41-50.
Cremonini F. et al., "Performance characteristics of scintigraphic transit measurements for studies of experimental therapies", *Aliment. Pharmacol. Ther.*, 2002;16:1781-1790.
Cruz et al., "Incidence and Predictors of Development of Acute Renal Failure Related to the Treatment of Congestive Heart Failure with ACE Inhibitors", *Nephron Clin. Pract.*, v. 105, No. 2, pp. c77-c83 (2007).
Davenport, A. et al. "Blood pressure control and symptomatic intradialytic hypotension in diabetic haemodialysis patients: a cross-sectional survey" *Nephron Clin. Pract.*, v. 109, No. 2, p. c65-c71 (2008).
Eherer, A. J. et al. "Effect of Psyllium, Calcium Polycarbophil, and Wheat Bran on Secretory Diarrhea Induced by Phenolphthalein", 1993, *Gastroenterology*, vol. 104, No. 4, p. 1007-1012.
Fischer M., "The gel-forming polysaccharide of psyllium husk (Plantago ovata Forsk)", Carbohydrate Research, 339, 2009-2012 (2004).
Horkay, F. "Effect of Cross-Links on the Swelling Equation of State: Polyacrylamide Hydrogels", *Macromolecules*, 22, pp. 2007-2009 (1989).
Geibel, J. P. "Secretion and absorption by colonic crypts", Annu. Rev. Physiol, v. 67, p. 471-490 (2005).

(56) References Cited

OTHER PUBLICATIONS

Gershon and Tack, "The Serotonin Signaling System: From Basic Understanding To Drug Development for Functional GI Disorders", 2007, *Gastroenterology* 132(1):397-414.
Griffin, et al., "Multivalent Drug Design. Synthesis and In Vitro Analysis of an Array of Vancomycin Dimers", *J. Am. Chem. Soc.*, 2003, 125, 6517-6531.
Hammerle and Surawicz, "Updates on treatment of irritable bowel syndrome", 2008, *World J. Gastroenterol.* 14(17):2639-2649.
International Search Report and Written Opinion issued for PCT/BG2013/052193 dated Oct. 31, 2013.
International Search Report and Written Opinion issued for PCT/BG2013/052192 dated Oct. 31, 2013.
Jacobsen, E.N. et al., "Highly Enantioselective Epoxidation Catalysts Derived from 1,2-Diaminocyclohexane", *J. Am. Chem. Soc.* 1991, 113, 7063-7064.
Jain, A. et al., "Perspectives of Biodegradable Natural Polysaccharides for Site-specific Drug Delivery to the Colon", *J. Pharm. Sci.*, 2007, 10 (1), 86-128.
Jain, S. K. et al. "Target-specific Drug Release to the Colon", *Expert Opin. Drug Deliv.*, 2008, 5 (5), 483-498.
Johanson and Kralstein, "Chronic constipation: a survey of the patient perspective", 2007, *Aliment. Pharmacol. Ther.* 25(5):599-608.
Kashani et al., "Fluid retention in cirrhosis: pathophysiology and management", QJM, v. 101, No. 2, p. 71-85 (2008).
Kiela, P. R., et al.; *Apical NA+/H+ exchangers in the mammalian gastrointestinal tract*; J. Physiol. Pharmacol., v. 57 Suppl 7, p. 51-79 (2006).
Kumar, P. et al., Colon Targeted Drug Delivery Systems—An Overview, Curr. Drug Deliv., 2008, 5 (3), 186-198.
Kunzelmann et al., *Electrolyte transport in the mammalian colon: mechanisms and implications for disease*; Physiol. Rev., v. 82, No. 1, p. 245-289 (2002).
Ledoussal, Clara, et al. "Renal salt wasting in mice lacking NHE3 Na+lH+ exchanger but not in mice lacking NHE2." American Journal of Physiology-Renal Physiology, vol. 281, No. 4 (2001): F718-F727.
Li, Xiaoling "Biodegradable polymeric prodrugs of antihypertensive agents," 1991, University of Utah, Department of Pharmaceutics, pp. 1-241.
Li et al. "Lysophosphatidic acid inhibits cholera toxin-induced secretory diarrhea through CFTR-dependent protein interactions", *J. Exp. Med.*, vol. 202 (2005), pp. 975-986.
Mammen et al. "Effective Inhibitors of Hemagglutination by Influenza Virus Synthesized from Polymers Having Active Ester Groups. Insight into Mechanism of Inhibition", *Journal of Mediciani Chemistry*, (1995); 38; 4179-4190.
Marlett, J. et al. "The active fraction of psyllium seed husk", *Proceedings of the Nutrition Society*, 62, pp. 207-209 (2003).
McKie, A. T. et al. "Mechanical aspects of rabbit fecal dehydration", 1990, *Am J Physiol*, vol. 258, No. 3 Pt 1, p. G391-G394.
Medline Plus entry for Irritable Bowel Syndrome, retrieved from medlineplus/irritablebowelsyndrome.html> on Aug. 6, 2015, pp. 1-6.
Medline Plus entry for Chronic Kidney Disease, retrived from <www.nlm.nih.gov/medlineplus/ency/article/000471.htm> on Aug. 6, 2015, pp. 1-8.
Medline Plus entry for End-stage Kidney Diseaes, retrieved from <www.nlm.nih.gov/medlineplus/ency/article/000500.htm> on Aug. 6, 2015, pp. 1-6.
Musso, David L.et al. "Indanylidenes. 2. Design and Synthesis of E)-2-(4-Chloro-6-fluoro-1-indanylidene)-N-methylacetamide, a Potent Antiinflammatory and Analgesic Agent without Centrally Acting Muscle Relaxant Activity", *J. Med. Chem.* 2003, 46, (3), 409-416.
Ogden, CL et al, "Prevalence of overweight and obesity in the united states, 1999-2004" *JAMA* 2006, 295, 1549-1555.
Oh K. et al. "Swelling Behavior of Submicron Gel Particles", *Journal of Applied Polymer Science*, 69, pp. 109-114 (1998).

Pappagallo, "Incidence, Prevalence, and Management of Opioid Bowel Dysfunction", 2001, *Am. J. Surg.* 182(5A Suppl.): 11S-18S.
Patil, S.B. et al., "Mucoadhesive Microspheres: A Promising Tool in Drug Delivery", *Curr. Drug. Deliv.*, Oct. 2008, 5(4), pp. 312-318.
Posserud, I. et al, Altered Rectal Perception in Irritable Bowel Syndrome Is Associated With Symptom Severity, *Gastroenterology*, 2007; 133:1113-1123.
Prather CM, et al., "Tegaserod Accelerates Orocecal Transit in Patients With Constipation-Predominant Irritable Bowel Syndrome", Gastroenterology, 2000; 118:463-468.
Pelton R., "Temperature-sensitive aqueous microgels", Advances in Colloid and Interface Science, 85, pp. 1-33, (2000).
Schocken, D. D. et al., "Prevention of heart failure: a scientific statement from the American Heart Association Councils on Epidemiology and Prevention, Clinical Cardiology, Cardiovascular Nursing, and High Blood Pressure Research", Quality of Care and Outcomes Research Interdisciplinary Working Group; and Functional Genomics and Translational Biology Interdisciplinary Working Group, *Circulation*, v. 117, No. 19, p. 2544-2565 (2008).
Shareef, M. A. et al., "Colonic Drug Delivery: An Updated Review", *AAPS Pharm. Sci.* 2003, 5 (2), E17.
Sinha, V. R. et al., "Colonic Drug Delivery: Prodrug Approach", *Pharm. Res.* 2001, 18 (5), 557-564.
Spencer, Andrew G., et al. "Intestinal Inhibition of the Na+/H+ Exchanger 3 Prevents Cardiorenal Damage in Rats and Inhibits Na+ Uptake in Humans," *Science translational medicine*, vol. 6, No. 227 (2014): 227ra36-27ra36.
Townsend, R. R. et al "Metabolic Syndrome, Components, and Cardiovascular Disease Prevalence in Chronic Kidney Disease: Findings from the Chronic Renal Insufficiency Cohort (CRIC) Study" *American Journal of Nephrology* 2011, 33, 477-484.
Ueda, H. et al. "Kyotorphin (Tyrosine-Arginine) Synthetase in Rat Brain Synaptosome", *J. Biol. Chem.* 262:8165, 1987.
Van den Mooter, G. "Colon Drug Delivery", *Expert Opin. Drug Deliv.*, 2006, 3 (1), 111-125.
Weinman, Edward et al.; "Fibroblast Growth Factor-23-mediated Inhibition of Renal Phosphate Transport in Mice Requires Sodium-Hydrogen Exchanger Regulatory Factor-1 (NHERF-1) and Synergizes with Parathyroid Hormone," 2011, ASBMB, *The Journal of Biological Chemistry*, vol. 286, No. 43, pp. 37216-37221.
W. McPhee, Journal of Colloid and Interface Science, 156, pp. 24-30 (1993).
Wahba, I. M. et al "Obesity and obesity-initiated metabolic syndrome: mechanistic links to chronic kidney disease", *Clinical Journal of the American Society of Nephrology* 2007, 2, 550-562.
Wenzl et al. "Determinants of decreased fecal consistency in patients with diarrhea", *Gastroenterology*, v. 108, No. 6, p. 1729-1738 (1995).
Yang, T. et al. "Renal and Vascular Mechanisms of Thiazolidinedione-Induced Fluid Retention", *PPAR Research* vol. 2008, article ID 943614, 8 pages in total.
Yang, L., "Biorelevant Dissolution Testing of Colon-Specific Delivery Systems Activated by Colonic Microflora", *J. Controlled Release*, 2008, 125 (2), 77-86.
Zachos et al., "Molecular physiology of intestinal Na+/H+ exchange", *Annu. Rev. Physiol.*, v. 67, p. 411-443 (2005).
Zammit, P. S. et al. "Effects on fluid and Na+ flux of varying luminal hydraulic resistance in rat colon in vivo", 1994, *J Physiol*, v. 477 ( Pt 3), p. 539-548.
Giral, Hector et al. "NHE3 Regulatory Factor 1 (NHERF1)Modulates Intestinal Sodium-dependent Phosphate Transporter (NaPi-2b) Expression in Apical Microvilli", the Journal of Biological Chemistry, vol. 287, No. 42, p. 35047-35056.
Mahon M. et al. "Na+/H+ Exchanger-Regulatory Factor 1 Mediates Inhibition of Phosphate Transport by Parathyroid Hormone and Second Messengers by Acting at Multiple Sites in Opossum Kidney Cells", Molecular Endocrinology, vol. 17, No. 11, p. 2355-2364 (2003).
Lopes, et al., "Phosphate Binder Use and Mortality Among Hemodialysis Patients in the Dopps: Evaluation of Possible Confounding by Nutritional Status", Am J Kidney Dis 60(1), 90-101 (2012).

(56) References Cited

OTHER PUBLICATIONS

Merck Manual, "Hyperphosphatemia", www.merckmanuals.com/professional/endocrine-and-metabolic-disorders/electrolyte-disorders/hyperphosphatemia, 4 pages (Last full review/revision Mar. 2018).
Spherix Global Insights Report, "RealWorld Dynamix—Exploring the Patient Journey", Dialysis Market, 2018, CKD, Non-dialysis Market 2017 (Slides 1-5).

* cited by examiner

NHE3-BINDING COMPOUNDS AND METHODS FOR INHIBITING PHOSPHATE TRANSPORT

RELATED APPLICATIONS

This application claims the benefit of priority under 35 U.S.C. §119(e) to U.S. Provisional Patent Application No. 61/888,879, filed Oct. 9, 2013 and U.S. Provisional Patent Application No. 81/811,613, filed Apr. 12, 2013. The entire contents of the foregoing applications are hereby incorporated expressly by reference.

BACKGROUND

Technical Field

The present invention relates to NHE3-binding and/or NHE3-modulating agents having activity as phosphate transport inhibitors, including inhibitors of phosphate transport in the gastrointestinal tract and the kidneys, and methods for their use as therapeutic or prophylactic agents.

Description of the Related Art

Patients with inadequate renal function, hypoparathyroidism, or certain other medical conditions (such as hereditary hyperphosphatemia, Albright hereditary osteodystrophy, amyloidosis, etc.) often have hyperphosphatemia, or elevated serum phosphate levels (wherein the level, for example, is more than about 6 mg/dL). Hyperphosphatemia, especially if present over extended periods of time, leads to severe abnormalities in calcium and phosphorus metabolism, often manifested by secondary hyperparathyroidism, bone disease and ectopic calcification in the cardiovascular system, joints, lungs, eyes and other soft tissues. Higher serum phosphorus levels are strongly associated with the progression of renal failure, cardiovascular calcification and mortality in end-stage renal disease (ESRD) patients. High-normal serum phosphorus levels have been associated with cardiovascular events and mortality among individuals who have chronic kidney disease (CKD) and among those who have normal kidney function (see, e.g., Joy et al., *J. Manag. Care Pharm.*, 13(5):397-411 (2007)) The progression of kidney disease can be slowed by reducing phosphate retention. Thus, for renal failure patients who are hyperphosphatemic and for chronic kidney disease patients who have serum phosphate levels within the normal range or only slightly elevated, therapy to reduce phosphate retention is beneficial.

For patients who experience hyperphosphatemia, calcium salts have been widely used to bind intestinal phosphate and prevent its absorption. Different types of calcium salts, including calcium carbonate, acetate, citrate, alginate, and ketoacid salts have been utilized for phosphate binding. However, these therapies often cause hypercalcemia, a condition which results from absorption of high amounts of ingested calcium. Hypercalcemia causes serious side effects such as cardiac arrhythmias, renal failure, and skin and vascular calcification. Frequent monitoring of serum calcium levels is required during therapy with calcium-based phosphate binders. Other calcium and aluminum-free phosphate binders, such as sevelamer, a crosslinked polyamine polymer, have drawbacks that include the amount and frequency of dosing required to be therapeutically active. The relatively modest phosphate binding capacity of those drugs in vivo obliges patients to escalate the dose (up to 7 grs per day or more). Such quantities have been shown to produce gastrointestinal discomfort, such as dyspepsia, abdominal pain and, in some extreme cases, bowel perforation.

An alternative approach to the prevention of phosphate absorption from the intestine in patients with elevated phosphate serum levels is through inhibition of the intestinal transport system which mediates phosphate uptake in the intestine. It is understood that phosphate absorption in the upper intestine is mediated at least in part by a carrier-mediated mechanism which couples the absorption of phosphate to that of sodium Inhibition of intestinal phosphate transport will reduce body phosphorus overload. In patients with advanced kidney disease (e.g. stage 4 and 5), the body phosphorus overload manifests itself by serum phosphate concentration above normal levels, i.e. hyperphosphatemia. Hyperphosphatemia is directly related to mortality and morbidity Inhibition of intestinal phosphate transport will reduce serum phosphate concentration and therefore improve outcome in those patients. In chronic kidney disease patients at stage 2 or 3, the body phosphorus overload does not necessarily lead to hyperphosphatemia, i.e., some patients remain normophosphatemic, but there is a need to reduce or prevent body phosphorus overload even at those early stages to avoid associated bone and vascular disorders, and ultimately improve mortality rate. Similarly, inhibition of intestinal phosphate transport would be particularly advantageous in patients that have a disease that is treatable by inhibiting the uptake of phosphate from the intestines. Inhibition of phosphate absorption from the glomerular filtrate within the kidneys would also be advantageous for treating chronic renal failure. Furthermore, inhibition of phosphate transport may slow the progression of renal failure and reduce risk of cardiovascular events.

While progress has been made in this field, there remains a need in the art for improved phosphate transport inhibitors. The present invention fulfills this need and provides further related advantages.

BRIEF SUMMARY

The present invention relates generally to NHE3-binding and/or NHE-modulating compounds having activity as phosphate transport inhibitors, including, for example, inhibitors of phosphate transport in the gastrointestinal tract and the kidneys, including stereoisomers, pharmaceutically acceptable salts and prodrugs thereof, and the use of such compounds to inhibit phosphate uptake and to thereby treat any of a variety of conditions or diseases in which modulation of phosphate uptake provides a therapeutic benefit.

Embodiments of the present invention include methods for inhibiting phosphate uptake in the gastrointestinal tract or kidneys of a patient in need of phosphate lowering, comprising administering to the patient a compound that binds to NHE3 and is substantially active in the gastrointestinal tract or kidneys to inhibit transport of phosphate ions (Pi) therein upon administration to the patient in need thereof.

Certain embodiments include methods for inhibiting phosphate uptake in the gastrointestinal tract of a patient in need of phosphate lowering, comprising enterally administering to the patient a substantially systemically non-bioavailable compound that binds to NHE3 and is substantially active in the gastrointestinal tract to inhibit transport of phosphate ions (Pi) therein upon administration to the patient in need thereof. In some embodiments, the method is selected from one or more of: (a) a method for treating hyperphosphatemia, optionally postprandial hyperphosphatemia; (b) a method for treating a renal disease, optionally chronic kidney disease (CKD) or end-stage renal disease (ESRD); (c) a method for reducing serum creatinine levels; (d) a method for treating proteinuria; (e) a method for delaying time to renal replacement therapy (RRT), optionally dialysis; (f) a method for reducing FGF23 levels; (g) a method for reducing the hyperphosphatemic effect of active vitamin D; (h) a method for attenuating hyperparathyroidism, optionally secondary hyperparathyroidism; (i) a method for reducing serum parathyroid hormone (PTH); (j) a method for reducing inderdialytic weight gain (IDWG); (k) a method for improving endothelial dysfunction, optionally induced by postprandial serum phosphate; (l) a method for reducing vascular calcification, optionally intima-localized vascular calcification; (m) a method for reducing urinary phosphorous; (n) a method for normalizing serum phosphorus levels; (o) a method for reducing phosphate burden in an elderly patient; (p) a method for decreasing dietary phosphate uptake; (q) a method for reducing renal hypertrophy; (r) a method for reducing heart hypertrophy; and (s) a method for treating obstructive sleep apnea.

In some embodiments, the compound is substantially active on the apical side of the epithelium of the gastrointestinal tract to inhibit transport of Pi therein. In certain embodiments, the compound is substantially impermeable to the epithelium of the gastrointestinal tract.

In certain embodiments, upon administration of the compound to the patient in need thereof, the compound exhibits a maximum concentration detected in the serum, defined as $C_{max}$, that is less than the Pi transport inhibitory concentration $IC_{50}$ of the compound.

In some embodiments, systemic exposure to the compound is less than 10% $pIC_{50}$ at PD dose, with fecal recovery of greater than about 80%, greater than about 90%, or greater than about 95%. In certain embodiments, the compound is substantially active in the small intestine to inhibit transport of Pi therein.

In certain embodiments, administration to the patient in need thereof (a) reduces serum phosphate concentrations or levels to about 150% or less of normal serum phosphate levels, and/or (b) reduces uptake of dietary phosphorous by at least about 10% relative to an untreated state. In some embodiments, administration to the patient in need thereof reduces urinary phosphate concentrations or levels by at least about 10% relative to an untreated state. In certain embodiments, administration to the patient in need thereof increases phosphate levels in fecal excretion by at least about 10% relative to an untreated state.

In some embodiments, the compound is a persistent inhibitor of NHE3-mediated antiport of sodium and hydrogen ions. In certain embodiments, the compound is substantially active in the gastrointestinal tract to inhibit NHE3-mediated antiport of sodium and hydrogen ions therein upon administration to the patient in need thereof. In some embodiments, the compound is substantially active on the apical side of the epithelium of the gastrointestinal tract to inhibit NHE3-mediated antiport of sodium ions and hydrogen ions. In certain embodiments, the compound is substantially active in the large intestine to inhibit NHE3-mediated antiport of sodium and hydrogen ions therein upon administration to the patient in need thereof.

In certain embodiments, persistent inhibition is characterized by the time-dependent inhibitory activity of the compound in an in vitro inhibition assay of NHE3-mediated antiport of sodium and hydrogen ions, wherein the $pIC_{50}$ of the compound under prompt conditions ($pIC_{50promp}$) is substantially comparable to the $pIC_{50}$ of the compound under persistent conditions ($pIC_{50pers}$). In some embodiments, persistent inhibition is characterized by the time-dependent inhibitory activity of the compound in an in vitro inhibition assay of NHE3-mediated antiport of sodium and hydrogen ions, wherein the $pIC_{50}$ of the compound under prompt conditions ($pIC_{50promp}$) and under persistent conditions ($pIC_{50pers}$) is about or greater than about 7.0. In some embodiments, the compound has an $EC_{50}$ for increasing fecal output of phosphate ions ($EC_{50}P_f$) and an $EC_{50}$ for inhibiting NHE3-mediated antiport of sodium and hydrogen ions ($EC_{50}Na$) that is defined by the formula $EC_{50}P_f=(r) EC_{50}Na$, wherein r is about 0.7 to about 1.3. In some embodiments, the compound has an $EC_{50}$ for reducing urinary output of phosphate ions ($EC_{50}P_u$) and an $EC_{50}$ for inhibiting NHE3-mediated antiport of sodium and hydrogen ions ($EC_{50}Na$) that is defined by the formula $EC_{50}P_u=(r) EC_{50}Na$, wherein r is about 0.7 to about 1.3. In certain embodiments, the compound has an $EC_{50}$ for inhibiting transport of phosphate ions ($EC_{50}P$) and an $EC_{50}$ for inhibiting NHE3-mediated antiport of sodium and hydrogen ions ($EC_{50}Na$) that is defined by the formula $EC_{50}P=(r)EC_{50}Na$, wherein r is about 0.7 to about 1.3.

In some embodiments, administration to the patient in need thereof increases the patient's daily fecal output of sodium and/or fluid. In certain embodiments, the compound, upon administration at a dose resulting in at least about a 10% increase in fecal water content, has a $C_{max}$ that is less than the $IC_{50}$ for NHE3, less than about 10× the $IC_{50}$, or less than about 100× the $IC_{50}$.

In certain embodiments, the patient in need thereof has ESRD, and administration to the patient (a) reduces serum phosphate concentrations or levels to about 150% or less of normal serum phosphate levels, and (b) reduces inderdialytic weight gain (IDWG) by at least about 10% relative to an untreated state.

In some embodiments, the patient in need thereof has CKD, and administration to the patient (a) reduces FGF23 levels and serum intact parathyroid hormone (iPTH) levels by at least about 10% relative to an untreated state, and (b) reduces blood pressure and proteinuria by at least about 10% relative to an untreated state.

In some embodiments, the compound is a non-persistent ligand of NHE3. In certain embodiments, the compound has a maximum inhibition of NHE3-mediated antiport of sodium and hydrogen ions of less than about 50%, less than about 20%, or less than about 10%, wherein maximum inhibition is characterized by the inhibitory activity of the compound in an in vitro inhibition assay of NHE3-mediated antiport of sodium and hydrogen ions and is relative to sodium-free conditions. In some embodiments, the compound is substantially inactive in the gastrointestinal tract to inhibit NHE3-mediated antiport of sodium and hydrogen ions therein upon administration to the patient in need thereof. In certain embodiments, the compound is substantially inactive in the large intestine to inhibit NHE3-mediated antiport of sodium and hydrogen ions therein.

In certain embodiments, non-persistence is characterized by the time-dependent inhibitory activity of the compound in an in vitro inhibition assay of NHE3-mediated antiport of sodium and hydrogen ions, wherein the $pIC_{50}$ of the compound under prompt conditions ($pIC_{50promp}$) is (substantially) greater than the $pIC_{50}$ of the compound under persistent conditions ($pIC_{50pers}$). In some embodiments, non-persistence is characterized by the time-dependent inhibitory activity of the compound in an in vitro inhibition assay of NHE3-mediated antiport of sodium and hydrogen ions, wherein the $pIC_{50}$ of the compound under prompt conditions ($pIC_{50promp}$) is about or greater than about 7.0, and wherein the $pIC_{50}$ of the compound under persistent conditions ($pIC_{50pers}$) is about or less than about 6.0. In certain embodiments, the compound has an $EC_{50}$ for increasing fecal output of phosphate ions ($EC_{50}P_f$) and an $EC_{50}$ for inhibiting NHE3-mediated antiport of sodium and hydrogen ions ($EC_{50}Na$) that is defined by the formula $EC_{50}P_f=(r)EC_{50}Na$, wherein r is about 0.1 to about 0.5. In some embodiments, the compound has an $EC_{50}$ for reducing urinary output of phosphate ions ($EC_{50}P_u$) and an $EC_{50}$ for inhibiting NHE3-mediated antiport of sodium and hydrogen ions ($EC_{50}Na$) that is defined by the formula $EC_{50}P_u=(r)EC_{50}Na$, wherein r is about 0.1 to about 0.5. In some embodiments, the compound has an $EC_{50}$ for inhibiting transport of phosphate ions ($EC_{50}P$) and an $EC_{50}$ for inhibiting NHE-mediated antiport of sodium and hydrogen ions ($EC_{50}Na$) that is defined by the formula $EC_{50}P=(r)EC_{50}Na$, wherein r is about 0.1 to about 0.5.

In certain embodiments, administration to the patient in need thereof increases the ratio of phosphate/sodium in fecal excretion by at least about 10% relative to an untreated state. In some embodiments, administration to the patient in need thereof increases the daily fecal output of phosphate without substantially modulating the stool form or water content of the feces. In certain embodiments, administration to a rodent increases the ratio of sodium in the small intestine ($Na_{SI}$)/cecum ($Na_C$) by at least about 10% relative to an untreated state.

Also included are methods for increasing phosphaturia in a patient in need of phosphate lowering, comprising administering to the patient (a) a substantially systemically bioavailable compound, or (b) a substantially systemically non-bioavailable compound via a route excluding enteral administration; wherein the compound binds to NHE3 and is substantially active in the kidneys to inhibit transport of phosphate ions (Pi) therein upon administration to the patient in need thereof. In some embodiments, the method is selected from one or more of: (a) a method for treating hyperphosphatemia, optionally postprandial hyperphosphatemia; (b) a method for treating a renal disease, optionally chronic kidney disease (CKD) or end-stage renal disease (ESRD); (c) a method for reducing serum creatinine levels; (d) a method for treating proteinuria; (e) a method for delaying time to renal replacement therapy (RRT), optionally dialysis; (f) a method for reducing FGF23 levels; (g) a method for reducing the hyperphosphatemic effect of active vitamin D; (h) a method for attenuating hyperparathyroidism, optionally secondary hyperparathyroidism; (i) a method for reducing serum parathyroid hormone (PTH); (j) a method for reducing interdialytic weight gain (IDWG); (k) a method for improving endothelial dysfunction, optionally induced by postprandial serum phosphate; (l) a method for reducing vascular calcification, optionally intima-localized vascular calcification; (m) a method for increasing urinary phosphorous; (n) a method for normalizing serum phosphorus levels; (o) a method for reducing phosphate burden in an elderly patient; (p) a method for decreasing dietary phosphate uptake; (q) a method for reducing renal hypertrophy; (r) a method for reducing heart hypertrophy; and (s) a method for treating obstructive sleep apnea.

In some embodiments, the compound is substantially permeable to the epithelium of the gastrointestinal tract. In certain embodiments, administration to the patient in need thereof reduces serum phosphate concentrations or levels to about 150% or less of normal serum phosphate levels. In some embodiments, administration to the patient in need thereof increases urinary phosphate concentrations or levels by at least about 10% relative to an untreated state.

In certain embodiments, the compound has (i) a tPSA of at least about 200 Å$^2$ and a molecular weight of at least about 710 Daltons in the non-salt form, or (ii) a tPSA of at least about 270 Å$^2$. In certain embodiments, the compound has a tPSA of at least about 250 Å$^2$, or a tPSA of at least about 270 Å$^2$, or a tPSA of at least about 300 Å$^2$, or a tPSA of at least about 350 Å$^2$, or a tPSA of at least about 400 Å$^2$, or a tPSA of at least about 500 Å$^2$. In certain embodiments, the compound has a molecular weight of at least about 500 Da, or a molecular weight of at least about 1000 Da, or a molecular weight of at least about 2500 Da, or a molecular weight of at least about 5000 Da.

In some embodiments, the compound has (i) a total number of NH and/or OH and/or other potential hydrogen bond donor moieties greater than about 5; (ii) a total number of O atoms and/or N atoms and/or other potential hydrogen bond acceptors greater than about 10; and/or (iii) a Moriguchi partition coefficient greater than about 10$^5$ or less than about 10. In certain embodiments, the compound has a permeability coefficient, $P_{app}$, of less than about $100\times10^{-6}$ cm/s, or less than about $10\times10^{-6}$ cm/s, or less than about $1\times10^{-6}$ cm/s, or less than about $0.1\times10^{-6}$ cm/s.

In some embodiments, the compound has a structure of Formula (I) or (IX):

wherein: NHE is a NHE-binding small molecule that comprises (i) a hetero-atom containing moiety, and (ii) a cyclic or heterocyclic scaffold or support moiety bound directly or indirectly thereto, the heteroatom-containing moiety being selected from a substituted guanidinyl moiety and a substituted heterocyclic moiety, which may optionally be fused with the scaffold or support moiety to form a fused bicyclic structure; and, Z is a moiety having at least one site thereon for attachment to the NHE-binding small molecule, the resulting NHE-Z molecule possessing overall physicochemical properties that render it substantially impermeable or substantially systemically non-bioavailable; and, E is an integer having a value of 1 or more.

In some embodiments, the compound is an oligomer, dendrimer or polymer, and further wherein Z is a Core moiety having two or more sites thereon for attachment to multiple NHE-binding small molecules, either directly or indirectly through a linking moiety, L, the compound having the structure of Formula (X):

wherein L is a bond or linker connecting the Core to the NHE-binding small molecule, and n is an integer of 2 or more, and further wherein each NHE-binding small molecule may be the same or differ from the others, or a pharmaceutically acceptable salt thereof.

In certain embodiments, the total number of freely rotatable bonds in the NHE-Z molecule is at least about 10. In certain embodiments, the total number hydrogen bond donors in the NHE-Z molecule is at least about 5. In some embodiments, the total number of hydrogen bond acceptors in the NHE-Z molecule is at least about 10. In certain embodiments, the total number of hydrogen bond donors and hydrogen bond acceptors in the NHE-Z molecule is at least about 10. In some embodiments, the Log P of the NHE-Z binding compound is at least about 5. In certain embodiments, the log P of the NHE-Z binding compound is less than about 1, or less than about 0. In certain embodiments, the scaffold is a 5-member or 6-member cyclic or heterocyclic moiety. In certain embodiments, the scaffold is aromatic.

In some embodiments, the scaffold of the NHE-binding small molecule is bound to the moiety, Z, the compound having the structure of Formula (II):

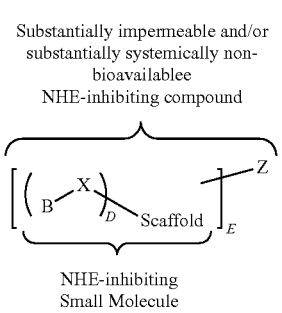

(II)

wherein: Z is a Core having one or more sites thereon for attachment to one or more NHE-binding small molecules, the resulting NHE-Z molecule possessing overall physicochemical properties that render it substantially impermeable or substantially systemically non-bioavailable; B is the heteroatom-containing moiety of the NHE-binding small molecule, and is selected from a substituted guanidinyl moiety and a substituted heterocyclic moiety, which may optionally be fused with the Scaffold moiety to form a fused, bicyclic structure; Scaffold is the cyclic or heterocyclic scaffold or support moiety of the NHE-binding small molecule, which is bound directly or indirectly to heteroatom-containing moiety, B, and which is optionally substituted with one or more additionally hydrocarbyl or heterohydrocarbyl moieties; X is a bond or a spacer moiety selected from a group consisting of substituted or unsubstituted hydrocarbyl or heterohydrocarbyl moieties, and in particular substituted or unsubstituted $C_{1-7}$ hydrocarbyl or heterohydrocarbyl, and substituted or unsubstituted, saturated or unsaturated, cyclic or heterocyclic moieties, which links B and the Scaffold; and D and E are integers, each independently having a value of 1 or more.

In some embodiments, the NHE-binding small molecule has the structure of Formula (IV):

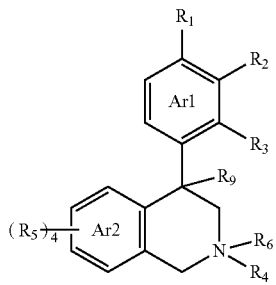

(IV)

or a stereoisomer, prodrug or pharmaceutically acceptable salt thereof, wherein: each $R_1$, $R_2$, $R_3$, $R_5$ and $R_9$ are independently selected from H, halogen, —$NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H or a bond linking the NHE-binding small molecule to L, provided at least one is a bond linking the NHE-binding small molecule to L; $R_4$ is selected from H, $C_1$-$C_7$ alkyl, or a bond linking the NHE-binding small molecule to L; $R_6$ is absent or selected from H and $C_1$-$C_7$ alkyl; and Ar1 and Ar2 independently represent an aromatic ring or a heteroaromatic ring.

In certain embodiments, the NHE-binding small molecule has the following structure:

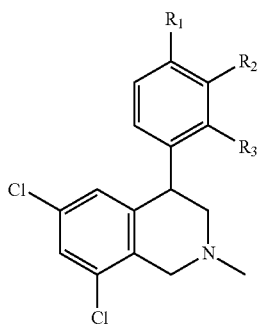

or a stereoisomer, prodrug or pharmaceutically acceptable salt thereof, wherein: each $R_1$, $R_2$ and $R_3$ are independently selected from H, halogen, —$NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H or a bond linking the NHE-binding small molecule to L, provided at least one is a bond linking the NHE-binding small molecule to L.

In some embodiments, the NHE-binding small molecule has one of the following structures:

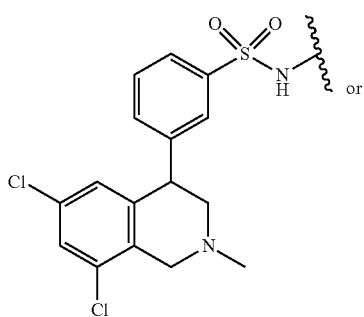

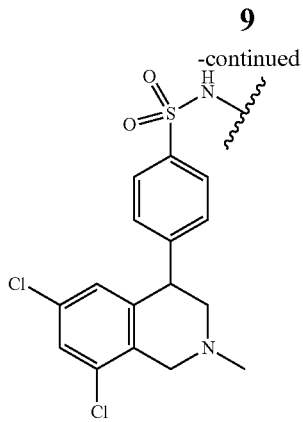

or a stereoisomer, prodrug or pharmaceutically acceptable salt thereof. In certain embodiments, L is a polyalkylene glycol linker. In certain embodiments, L is a polyethylene glycol linker. In some embodiments, n is 2.

In certain embodiments, the Core has the following structure:

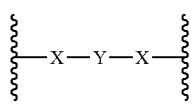

wherein: X is selected from the group consisting of a bond, —O—, —NH—, —S—, $C_{1-6}$alkylene, —NHC(=O)—, —C(=O)NH—, —NHC(=O)NH—, —SO$_2$NH—, and —NHSO$_2$—; Y is selected from the group consisting of a bond, optionally substituted $C_{1-8}$alkylene, optionally substituted aryl, optionally substituted heteroaryl, a polyethylene glycol linker, —(CH$_2$)$_{1-6}$O(CH$_2$)$_{1-6}$— and —(CH$_2$)$_{1-6}$NY$_1$(CH$_2$)$_{1-6}$—; and Y$_1$ is selected from the group consisting of hydrogen, optionally substituted $C_{1-8}$alkyl, optionally substituted aryl or optionally substituted heteroaryl, or a pharmaceutically acceptable salt thereof.

In some embodiments, the Core is selected from the group consisting of:

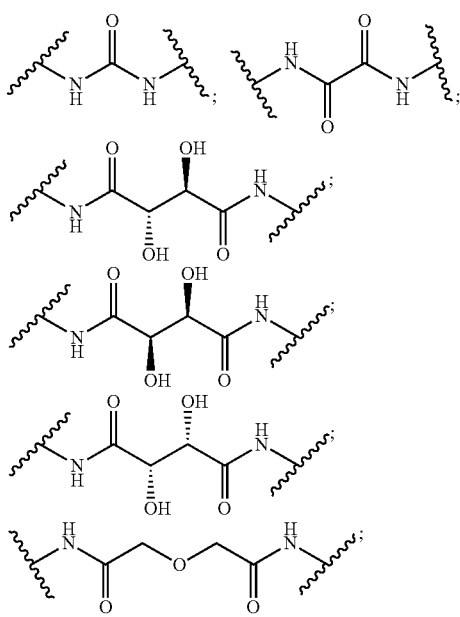

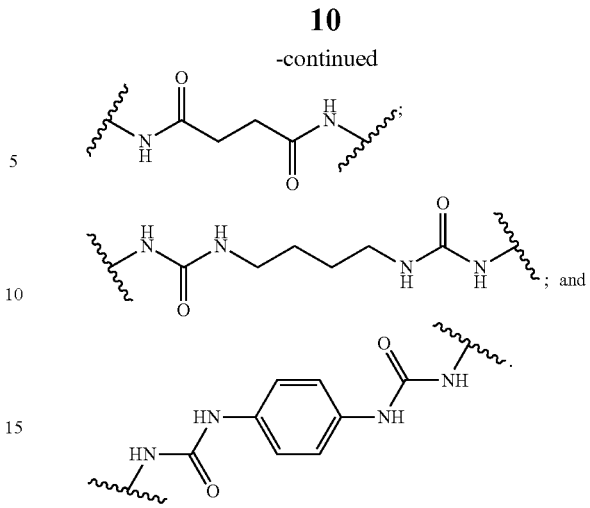

In some embodiments, the compound has the following structure of Formula (I-H):

Core—(L-NHE)$_n$ (I-H)

or a stereoisomer, prodrug or pharmaceutically acceptable salt thereof, wherein: (a) n is an integer of 2 or more; (b) Core is a Core moiety having two or more sites thereon for attachment to two or more NHE-binding small molecule moieties; (c) L is a bond or linker connecting the Core moiety to the two or more NHE-binding small molecule moieties; and (d) NHE is a NHE-binding small molecule moiety having the following structure of Formula (XI-H):

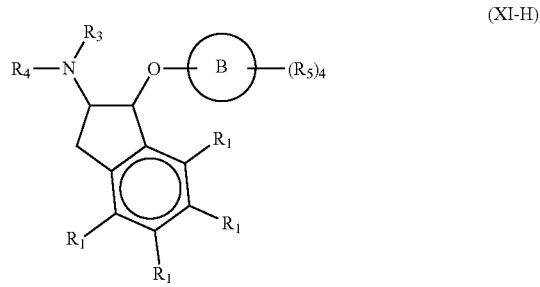

wherein: B is selected from the group consisting of aryl and heterocyclyl; each R$_5$ is independently selected from the group consisting of hydrogen, halogen, optionally substituted $C_{1-4}$alkyl, optionally substituted $C_{1-4}$alkoxy, optionally substituted $C_{1-4}$thioalkyl, optionally substituted heterocyclyl, optionally substituted heterocyclylalkyl, optionally substituted aryl, optionally substituted heteroaryl, hydroxyl, oxo, cyano, nitro, —NR$_7$R$_8$, —NR$_7$C(=O)R$_8$, —NR$_7$C(=O)OR$_8$, —NR$_7$C(=O)NR$_8$R$_9$, —NR$_7$SO$_2$R$_8$, —NR$_7$S(O)$_2$NR$_8$R$_9$, —C(=O)OR$_7$, —C(=O)R$_7$, —C(=O)NR$_7$R$_8$, —S(O)$_{1-2}$R$_7$, and —SO$_2$NR$_7$R$_8$, wherein R$_7$, R$_8$, and R$_9$ are independently selected from the group consisting of hydrogen, $C_{1-4}$alkyl, or a bond linking the NHE-binding small molecule moiety to L, provided at least one is a bond linking the NHE-binding small molecule moiety to L; R$_3$ and R$_4$ are independently selected from the group consisting of hydrogen, optionally substituted $C_{1-4}$alkyl, optionally substituted cycloalkyl, optionally substituted cycloalkylalkyl, optionally substituted aryl, optionally substituted aralkyl, optionally substituted heterocyclyl and optionally substituted heteroaryl; or R$_3$ and R$_4$ form together with the nitrogen to which they are bonded an optionally substituted 4-8 membered heterocyclyl; and each $R_1$ is independently selected from the group consisting of hydrogen, halogen, optionally substituted $C_{1-6}$alkyl and optionally substituted $C_{1-6}$alkoxy. In some embodiments, n is 2. In certain embodiments, L is a polyalkylene glycol linker. In certain embodiments, L is a polyethylene glycol linker.

In certain embodiments, the Core has the following structure:

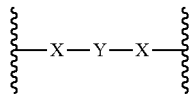

wherein: X is selected from the group consisting of a bond, —O—, —NH—, —S—, $C_{1-6}$alkylene, —NHC(═O)—, —C(═O)NH—, —NHC(═O)NH—, —SO$_2$NH—, and —NHSO$_2$—; Y is selected from the group consisting of a bond, optionally substituted $C_{1-8}$alkylene, optionally substituted aryl, optionally substituted heteroaryl, a polyethylene glycol linker, —(CH$_2$)$_{1-6}$O(CH$_2$)$_{1-6}$— and —(CH$_2$)$_{1-6}$NY$_1$(CH$_2$)$_{1-6}$—; and $Y_1$ is selected from the group consisting of hydrogen, optionally substituted $C_{1-8}$alkyl, optionally substituted aryl or optionally substituted heteroaryl, or a pharmaceutically acceptable salt thereof.

In some embodiments, the Core is selected from the group consisting of

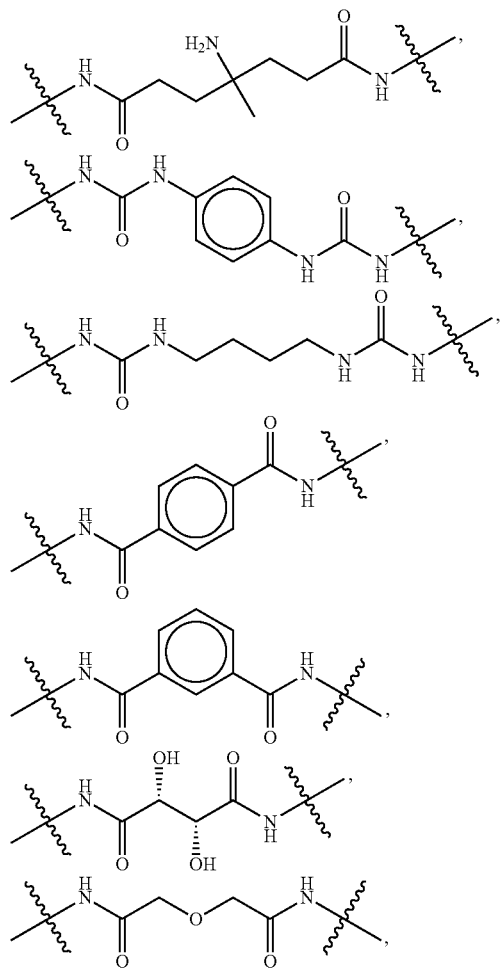

In certain embodiments, the NHE-binding small molecule moiety has the following structure of Formula (XII-H):

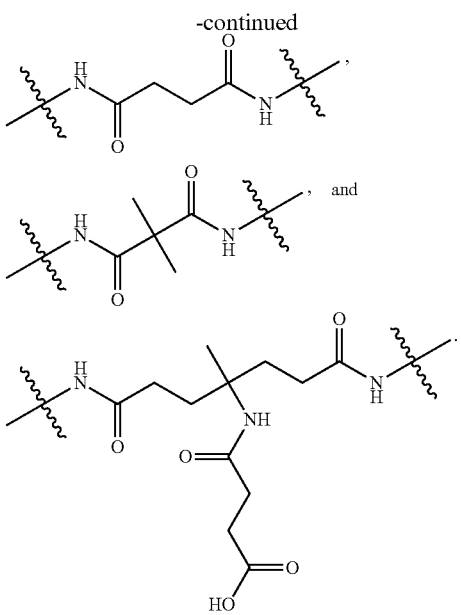

(XII-H)

wherein: each $R_3$ and $R_4$ are independently selected from the group consisting of hydrogen and optionally substituted $C_{1-4}$alkyl, or $R_3$ and $R_4$, taken together with the nitrogen to which they are bonded, form an optionally substituted 4-8 membered heterocyclyl; each $R_1$ is independently selected from the group consisting of hydrogen, halogen, $C_{1-6}$alkyl, and $C_{1-6}$haloalkyl; and $R_5$ is selected from the group consisting of —SO$_2$—NR$_7$— and —NHC(═O)NH—, wherein $R_7$ is hydrogen or $C_{1-4}$alkyl.

In some embodiments, $R_3$ and $R_4$, taken together with the nitrogen to which they are bonded, form an optionally substituted 5 or 6 membered heterocyclyl. In certain embodiments, the optionally substituted 5 or 6 membered heterocyclyl is pyrrolidinyl or piperidinyl. In certain embodiments, the optionally substituted 5 or 6 membered heterocyclyl is pyrrolidinyl or piperidinyl, each substituted with at least one amino or hydroxyl. In some embodiments, $R_3$ and $R_4$ are independently $C_{1-4}$alkyl. In certain embodiments, $R_3$ and $R_4$ are methyl. In some embodiments, each $R_1$ is independently selected from the group consisting of hydrogen or halogen. In certain embodiments, each $R_1$ is independently selected from the group consisting of hydrogen, F and Cl.

In certain embodiments, the compound has the following structure of Formula (I-I):

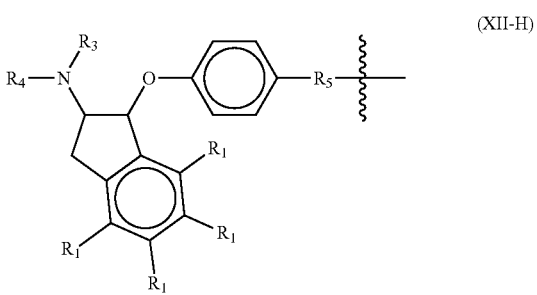

(I-I)

or a stereoisomer, prodrug or pharmaceutically acceptable salt thereof, wherein: (a) NHE is a NHE-binding small molecule moiety having the following structure of Formula (A-I):

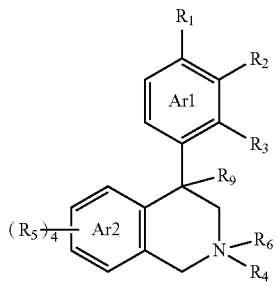

(A-I)

wherein: each $R_1$, $R_2$, $R_3$, $R_5$ and $R_9$ are independently selected from H, halogen, —$NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H, $C_{1-6}$alkyl, —$C_{1-6}$alkyl-OH or a bond linking the NHE-binding small molecule to L, provided at least one is a bond linking the NHE-binding small molecule to L; $R_4$ is selected from H, $C_1$-$C_7$ alkyl, or a bond linking the NHE-binding small molecule to L; $R_6$ is absent or selected from H and $C_1$-$C_7$ alkyl; and Ar1 and Ar2 independently represent an aromatic ring or a heteroaromatic ring; (b) Core is a Core moiety having the following structure of Formula (B-I):

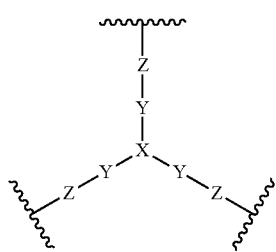

(B-I)

wherein: X is selected from $C(X_1)$, N and $N(C_{1-6}$alkyl); $X_1$ is selected from hydrogen, optionally substituted alkyl, —$NX_aX_b$, —$NO_2$, —$NX_c$—$C(=O)$—$NX_c$—$X_a$, —$C(=O)NX_c$—$X_a$, —$NX_c$—$C(=O)$—$X_a$, —$NX_c$—$SO_2$—$X_a$, —$C(=O)$—$X_a$ and —$OX_a$, each $X_a$ and $X_b$ are independently selected from hydrogen, optionally substituted alkyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl and optionally substituted heteroarylalkyl; Y is $C_{1-6}$alkylene; Z is selected from —$NZ_a$—$C(=O)$—$NZ_a$—, —$C(=O)NZ_a$—, —$NZ_a$—$C(=O)$— and heteroaryl when X is $CX_1$; Z is selected from —$NZ_a$—$C(=O)$—$NZ_a$—, —$NZ_a$—$C(=O)$— and heteroaryl when X is N or $N(C_{1-6}$alkyl); and each $X_c$ and $Z_a$ is independently selected from hydrogen and $C_{1-6}$alkyl; and (c) L is a bond or linker connecting the Core moiety to the NHE-binding small molecule moieties.

In some embodiments, the NHE-binding small molecule moiety has the following structure:

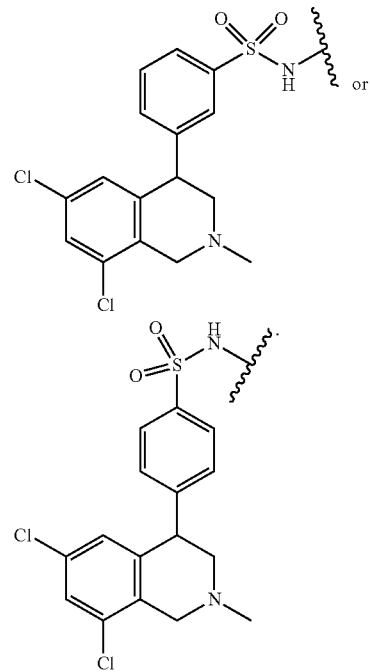

wherein: each $R_1$, $R_2$ and $R_3$ are independently selected from H, halogen, —$NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H, $C_{1-6}$alkyl, —$C_{1-6}$alkyl-OH or a bond linking the NHE-binding small molecule to L, provided at least one is a bond linking the NHE-binding small molecule to L.

In some embodiments, the NHE-binding small molecule moiety has one of the following structures:

In some embodiments, L is a polyalkylene glycol linker. In certain embodiments, L is a polyethylene glycol linker. In some embodiments, X is $C(X_1)$. In some embodiments, each $X_c$ is hydrogen. In certain embodiments, X is N. In certain embodiments, each $Z_a$ is hydrogen.

In some embodiments, the compound has the structure of Formula (II-I):

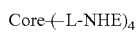

Core—(—L—NHE)$_4$        (II-I)

or a stereoisomer, prodrug or pharmaceutically acceptable salt thereof, wherein: (a) NHE is a NHE-binding small molecule moiety having the structure of Formula (A-I):

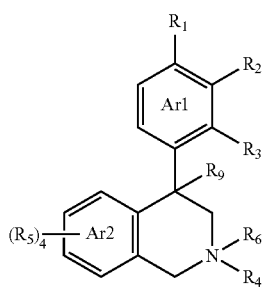
(A-1)

wherein: each $R_1$, $R_2$, $R_3$, $R_5$ and $R_9$ are independently selected from H, halogen, —$NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H, $C_{1-6}$alkyl, —$C_{1-6}$alkyl-OH or a bond linking the NHE-binding small molecule to L, provided at least one is a bond linking the NHE-binding small molecule to L; $R_4$ is selected from H, $C_1$-$C_7$ alkyl, or a bond linking the NHE-binding small molecule to L; $R_6$ is absent or selected from H and $C_1$-$C_7$ alkyl; and Ar1 and Ar2 independently represent an aromatic ring or a heteroaromatic ring; (b) Core is a Core moiety having the following structure of Formula (C-I):

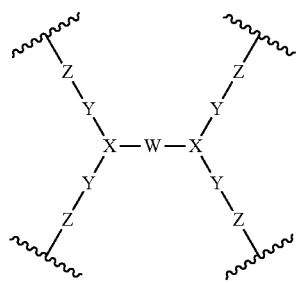
(C-I)

wherein: W is selected from alkylene, polyalkylene glycol, —C(=O)—NH-(alkylene)-NH—C(=O)—, —C(=O)—NH-(polyalkylene glycol)-NH—C(=O)—, —C(=O)-(alkylene)-C(=O)—, —C(=O)-(polyalkylene glycol)-C(=O)— and cycloalkyl; X is N; Y is $C_{1-6}$alkylene; Z is selected from —$NZ_a$—C(=O)—$NZ_a$—, —C(=O)$NZ_a$—, —$NZ_a$—C(=O)— and heteroaryl; each $Z_a$ is independently selected from hydrogen and $C_{1-6}$alkyl; and (c) L is a bond or linker connecting the Core moiety to the NHE-binding small molecules.

In certain embodiments, the NHE-binding small molecule moiety has the following structure:

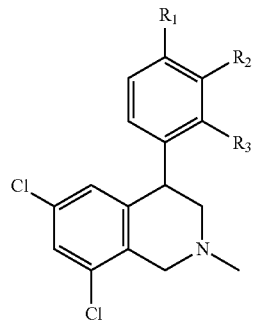

wherein: each $R_1$, $R_2$ and $R_3$ are independently selected from H, halogen, —$NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H, $C_{1-6}$alkyl, —$C_{1-6}$alkyl-OH or a bond linking the NHE-binding small molecule to L, provided at least one is a bond linking the NHE-binding small molecule to L.

In certain embodiments, the NHE-binding small molecule moiety has one of the following structures:

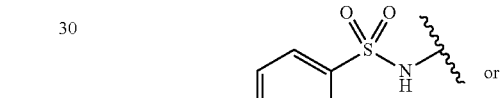

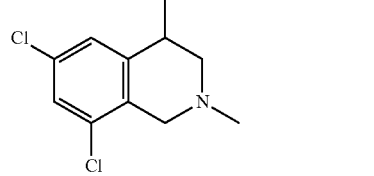

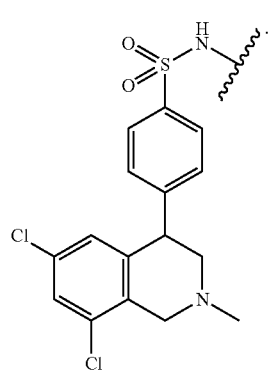

In specific embodiments, the compound is selected from a compound of Table E3 or Table E4, or a pharmaceutically acceptable salt thereof.

In particular embodiments, the compound is:

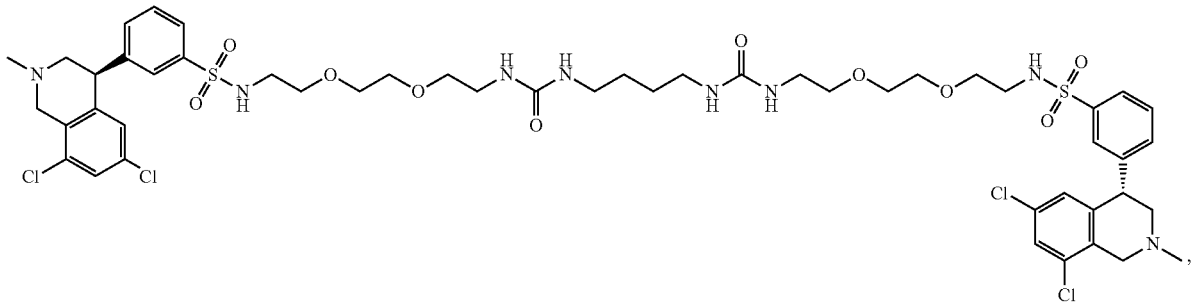

or a pharmaceutically acceptable salt thereof.

In particular embodiments, the compound is:

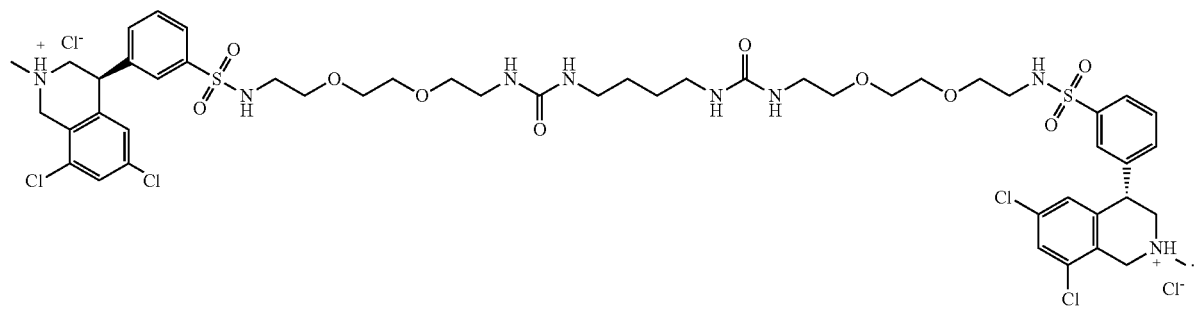

Certain methods further comprise administering one or more additional biologically active agents. In certain embodiments, the compound and the one or more additional biologically active agents are administered as part of a single pharmaceutical composition. In some embodiments, the compound and the one or more additional biologically active agents are administered as individual pharmaceutical compositions. In some embodiments, the individual pharmaceutical compositions are administered sequentially. In some embodiments, the individual pharmaceutical compositions are administered simultaneously.

In certain embodiments, the additional biologically active agent is selected from vitamin $D_2$ (ergocalciferol), vitamin $D_3$ (cholecalciferol), active vitamin D (calcitriol) and active vitamin D analogs (e.g. doxercalciferol, paricalcitol).

In some embodiments, the additional biologically active agent is a phosphate binder. In certain embodiments, the phosphate binder is selected from the group consisting of sevelamer (e.g., Renvela® (sevelamer carbonate), Renagel® (sevelamer hydrochloride)), lanthanum carbonate (e.g., Fosrenol®), calcium carbonate (e.g., Calcichew®, Titralac®), calcium acetate (e.g. PhosLo®, Phosex®), calcium acetate/magnesium carbonate (e.g., Renepho®, OsvaRen®), MCI-196, ferric citrate (e.g., Zerenex™), magnesium iron hydroxycarbonate (e.g., Fermagate™), aluminum hydroxide (e.g., Alucaps®, Basaljel®), APS1585, SBR-759, and PA-21.

In some embodiments, the additional biologically active agent is a NaPi2b inhibitor. In certain embodiments, the additional biologically active agent is niacin or nicotinamide.

In some embodiments, the compound or composition is administered orally. In certain embodiments, the compound or composition is administered orally once-a-day.

These and other aspects of the invention will be apparent upon reference to the following detailed description.

BRIEF DESCRIPTION OF THE DRAWINGS

FIGS. 1A-B shows the effects of test compounds on reducing phosphate uptake in normal-function rats (see Example 3). FIG. 1A shows that Cpd 004, a non-persistent NHE3 inhibitor, was as potent at reducing Pi uptake as a persistent inhibitor such as Cpd 003. FIGS. 1B-C show that Cpd 003 significantly reduced Pi uptake in the presence of glucose/Ca (1B) and Ca (1C).

DETAILED DESCRIPTION

Figure 1:
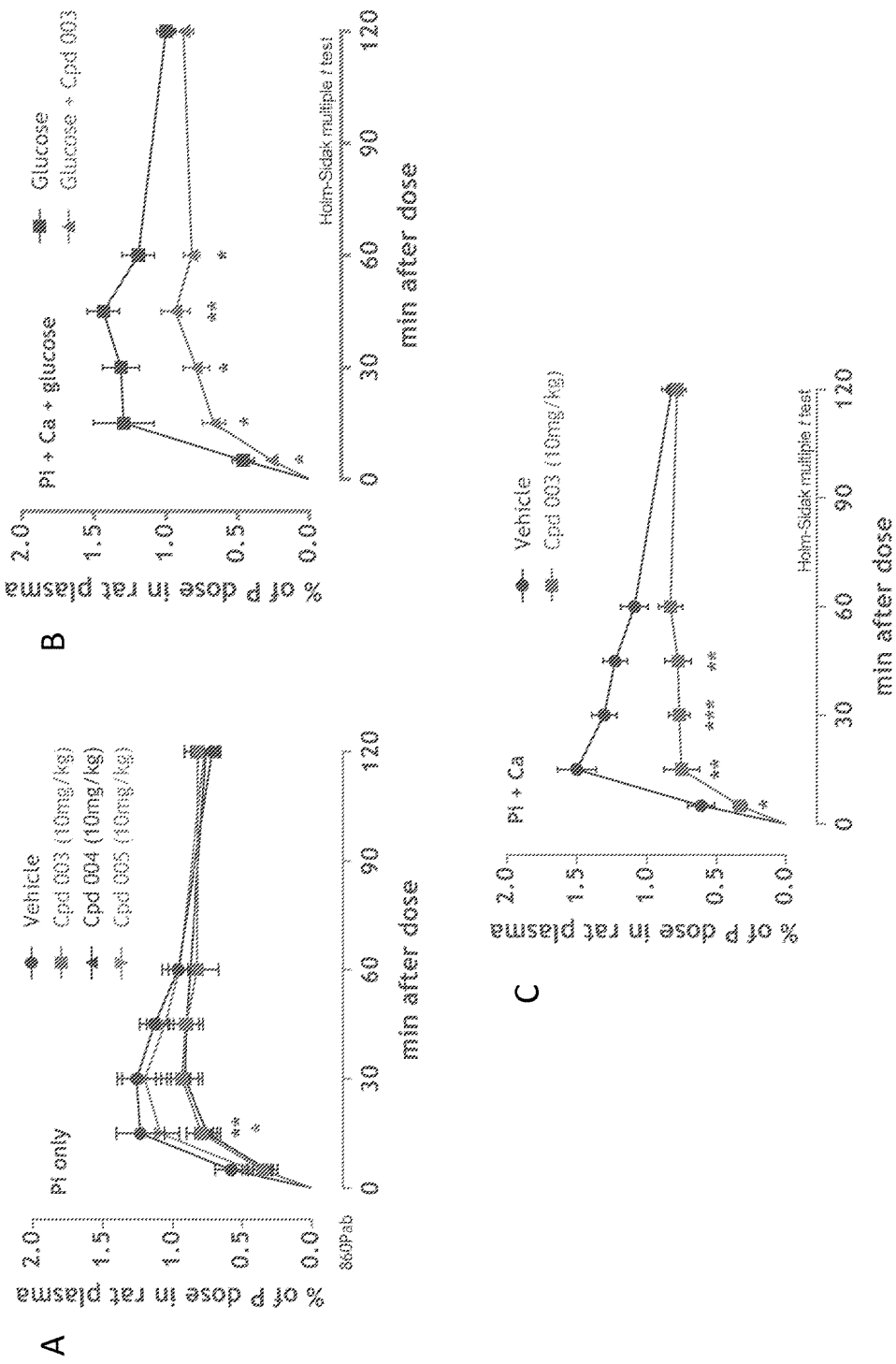

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Certain embodiments relate to the unexpected discovery that phosphate absorption from the intestine in subjects with elevated phosphate serum levels may be limited, and preferably substantially prevented, through the use of NHE3-binding and/or NHE3-modulating agents to inhibit the intestinal transport system which mediates phosphate uptake in the intestine. It has also been unexpectedly discovered that such NHE3-binding and/or NHE3-modulating agents can inhibit the renal transport system which mediates phosphate uptake in the kidneys.

In some aspects, inhibition of phosphate uptake in the gastrointestinal tract may be achieved by the administration of certain compounds, and/or pharmaceutical compositions comprising them, which may advantageously be designed such that little, or substantially none, of the compound is absorbed into the blood stream (that is, it is designed to be non-systemic or substantially non-systemic). In this regard, the compounds have features that give rise to little or substantially no systemic availability upon enteral administration, including oral administration. In other words, the compounds are not absorbed into the bloodstream at meaningful levels and therefore have no activity there, but instead have their activity localized substantially within the GI tract.

Therefore, in certain illustrative embodiments as further described herein, the compounds of the invention generally require a combination of structural and/or functional features relating or contributing to their activity in the GI tract and/or their substantial non-systemic bioavailability. Such features may include, for example, one or more of (i) specific tPSA and/or MW values (e.g., at least about 190 $Å^2$ and/or at least about 736 Daltons, respectively), (ii) specific levels of fecal recovery of the compound and/or its metabolites after administration (e.g., greater than 50% at 72 hours); (iii) specific numbers of NH and/or OH and/or potentially hydrogen bond donor moieties (e.g., greater than about five); (iv) specific numbers of rotatable bonds (e.g., greater than about five); (iv) specific permeability features (e.g., $P_{app}$ less than about $100 \times 10^{-6}$ cm/s); and/or any of a number of other features and characteristics as described herein.

The substantially non-systemic compounds described herein offer numerous advantages in the treatment of GI tract and other disorders. For instance, the compounds are active on the phosphate transporter apically located in the intestine and essentially do not reach other phosphate transporters expressed in other tissues and organs. Because NHE3 is expressed on cells many systemic tissues or organs, the use of NHE3-binding or modulating agents can raise concerns about systemic effects, whether on-target or off-target. These particular compounds do not give rise to such concerns because of their limited systemic availability.

As noted above, certain embodiments relate to the discovery that phosphate absorption from the glomerular filtrate within the kidneys of patients with elevated phosphate serum levels may be limited, and preferably substantially prevented, through inhibition of the renal tubule transport system which mediates phosphate uptake in the kidneys. In some aspects, inhibition of phosphate uptake in the kidneys may be achieved by the administration of an otherwise substantially systemically non-bioavailable compound described herein, by a route that optionally excludes enteral or enteric administration, that is, by a route that optionally excludes administration via the gastrointestinal tract. Non-limiting examples include parenteral administration such as intravenous, intra-arterial, intramuscular, and subcutaneous administration, among others described herein and known in the art.

In some aspects, inhibition of phosphate uptake in the kidneys may be achieved by the administration of certain compounds, and/or pharmaceutical compositions comprising them, which may advantageously be designed such that most of the compound is absorbed into the blood stream (that is, it is designed to be systemic or substantially systemic). In this regard, the compounds have features that give rise to systemic availability, including oral availability. In other words, the compounds are absorbed into the bloodstream at meaningful levels and therefore have most if not all of their activity systemically, for example, within organs such as the kidney, relative to having their activity localized substantially within the GI tract. Therefore, in certain embodiments, particularly for targeting systemic tissues via oral or other form of enteral administration, the compounds described herein may have a combination of structural and/or functional features relating or contributing to their substantial systemic bioavailability. Functional features include, for example, wherein the compound is substantially permeable to the epithelium of the gastrointestinal tract, including the mouth, esophagus, stomach, upper intestine, lower intestine, etc.

As further detailed below, phosphate absorption in the upper intestine is mediated, at least in part, by a carrier-mediated mechanism which couples the absorption of phosphate to that of sodium. Renal phosphate transport is mediated, at least in part, by the activity of the sodium-dependent phosphate transporters, Npt2a, Npt2c, and PiT-2, present within the apical brush border membrane of the proximal tubule. Accordingly, inhibition of intestinal or renal phosphate transport will reduce body phosphorus overload.

In patients with advanced kidney disease (e.g. stage 4 and 5), the body phosphorus overload manifests itself by serum phosphate concentration above normal levels, i.e., hyperphosphatemia. Hyperphosphatemia is directly related to mortality and morbidity Inhibition of intestinal or renal phosphate transport will reduce serum phosphate concentration and therefore improve outcome in those patients. In stage 2 and 3 chronic kidney disease patients, the body phosphorus overload does not necessarily lead to hyperphosphatemia, i.e., patients remain normophosphatemic, but there is a need to reduce body phosphorus overload even at those early stages to avoid associated bone and vascular disorders, and ultimately improve mortality rate.

Inhibition of intestinal phosphate transport will be particularly advantageous in patients that have a disease that is treatable by inhibiting the uptake of phosphate from the intestines. Likewise, inhibition of phosphate absorption from the glomerular filtrate within the kidneys would also be advantageous for treating or preventing chronic renal failure and other renal disease conditions. Furthermore, inhibition of phosphate transport may slow the progression of renal failure and reduce the risk of cardiovascular events, among other diseases or conditions associated with the need for phosphate lowering.

I. Compounds that Inhibit Phosphate Transport

Embodiments of the present invention relate generally to the discovery that NHE3-binding and/or NHE3-modulating compounds inhibit transport or uptake of phosphate ions (Pi) in tissues such as the gastrointestinal tract and/or the kidneys. A compound's Pi transport inhibitory activity in a given tissue will depend generally, for example, on the systemic bioavailability or systemic non-bioavailability of the compound, the route of administration, or any combination thereof.

Accordingly, embodiments of the present invention include compounds that bind to and/or modulate NHE3 (e.g., NHE inhibitors) and are substantially active to inhibit transport or uptake of Pi, for instance, in a human subject, an animal model, and/or a cell-based or biochemical assay.

In some embodiments, a compound binds to NHE3. In these and related embodiments, a compound is said to "bind" or "specifically bind" to an NHE3 protein if it reacts at a detectable level with the protein, and optionally does not react detectably in a statistically significant manner with unrelated proteins under similar conditions. In certain illustrative embodiments, a compound may have a binding "affinity" (e.g., as measured by the dissociation constant, or $K_d$) for an NHE3 protein of about or less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 200, 300, 400, 500, 600, 700, 800, 900, 1000 nM.

In some embodiments, one or more of the compounds described herein, when administered either alone or in combination with one or more additional pharmaceutically active compounds or agents to a subject in need thereof, or measured in an animal model or cell-based assay, may have an $IC_{50}$ for inhibiting Pi transport or uptake of about or less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 200, 300, 400, 500, 600, 700, 800, 900, 1000 nM. In certain embodiments, one or more of the compounds detailed herein, when administered either alone or in combination with one or more additional pharmaceutically active compounds or agents to a subject in need thereof, or measured in an animal model or cell-based assay, may have a $pIC_{50}$ for inhibiting Pi transport or uptake of about or greater than about 6.0, 6.05, 6.1, 6.15, 6.2, 6.25, 6.3, 6.35, 6.4, 6.45, 6.5, 6.55, 6.6, 6.65, 6.7, 6.75, 6.8, 6.85, 6.9, 6.95, 7.0, 7.05, 7.1, 7.15, 7.2, 7.25, 7.3, 7.35, 7.4, 7.45, 7.5, 7.55, 7.6, 7.65. 7.7, 7.75, 7.8, 7.85, 7.9, 7.95, 8.0, 8.05, 8.1, 8.15, 8.2, 8.25, 8.3, 8.35, 8.4, 8.45, 8.5, 8.55, 8.6, 8.65, 8.7, 8.75, 8.8, 8.85, 8.9, 8.95, or 9.0.

As used herein, the $IC_{50}$ is defined as the quantitative measure indicating the concentration of a compound where 50% of its maximal inhibitory effect is observed, for example, in a human subject, an animal model, and/or a cell-based or biochemical assay. The $pIC_{50}$ refers to the inverse logarithm of the $IC_{50}$ (or $pIC_{50} = -\log (IC_{50})$ (see Selvaraj et al., *Current Trends in Biotechnology and Pharmacy*. 5:1104-1109, 2011). Assays for measuring the activity of inhibitors of phosphate transport or uptake are described in the accompanying Examples.

For inhibiting transport or uptake of Pi in the gastrointestinal tract, and treatment of related conditions in a subject in need of phosphate lowering, embodiments of the present invention will generally employ substantially systemically non-bioavailable compounds. Such compounds are preferably formulated or suitable for enteral administration, including oral administration. Examples of substantially systemically non-bioavailable compounds and their related features are provided elsewhere herein. In these and related embodiments, administration of the compound to a subject in need thereof reduces any one or more of serum phosphate concentrations or levels, dietary phosphorus, and/or urinary phosphate concentrations or levels. In some embodiments, serum phosphate concentrations or levels in a hyperphosphatemic subject are reduced to about or less than about 150%, 145%, 140%, 135%, 130%, 125%, 120%, 115%, 110%, 105%, or 100% (normalized) of the normal serum phosphate levels (of a healthy subject, e.g., 2.5-4.5 mg/dL or 0.81-1.45 mmol/L for a human adult). In some embodiments, uptake of dietary phosphorous is reduced by about or at least about 5%, 10%, 20%, 30%, 40%, 50%, 60%, 70%, 80% or more relative to an untreated state. In some embodiments, urinary phosphate concentrations or levels are reduced by about or at least about 5%, 10%, 20%, 30%, 40%, 50%, 60%, 70%, 80%, 90%, 100% or more, preferably about 20%, 30%, 40%, 50%, or 60%, relative to an untreated state. In some embodiments, administration of the compound to a subject in need thereof increases phosphate levels in fecal excretion by at least about 5%, 10%, 20%, 30%, 40%, 50%, 60%, 70%, 80%, 90%, 100%, 200% or more relative to an untreated state.

For inhibiting transport or uptake of Pi in the kidneys, and treatment of related conditions in a subject in need of phosphate lowering, embodiments of the present invention will generally employ substantially systemically bioavailable compounds, optionally by any route of administration, or the substantially systemically non-bioavailable compounds described herein, preferably by a route of administration that excludes enteral administration. In these and related embodiments, administration of a compound reduces serum phosphate concentrations or levels in a hyperphosphatemic subject to about or less than about 150%, 145%, 140%, 135%, 130%, 125%, 120%, 115%, 110%, 105%, or 100% (normalized) of the normal serum phosphate levels (of a healthy subject, e.g., 2.5-4.5 mg/dL or 0.81-1.45 mmol/L for a human adult). In some embodiments, administration of a compound to a subject in need thereof increases urinary phosphate concentrations or levels by at least about 5%, 10%, 20%, 30%, 40%, 50%, 60%, 70%, 80%, 90%, 100% or more relative to an untreated state.

In certain embodiments, the NHE3-binding compounds of the present invention are further characterized by their activity towards NHE3-mediated antiport of sodium and hydrogen ions. For instance, certain compounds are substantially active to inhibit NHE3-mediated antiport of sodium ions and hydrogen ions. Such "dual-active" compounds can thus be used to inhibit both phosphate and sodium transport or uptake in the gastrointestinal tract and/or in the kidneys. In other embodiments, the compounds are substantially inactive to inhibit NHE3-mediated antiport of sodium ions and hydrogen ions. Such "mono-active" compounds can be used to inhibit phosphate uptake in the gastrointestinal tract and/or in the kidneys without significantly modulating sodium transport or uptake in those or other tissues.

Without wishing to be bound by any one theory, it is believed that "persistent" NHE3 inhibitor compounds (e.g., compounds that bind to NHE3 and inhibit NHE3-mediated antiport of sodium and hydrogen ions under both "prompt" conditions and "persistent" conditions) are substantially active in tissues to inhibit both transport of Pi and NHE3-mediated antiport of sodium and hydrogen ions. In contrast, it is believed that non-persistent NHE3 ligands (e.g., compounds that bind to or otherwise interact with NHE3 and might inhibit NHE3-mediated antiport of sodium and hydrogen ions under "prompt" conditions but do not substantially inhibit the same under "persistent" conditions) are active in tissues to inhibit transport of Pi but are not substantially active in tissues to inhibit NHE3-mediated antiport of sodium and hydrogen ions. Certain characteristics of these compounds are described below.

A. Dual-Active Compounds

Certain embodiments relate to NHE3-binding and/or NHE3-modulating compounds that inhibit both the transport of phosphate ions (Pi) and the NHE3-mediated antiport of sodium and hydrogen ions. These and related embodiments include, for example, compounds that are substantially active in the gastrointestinal tract and/or kidneys to inhibit Pi transport and NHE3-mediated antiport of sodium and hydrogen ions therein upon administration to a subject in need thereof. In particular embodiments, the compounds are substantially active on the apical side of the epithelium of the gastrointestinal tract (e.g., upon enteral administration) to inhibit NHE3-mediated antiport of sodium ions and hydrogen ions. Also included are compounds that are substantially active in the large intestine (e.g., cecum, ascending colon, transverse colon, descending colon, sigmoid colon) to inhibit NHE3-mediated antiport of sodium and hydrogen ions therein upon administration to the subject in need thereof.

In some aspects, the dual-active compounds are characterized by their "persistence" towards binding to NHE3 and inhibiting NHE3-mediated antiport of sodium and hydrogen ions, i.e., their "persistent inhibition" of NHE-mediated antiport of sodium and hydrogen ions. In particular aspects, persistent inhibition is characterized by the time-dependent inhibitory activity of the compound in an in vitro inhibition assay of NHE3-mediated antiport of sodium and hydrogen ions, for instance, as measured under "persistent" conditions optionally relative to "prompt" conditions (see, e.g., *PNAS USA*. (1984) 81(23): 7436-7440; and Examples 1-2).

Persistent conditions include, for instance, where a test compound is pre-incubated with cells, e.g., for about 10, 20, 30, 40, 50, 60, 80, 100, 120 minutes or more, and washed-out prior to lowering intracellular pH and testing for NHE3-mediated recovery of neutral intracellular pH. Post-incubation washout can be performed, for example, about 10, 20, 30, 40, 50, 60, 80, 100, 120 minutes or more before lowering intracellular pH and testing for NHE3-mediated recovery of neutral intracellular pH. In some persistent conditions, a test compound is pre-incubated with cells for a desired time and then washed-out of the cell medium, a buffer is added to lower intracellular pH (e.g., incubated for about 10, 20, 30, 40, 50, or 60 minutes or more), and NHE3-mediated recovery of neutral intracellular pH is initiated by addition of an appropriate buffer without any test compound.

Prompt conditions include, for example, where a test compound is incubated with cells during testing for NHE3-mediated recovery of neutral intracellular pH, i.e., the compound is not washed-out before or during initiating recovery of intracellular pH. Under certain prompt conditions, a buffer is added to lower intracellular pH (e.g., incubated for about 10, 20, 30, 40, 50, or 60 minutes or more), and NHE3-mediated recovery of neutral intracellular pH is initiated by addition of an appropriate buffer that contains the test compound. In one exemplary cell-based assay, recovery of intracellular pH can be measured, for instance, by monitoring the pH sensitive changes in fluorescence of a marker normalized to the pH insensitive fluorescence of the marker. Exemplary markers include bis(acetoxymethyl) 3,3'-(3',6'-bis(acetoxymethoxy)-5-((acetoxymethoxy)carbonyl)-3-oxo-3H-spiro[isobenzofuran-1,9'-xanthene]-2',7'-diyl) dipropanoate (BCECF).

In certain aspects, a dual-active compound is characterized by the time-dependent inhibitory activity of the compound in an in vitro inhibition assay of NHE3-mediated antiport of sodium and hydrogen ions, wherein the $pIC_{50}$ of the compound under prompt conditions ($pIC_{50promp}$) is substantially comparable to the $pIC_{50}$ of the compound under persistent conditions ($pIC_{50pers}$). Substantially comparable includes, for example, where the $pIC_{50promp}$ and $pIC_{50pers}$ values are within about 1%, 2%, 3%, 4%, 5%, 6%, 7%, 8%, 9%, or 10%. In particular aspects, the $pIC_{50promp}$ and the $pIC_{50pers}$ are about or at least about 7.0, including about or at least about 6.5, 6.55. 6.6, 6.65, 6.7. 6.75, 6.8, 6.85, 6.9, 6.95, 7.0, 7.05, 7.1, 7.15, 7.2, 7.25, 7.3, 7.35, 7.4, 7.45, 7.5, 7.55, 7.6, 7.65. 7.7, 7.75, 7.8, 7.85, 7.9, 7.95, 8.0, 8.05, 8.1, 8.15, 8.2, 8.25, 8.3, 8.35, 8.4, 8.45, 8.5, 8.55, 8.6, 8.65, 8.7, 8.75, 8.8, 8.85, 8.9, 8.95, or 9.0. In some aspects, the $IC_{50}$ of the compound under prompt conditions ($IC_{50promp}$) is substantially comparable to the $IC_{50}$ of the compound under persistent conditions ($IC_{50pers}$). Substantially comparable includes, for example, where the $IC_{50promp}$ and $IC_{50pers}$ values are within about 1%, 2%, 3%, 4%, 5%, 6%, 7%, 8%, 9%, or 10%. In particular aspects, the $IC_{50promp}$ and the $IC_{50pers}$ are about or less than about 0.3, 0.2, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002, or 0.001 µM, or range from about 0.001-0.3, 0.001-0.2, 0.001-0.1, 0.001-0.05, 0.001-0.01, 0.001-0.005 µM, or range from about 0.005-0.3, 0.005-0.2, 0.005-0.1, 0.005-0.05, 0.005-0.01, or range from about 0.01-0.3, 0.01-0.2, 0.01-0.1, or 0.01-0.05 µM, or range from about 0.1-0.3 or 0.1-0.2 µM.

In some aspects, the dual-active compounds are characterized by their relative activity towards inhibiting phosphate transport and inhibiting NHE3-mediated antiport of sodium and hydrogen ions. For instance, upon enteral administration to a subject in need of phosphate lowering, certain compounds may have an $EC_{50}$ for increasing fecal output of phosphate ions ($EC_{50}P_f$) and an $EC_{50}$ for inhibiting NHE3-mediated antiport of sodium and hydrogen ions ($EC_{50}Na$) that is defined by the formula $EC_{50}P_f=(r)EC_{50}Na$, wherein r is about 0.6 to about 1.5, preferably about 0.7 to about 1.3, or about 0.6, 0.65, 0.7, 0.75, 0.8, 0.85, 0.9, 0.95, 1.0, 1.1, 1.2, 1.3, 1.4, or 1.5, including all ranges in between. In some embodiments, for example, upon enteral administration to a subject in need of phosphate lowering, certain compounds may have an $EC_{50}$ for reducing urinary output of phosphate ions ($EC_{50}P_u$) and a $EC_{50}$ for inhibiting NHE3-mediated antiport of sodium and hydrogen ions ($EC_{50}Na$) that is defined by the formula $EC_{50}P_u=(r)EC_{50}Na$, wherein r is about 0.6 to about 1.5, preferably about 0.7 to about 1.3, or about 0.6, 0.65, 0.7, 0.75, 0.8, 0.85, 0.9, 0.95, 1.0, 1.1, 1.2, 1.3, 1.4, or 1.5, including all ranges in between. In some embodiments, for instance, upon administration that achieves systemic availability (e.g., leads to activity in the kidneys), certain compounds may have an $EC_{50}$ for increasing urinary output of phosphate ions ($EC_{50}P_u$) and an $EC_{50}$ for inhibiting NHE3-mediated antiport of sodium and hydrogen ions ($EC_{50}Na$) that is defined by the formula $EC_{50}P_u=(r)EC_{50}Na$, wherein r is about 0.6 to about 1.5, preferably about 0.7 to about 1.3, or about 0.6, 0.65, 0.7, 0.75, 0.8, 0.85, 0.9, 0.95, 1.0, 1.1, 1.2, 1.3, 1.4, or 1.5, including all ranges in between. In particular embodiments, for example, upon administration to a subject in need of phosphate lowering or in a cell-based assay, certain compounds may have an $EC_{50}$ for inhibiting transport of phosphate ions ($EC_{50}P$) and an $EC_{50}$ for inhibiting NHE3-mediated antiport of sodium and hydrogen ions ($EC_{50}Na$) that is defined by the formula $EC_{50}P=(r)EC_{50}Na$, wherein r is about 0.6 to about 1.5, preferably about 0.7 to about 1.3, or about 0.6, 0.65, 0.7, 0.75, 0.8, 0.85, 0.9, 0.95, 1.0, 1.1, 1.2, 1.3, 1.4, or 1.5, including all ranges in between.

In some embodiments, and further to its effects on Pi levels, administration of a dual-active compound (or at a dosage that allows dual-activity) to a subject in need thereof (e.g., via enteral administration) increases the subject's daily fecal daily output of sodium and/or fluid. In certain instances, the fecal output of sodium is increased by about or at least about 5%, 10%, 20%, 30%, 40%, 50%, 60%, 70%, 80%, 90%, 100%, 200%, 300%, 400%, 500%, 600%, 700%, 800%, 900%, 1000%, 1100%, 1200%, 1300%, 1400%, 1500%, 1600%, 1700%, 1800%, 1900%, or 2000% or more relative to an untreated state. In some instances, the output of fluid or the fecal water content is increased by about or at least about 5%, 10%, 20%, 30%, 40%, 50%, 60%, 70%, 80%, 90%, 100%, 200%, 300%, 400%, 500%, 600%, 700%, 800%, 900%, 1000%, 1100%, 1200%, 1300%, 1400%, 1500%, 1600%, 1700%, 1800%, 1900%, or 2000% or more relative to an untreated state.

B. Mono-Active Compounds

Certain embodiments relate to NHE3-binding compounds that inhibit transport of phosphate ions (Pi) and but do not substantially inhibit NHE3-mediated antiport of sodium and hydrogen ions, for instance, at a given dosage. These and related embodiments include, for example, non-persistent ligands of NHE3 that are substantially active to inhibit Pi transport but are substantially inactive in the gastrointestinal tract and/or kidneys to inhibit NHE3-mediated antiport of sodium and hydrogen ions therein upon administration to a subject in need thereof. In some embodiments, the non-persistent ligands of NHE3 are substantially inactive in the large intestine (e.g., upon enteral administration) to inhibit NHE3-mediated antiport of sodium and hydrogen ions therein.

In some aspects, a non-persistent NHE3 ligand is characterized by its maximum inhibitory activity towards NHE3-mediated antiport of sodium and hydrogen ions, for instance, in a cell-based assay or other in vitro assay. In one example, a non-persistent NHE3 ligand has a maximum inhibition of NHE3-mediated antiport of sodium and hydrogen ions of about or less than about 50%, 40%, 30%, 35%, 20%, 15%, 10%, or 5%, wherein maximum inhibition is characterized by the inhibitory activity of the compound in an in vitro inhibition assay of NHE3-mediated antiport of sodium and hydrogen ions and is relative to sodium-free conditions. In these and related embodiments, sodium-free conditions essentially represent zero activity for NHE3-mediated antiport of sodium and hydrogen ions, and can thus be used to set the value for 100% or maximum inhibition.

In some aspects, the non-persistent NHE3 ligands are characterized by their "non-persistence" towards binding to NHE3 and inhibiting NHE3-mediated antiport of sodium and hydrogen ions, i.e., their relative lack of or reduced "persistent inhibition" of NHE-mediated antiport of sodium and hydrogen ions. In particular aspects, persistent inhibition is characterized by the time-dependent inhibitory activity of the compound in an in vitro inhibition assay of NHE3-mediated antiport of sodium and hydrogen ions, for instance, as measured under "persistent" conditions optionally relative to "prompt" conditions (see, e.g., *PNAS USA*. (1984) 81(23): 7436-7440; and Examples 1-2). Examples of persistent and prompt conditions are described supra.

In certain aspects, the non-persistent NHE3 ligands are characterized by the time-dependent inhibitory activity of the compound in an in vitro inhibition assay of NHE3-mediated antiport of sodium and hydrogen ions, wherein the $pIC_{50}$ of the compound under prompt conditions ($pIC_{50promp}$) is greater than or substantially greater than the $pIC_{50}$ of the compound under persistent conditions ($pIC_{50pers}$). Substantially greater includes, for example, where the $pIC_{50promp}$ is greater than the $pIC_{50pers}$ by about or at least about 10%, 20%, 30%, 40%, 50%, 60%, 70%, 80%, 90%, 100%, 200% or more. In particular aspects, the $pIC_{50promp}$ is about or at least about 7.0, including about or at least about 6.5, 6.55. 6.6, 6.65, 6.7. 6.75, 6.8, 6.85, 6.9, 6.95, 7.0, 7.05, 7.1, 7.15, 7.2, 7.25, 7.3, 7.35, 7.4, 7.45, 7.5, 7.55, 7.6, 7.65. 7.7, 7.75, 7.8, 7.85, 7.9, 7.95, 8.0, 8.05, 8.1, 8.15, 8.2, 8.25, 8.3, 8.35, 8.4, 8.45, 8.5, 8.55, 8.6, 8.65, 8.7, 8.75, 8.8, 8.85, 8.9, 8.95, or 9.0, and the $pIC_{50pers}$ is about or less than about 6.0, including about or less than about 6.4, 6.35, 6.3, 6.25, 6.2, 6.15, 6.1, 6.05, 6.0, 5.95, 5.9, 5.85, 5.7, 5.75, 5.6, 5.65, 5.5, 5.45, 5.4, 5.35, 5.3, 5.25, 5.2, 5.15, 5.1, 5.05, 5.0, 4.95, 4.9, 4.85, 4.8, 4.75, 4.7, 4.65, 4.6, 4.55, 4.5, 4.45, 4.4, 4.35, 4.3, 4.25, 4.2, 4.15, 4.1, 4.05, 4.0, 3.9, 3.8, 3.7, 3.6, 3.5, 3.4, 3.3, 3.2, 3.1, or 3.0.

In some aspects, the $IC_{50}$ of the non-persistent NHE3 ligand under prompt conditions ($IC_{50promp}$) is substantially less than the $IC_{50}$ of the compound under persistent conditions ($IC_{50pers}$). Substantially less includes, for example, where the $IC_{50promp}$ is less than the $IC_{50pers}$ by about or at least about 10%, 20%, 30%, 40%, 50%, 60%, 70%, 80%, 90%, 100%, 200%, 300%, 400%, 500%, or 1000%. For instance, in some aspects, the $IC_{50promp}$ is about or less than about 0.3, 0.2, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002, or 0.001 µM, or ranges from about 0.001-0.3, 0.001-0.2, 0.001-0.1, 0.001-0.05, 0.001-0.01, 0.001-0.005 µM, or ranges from about 0.005-0.3, 0.005-0.2, 0.005-0.1, 0.005-0.05, 0.005-0.01, or ranges from about 0.01-0.3, 0.01-0.2, 0.01-0.1, or 0.01-0.05 µM, or ranges from about 0.1-0.3 or 0.1-0.2 µM, and the $IC_{50pers}$ is about or greater than about 1, 2, 3, 4, 5, 6, 7, 8, 9, 10, 15, 20, 25, 30, 40, 50, 60, 70, 80, 90, 100, 200, 300, 400, 500, 600, 700, 800, 900, or 1000 µM or more, or ranges from about 1-10, 1-20, 1-30, 1-40, 1-50, 1-100, 1-500, 1-1000 µM, or ranges from about 2-10, 2-20, 2-30, 2-40, 2-50, 2-100, 2-500, 2-1000 µM, or ranges from about 5-10, 5-20, 5-30, 5-40, 5-50, 5-100, 5-500, 5-1000 µM, or ranges from about 10-20, 10-30, 10-40, 10-50, 10-100, 10-500, 10-1000 µM, or ranges from about 20-30, 20-40, 20-50, 20-100, 20-500, 20-1000 µM, or ranges from about 50-100, 50-500, 50-1000 µM, or ranges from about 100-500 or 100-1000 µM.

In some aspects, the non-persistent NHE3 ligands are characterized by their relative activity towards inhibiting phosphate transport and inhibiting NHE3-mediated antiport of sodium and hydrogen ions. For instance, upon enteral administration to a subject in need of phosphate lowering, certain compounds may have an $EC_{50}$ for increasing fecal output of phosphate ions ($EC_{50}P_f$) and an $EC_{50}$ for inhibiting NHE3-mediated antiport of sodium and hydrogen ions ($EC_{50}Na$) that is defined by the formula $EC_{50}P_f=(r)EC_{50}Na$, wherein r is about 0.1 to about 0.5, or about 0.05, 0.1, 0.15, 0.2, 0.25, 0.3, 0.35, 0.4, 0.45, 0.5, or 0.55, including all ranges in between. In some embodiments, for example, upon enteral administration to a subject in need of phosphate lowering, certain compounds may have an $EC_{50}$ for reducing urinary output of phosphate ions ($EC_{50}P_u$) and an $EC_{50}$ for inhibiting NHE3-mediated antiport of sodium and hydrogen ions ($EC_{50}Na$) that is defined by the formula $EC_{50}P_u=(r)EC_{50}Na$, wherein r is about 0.1 to about 0.5, or about 0.05, 0.1, 0.15, 0.2, 0.25, 0.3, 0.35, 0.4, 0.45, 0.5, or 0.55, including all ranges in between. In particular embodiments, for example, upon enteral administration to a subject in need of phosphate lowering or in a cell-based assay, certain compounds may have an $EC_{50}$ for inhibiting transport of phosphate ions ($EC_{50}P$) and an $EC_{50}$ for inhibiting NHE3-mediated antiport of sodium and hydrogen ions ($EC_{50}Na$) that is defined by the formula $EC_{50}P=(r)EC_{50}Na$, wherein r is about 0.05 or 0.1 to about 0.5 or 0.55 or so, or about 0.05, 0.1, 0.15, 0.2, 0.25, 0.3, 0.35, 0.4, 0.45, 0.5, or 0.55, including all ranges in between. In some embodiments, for instance, upon administration that achieves systemic availability (e.g., leads to significant activity in the kidneys), certain non-persistent NHE3 ligand compounds may have an $EC_{50}$ for increasing urinary output of phosphate ions ($EC_{50}P_u$) and an $EC_{50}$ for inhibiting NHE3-mediated antiport of sodium and hydrogen ions ($EC_{50}Na$) that is defined by the formula $EC_{50}P_u=(r)EC_{50}Na$, wherein r is about 0.1 to about 0.5, or about 0.05, 0.1, 0.15, 0.2, 0.25, 0.3, 0.35, 0.4, 0.45, 0.5, or 0.55, including all ranges in between.

In certain embodiments, administration a non-persistent NHE3 ligand to a subject in need thereof (e.g., via enteral administration) increases the ratio of phosphate/sodium in fecal excretion by about or at least about 5%, 10%, 20%, 30%, 40%, 50%, 60%, 70%, 80%, 90%, 100%, 200% or more relative to an untreated state. In some embodiments, administration to a subject in need thereof (e.g., via enteral administration) increases the daily fecal output of phosphate without substantially modulating the stool form or water content of the feces. For instance, in these and related embodiments, the stool form of the feces can be about or within about 1%, 2%, 3%, 4%, 5%, 6%, 7%, 8%, 9%, 10%, 15%, or 20% of the stool form of the feces relative to an untreated state. In some aspects, the fecal form under the Bristol stool scale (Types 1, 2, 3, 4, 5, 6, and 7; Type 1 being hard and Type 7 being watery) can be the same or within about 1-2 units relative to an untreated state (see, e.g., Rao et al., *Neurogastroenterol Motil.* 23:8-23, 2011; and Lewis and Heaton, *Scand. J. Gastroenterol.* 32:920-4, 1997). In specific aspects, the fecal form under the Bristol scale is Type 3 or Type 4. In some embodiments, administration to a rodent (e.g., rat, mouse) increases the ratio of sodium in the small intestine ($Na_{SI}$)/cecum (NO by at least about 5%, 10%, 20%, 30%, 40%, 50%, 60%, 70%, 80%, 90%, 100%, 200% or more relative to an untreated state.

II. Substantially Systemically Non-Bioavailable Compounds

A. Physical and Performance Properties of Compounds Localizable to the GI Tract

Certain of the compounds described herein are designed to be substantially active or localized in the gastrointestinal lumen of a human or animal subject. The term "gastrointestinal lumen" is used interchangeably herein with the term "lumen," to refer to the space or cavity within a gastrointestinal tract (GI tract, which can also be referred to as the gut), delimited by the apical membrane of GI epithelial cells of the subject. In some embodiments, the compounds are not absorbed through the layer of epithelial cells of the GI tract (also known as the GI epithelium). "Gastrointestinal mucosa" refers to the layer(s) of cells separating the gastrointestinal lumen from the rest of the body and includes gastric and intestinal mucosa, such as the mucosa of the small intestine. A "gastrointestinal epithelial cell" or a "gut epithelial cell" as used herein refers to any epithelial cell on the surface of the gastrointestinal mucosa that faces the lumen of the gastrointestinal tract, including, for example, an epithelial cell of the stomach, an intestinal epithelial cell, a colonic epithelial cell, and the like.

"Substantially systemically non-bioavailable" and/or "substantially impermeable" as used herein (as well as variations thereof) generally refer to situations in which a statistically significant amount, and in some embodiments essentially all of the compound remains in the gastrointestinal lumen. For example, in accordance with one or more embodiments of the present disclosure, preferably at least about 60%, about 70%, about 75%, about 80%, about 85%, about 90%, about 95%, about 96%, about 97%, about 98%, about 99%, or even about 99.5%, of the compound remains in the gastrointestinal lumen. In such cases, localization to the gastrointestinal lumen refers to reducing net movement of a compound across a gastrointestinal layer of epithelial cells, for example, by way of both transcellular and paracellular transport, as well as by active and/or passive transport. The compound in such embodiments is hindered from net permeation of a layer of gastrointestinal epithelial cells in transcellular transport, for example, through an apical membrane of an epithelial cell of the small intestine. The compound in these embodiments is also hindered from net permeation through the "tight junctions" in paracellular transport between gastrointestinal epithelial cells lining the lumen.

In this regard it is to be noted that, in one particular embodiment, the compound is essentially not absorbed at all by the GI tract or gastrointestinal lumen. As used herein, the terms "substantially impermeable" or "substantially systemically non-bioavailable" includes embodiments wherein no detectable amount of absorption or permeation or systemic exposure of the compound is detected, using means generally known in the art.

In this regard it is to be further noted, however, that in alternative embodiments "substantially impermeable" or "substantially systemically non-bioavailable" provides or allows for some limited absorption in the GI tract, and more particularly the gut epithelium, to occur (e.g., some detectable amount of absorption, such as for example at least about 0.1%, 0.5%, 1% or more and less than about 30%, 20%, 10%, 5%, etc., the range of absorption being for example between about 1% and 30%, or 5% and 20%, etc.); stated another way, "substantially impermeable" or "substantially systemically non-bioavailable" may refer to compounds that exhibit some detectable permeability to an epithelial layer of cells in the GI tract of less than about 20% of the administered compound (e.g., less than about 15%, about 10%, or even about 5%, 4%, 3%, or 2%, and for example greater than about 0.5%, or 1%), but then are cleared by the liver (i.e., hepatic extraction) and/or the kidney (i.e., renal excretion).

In this regard it is to be further noted, that in certain embodiments, due to the substantial impermeability and/or substantial systemic non-bioavailability of the compounds of the present invention, greater than about 50%, 60%, 70%, 80%, 90%, or 95% of a compound of the invention is recoverable from the feces over, for example, a 24, 36, 48, 60, 72, 84, or 96 hour period following administration to a subject in need thereof. In this respect, it is understood that a recovered compound can include the sum of the parent compound and its metabolites derived from the parent compound, e.g., by means of hydrolysis, conjugation, reduction, oxidation, N-alkylation, glucuronidation, acetylation, methylation, sulfation, phosphorylation, or any other modification that adds atoms to or removes atoms from the parent compound, wherein the metabolites are generated via the action of any enzyme or exposure to any physiological environment including, pH, temperature, pressure, or interactions with foodstuffs as they exist in the digestive milieu.

Measurement of fecal recovery of compound and metabolites can be carried out using standard methodology. For example, a compound can be administered orally at a suitable dose (e.g., 10 mg/kg) and feces are then collected at predetermined times after dosing (e.g., 24 hours, 36 hours, 48 hours, 60 hours, 72 hours, 96 hours). Parent compound and metabolites can be extracted with organic solvent and analyzed quantitatively using mass spectrometry. A mass balance analysis of the parent compound and metabolites (including, parent=M, metabolite 1 [M+16], and metabolite 2 [M+32]) can be used to determine the percent recovery in the feces.

(i) Permeability

In this regard it is to be noted that, in various embodiments, the ability of the compound to be substantially systemically non-bioavailable is based on the compound charge, size, and/or other physicochemical parameters (e.g., polar surface area, number of hydrogen bond donors and/or acceptors therein, number of freely rotatable bonds, etc.). More specifically, it is to be noted that the absorption character of a compound can be selected by applying principles of pharmacokinetics, for example, by applying Lipinski's rule, also known as "the rule of five." Although not a rule, but rather a set of guidelines, Lipinski shows that small molecule drugs with (i) a molecular weight, (ii) a number of hydrogen bond donors, (iii) a number of hydrogen bond acceptors, and/or (iv) a water/octanol partition coefficient (Moriguchi Log P), greater than a certain threshold value, generally do not show significant systemic concentration (i.e., are generally not absorbed to any significant degree). (See, e.g., Lipinski et al., *Advanced Drug Delivery Reviews,* 46:3-26, 2001 incorporated herein by reference.) Accordingly, substantially systemically non-bioavailable compounds can be designed to have molecular structures exceeding one or more of Lipinski's threshold values. (See also Lipinski et al., *Experimental and Computational Approaches to Estimate Solubility and Permeability in Drug Discovery and Development Settings*, Adv. Drug Delivery Reviews, 46:3-26 (2001); and Lipinski, *Drug-like Properties and the Causes of Poor Solubility and Poor Permeability*, J. Pharm. & Toxicol. Methods, 44:235-249 (2000), incorporated herein by reference.).

In some embodiments, for example, a substantially impermeable or substantially systemically non-bioavailable compound of the present disclosure can be constructed to feature one or more of the following characteristics: (i) a MW greater than about 500 Da, about 600 Da, about 700 Da, about 800 Da, about 900 Da, about 1000 Da, about 1200 Da, about 1300 Da, about 1400 Da, about 1500 Da, about 1600 Da, about 1800 Da, about 2000 Da, about 2500 Da, about 3000 Da, about 4000 Da, about 5000 Da, about 7500 Da, about 10,000 Da or more (in the non-salt form of the compound); (ii) a total number of NH and/or OH and/or other potential hydrogen bond donors greater than about 5, about 6, about 7, about 8, about 9, about 10, about 11, about 12, about 13, about 14, about 15, about 20 or more; (iii) a total number of O atoms and/or N atoms and/or other potential hydrogen bond acceptors greater than about 5, about 6, about 7, about 8, about 9, about 10, about 11, about 12, about 13, about 14, about 15, about 20 or more; (iv) a Moriguchi partition coefficient greater than about $10^5$ (i.e., Log P greater than about 5, about 6, about 7, about 8, about 9, about 10 etc.), or alternatively less than about 10 (i.e., a Log P of less than 1, or even 0); and/or (v) a total number of rotatable bonds greater than about 5, about 10 or about 15, or more. In specific embodiments, the compound has a Log P that is not 14 or is less than about 14, for instance, a Log P that is in the range of about 6-7, 6-8, 6-9, 6-10, 6-11, 6-12, 6-13, 7-8, 7-9, 7-10, 7-11, 7-12, 7-13, 8-9, 8-10, 8-11, 8-12, 8-13, 9-10, 9-11, 9-12, 9-13, 10-11, 10-12, 10-13, 11-12, 11-13, or 12-13.

In addition to the parameters noted above, the molecular polar surface area (i.e., "PSA"), which may be characterized as the surface belonging to polar atoms, is a descriptor that has also been shown to correlate well with passive transport through membranes and, therefore, allows prediction of transport properties of drugs. It has been successfully applied for the prediction of intestinal absorption and Caco2 cell monolayer penetration. For exemplary Caco2 cell monolayer penetration test details, see for example the description of the Caco2 Model provided in U.S. Pat. No. 6,737,423, incorporated by reference, particularly the text describing the Caco2 Model, which may be applied for example to the evaluation or testing of the compounds of the present invention. PSA is expressed in $Å^2$ (squared angstroms) and is computed from a three-dimensional molecular representation. A fast calculation method is also available (see, e.g., Ertl et al., *Journal of Medicinal Chemistry*, 2000, 43, 3714-3717, the entire contents of which are incorporated herein by reference for all relevant and consistent purposes) using a desktop computer and commercially available chemical graphic tools packages, such as ChemDraw. The term "topological PSA" (tPSA) has been coined for this fast-calculation method. tPSA is well correlated with human absorption data with common drugs (see Table 1, from Ertl et al., *J. Med. Chem.*, 2000, 43:3714-3717):

TABLE 1

| name | % FA[a] | TPSA[b] |
| --- | --- | --- |
| metoprolol | 102 | 50.7 |
| nordiazepam | 99 | 41.5 |
| diazepam | 97 | 32.7 |
| oxprenolol | 97 | 50.7 |
| phenazone | 97 | 26.9 |
| oxazepam | 97 | 61.7 |
| alprenolol | 96 | 41.9 |
| practolol | 95 | 70.6 |
| pindolol | 92 | 57.3 |
| ciprofloxacin | 69 | 74.6 |
| metolazone | 64 | 92.5 |
| tranexamic acid | 55 | 63.3 |
| atenolol | 54 | 84.6 |
| sulpiride | 36 | 101.7 |
| mannitol | 26 | 121.4 |
| foscarnet | 17 | 94.8 |
| sulfasalazine | 12 | 141.3 |
| olsalazine | 2.3 | 139.8 |
| lactulose | 0.6 | 197.4 |
| raffinose | 0.3 | 268.7 |

Accordingly, in some embodiments, the compounds of the present disclosure may be constructed to exhibit a tPSA value greater than about 100 $Å^2$, about 116 $Å^2$, about 120 $Å^2$, about 130 $Å^2$, or about 140 $Å^2$, and in some instances about 150 $Å^2$, about 160 $Å^2$, about 170 $Å^2$, about 180 $Å^2$, about 190 $Å^2$, about 200 $Å^2$, about 225 $Å^2$, about 250 $Å^2$, about 270 $Å^2$, about 300 $Å^2$, about 350 $Å^2$, about 400 $Å^2$, about 450 $Å^2$, about 500 $Å^2$, about 750 $Å^2$, or even about 1000 $Å^2$, or in the range of about 100-120 $Å^2$, 100-130 $Å^2$, 100-140 $Å^2$, 100-150 $Å^2$, 100-160 $Å^2$, 100-170 $Å^2$, 100-170 $Å^2$, 100-190 $Å^2$, 100-200 $Å^2$, 100-225 $Å^2$, 100-250 $Å^2$, 100-300 $Å^2$, 100-400 $Å^2$, 100-500 $Å^2$, 100-750 $Å^2$, 100-1000 $Å^2$, 116-120 $Å^2$, 116-130 $Å^2$, 116-140 $Å^2$, 116-150 $Å^2$, 116-160 $Å^2$, 116-170 $Å^2$, 116-170 $Å^2$, 116-190 $Å^2$, 116-200 $Å^2$, 116-225 $Å^2$, 116-250 $Å^2$, 116-300 $Å^2$, 116-400 $Å^2$, 116-500 $Å^2$, 116-750 $Å^2$, 116-1000 $Å^2$, 120-130 $Å^2$, 120-140 $Å^2$, 120-150 $Å^2$, 120-160 $Å^2$, 120-170 $Å^2$, 120-170 $Å^2$, 120-190 $Å^2$, 120-200 $Å^2$, 120-225 $Å^2$, 120-250 $Å^2$, 120-300 $Å^2$, 120-400 $Å^2$, 120-500 $Å^2$, 120-750 $Å^2$, 120-1000 $Å^2$, 130-140 $Å^2$, 130-150 $Å^2$, 130-160 $Å^2$, 130-170 $Å^2$, 130-170 $Å^2$, 130-190 $Å^2$, 130-200 $Å^2$, 130-225 $Å^2$, 130-250 $Å^2$, 130-300 $Å^2$, 130-400 $Å^2$, 130-500 $Å^2$, 130-750 $Å^2$, 130-1000 $Å^2$, 140-150 $Å^2$, 140-160 $Å^2$, 140-170 $Å^2$, 140-170 $Å^2$, 140-190 $Å^2$, 140-200 $Å^2$, 140-225 $Å^2$, 140-250 $Å^2$, 140-300 $Å^2$, 140-400 $Å^2$, 140-500 $Å^2$, 140-750 $Å^2$, 140-1000 $Å^2$, 150-160 $Å^2$, 150-170 $Å^2$, 150-170 $Å^2$, 150-190 $Å^2$, 150-200 $Å^2$, 150-225 $Å^2$, or 150-250 $Å^2$, 150-300 $Å^2$, 150-400 $Å^2$, 150-500 $Å^2$, 150-750 $Å^2$, 150-1000 $Å^2$, 200-250 $Å^2$, 200-300 $Å^2$, 200-400 $Å^2$, 200-500 $Å^2$, 200-750 $Å^2$, 200-1000 $Å^2$, 250-250 $Å^2$, 250-300 $Å^2$, 250-400 $Å^2$, 20-500 $Å^2$, 250-750 $Å^2$, or 250-1000 $Å^2$, such that the compounds are substantially impermeable (e.g., cell impermeable) or substantially systemically non-bioavailable (as defined elsewhere herein).

Because there are exceptions to Lipinski's "rule," or the tPSA model, the permeability properties of the compounds of the present disclosure may be screened experimentally. The permeability coefficient can be determined by methods known to those of skill in the art, including for example by Caco-2 cell permeability assay and/or using an artificial membrane as a model of a gastrointestinal epithelial cell. A synthetic membrane impregnated with, for example, lecithin and/or dodecane to mimic the net permeability characteristics of a gastrointestinal mucosa may be utilized as a model of a gastrointestinal mucosa. The membrane can be used to separate a compartment containing the compound of the present disclosure from a compartment where the rate of permeation will be monitored. Also, parallel artificial membrane permeability assays (PAMPA) can be performed. Such in vitro measurements can reasonably indicate actual permeability in vivo (see Wohnsland et al., *J. Med. Chem.* 44:923-930, 2001; Schmidt et al., Millipore Corp. Application Note, 2002, n AN1725EN00, and n AN1728EN00, incorporated herein by reference).

Accordingly, in some embodiments, the compounds utilized in the methods of the present disclosure may have a permeability coefficient, $P_{app}$, of less than about $100 \times 10^{-6}$ cm/s, or less than about $10 \times 10^{-6}$ cm/s, or less than about $1 \times 10^{-6}$ cm/s, or less than about $0.1 \times 10^{-6}$ cm/s, when measured using means known in the art (such as for example the permeability experiment described in Wohnsland et al., 2001, supra).

As previously noted, in accordance with the present disclosure, compounds may be modified to hinder their net absorption through a layer of gut epithelial cells, rendering them substantially systemically non-bioavailable. In some particular embodiments, the compounds of the present disclosure comprise a compound that is linked, coupled or otherwise attached to a non-absorbable moiety, which may be an oligomer moiety, a polymer moiety, a hydrophobic moiety, a hydrophilic moiety, and/or a charged moiety, which renders the overall compound substantially impermeable or substantially systemically non-bioavailable. In some preferred embodiments, the compound is coupled to a multimer or polymer portion or moiety, such that the resulting molecule is substantially impermeable or substantially systemically non-bioavailable. The multimer or polymer portion or moiety may be of a molecular weight greater than about 500 Daltons (Da), about 1000 Da, about 2500 Da, about 5000 Da, about 10,000 Da or more, and in particular may have a molecular weight in the range of about 1000 Daltons (Da) to about 500,000 Da, preferably in the range of about 5000 to about 200,000 Da, and more preferably may have a molecular weight that is sufficiently high to essentially preclude any net absorption through a layer of gut epithelial cells of the compound. In these or other particular embodiments, the compound is modified to substantially hinder its net absorption through a layer of gut epithelial cells.

(ii) $C_{max}$ and $IC_{50}$ or $EC_{50}$

In some embodiments, the substantially systemically non-bioavailable compounds detailed herein, when administered (e.g., enterally) either alone or in combination with one or more additional pharmaceutically active compounds or agents to a subject in need thereof, exhibit a maximum concentration detected in the serum, defined as $C_{max}$, that is about the same as or less than the phosphate ion (Pi) transport or uptake inhibitory concentration $IC_{50}$ of the compound. In some embodiments, for instance, the $C_{max}$ is about or at least about 5%, 10%, 20%, 30%, 40%, 50%, 60%, 70%, 80%, 90%, or 100% less than the $IC_{50}$ for inhibiting Pi transport or uptake. In some embodiments, the $C_{max}$ is about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9× (0.9 times) the $IC_{50}$ for inhibiting Pi transport or uptake.

In certain embodiments, one or more of the substantially systemically non-bioavailable compounds detailed herein, when administered (e.g., enterally) to a subject in need thereof, may have a ratio of $C_{max}:IC_{50}$ (for inhibiting Pi transport or update), wherein $C_{max}$ and $IC_{50}$ are expressed in terms of the same units, of at about or less than about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1.0, or a range in between about 0.01-1.0, 0.01-0.9, 0.01-0.8, 0.01-0.7, 0.01-0.6, 0.01-0.5, 0.01-0.4, 0.01-0.3, 0.01-0.2, or 0.01-0.1, or a range in between about 0.1-1.0, 0.1-0.9, 0.1-0.8, 0.1-0.7, 0.1-0.6, 0.1-0.5, 0.1-0.4, 0.1-0.3, or 0.1-0.2.

In some embodiments, the substantially systemically non-bioavailable compounds detailed herein, when administered (e.g., enterally) either alone or in combination with one or more additional pharmaceutically active compounds or agents to a subject in need thereof, exhibit a maximum concentration detected in the serum, defined as $C_{max}$, that is about the same as or less than $EC_{50}$ of the compound for increasing fecal output of phosphate, where fecal output is increased by about or at least about 5%, 10%, 20%, 30%, 40%, 50%, 60%, 70%, 80%, 90%, or 100%. In some embodiments, for instance, the $C_{max}$ is about or at least about 5%, 10%, 20%, 30%, 40%, 50%, 60%, 70%, 80%, 90%, or 100% less than the $EC_{50}$ for increasing fecal output of phosphate. In some embodiments, the $C_{max}$ is about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9× (0.9 times) the $EC_{50}$ for increasing fecal output of phosphate.

In some embodiments, one or more of the substantially systemically non-bioavailable compounds detailed herein, when administered (e.g., enterally) either alone or in combination with one or more additional pharmaceutically active compounds or agents to a subject in need thereof, or measured in an animal model or cell-based assay, may have an $EC_{50}$ for increasing fecal output of phosphate of about or less than about 10 μM, 9 μM, 8 μM, 7 μM, 7.5 μM, 6 μM, 5 μM, 4 μM, 3 μM, 2.5 μM, 2 μM, 1 μM, 0.5 μM, 0.1 μM, 0.05 μM, or 0.01 μM, or less, the $IC_{50}$ being, for example, within the range of about 0.01 μM to about 10 μM, or about 0.01 μM to about 7.5 μM, or about 0.01 μM to about 5 μM, or about 0.01 μM to about 2.5 μM, or about 0.01 μM to about 1.0, or about 0.1 μM to about 10 μM, or about 0.1 μM to about 7.5 μM, or about 0.1 μM to about 5 μM, or about 0.1 μM to about 2.5 μM, or about 0.1 μM to about 1.0, or about μM 0.5 μM to about 10 μM, or about 0.5 μM to about 7.5 μM, or about 0.5 μM to about 5 μM, or about 0.5 μM to about 2.5 μM, or about 0.5 μM to about 1.0 μM.

In particular embodiments, the substantially systemically non-bioavailable compounds detailed herein, when administered (e.g., enterally) either alone or in combination with one or more additional pharmaceutically active compounds or agents to a subject in need thereof, exhibit a maximum concentration detected in the serum, defined as $C_{max}$, that is about the same as or less than $EC_{50}$ of the compound for reducing urinary output of phosphate, where urinary output is reduced by about or at least about 5%, 10%, 20%, 30%, 40%, 50%, 60%, 70%, 80%, 90%, or 100%. In some embodiments, for instance, the $C_{max}$ is about or at least about 5%, 10%, 20%, 30%, 40%, 50%, 60%, 70%, 80%, 90%, or 100% less than the $EC_{50}$ for reducing urinary output of phosphate. In some embodiments, the $C_{max}$ is about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9× (0.9 times) the $EC_{50}$ for reducing urinary output of phosphate.

In some embodiments, one or more of the substantially systemically non-bioavailable compounds detailed herein, when administered (e.g., enterally) either alone or in combination with one or more additional pharmaceutically active compounds or agents to a subject in need thereof, or measured in an animal model or cell-based assay, may have an $EC_{50}$ for reducing urinary output of phosphate of about or less than about 10 μM, 9 μM, 8 μM, 7 μM, 7.5 μM, 6 μM, 5 μM, 4 μM, 3 μM, 2.5 μM, 2 μM, 1 μM, 0.5 μM, 0.1 μM, 0.05 μM, or 0.01 μM, or less, the $IC_{50}$ being, for example, within the range of about 0.01 μM to about 10 μM, or about 0.01 μM to about 7.5 μM, or about 0.01 μM to about 5 μM, or about 0.01 μM to about 2.5 μM, or about 0.01 μM to about 1.0, or about 0.1 μM to about 10 μM, or about 0.1 μM to about 7.5 μM, or about 0.1 μM to about 5 μM, or about 0.1 μM to about 2.5 μM, or about 0.1 μM to about 1.0, or about μM 0.5 μM to about 10 μM, or about 0.5 μM to about 7.5 μM, or about 0.5 μM to about 5 μM, or about 0.5 μM to about 2.5 μM, or about 0.5 μM to about 1.0 μM.

In certain embodiments, one or more of the substantially systemically non-bioavailable compounds detailed herein, when administered (e.g., enterally) to a subject in need thereof, may have a ratio of $C_{max}:EC_{50}$ (e.g., for increasing fecal output of phosphate, for decreasing urinary output of phosphate), wherein $C_{max}$ and $EC_{50}$ are expressed in terms of the same units, of at about or less than about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1.0, or a range in between about 0.01-1.0, 0.01-0.9, 0.01-0.8, 0.01-0.7, 0.01-0.6, 0.01-0.5, 0.01-0.4, 0.01-0.3, 0.01-0.2, or 0.01-0.1, or a range in between about 0.1-1.0, 0.1-0.9, 0.1-0.8, 0.1-0.7, 0.1-0.6, 0.1-0.5, 0.1-0.4, 0.1-0.3, or 0.1-0.2.

Additionally, or alternatively, one or more of the substantially systemically non-bioavailable compounds detailed herein, when administered (e.g., enterally) either alone or in combination with one or more additional pharmaceutically active compounds or agents to a subject in need thereof, may have a $C_{max}$ of about or less than about 10 ng/ml, about 7.5 ng/ml, about 5 ng/ml, about 2.5 ng/ml, about 1 ng/ml, or about 0.5 ng/ml, the $C_{max}$ being for example within the range of about 1 ng/ml to about 10 ng/ml, or about 2.5 ng/ml to about 7.5 ng/ml.

B. Exemplary Structures

Generally speaking, the present disclosure encompasses essentially any small molecule, which may be monovalent or polyvalent, that binds to and/or modulates NHE3 and has activity as a phosphate transport inhibitor, including small molecules that are substantially impermeable or substantially systemically non-bioavailable in the gastrointestinal tract, including known NHE-binding compounds that may be modified or functionalized in accordance with the present disclosure to alter the physicochemical properties thereof so as to render the overall compound substantially active in the GI tract.

Accordingly, the compounds of the present disclosure may be generally represented by Formula (I):

NHE-Z  (I)

wherein: (i) NHE represents a NHE-binding small molecule, and (ii) Z represents a moiety having at least one site thereon for attachment to an NHE-binding small molecule, the resulting NHE-Z molecule possessing overall physicochemical properties that render it substantially impermeable or substantially systemically non-bioavailable. The NHE-binding small molecule generally comprises a heteroatom-containing moiety and a cyclic or heterocyclic scaffold or support moiety bound directly or indirectly thereto. In particular, examination of the structures of small molecules reported to-date to be NHE-binders or inhibitors suggest, as further illustrated herein below, that most comprise a cyclic or heterocyclic support or scaffold bound directly or indirectly (by, for example, an acyl moiety or a hydrocarbyl or heterohydrocarbyl moiety, such as an alkyl, an alkenyl, a heteroalkyl or a heteroalkenyl moiety) to a heteroatom-containing moiety that is capable of acting as a sodium atom or sodium ion mimic, which is typically selected from a substituted guanidinyl moiety and a substituted heterocyclic moiety (e.g., a nitrogen-containing heterocyclic moiety). Optionally, the heteroatom-containing moiety may be fused with the scaffold or support moiety to form a fused, bicyclic structure, and/or it may be capable of forming a positive charge at a physiological pH.

In this regard it is to be noted that, while the heteroatom-containing moiety that is capable of acting as a sodium atom or ion mimic may optionally form a positive charge, this should not be understood or interpreted to require that the overall compound have a net positive charge, or only a single positively charged moiety therein. Rather, in various embodiments, the compound may have no charged moieties, or it may have multiple charged moieties therein (which may have positive charges, negative charges, or a combination thereof, the compound for example being a zwitterion). Additionally, it is to be understood that the overall compound may have a net neutral charge, a net positive charge (e.g., +1, +2, +3, etc.), or a net negative charge (e.g., −1, −2, −3, etc.).

The Z moiety may be bound to essentially any position on, or within, the NHE small molecule, and in particular may be: (i) bound to the scaffold or support moiety, (ii) bound to a position on, or within, the heteroatom-containing moiety, and/or (iii) bound to a position on, or within, a spacer moiety that links the scaffold to the heteroatom-containing moiety, provided that the installation of the Z moiety does not significantly adversely impact NHE-binding activity. In one particular embodiment, Z may be in the form of an oligomer, dendrimer or polymer bound to the NHE small molecule (e.g., bound for example to the scaffold or the spacer moiety), or alternatively Z may be in the form of a linker that links multiple NHE small molecules together, and therefore that acts to increase: (i) the overall molecular weight and/or polar surface area of the NHE-Z molecule; and/or, (ii) the number of freely rotatable bonds in the NHE-Z molecule; and/or, (iii) the number of hydrogen-bond donors and/or acceptors in the NHE-Z molecule; and/or, (iv) the Log P value of the NHE-Z molecule to a value of at least about 5 (or alternatively less than 1, or even about 0), all as set forth herein; such that the overall NHE-binding compound (i.e., the NHE-Z compound) is substantially impermeable or substantially systemically non-bioavailable.

The present disclosure is more particularly directed to such a substantially impermeable or substantially systemically non-bioavailable, NHE-binding compound, or a pharmaceutical salt thereof, wherein the compound has the structure of Formula (II):

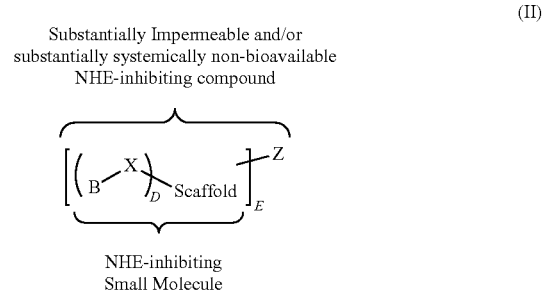

(II)

Substantially Impermeable and/or substantially systemically non-bioavailable NHE-inhibiting compound NHE-inhibiting Small Molecule wherein: (i) Z, as previously defined above, is a moiety bound to or incorporated in the NHE-binding small molecule, such that the resulting NHE-Z molecule possesses overall physicochemical properties that render it substantially impermeable or substantially systemically non-bioavailable; (ii) B is the heteroatom-containing moiety of the NHE-binding small molecule, and in one particular embodiment is selected from a substituted guanidinyl moiety and a substituted heterocyclic moiety, which may optionally be fused with the Scaffold moiety to form a fused, bicyclic structure; (iii) Scaffold is the cyclic or heterocyclic moiety to which is bound directly or indirectly the hetero-atom containing moiety (e.g., the substituted guanidinyl moiety or a substituted heterocyclic moiety), B, and which is optionally substituted with one or more additionally hydrocarbyl or heterohydrocarbyl moieties; (iv) X is a bond or a spacer moiety selected from a group consisting of substituted or unsubstituted hydrocarbyl or heterohydrocarbyl moieties, and in particular substituted or unsubstituted $C_1$-$C_7$ hydrocarbyl or heterohydrocarbyl (e.g., $C_1$-$C_7$ alkyl, alkenyl, heteroalkyl or heteroalkenyl), and substituted or unsubstituted, saturated or unsaturated, cyclic or heterocyclic moieties (e.g., $C_4$-$C_7$ cyclic or heterocyclic moieties), which links B and the Scaffold; and, (v) D and E are integers, each independently having a value of 1, 2 or more.

In one or more particular embodiments, as further illustrated herein below, B may be selected from a guanidinyl moiety or a moiety that is a guanidinyl bioisostere selected from the group consisting of substituted cyclobutenedione, substituted imidazole, substituted thiazole, substituted oxadiazole, substituted pyrazole, or a substituted amine More particularly, B may be selected from guanidinyl, acylguanidinyl, sulfonylguanidinyl, or a guanidine bioisostere such as a cyclobutenedione, a substituted or unsubstituted 5- or 6-member heterocycle such as substituted or unsubstituted imidazole, aminoimidazole, alkylimidizole, thiazole, oxadiazole, pyrazole, alkylthioimidazole, or other functionality that may optionally become positively charged or function as a sodium mimetic, including amines (e.g., tertiary amines), alkylamines, and the like, at a physiological pH. In one particularly preferred embodiment, B is a substituted guanidinyl moiety or a substituted heterocyclic moiety that may optionally become positively charged at a physiological pH to function as a sodium mimetic. In one exemplary embodiment, the compound of the present disclosure (or more particularly the pharmaceutically acceptable HCl salt thereof, as illustrated) may have the structure of Formula (III):

(III)

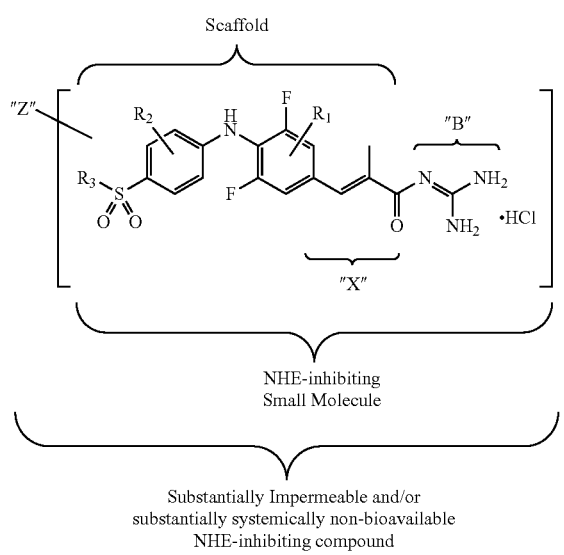

NHE-inhibiting Small Molecule

Substantially Impermeable and/or substantially systemically non-bioavailable NHE-inhibiting compound wherein Z may be optionally attached to any one of a number of sites on the NHE-binding small molecule, and further wherein the $R_1$, $R_2$ and $R_3$ substituents on the aromatic rings are as detailed elsewhere herein, and/or in U.S. Pat. No. 6,399,824, the entire contents of which are incorporated herein by reference for all relevant and consistent purposes.

In this regard it is to be noted, however, that the substantially impermeable or substantially systemically non-bioavailable NHE-binding compounds of the present disclosure may have a structure other than illustrated above, without departing from the scope of the present disclosure. For example, in various alternative embodiments, one or both of the terminal nitrogen atoms in the guanidine moiety may be substituted with one or more substituents, and/or the modifying or functionalizing moiety Z may be attached to the NHE-binding compound by means of (i) the Scaffold, (ii) the spacer X, or (iii) the heteroatom-containing moiety, B, as further illustrated generally in the structures provided below:

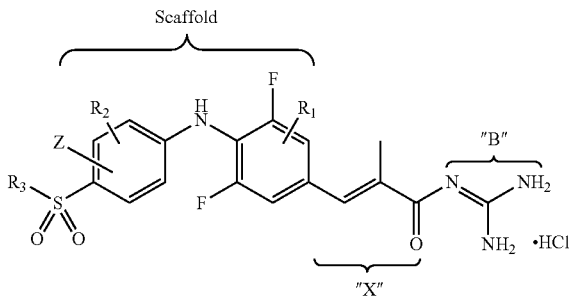

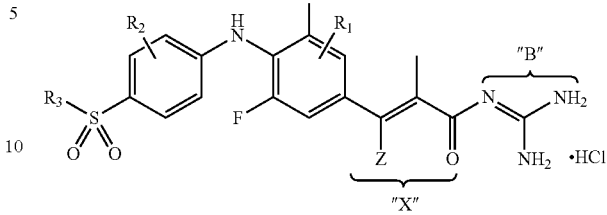

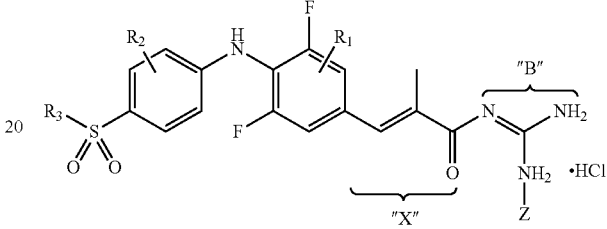

In this regard it is to be further noted that, as used herein, "bioisostere" generally refers to a moiety with similar physical and chemical properties to a guanidine moiety, which in turn imparts biological properties to that given moiety similar to, again, a guanidine moiety, in this instance. (See, for example, Ahmad, S. et al., Aminoimidazoles as Bioisosteres of Acylguanidines: Novel, Potent, Selective and Orally Bioavailable Inhibitors of the Sodium Hydrogen Exchanger Isoform-1, *Boorganic & Med. Chem. Lett.*, pp. 177-180 (2004), the entire contents of which is incorporated herein by reference for all relevant and consistent purposes.)

As further detailed below, known NHE-binding small molecules or chemotypes that may serve as suitable starting materials (for modification or functionalization, in order to render the small molecules substantially impermeable or substantially systemically non-bioavailable, and/or used in pharmaceutical preparations) may generally be organized into a number of subsets, such as for example:

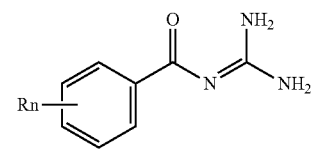

Benzoylguanidines

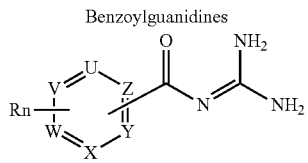

Heteroaroylguanidines

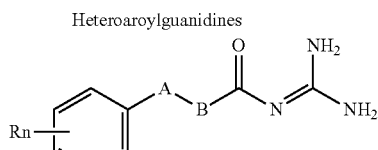

"Spacer-Stretched"
Aroylguanidines

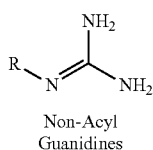

Non-Acyl Guanidines

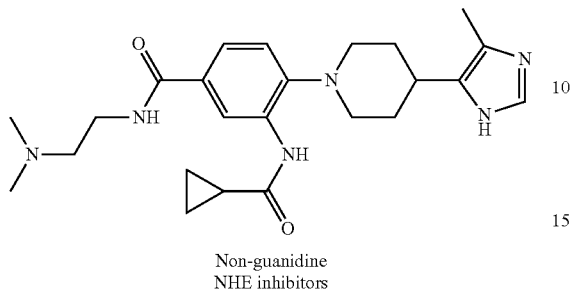

Non-guanidine NHE inhibitors wherein: the terminal ring (or, in the case of the non-acyl guanidines, "R"), represent the scaffold or support moiety; the guanidine moiety (or the substituted heterocycle, and more specifically the piperidine ring, in the case of the non-guanidine inhibitors) represents B; and, X is the acyl moiety, or the -A-B-acyl- moiety (or a bond in the case of the non-acyl guanidines and the non-guanidine inhibitors). (See, e.g., Lang, H. J., "*Chemistry of NHE Inhibitors*" in The Sodium-Hydrogen Exchanger, Harmazyn, M., Avkiran, M. and Fliegel, L., Eds., Kluwer Academic Publishers 2003. See also B. Masereel et al., An Overview of Inhibitors of Na+/H+Exchanger, *European J. of Med. Chem.*, 38, pp. 547-554 (2003), the entire contents of which is incorporated by reference here for all relevant and consistent purposes). Without being held to any particular theory, it has been proposed that a guanidine group, or an acylguanidine group, or a charged guanidine or acylguanidine group (or, in the case of non-guanidine inhibitors, a heterocycle or other functional group that can replicate the molecular interactions of a guanidinyl functionality including, but not limited to, a protonated nitrogen atom in a piperidine ring) at physiological pH may mimic a sodium ion at the binding site of the exchanger or antiporter (See, e.g., Vigne et al., *J. Biol. Chem.* 1982, 257, 9394).

Although the heteroatom-containing moiety may be capable of forming a positive charge, this should not be understood or interpreted to require that the overall compound have a net positive charge, or only a single positively charged moiety therein, or even that the heteroatom-containing moiety therein be capable of forming a positive charge in all instances. Rather, in various alternative embodiments, the compound may have no charged moieties therein, or it may have multiple charged moieties therein (which may have positive charges, negative charges, or a combination thereof). Additionally, it is to be understood that the overall compound may have a net neutral charge, a net positive charge, or a net negative charge.

In this regard it is to be noted that the U.S. patents and U.S. Published applications cited above, or elsewhere herein, are incorporated herein by reference in their entirety, for all relevant and consistent purposes.

In addition to the structures illustrated above, and elsewhere herein, it is to be noted that bioisosteric replacements for guanidine or acylguanidine may also be used. Potentially viable bioisosteric "guanidine replacements" identified to-date have a five- or six-membered heterocyclic ring with donor/acceptor and pKa patterns similar to that of guanidine or acylguanidine (see for example Ahmad, S. et al., Aminoimidazoles as Bioisosteres of Acylguanidines: Novel, Potent, Selective and Orally Bioavailable Inhibitors of the Sodium Hydrogen Exchanger Isoform-1, *Boorganic & Med. Chem. Lett.*, pp. 177-180 (2004), the entire contents of which is incorporated herein by reference for all relevant and consistent purposes), and include those illustrated below:

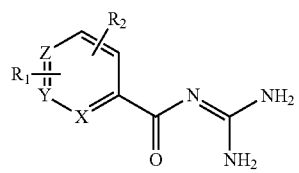

"Scaffold"  Acylguanidine or "sodium bioisostere"

Examples of acyl guanidine isosteres:

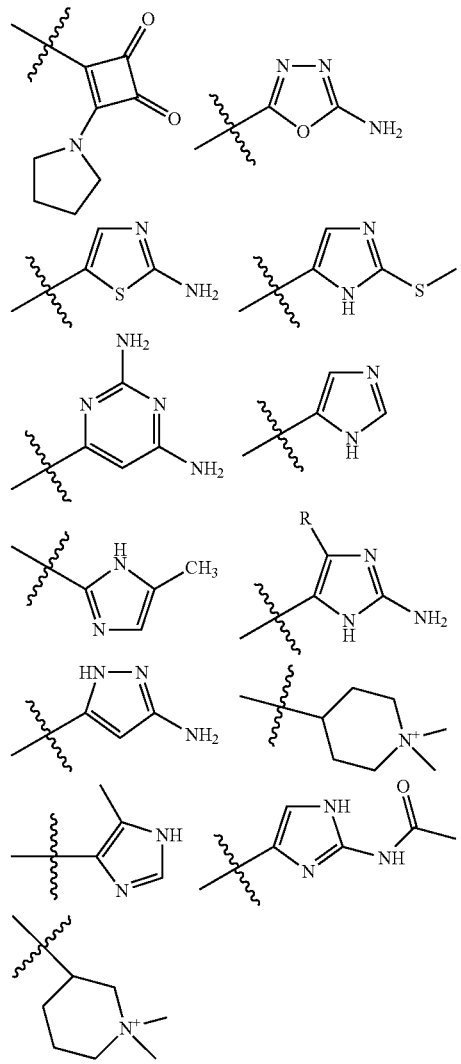

The above bioisosteric embodiments (i.e., the group of structures above) correspond to "B" in the structure of Formula (II), the broken bond therein being attached to "X"

(e.g., the acyl moiety, or alternatively a bond linking the bioisostere to the scaffold), with bonds to Z in Formula (III) not shown here.

It is to be noted that, in the many structures illustrated herein, all of the various linkages or bonds will not be shown in every instance. For example, in one or more of the structures illustrated above, a bond or connection between the NHE-binding small molecule and the modifying or functionalizing moiety Z is not always shown. However, this should not be viewed in a limiting sense. Rather, it is to be understood that the NHE-binding small molecule is bound or connected in some way (e.g., by a bond or linker of some kind) to Z, such that the resulting NHE-Z molecule is suitable for use (i.e., substantially impermeable or substantially systemically non-bioavailable in the GI tract). Alternatively, Z may be incorporated into the NHE-binding small molecule, such as for example by positioning it between the guanidine moiety and scaffold.

It is to be further noted that a number of structures are provided herein for substantially impermeable or substantially systemically non-bioavailable NHE-binding compounds, and/or for NHE-binding small molecules suitable for modification or functionalization in accordance with the present disclosure so as to render them substantially impermeable or substantially systemically non-bioavailable. Due to the large number of structures, various identifiers (e.g., atom identifiers in a chain or ring, identifiers for substituents on a ring or chain, etc.) may be used more than once. An identifier in one structure should therefore not be assumed to have the same meaning in a different structure, unless specifically stated (e.g., "$R_1$" in one structure may or may not be the same as "$R_1$" in another structure). Additionally, it is to be noted that, in one or more of the structures further illustrated herein below, specific details of the structures, including one or more of the identifiers therein, may be provided in a cited reference, the contents of which are specifically incorporated herein by reference for all relevant and consistent purposes.

C. Illustrative Small Molecule Embodiments

The substantially impermeable or substantially systemically non-bioavailable NHE3-binding compounds of the present disclosure may in general be derived or prepared from essentially any small molecule possessing the ability to bind to and/or modulate NHE3, including small molecules that have already been reported or identified as binding to and/or modulating NHE3 activity but lack impermeability (i.e., are not substantially impermeable). In one particularly preferred embodiment, the compounds utilized in the various methods of the present disclosure are derived or prepared from small molecules that bind to the NHE3, -2, and/or -8 isoforms. Although the present disclosure relates generally to NHE3-binding compounds, compounds exhibiting NHE-2 and/or -8 binding or inhibition are also of interest. However, while it is envisioned that appropriate starting points may be the modification of known NHE3, -2, and/or -8 binding or inhibiting small molecules, small molecules identified for the binding or inhibition of other NHE subtypes, including NHE-1, may also be of interest, and may be optimized for selectivity and binding to the NHE3 subtype antiporter.

Small molecules suitable for use (i.e., suitable for use as substantially bioavailable compounds, suitable for modification or functionalization to generate substantially systemically non-bioavailable compounds) include those illustrated below. In this regard it is to be noted a bond or link to Z (i.e., the modification or functionalization that renders the small molecules substantially impermeable or substantially systemically non-bioavailable) is not specifically shown. As noted, the Z moiety may be attached to, or included within, the small molecule at essentially any site or position that does not interfere (e.g., sterically interfere) with the ability of the resulting compound to effectively bind the NHE antiport of interest. More particularly, Z may be attached to essentially any site on the NHE-binding small molecule, Z for example displacing all or a portion of a substituent initially or originally present thereon and as illustrated below, provided that the site of installation of the Z moiety does not have a substantially adversely impact on the NHE-binding activity thereof. In one particular embodiment, however, a bond or link extends from Z to a site on the small molecule that effectively positions the point of attachment as far away (based, for example, on the number of intervening atoms or bonds) from the atom or atoms present in the resulting compound that effectively act as the sodium ion mimic (for example, the atom or atoms capable of forming a positive ion under physiological pH conditions). In a preferred embodiment, the bond or link will extend from Z to a site in a ring, and more preferably an aromatic ring, within the small molecule, which serves as the scaffold.

In view of the foregoing, in one particular embodiment, the following small molecule, disclosed in U.S. Patent Application No. 2005/0054705, the entire content of which (and in particular the text of pages 1-2 therein) is incorporated herein by reference for all relevant and consistent purposes, may be suitable for use or modification in accordance with the present disclosure (e.g., bound to or modified to include Z, such that the resulting NHE-Z molecule is substantially impermeable or substantially systemically non-bioavailable).

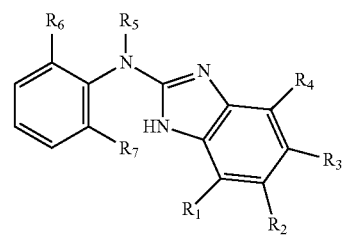

The variables in the structure are defined in the cited patent application, the details of which are incorporated herein by reference. In one particularly preferred embodiment, $R_6$ and $R_7$ are a halogen (e.g., Cl), $R_5$ is lower alkyl (e.g., $CH_3$), and $R_1$-$R_4$ are H, the compound having for example the structure:

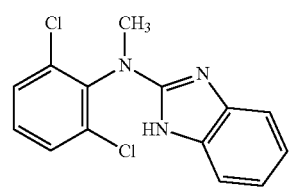 [SMILES: CN(c1nc2ccccc2[nH]1)c1c(Cl)cccc1Cl]

In yet another particular embodiment, the following small molecule, disclosed in Canadian Patent Application No. 2,241,531 (or International Patent Publication No. WO 97/24113), the entire content of which (and in particular pages 1-2 therein) is incorporated herein for all relevant and consistent purposes, may be suitable for use or modification in accordance with the present disclosure (e.g., bound to or modified to include Z, such that the resulting NHE-Z molecule is substantially impermeable or substantially systemically non-bioavailable).

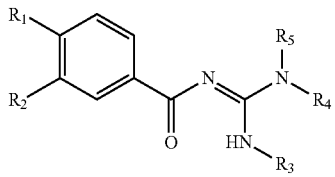

The variables in the structure are defined in the cited patent application, the details of which are incorporated herein by reference.

In yet another particular embodiment, the following small molecule, disclosed in Canadian Patent Application No. 2,241,531 (or International Patent Publication No. WO 97/24113), the entire content of which (and in particular page 49 therein) is incorporated herein for all relevant and consistent purposes, may be suitable for use or modification in accordance with the present disclosure (e.g., bound to or modified to include Z, such that the resulting NHE-Z molecule is substantially impermeable or substantially systemically non-bioavailable).

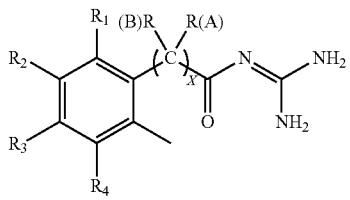

The variables in the structure are defined in the cited patent application, the details of which are incorporated herein by reference.

In yet another particular embodiment, the following small molecule, disclosed in Canadian Patent Application No. 2,241,531 (or International Patent Publication No. WO 97/24113), the entire content of which (and in particular pages 118-120 and 175-177 therein) is incorporated herein for all relevant and consistent purposes, may be suitable for use or modification in accordance with the present disclosure (e.g., bound to or modified to include Z, such that the resulting NHE-Z molecule is substantially impermeable or substantially systemically non-bioavailable).

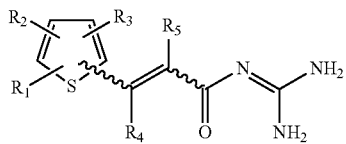

The variables in the structure are defined in the cited patent application, the details of which are incorporated herein by reference.

In yet another particular embodiment, the following small molecule, disclosed in Canadian Patent Application No. 2,241,531 (or International Patent Publication No. WO 97/24113), the entire content of which (and in particular pages 129-131 therein) is incorporated herein for all relevant and consistent purposes, may be suitable for use or modification in accordance with the present disclosure (e.g., bound to or modified to include Z, such that the resulting NHE-Z molecule is substantially impermeable or substantially systemically non-bioavailable).

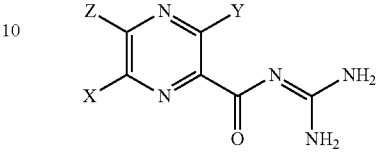

The variables in the structure are defined in the cited patent application, the details of which are incorporated herein by reference. (In this regard it is to be noted that the substituent Z within the structure illustrated above is not to be confused with the moiety Z that, in accordance with the present disclosure, is attached to the NHE-binding small molecule in order effective render the resulting "NHE-Z" molecule substantially impermeable.).

In yet another particular embodiment, the following small molecule, disclosed in Canadian Patent Application No. 2,241,531 (or International Patent Publication No. WO 97/24113), the entire content of which (and in particular pages 127-129 therein) is incorporated herein for all relevant and consistent purposes, may be suitable for use or modification in accordance with the present disclosure (e.g., bound to or modified to include Z, such that the resulting NHE-Z molecule is substantially impermeable or substantially systemically non-bioavailable).

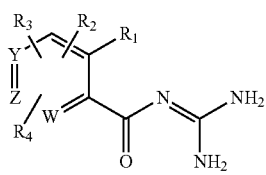

The variables in the structure are defined in the cited patent application, the details of which are incorporated herein by reference. (In this regard it is to be noted that Z within the ring of the structure illustrated above is not to be confused with the moiety Z that, in accordance with the present disclosure, is attached to the NHE-binding small molecule in order effective render the resulting "NHE-Z" molecule substantially impermeable.)

In yet another particular embodiment, the following small molecule, disclosed in Canadian Patent Application No. 2,241,531 (or International Patent Publication No. WO 97/24113), the entire content of which (and in particular pages 134-137 therein) is incorporated herein for all relevant and consistent purposes, may be suitable for use or modification in accordance with the present disclosure (e.g., bound to or modified to include Z, such that the resulting NHE-Z molecule is substantially impermeable or substantially systemically non-bioavailable).

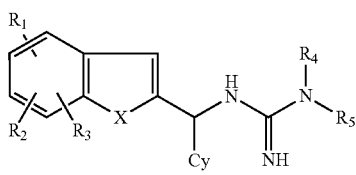

The variables in the structure are defined in the cited patent application, the details of which are incorporated herein by reference.

In yet another particular embodiment, the following small molecule, disclosed in Canadian Patent Application No. 2,241,531 (or International Patent Publication No. WO 97/24113), the entire content of which (and in particular pages 31-32 and 137-139 therein) is incorporated herein for all relevant and consistent purposes, may be suitable for use or modification in accordance with the present disclosure (e.g., bound to or modified to include Z, such that the resulting NHE-Z molecule is substantially impermeable or substantially systemically non-bioavailable).

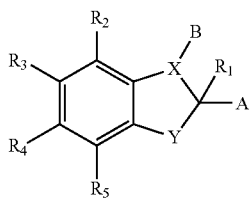

The variables in the structure are defined in the cited patent application, the details of which are incorporated herein by reference.

In yet another particular embodiment, the following small molecule, disclosed in Canadian Patent Application No. 2,241,531 (or International Patent Publication No. WO 97/24113), the entire content of which (and in particular pages 37-45 therein) is incorporated herein for all relevant and consistent purposes, may be suitable for use or modification in accordance with the present disclosure (e.g., bound to or modified to include Z, such that the resulting NHE-Z molecule is substantially impermeable or substantially systemically non-bioavailable).

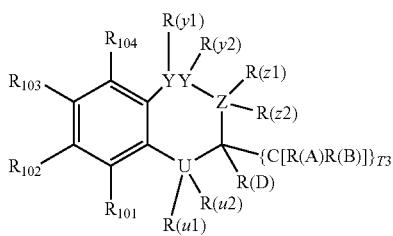

The variables in the structure are defined in the cited patent application, the details of which are incorporated herein by reference. (In this regard it is to be noted that Z within the ring structure illustrated above is not to be confused with the moiety Z that, in accordance with the present disclosure, is attached to the NHE-binding small molecule in order effective render the resulting "NHE-Z" molecule substantially impermeable.)

In yet another particular embodiment, the following small molecule, disclosed in Canadian Patent Application No. 2,241,531 (or International Patent Publication No. WO 97/24113), the entire content of which (and in particular pages 100-102 therein) is incorporated herein for all relevant and consistent purposes, may be suitable for use or modification in accordance with the present disclosure (e.g., bound to or modified to include Z, such that the resulting NHE-Z molecule is substantially impermeable or substantially systemically non-bioavailable).

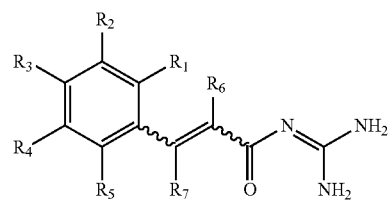

The variables in the structure are defined in the cited patent application, the details of which are incorporated herein by reference (wherein, in particular, the wavy bonds indicate variable length, or a variable number of atoms, therein).

In yet another particular embodiment, the following small molecule, disclosed in Canadian Patent Application No. 2,241,531 (or International Patent Publication No. WO 97/24113), the entire content of which (and in particular pages 90-91 therein) is incorporated herein for all relevant and consistent purposes, may be suitable for use or modification in accordance with the present disclosure (e.g., bound to or modified to include Z, such that the resulting NHE-Z molecule is substantially impermeable or substantially systemically non-bioavailable).

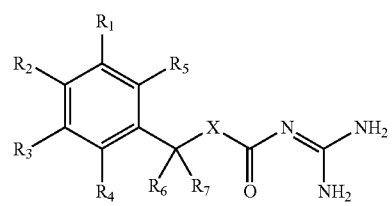

The variables in the structure are defined in the cited patent application, the details of which are incorporated herein by reference.

In yet another particular embodiment, the following small molecule, disclosed in U.S. Pat. No. 5,900,436 (or EP 0822182 B1), the entire contents of which (and in particular column 1, lines 10-55 therein) are incorporated herein by reference for all relevant and consistent purposes, may be suitable for use or modification in accordance with the present disclosure (e.g., bound to or modified to include Z, such that the resulting NHE-Z molecule is substantially impermeable or substantially systemically non-bioavailable).

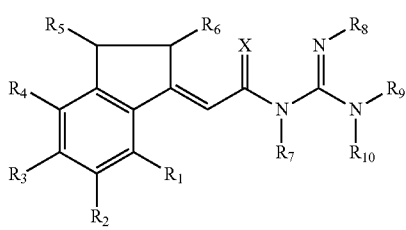

The variables in the structures are defined in the cited patents, the details of which are incorporated herein by reference.

In yet another particular embodiment, the following small molecule, disclosed in Canadian Patent Application No. 2,241,531 (or International Patent Publication No. WO 97/24113), the entire content of which (and in particular pages 35-47 therein) is incorporated herein for all relevant and consistent purposes, may be suitable for use or modification in accordance with the present disclosure (e.g., bound to or modified to include Z, such that the resulting NHE-Z molecule is substantially impermeable or substantially systemically non-bioavailable).

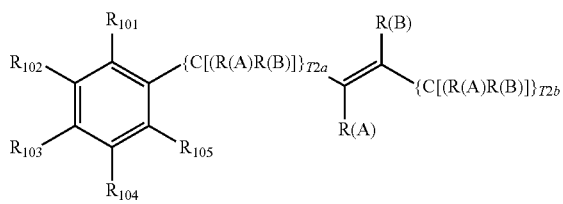

The variables in the structure are defined in the cited patent application, the details of which are incorporated herein by reference.

In yet another particular embodiment, the following small molecule, disclosed in Canadian Patent Application No. 2,241,531 (or International Patent Publication No. WO 97/24113), the entire content of which (and in particular pages 154-155 therein) is incorporated herein for all relevant and consistent purposes, may be suitable for use or modification in accordance with the present disclosure (e.g., bound to or modified to include Z, such that the resulting NHE-Z molecule is substantially impermeable or substantially systemically non-bioavailable).

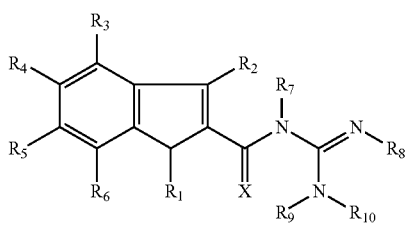

The variables in the structure are defined in the cited patent application, the details of which are incorporated herein by reference.

In yet another particular embodiment, the following small molecule, disclosed in Canadian Patent Application No. 2,241,531 (or International Patent Publication No. WO 97/24113), the entire content of which (and in particular pages 132-133 therein) is incorporated herein for all relevant and consistent purposes, may be suitable for use or modification in accordance with the present disclosure (e.g., bound to or modified to include Z, such that the resulting NHE-Z molecule is substantially impermeable or substantially systemically non-bioavailable).

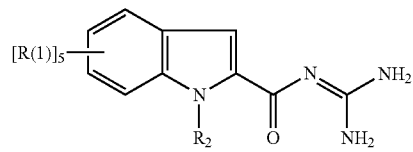

The variables in the structure are defined in the cited patent application, the details of which are incorporated herein by reference.

In yet another particular embodiment, the following small molecule, disclosed in Canadian Patent Application No. 2,241,531 (or International Patent Publication No. WO 97/24113), the entire content of which (and in particular pages 58-65 AND 141-148 therein) is incorporated herein for all relevant and consistent purposes, may be suitable for use or modification in accordance with the present disclosure (e.g., bound to or modified to include Z, such that the resulting NHE-Z molecule is substantially impermeable or substantially systemically non-bioavailable).

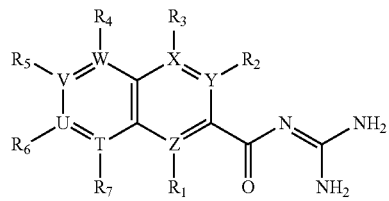

The variables in the structure are defined in the cited patent application, the details of which are incorporated herein by reference. (In this regard it is to be noted that Z within the ring structure illustrated above is not to be confused with the moiety Z that, in accordance with the present disclosure, is attached to the NHE-binding small molecule in order effective render the resulting "NHE-Z" molecule substantially impermeable.)

In yet another particular embodiment, the following small molecule, disclosed in U.S. Pat. Nos. 6,911,453 and 6,703,405, the entire contents of which (and in particular the text of columns 1-7 and 46 of U.S. Pat. No. 6,911,453 and columns 14-15 of U.S. Pat. No. 6,703,405) are incorporated herein by reference for all relevant and consistent purposes, may be suitable for use or modification in accordance with the present disclosure (e.g., bound to or modified to include Z, such that the resulting NHE-Z molecule is substantially impermeable or substantially systemically non-bioavailable).

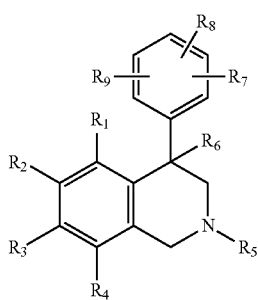

The variables in the structure are defined in the cited patents, the details of which are incorporated herein by reference. A particularly preferred small molecule falling within the above-noted structure is further illustrated below (see, e.g., Example 1 of the U.S. Pat. No. 6,911,453 patent, the entire contents of which are specifically incorporated herein by reference):

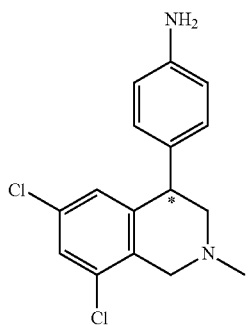 [SMILES: CN1Cc2c(Cl)cc(Cl)cc2C(c2ccc(N)cc2)C1]

In yet another particular embodiment, the following small molecules, disclosed in U.S. Patent Publication Nos. 2004/0039001, 2004/0224965, 2005/0113396 and 2005/0020612, the entire contents of which are incorporated herein by reference for all relevant and consistent purposes, may be suitable for use or modification in accordance with the present disclosure (e.g., bound to or modified to include Z, such that the resulting NHE-Z molecule is substantially impermeable or substantially systemically non-bioavailable).

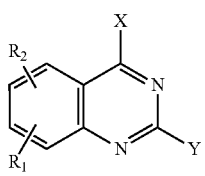

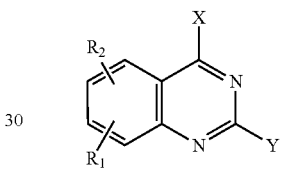

The variables in the structures are defined above and/or in one or more of the cited patent applications, the details of which are incorporated herein by reference, and/or as illustrated above (wherein the broken bonds indicate a point of attachment for the Y moiety to the fused heterocyclic ring). In particular, in various embodiments the combination of X and Y may be as follows:

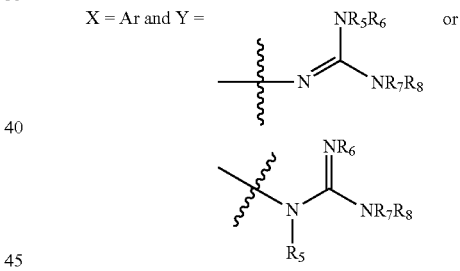

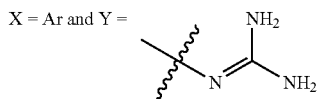

(see, e.g., US 2004/0039001, p. 1 therein)

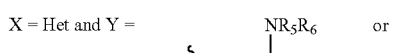

(see, e.g., US 2004/0224965, p. 1 therein)

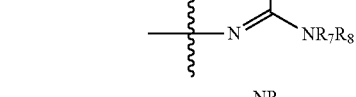

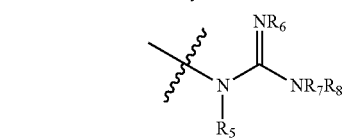

(see, e.g., US 2005/0113396, p. 1 therein)

X = Het and Y =

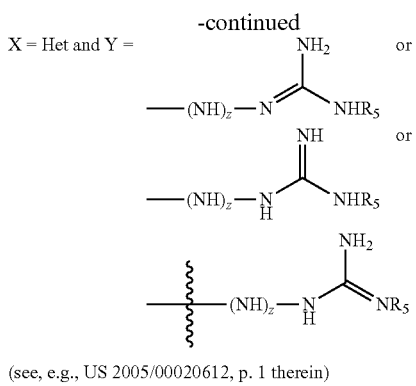

(see, e.g., US 2005/00020612, p. 1 therein)

In a particularly preferred embodiment of the above-noted structure, the small molecule has the general structure:

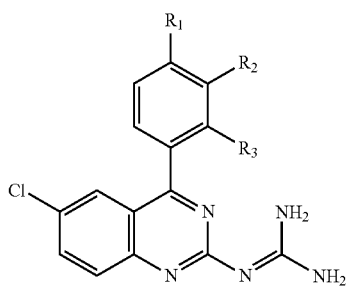

wherein $R_1$, $R_2$ and $R_3$ may be the same or different, but are preferably different, and are independently selected from H, NR'R" (wherein R' and R" are independently selected from H and hydrocarbyl, such as lower alkyl, as defined elsewhere herein) and the structure:

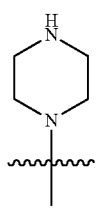

In a more particularly preferred embodiment of the above structure, a small molecule falling within the above-noted structure is further illustrated below (see, e.g., compound I1 on p. 5 of the 2005/0020612 patent application, the entire contents of which are specifically incorporated herein by reference):

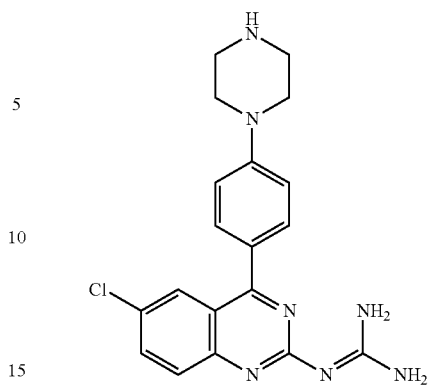

In another particularly preferred embodiment, the following small molecule, disclosed in U.S. Pat. No. 6,399,824, the entire content of which (and in particular the text of Example 1 therein) is incorporated herein by reference for all relevant and consistent purposes, may be particularly suitable for use or modification in accordance with the present disclosure (e.g., bound to or modified to include Z, such that the resulting NHE-Z molecule is substantially impermeable or substantially systemically non-bioavailable).

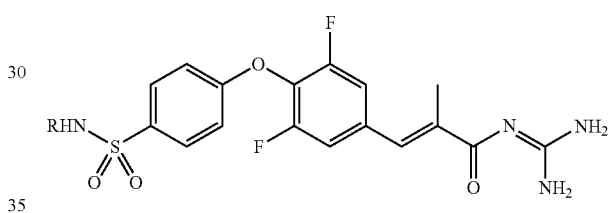

In the structure, R may be preferably selected from H and $(CH_3)_2NCH_2CH_2$—, with H being particularly preferred in various embodiments.

In yet another particular embodiment, the following small molecule, disclosed in U.S. Pat. No. 6,005,010 (and in particular columns 1-3 therein), and/or U.S. Pat. No. 6,166,002 (and in particular columns 1-3 therein), the entire contents of which are incorporated herein by reference for all relevant and consistent purposes, may be suitable for use or modification in accordance with the present disclosure (e.g., bound to or modified to include Z, such that the resulting NHE-Z molecule is substantially impermeable or substantially systemically non-bioavailable).

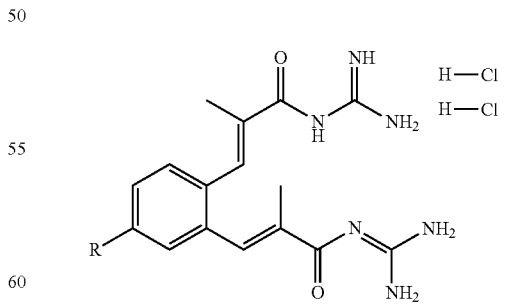

The variable ("R") in the structure is defined in the cited patent application, the details of which are incorporated herein by reference.

In yet another particularly preferred embodiment, the following small molecule, disclosed in U.S. Patent Application No. 2008/0194621, the entire content of which (and in particular the text of Example 1 therein) is incorporated herein by reference for all relevant and consistent purposes, may be particularly suitable for use or modification in accordance with the present disclosure (e.g., bound to or modified to include Z, such that the resulting NHE-Z molecule is substantially impermeable or substantially systemically non-bioavailable).

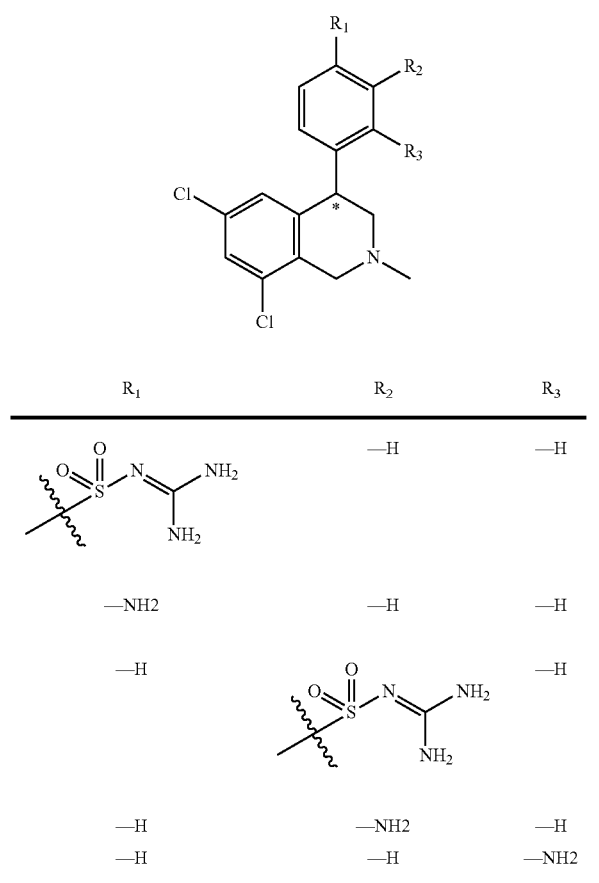

The variables ("$R_1$", "$R_2$ and "$R_3$") in the structure are as defined above, and/or as defined in the cited patent application, the details of which are incorporated herein by reference.

In yet another particularly preferred embodiment, the following small molecule, disclosed in U.S. Patent Application No. 2007/0225323, the entire content of which (and in particular the text of Example 36 therein) is incorporated herein by reference for all relevant and consistent purposes, may be particularly suitable for use or modification in accordance with the present disclosure (e.g., bound to or modified to include Z, such that the resulting NHE-Z molecule is substantially impermeable or substantially systemically non-bioavailable).

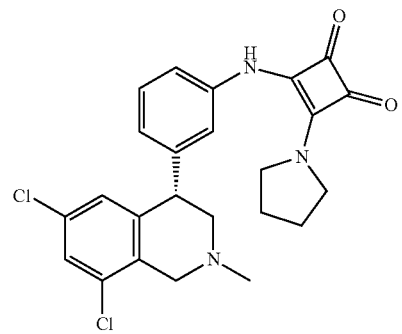 [SMILES: CN1Cc2c(Cl)cc(Cl)cc2[C@H](c2cccc(Nc3c(N4CCCC4)c(=O)c3=O)c2)C1]

In yet another particularly preferred embodiment, the following small molecule, disclosed in U.S. Pat. No. 6,911,453, the entire content of which (and in particular the text of Example 35 therein) is incorporated herein by reference for all relevant and consistent purposes, may be particularly suitable for use or modification in accordance with the present disclosure (e.g., bound to or modified to include Z, such that the resulting NHE-Z molecule is substantially impermeable or substantially systemically non-bioavailable).

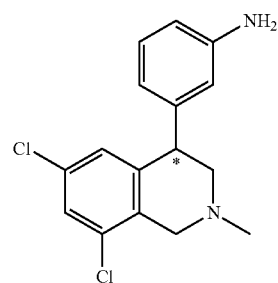 [SMILES: CN1Cc2c(Cl)cc(Cl)cc2C(c2cccc(N)c2)C1]

In one particularly preferred embodiment of the present disclosure, the small molecule may be selected from the group consisting of:

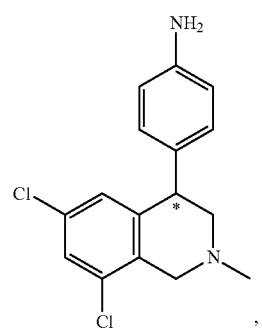

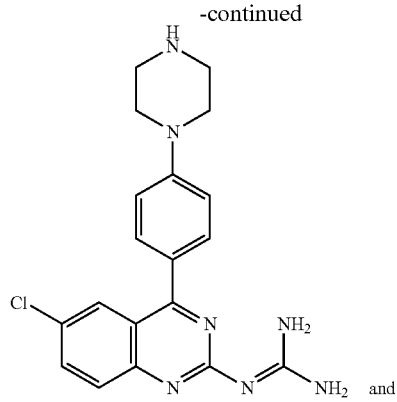 and

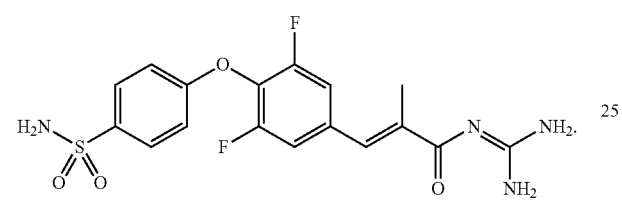

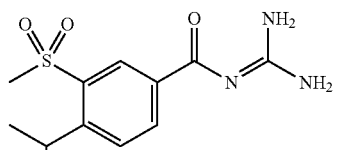

Cariporide

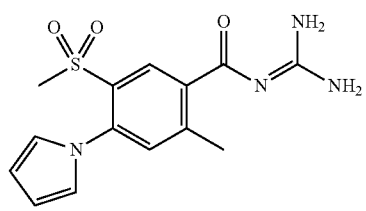

Eniporide

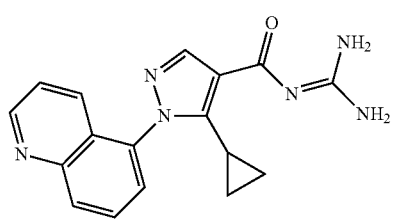

Zoniporide

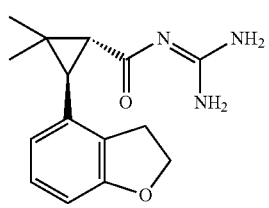

BMS-284640

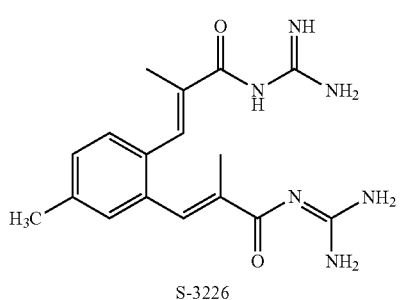

S-3226

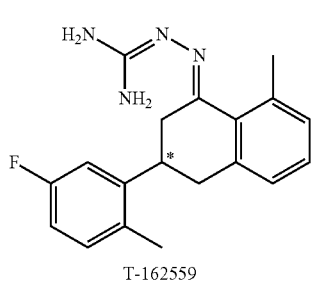

T-162559

In these structures, a bond or link (not shown) may extend, for example, between the Core and amine-substituted aromatic ring (first structure), the heterocyclic ring or the aromatic ring to which it is bound, or alternatively the chloro-substituted aromatic ring (second structure), or the difluoro-substituted aromatic ring or the sulfonamide-substituted aromatic ring (third structure).

D. Exemplary Small Molecule Selectivity

Shown below are examples of various NHE binding small molecules and their selectivity across the NHE-1, -2 and -3 isoforms. (See, e.g., B. Masereel et al., An Overview of Inhibitors of Na+/H+Exchanger, *European J. of Med. Chem.*, 38, pp. 547-554 (2003), the entire contents of which is incorporated by reference here for all relevant and consistent purposes). Most of these small molecules were optimized as NHE-1 inhibitors, and this is reflected in their selectivity with respect thereto (IC50's for subtype-1 are significantly more potent (numerically lower) than for subtype-3). However, the data in Table 2 indicates that NHE3 binding activity may be engineered into a compound series originally optimized against a different isoform. For example, amiloride is a poor NHE3 binder/inhibitor and was inactive against this antiporter at the highest concentration tested (IC50>100 μM); however, analogs of this compound, such as DMA and EIPA, have NHE3 IC50's of 14 and 2.4 μM, respectively. The cinnamoylguanidine S-2120 is over 500-fold more active against NHE-1 than NHE3; however, this selectivity is reversed in regioisomer S-3226. It is thus possible to engineer NHE3 binding selectivity into a chemical series optimized for potency against another antiporter isoform; that is, the inhibitor classes exemplified in the art may be suitably modified for activity and selectivity against NHE3 (or alternatively NHE-2 and/or NHE-8), as well as being optionally modified to be rendered substantially impermeable or substantially systemically non-bioavailable.

-continued

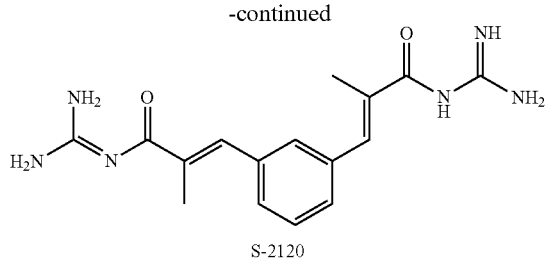

S-2120

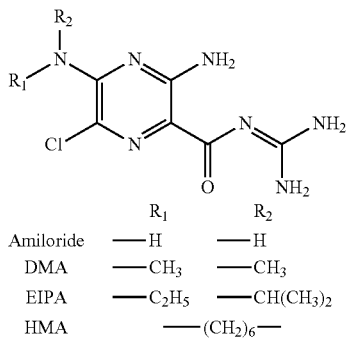

|  | $R_1$ | $R_2$ |
|---|---|---|
| Amiloride | —H | —H |
| DMA | —CH$_3$ | —CH$_3$ |
| EIPA | —C$_2$H$_5$ | —CH(CH$_3$)$_2$ |
| HMA | —(CH$_2$)$_6$— | |

TABLE 2

| | IC$_{50}$ or K$_i$ (μM) [b] | | | |
|---|---|---|---|---|
| Drug [a] | NHE-1 | NHE-2 | NHE-3 | NHE-5 |
| Amiloride | 1-1.6* | 1.0** | >100* | 21 |
| EIPA | 0.01*-0.02** | 0.08*-0.5** | 2.4* | 0.42 |
| HMA | 0.013* | — | 2.4* | 0.37 |
| DMA | 0.023* | 0.25* | 14* | — |
| Cariporide | 0.03-3.4 | 4.3-62 | 1->100 | >30 |
| Eniporide | 0.005-0.38 | 2-17 | 100-460 | >30 |
| Zoniporide | 0.059 | 12 | >500* | — |
| BMS-284640 | 0.009 | 1800 | >30 | 3.36 |
| T-162559 (S) | 0.001 | 0.43 | 11 | — |
| T-162559 (R) | 35 | 0.31 | >30 | — |
| S-3226 | 3.6 | 80** | 0.02 | |
| S-2120 | 0.002 | 0.07 | 1.32 | |

*from rat, **from rabbit.
NA = not active
[a] Table adapted from Masereel, B. et al., *European Journal of Medicinal Chemistry*, 2003, 38, 547-54.
[b] K$_i$ values are in italic As previously noted above, the NHE-binding small molecules disclosed herein, including those noted above, may advantageously be modified to render them substantially impermeable or substantially systemically non-bioavailable. The compounds as described herein are, accordingly, effectively localized in the gastrointestinal tract or lumen, and in one particular embodiment the colon. Since the various NHE isoforms may be found in many different internal organs (e.g., brain, heart, liver, etc.), localization of the NHE binding compounds in the intestinal lumen can be desirable in order to minimize or eliminate systemic effects (i.e., prevent or significantly limit exposure of such organs to these compounds). Accordingly, the present disclosure provides NHE binding compounds, and in particular NHE3, -2 and/or -8 inhibitors, which are substantially systemically non-bioavailable in the GI tract, and more specifically substantially systemically impermeable to the gut epithelium, as further described herein.

E. Exemplary Embodiments

In one or more particularly preferred embodiments of the present disclosure, the "NHE-Z" molecule is monovalent; that is, the molecule contains one moiety that effectively binds to and/or modulates NHE3 and also inhibits phosphate transport in the GI tract or kidneys. In such embodiments, the NHE-Z molecule may be selected, for example, from one of the following structures of Formulas (IV), (V), (VI) or (VII):

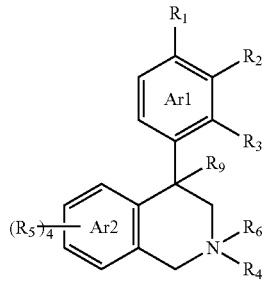

(IV)

wherein: each $R_1$, $R_2$, $R_3$, $R_5$ and $R_9$ are independently selected from H, halogen (e.g., Cl), —NR$_7$(CO)R$_8$, —(CO)NR$_7$R$_8$, —SO$_2$—NR$_7$R$_8$, —NR$_7$SO$_2$R$_8$, —NR$_7$R$_8$, —OR$_7$, —SR$_7$, —O(CO)NR$_7$R$_8$, —NR$_7$(CO)OR$_8$, and —NR$_7$SO$_2$NR$_8$, where $R_7$ and $R_8$ are independently selected from H or Z, where Z is selected from substituted or unsubstituted hydrocarbyl, heterohydrocarbyl, polyalkylene glycol and polyols, where substituents thereon are selected from hydroxyls, amines, amidines, carboxylates, phosphonates, sulfonates, and guanidines; $R_4$ is selected from H, $C_1$-$C_7$ alkyl or Z, where Z is selected from substituted or unsubstituted hydrocarbyl, heterohydrocarbyl, a polyalkylene glycol and polyols, where substituents thereon are selected from hydroxyls, amines, amidines, carboxylates, phosphonates, sulfonates, and guanidines; $R_6$ is absent or selected from H and $C_1$-$C_7$ alkyl; and, Ar1 and Ar2 independently represent an aromatic ring, or alternatively a heteroaromatic ring wherein one or more of the carbon atoms therein is replaced with a N, O or S atom;

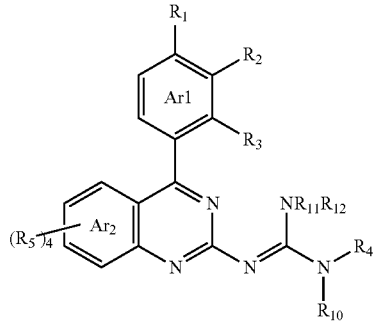

(V)

wherein: each $R_1$, $R_2$, $R_3$, and $R_5$ are independently selected from H, —NR$_7$(CO)R$_8$, —(CO)NR$_7$R$_8$, —SO$_2$—NR$_7$R$_8$, —NR$_7$SO$_2$R$_8$, —NR$_7$R$_8$, —OR$_7$, —SR$_7$, —O(CO)NR$_7$R$_8$, —NR$_7$(CO)OR$_8$, and —NR$_7$SO$_2$NR$_8$, where $R_7$ and $R_8$ are independently selected from H or Z, where Z is selected from substituted or unsubstituted hydrocarbyl, heterohydrocarbyl, polyalkylene glycol and polyols, where substituents thereon are selected from hydroxyls, amines, amidines, carboxylates, phosphonates, sulfonates, and guanidines, optionally linked to the ring Ar1 by a heterocyclic linker; $R_4$ and $R_{12}$ are independently selected from H and $R_7$, where $R_7$ is as defined above; $R_{10}$ and $R_{11}$, when presented, are independently selected from H and $C_1$-$C_7$ alkyl; and, Ar1 and Ar2 independently represent an aromatic ring, or alternatively a heteroaromatic ring wherein one or more of the carbon atoms therein is replaced with a N, O or S atom;

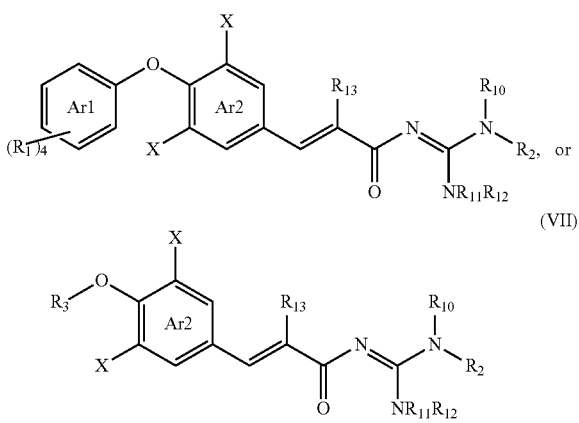

(VI)

(VII)

wherein: each X is a halogen atom, which may be the same or different; $R_1$ is selected from —$SO_2$—$NR_7R_8$, —$NR_7(CO)R_8$, —$(CO)NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H or Z, where Z is selected from substituted or unsubstituted hydrocarbyl, heterohydrocarbyl, polyalkylene glycol and polyols, where substituents thereon are selected from hydroxyls, amines, amidines, carboxylates, phosphonates, sulfonates, and guanidines; $R_3$ is selected from H or $R_7$, where $R_7$ is as described above; $R_{13}$ is selected from substituted or unsubstituted $C_1$-$C_8$ alkyl; $R_2$ and $R_{12}$ are independently selected from H or $R_7$, wherein $R_7$ is as described above; $R_{10}$ and $R_{11}$, when present, are independently selected from H and $C_1$-$C_7$ alkyl; Ar1 represents an aromatic ring, or alternatively a heteroaromatic ring wherein one or more of the carbon atoms therein is replaced with a N, O or S atom; and Ar2 represents an aromatic ring, or alternatively a heteroaromatic ring wherein one or more of the carbon atoms therein is replaced with a N, O or S atom.

In one particular embodiment for the structure of Formula (V), one of $R_1$, $R_2$ and $R_3$ is linked to the ring Ar1, and/or $R_5$ is linked to the ring Ar2, by a heterocyclic linker having the structure:

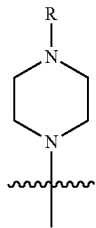

wherein R represents $R_1$, $R_2$, $R_3$, or $R_5$ bound thereto.

In another particular embodiment, the NHE-Z molecule of the present disclosure may have the structure of Formula (IV):

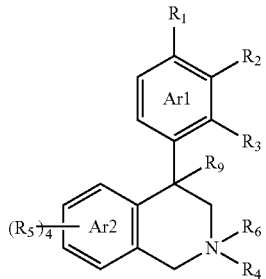

(IV)

wherein: each $R_1$, $R_2$, $R_3$, $R_5$ and $R_9$ are independently selected from H, halogen, $NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H or Z, where Z is selected from substituted hydrocarbyl, heterohydrocarbyl, or polyols and/or substituted or unsubstituted polyalkylene glycol, wherein substituents thereon are selected from the group consisting of phosphinates, phosphonates, phosphonamidates, phosphates, phosphonthioates and phosphonodithioates; $R_4$ is selected from H or Z, where Z is substituted or unsubstituted hydrocarbyl, heterohydrocarbyl, a polyalkylene glycol and a polyol, where substituents thereon are selected from hydroxyls, amines, amidines, carboxylates, phosphonates, sulfonates, and guanidines; $R_6$ is selected from —H and $C_1$-$C_7$ alkyl; and, Ar1 and Ar2 independently represent an aromatic ring, or alternatively a heteroaromatic ring wherein one or more of the carbon atoms therein is replaced with a N, O or S atom.

Additionally, or alternatively, in one or more embodiments of the compounds illustrated above, the compound may optionally have a tPSA of at least about 100 Å², about 150 Å², about 200 Å², about 250 Å², about 270 Å², or more and/or a molecular weight of at least about 710 Da.

F. Polyvalent Structures: Macromolecules and Oligomers (i). General Structure

As noted above, certain embodiments relate to NHE-binding small molecules that have been modified or functionalized structurally to alter its physicochemical properties (by the attachment or inclusion of moiety Z), and more specifically the physicochemical properties of the NHE-Z molecule, thus rendering it substantially impermeable or substantially systemically non-bioavailable. In one particular embodiment, and as further detailed elsewhere herein, the NHE-Z compound may be polyvalent (i.e., an oligomer, dendrimer or polymer moiety), wherein Z may be referred to in this embodiment generally as a "Core" moiety, and the NHE-binding small molecule may be bound, directly or indirectly (by means of a linking moiety) thereto, the polyvalent compounds having for example one of the following general structures of Formula (VIII), (IX) and (X):

NHE-Core (VIII)

[NHE—]$_E$-Z (IX)

Core—(L-NHE)$_n$ (X)

wherein: Core (or Z) and NHE are as defined above; L is a bond or linker, as further defined elsewhere herein below, and E and n are both an integer of 2 or more. In various alternative embodiments, however, the NHE-binding small molecule may be rendered substantially impermeable or substantially systemically non-bioavailable by forming a polymeric structure from multiple NHE-binding small molecules, which may be the same or different, connected or bound by a series of linkers, L, which also may be the same or different, the compound having for example the structure of Formula (XI):

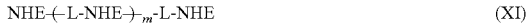  (XI)

wherein: Core (or Z) and NHE are as defined above; L is a bond or linker, as further defined elsewhere herein below, and m is 0 or an integer of 1 or more. In this embodiment, the physicochemical properties, and in particular the molecular weight or polar surface area, of the NHE-binding small molecule is modified (e.g., increased) by having a series of NHE-binding small molecules linked together, in order to render them substantially impermeable or substantially systemically non-bioavailable. In these or yet additional alternative embodiments, the polyvalent compound may be in dimeric, oligomeric or polymeric form, wherein for example Z or the Core is a backbone to which is bound (by means of a linker, for example) multiple NHE-binding small molecules. Such compounds may have, for example, the structures of Formulas (XIIA) or (XIIB):

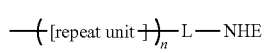  (XIIA)

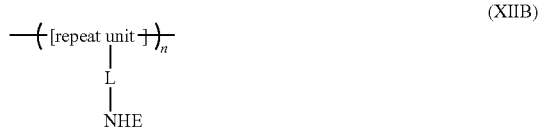  (XIIB)

wherein: L is a linking moiety; NHE is a NHE-binding small molecule, each NHE as described above and in further detail hereinafter; and n is a non-zero integer (i.e., an integer of 1 or more).

The Core moiety has one or more attachment sites to which NHE-binding small molecules are bound, and preferably covalently bound, via a bond or linker, L. The Core moiety may, in general, be anything that serves to enable the overall compound to be substantially impermeable or substantially systemically non-bioavailable (e.g., an atom, a small molecule, etc.), but in one or more preferred embodiments is an oligomer, a dendrimer or a polymer moiety, in each case having more than one site of attachment for L (and thus for the NHE-binding small molecule). The combination of the Core and NHE-binding small molecule (i.e., the "NHE-Z" molecule) may have physicochemical properties that enable the overall compound to be substantially impermeable or substantially systemically non-bioavailable.

In this regard it is to be noted that the repeat unit in Formulas (XIIA) and (XIIB) generally encompasses repeating units of various polymeric embodiments, which may optionally be produced by methods referred to herein. In each polymeric, or more general polyvalent, embodiment, it is to be noted that each repeat unit may be the same or different, and may or may not be linked to the NHE-binding small molecule by a linker, which in turn may be the same or different when present. In this regard it is to be noted that as used herein, "polyvalent" refers to a molecule that has multiple (e.g., 2, 4, 6, 8, 10 or more) NHE-binding moieties therein.

The above noted embodiments are further illustrated herein below. For example, the first representation below of an exemplary oligomer compound, wherein the various parts of the compound corresponding to the structure of Formula (X) are identified, is intended to provide a broad context for the disclosure provided herein. It is to be noted that while each "NHE" moiety (i.e., the NHE small molecule) in the structure below is the same, it is within the scope of this disclosure that each is independently selected and may be the same or different. In the illustration below, the linker moiety is a polyethylene glycol (PEG) motif. PEG derivatives are advantageous due in part to their aqueous solubility, which may help avoid hydrophobic collapse (the intramolecular interaction of hydrophobic motifs that can occur when a hydrophobic molecule is exposed to an aqueous environment (see, e.g., Wiley, R. A.; Rich, D. H. Medical Research Reviews 1993, 13(3), 327-384). The core moiety illustrated below is also advantageous because it provides some rigidity to the Core-(L-NHE)$_n$ molecule, allowing an increase in distance between the NHE-binding compounds while minimally increasing rotational degrees of freedom.

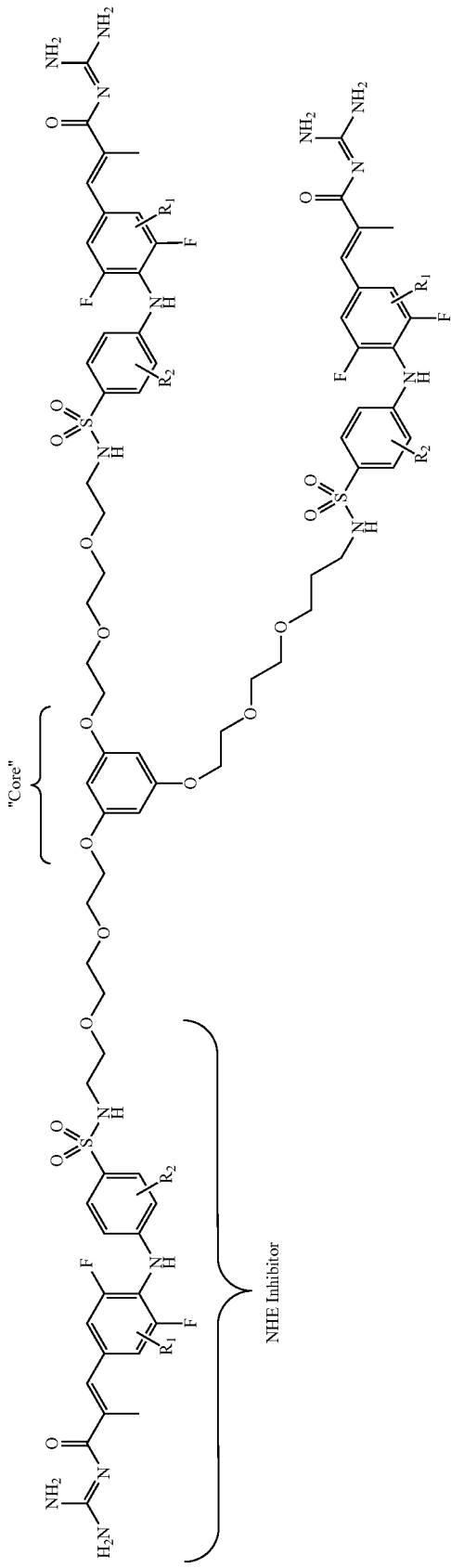

In an alternative embodiment (e.g., Formula (XI), wherein m=0), the structure may be for example:

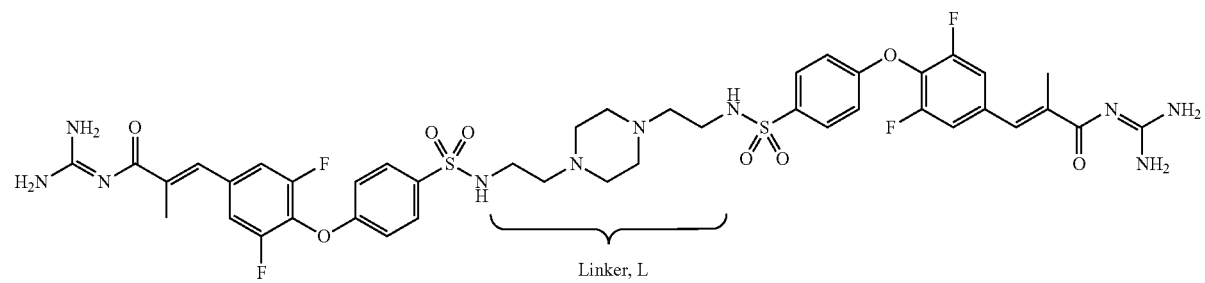

or

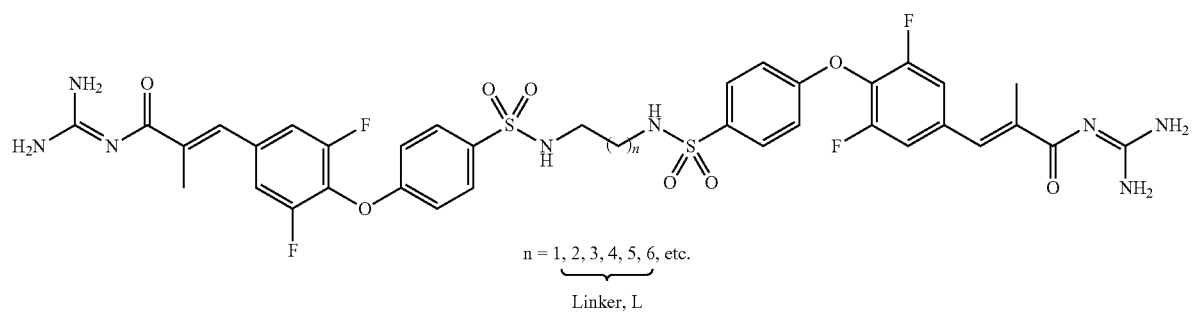

or

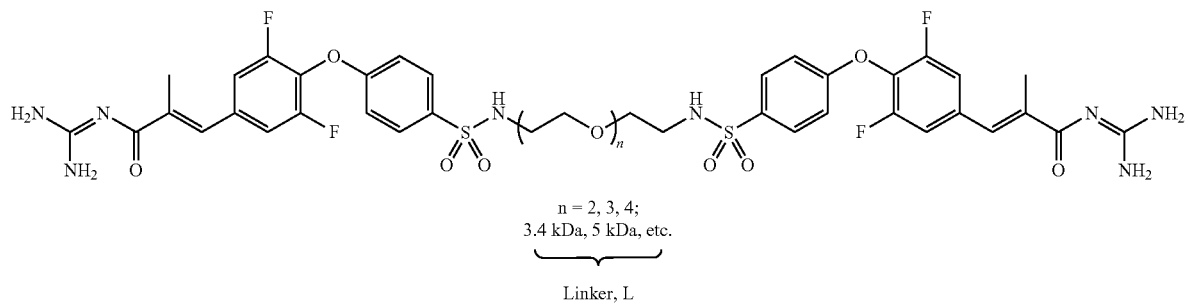

Within the polyvalent compounds utilized for treatments according to the present disclosure, n and m (when m is not zero) may be independently selected from the range of from about 1 to about 10, more preferably from about 1 to about 5, and even more preferably from about 1 to about 2. In alternative embodiments, however, n and m may be independently selected from the range of from about 1 to about 500, preferably from about 1 to about 300, more preferably from about 1 to about 100, and most preferably from about 1 to about 50. In these or other particular embodiments, n and m may both be within the range of from about 1 to about 50, or from about 1 to about 20.

The structures provided above are illustrations of one embodiment of compounds utilized for administration wherein absorption is limited (i.e., the compound is rendered substantially impermeable or substantially systemically non-bioavailable) by means of increasing the molecular weight of the NHE-binding small molecule. In an alternative approach, as noted elsewhere herein, the NHE-binding small molecule may be rendered substantially impermeable or substantially systemically non-bioavailable by means of altering, and more specifically increasing, the topological polar surface area, as further illustrated by the following structures, wherein a substituted aromatic ring is bound to the "scaffold" of the NHE-binding small molecule. The selection of ionizable groups such as phosphonates, sulfonates, guanidines and the like may be particularly advantageous at preventing paracellular permeability. Carbohydrates are also advantageous, and though uncharged, significantly increase tPSA while minimally increasing molecular weight.

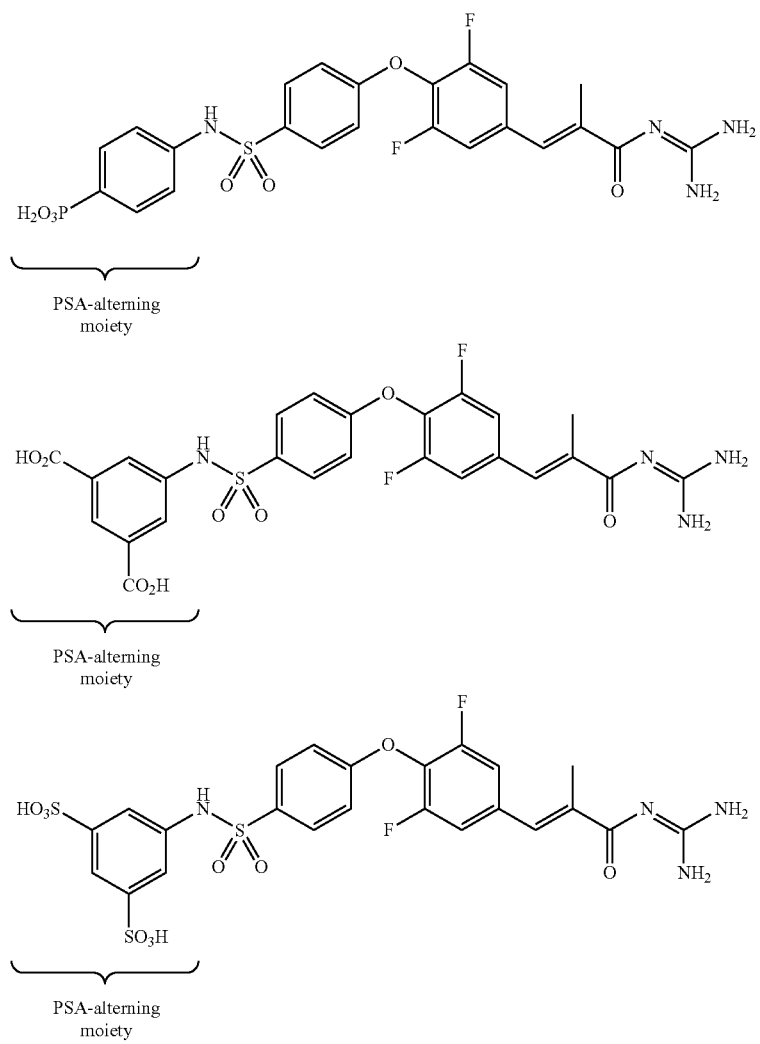

It is to be noted, within one or more of the various embodiments illustrated herein, NHE-binding small molecules suitable for use (i.e., suitable for use as substantially bioavailable compounds, suitable for modification or functionalization, in order to render them substantially impermeable or substantially systemically non-bioavailable) may, in particular, be selected independently from one or more of the small molecules described as benzoylguanidines, heteroaroylguanidines, "spacer-stretched" aroylguanidines, non-acyl guanidines and acylguanidine isosteres, above, and as discussed in further detail hereinafter and/or to the small molecules detailed in, for example: U.S. Pat. No. 5,866,610; 6,399,824; 6,911,453; 6,703,405; 6,005,010; 6,887,870; 6,737,423; 7,326,705; 5,582,4691 (WO94/026709); U.S. Pat. No. 6,399,824 (WO02/024637); US 2004/0339001 (WO02/020496); US 2005/0020612 (WO03/055490); WO01/072742; CA 2387529 (WO01021582); CA 02241531 (WO97/024113); US 2005/0113396 (WO03/051866); US2005/0020612; US2005/0054705; US2008/0194621; US2007/0225323; US2004/0039001; US2004/0224965; US2005/0113396; US2007/0135383; US2007/0135385; US2005/0244367; US2007/0270414; and CA 2177007 (EP0744397), the entire contents of which are incorporated herein by reference for all relevant and consistent purposes.

Again, it is to be noted that when it is said that NHE-binding small molecule is selected independently, it is intended that, for example, the oligomeric structures represented in Formulas (X) and (XI) above can include different structures of the NHE small molecules, within the same oligomer or polymer. In other words, each "NHE" within a given polyvalent embodiment may independently be the same or different than other "NHE" moieties within the same polyvalent embodiment.

In designing and making the substantially impermeable or substantially systemically non-bioavailable, NHE-binding compounds that may be utilized for the treatments detailed in the instant disclosure, it may in some cases be advantageous to first determine a likely point of attachment on a small molecule NHE-binding compound, where a core or linker might be installed or attached before making a series of candidate multivalent or polyvalent compounds. This may be done by one skilled in the art via known methods by systematically installing functional groups, or functional groups displaying a fragment of the desired core or linker, onto various positions of the NHE-binding small molecule and then testing these adducts to determine whether the modified compound still retains desired biological properties (e.g., NHE3 binding and/or modulation, inhibition of phosphate transport). An understanding of the SAR of the compound also allows the design of cores and/or linkers that contribute positively to the activity of the resulting compounds. For example, the SAR of an NHE-binding compound series may show that installation of an N-alkylated piperazine contributes positively to biochemical activity (increased potency) or pharmaceutical properties (increased solubility); the piperazine moiety may then be utilized as the point of attachment for the desired core or linker via N-alkylation. In this fashion, the resulting compound thereby retains the favorable biochemical or pharmaceutical properties of the parent small molecule. In another example, the SAR of an NHE-binding compound series might indicate that a hydrogen bond donor is important for activity or selectivity. Core or linker moieties may then be designed to ensure this H-bond donor is retained. These cores and/or linkers may be further designed to attenuate or potentiate the pKa of the H-bond donor, potentially allowing improvements in potency and selectivity. In another scenario, an aromatic ring in a compound could be an important pharmacophore, interacting with the biological target via a pi-stacking effect or pi-cation interaction. Linker and core motifs may be similarly designed to be isosteric or otherwise synergize with the aromatic features of the small molecule. Accordingly, once the structure-activity relationships within a molecular series are understood, the molecules of interest can be broken down into key pharmacophores which act as essential molecular recognition elements. When considering the installation of a core or linker motif, said motifs can be designed to exploit this SAR and may be installed to be isosteric and isoelectronic with these motifs, resulting in compounds that retain biological activity but have significantly reduced permeability.

Another way the SAR of a compound series can be exploited in the installation of core or linker groups is to understand which regions of the molecule are insensitive to structural changes. For example, X-ray co-crystal structures of protein-bound compounds can reveal those portions of the compound that are solvent exposed and not involved in productive interactions with the target. Such regions can also be identified empirically when chemical modifications in these regions result in a "flat SAR" (i.e., modifications appear to have minimal contribution to biochemical activity). Those skilled in the art have frequently exploited such regions to engineer in pharmaceutical properties into a compound, for example, by installing motifs that may improve solubility or potentiate ADME properties. In the same fashion, such regions are expected to be advantageous places to install core or linker groups to create compounds as described in the instant disclosure. These regions are also expected to be sites for adding, for example, highly polar functionality such as carboxylic acids, phosphonic acids, sulfonic acids, and the like in order to greatly increase tPSA.

Another aspect to be considered in the design of cores and linkers displaying an NHE-binding activity is the limiting or preventing of hydrophobic collapse. Compounds with extended hydrocarbon functionalities may collapse upon themselves in an intramolecular fashion, causing an increased enthalpic barrier for interaction with the desired biological target. Accordingly, when designing cores and linkers, these are preferably designed to be resistant to hydrophobic collapse. For example, conformational constraints such as rigid monocyclic, bicyclic or polycyclic rings can be installed in a core or linker to increase the rigidity of the structure. Unsaturated bonds, such as alkenes and alkynes, may also or alternatively be installed. Such modifications may ensure the NHE-binding compound is accessible for productive binding with its target. Furthermore, the hydrophilicity of the linkers may be improved by adding hydrogen bond donor or acceptor motifs, or ionic motifs such as amines that are protonated in the GI, or acids that are deprotonated. Such modifications will increase the hydrophilicity of the core or linker and help prevent hydrophobic collapse. Furthermore, such modifications will also contribute to the impermeability of the resulting compounds by increasing tPSA.

Specific examples of NHE-binding small molecules modified consistent with the principles detailed above are illustrated below. These moieties display functional groups that facilitate their appendage to "Z" (e.g., a core group, Core, or linking group, L). These functional groups can include electrophiles, which can react with nucleophilic cores or linkers, and nucleophiles, which can react with electrophilic cores or linkers. Small molecule NHE binding compounds may be similarly derivatized with, for example, boronic acid groups which can then react with appropriate cores or linkers via palladium mediated cross-coupling reactions. The NHE binding compound may also contain olefins which can then react with appropriate cores or linkers via olefin metathesis chemistry, or alkynes or azides which can then react with appropriate cores or linkers via [2+3] cycloaddition. One skilled in the art may consider a variety of functional groups that will allow the facile and specific attachment of an NHE-binding small molecule to a desired core or linker. Exemplary functionalized derivatives of NHEs include but are not limited to the following:

Scheme 1

Cinnamoylguanidine NHE-binding Moiety Functionalized to Display
Electrophilic or Nucleophilic Groups to Facilitate Reaction with Cores and Linkers

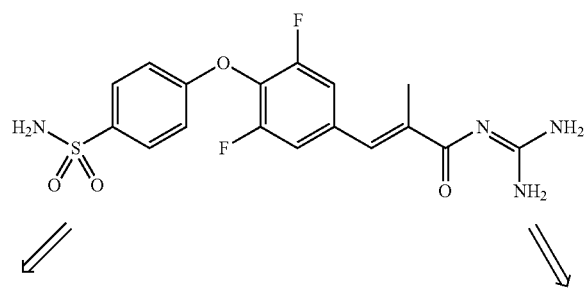

-continued

Electrophilic Intermediates:

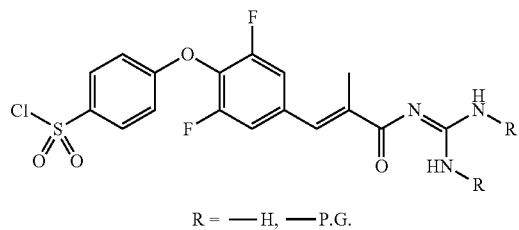

R = —H, —P.G.

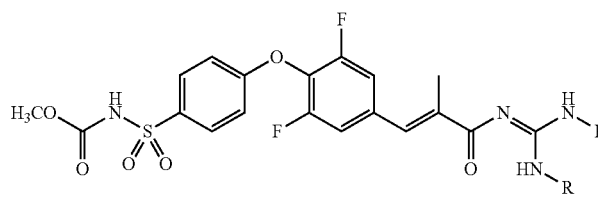

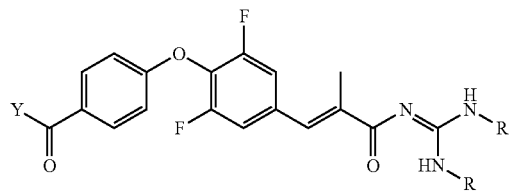

Y = —OH, —NHS, —Cl, etc.

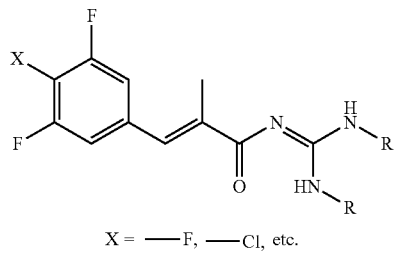

X = —F, —Cl, etc.

Nucleophilic Intermediates:

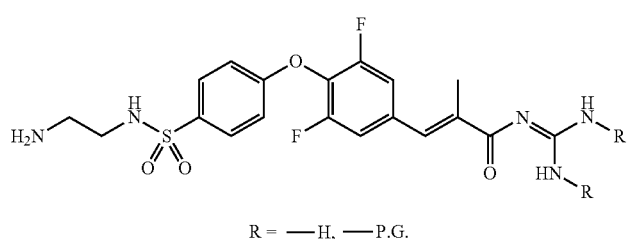

R = —H, —P.G.

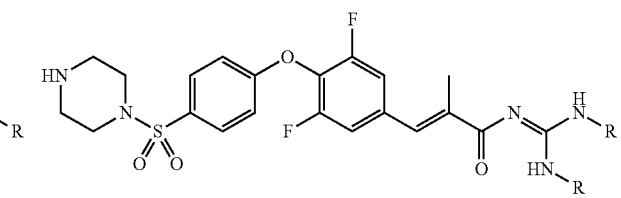

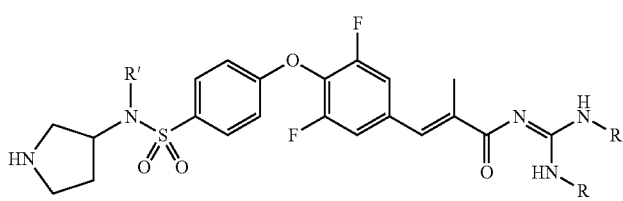

R' = —H, —CH₃

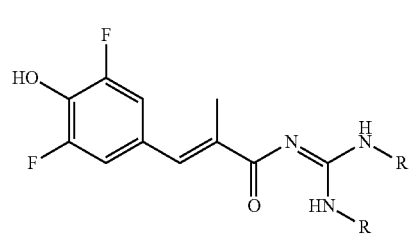

wherein the variables in the above-noted structures (e.g., R, etc.) are as defined in U.S. Pat. No. 6,399,824, the entire contents of which are incorporated herein by reference for all relevant and consistent purposes.

Scheme 2

Tetrahydroisoquinoline NHE-binding Moiety Functionalized to Display Electrophilic or Nucleophilic Groups to Facilitate Reaction with Cores and Linkders

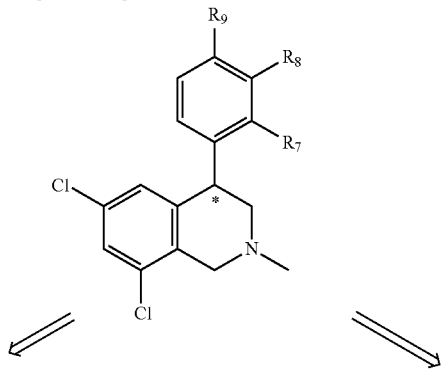

Nucleophilic Intermediates:
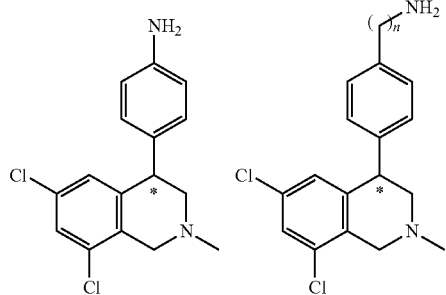
-continued
Electrophilic Intermediates:
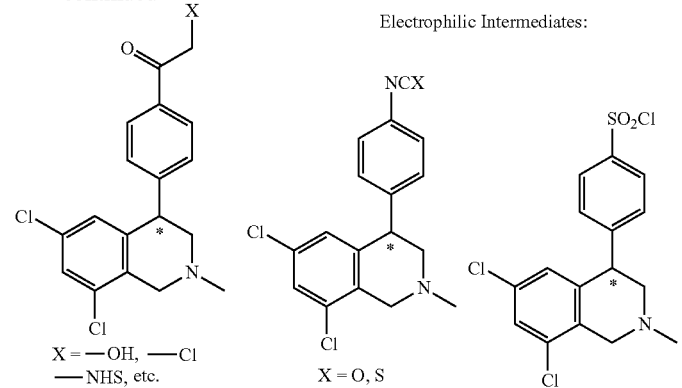
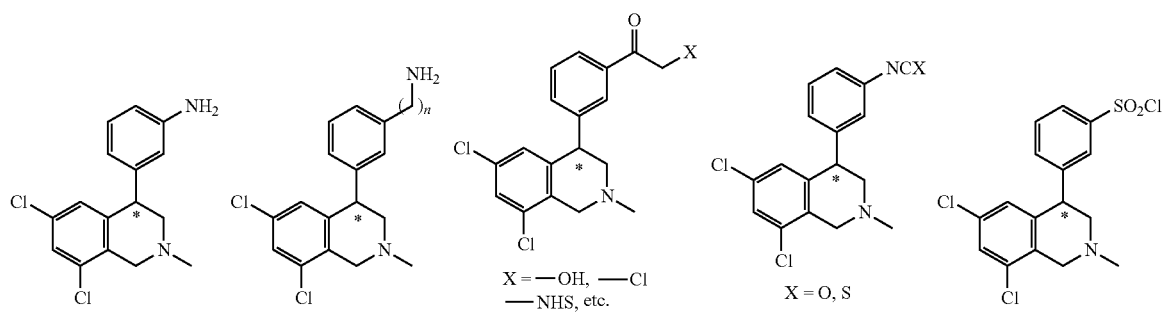
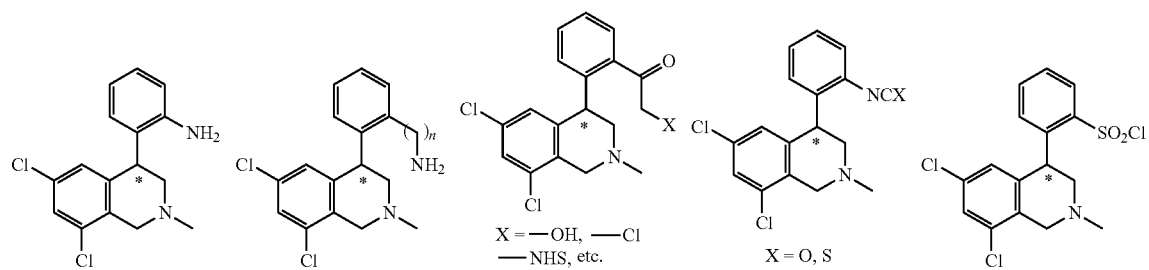
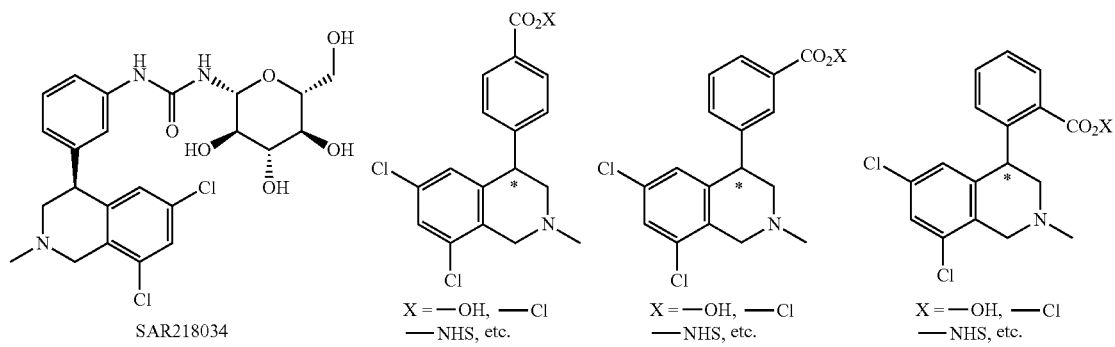
wherein the variables in the above-noted structures (e.g., $R_{7-9}$, etc.) are as defined in U.S. Pat. No. 6,911,453, the entire contents of which (and in particular the text of columns 1-4 therein) are incorporated herein by reference for all relevant and consistent purposes. See also Linz et al., *Hypertension*. 60:1560-7, 2012.

Scheme 3

Quinazoline NHE-binding Moiety Functionalized to Display
Electrophilic or Nucleophilic Groups to Facilitate Reaction with Cores and Linkers

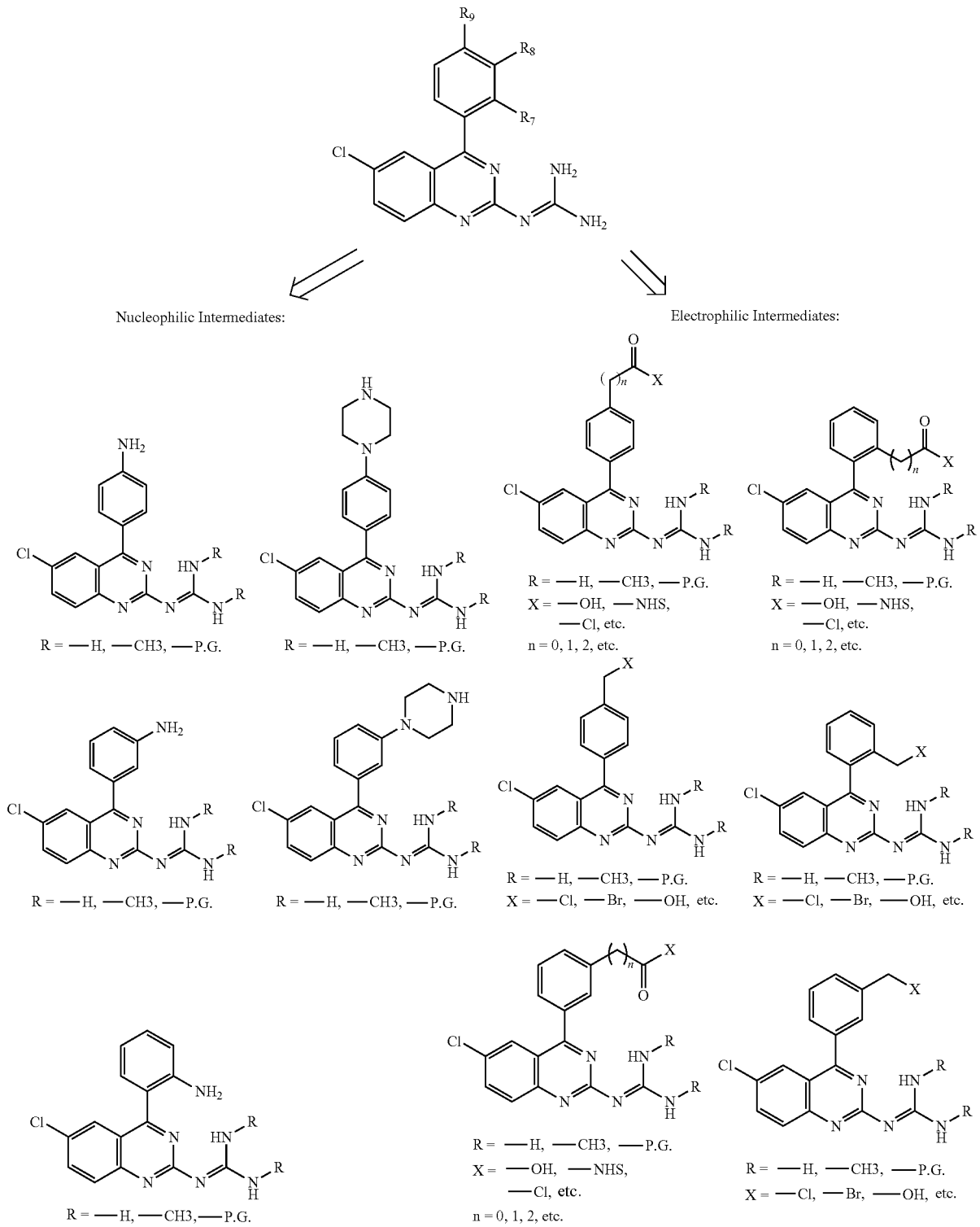

wherein the variables in the above-noted structures (e.g., $R_{7-9}$, etc.) are as defined in U.S. Patent Application No. 2005/0020612 and U.S. Pat. No. 6,911,453, the entire contents of which (and in particular the text of columns 1-4 therein) are incorporated herein by reference for all relevant and consistent purposes.

It is to be noted that one skilled in the art can envision a number of core or linker moieties that may be functionalized with an appropriate electrophile or nucleophile. Shown below are a series of such compounds selected based on several design considerations, including solubility, steric effects, and their ability to confer, or be consistent with, favorable structure-activity relationships. In this regard it is to be further noted, however, that the structures provided below, and above, are for illustration purposes only, and therefore should not be viewed in a limiting sense.

Exemplary electrophilic and nucleophilic linker moieties include, but are not limited to, the linker moieties illustrated by the following:

Nucleophilic Linkers (for Use with Electrophilic NHE-Inhibitory Derivatives)

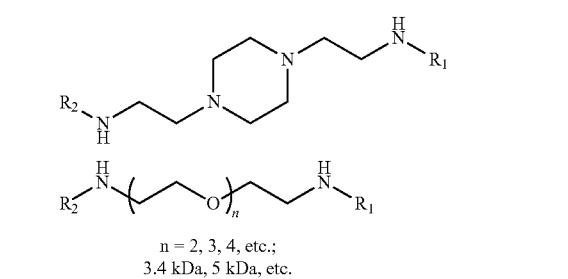

n = 2, 3, 4, etc.;
3.4 kDa, 5 kDa, etc.

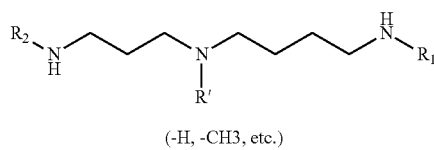

(-H, -CH3, etc.)

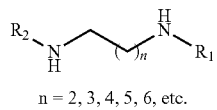

n = 2, 3, 4, 5, 6, etc.

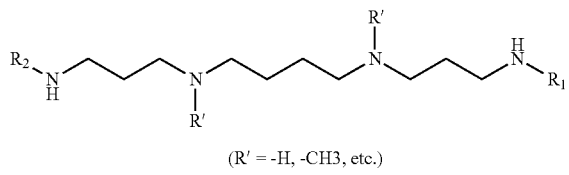

(R' = -H, -CH3, etc.)

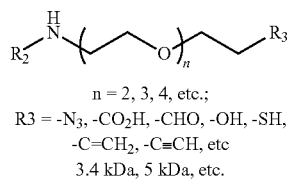

n = 2, 3, 4, etc.;
R3 = -N$_3$, -CO$_2$H, -CHO, -OH, -SH,
-C=CH$_2$, -C≡CH, etc
3.4 kDa, 5 kDa, etc.

Electrophilic Linkers (for Use with Nucleophilic NHE-Inhibitory Derivatives)

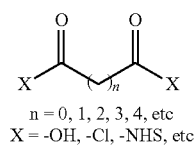

n = 0, 1, 2, 3, 4, etc
X = -OH, -Cl, -NHS, etc

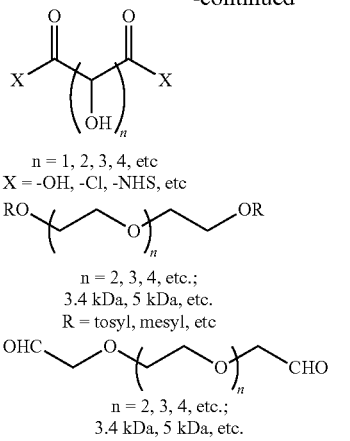

n = 1, 2, 3, 4, etc
X = -OH, -Cl, -NHS, etc n = 2, 3, 4, etc.;
3.4 kDa, 5 kDa, etc.
R = tosyl, mesyl, etc n = 2, 3, 4, etc.;
3.4 kDa, 5 kDa, etc.
R = tosyl, mesyl, etc

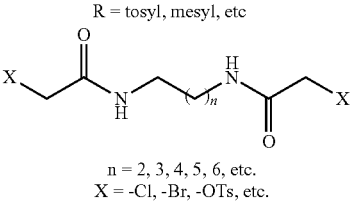

n = 2, 3, 4, 5, 6, etc.
X = -Cl, -Br, -OTs, etc.

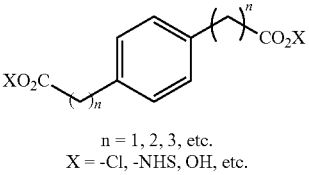

n = 1, 2, 3, etc.
X = -Cl, -NHS, OH, etc.

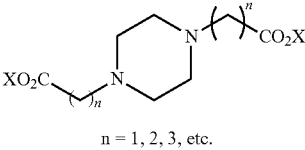

n = 1, 2, 3, etc.
X = -Cl, -NHS, OH, etc.

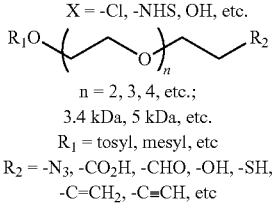

n = 2, 3, 4, etc.;
3.4 kDa, 5 kDa, etc.
R$_1$ = tosyl, mesyl, etc
R$_2$ = -N$_3$, -CO$_2$H, -CHO, -OH, -SH,
-C=CH$_2$, -C≡CH, etc The linking moiety, L, in each of the described embodiments (including embodiments in which a NHE-binding small molecule is linked to a core such as an atom, another small molecule, a polymer moiety, an oligomer moiety, or a non-repeating moiety) can be a chemical linker, such as a bond or other moiety, for example, comprising about 1 to about 200 atoms, or about 1 to about 100 atoms, or about 1 to about 50 atoms, that can be hydrophilic and/or hydrophobic. In one embodiment, the linking moiety can be a polymer moiety grafted onto a polymer backbone, for example, using living free radical polymerization approaches known in the art. Preferred L structures or moieties may also be selected from, for example, oligoethylene glycol, oligopeptide, oligoethyleneimine, oligotetramethylene glycol and oligocaprolactone.

As noted, the core moiety can be an atom, a small molecule, an oligomer, a dendrimer or a polymer moiety, in each case having one or more sites of attachment for L. For example, the core moiety can be a non-repeating moiety (considered as a whole including linking points to the compounds), selected for example from the group consisting of alkyl, phenyl, aryl, alkenyl, alkynyl, heterocyclic, amine, ether, sulfide, disulfide, hydrazine, and any of the foregoing substituted with oxygen, sulfur, sulfonyl, phosphonyl, hydroxyl, alkoxyl, amine, thiol, ether, carbonyl, carboxyl, ester, amide, alkyl, alkenyl, alkynyl, aryl, heterocyclic, and moieties comprising combinations thereof (in each permutation). A non-repeating moiety can include repeating units (e.g., methylene) within portions or segments thereof (e.g., within an alkyl segment), without having discrete repeat units that constitute the moiety as a whole (e.g., in the sense of a polymer or oligomer).

Exemplary core moieties include but are not limited to the core moieties illustrated in the Examples and ether moieties, ester moieties, sulfide moieties, disulfide moieties, amine moieties, aryl moieties, alkoxyl moieties, etc., such as, for example, the following:

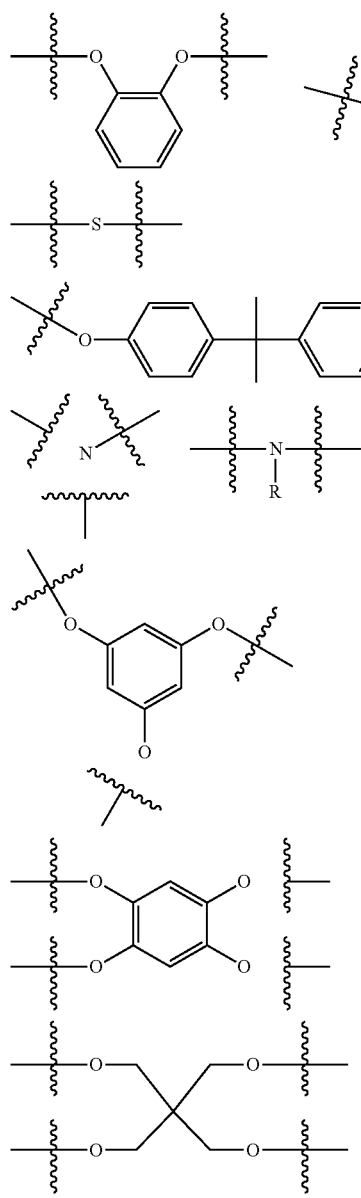

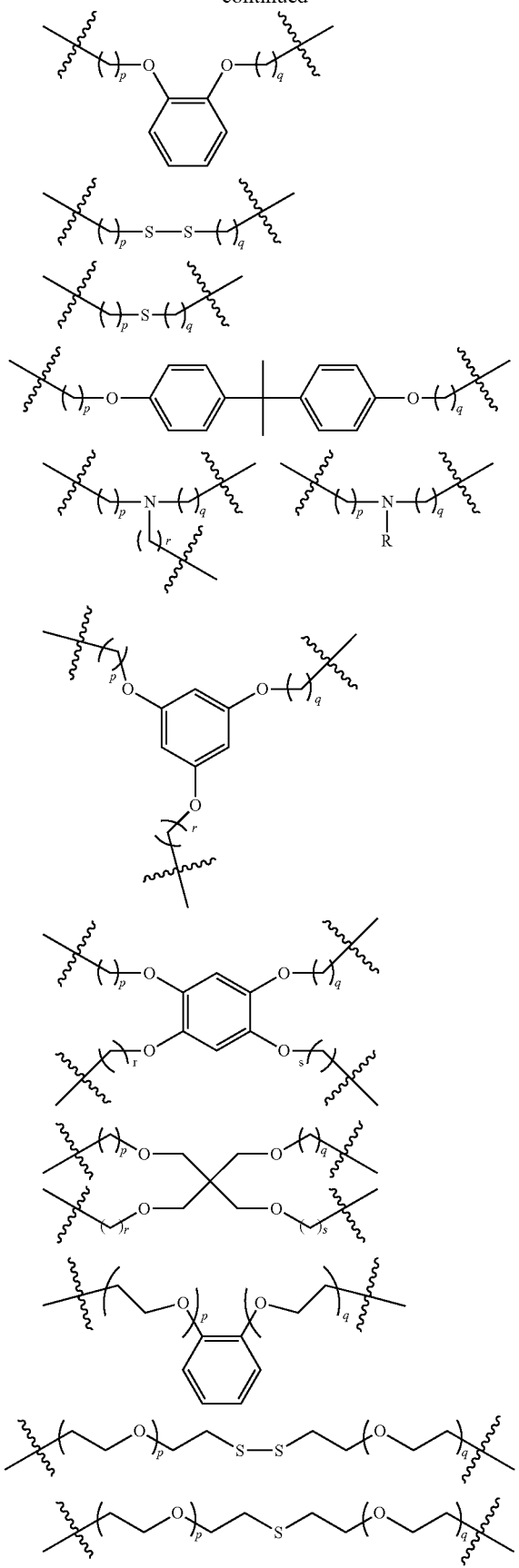

81
-continued
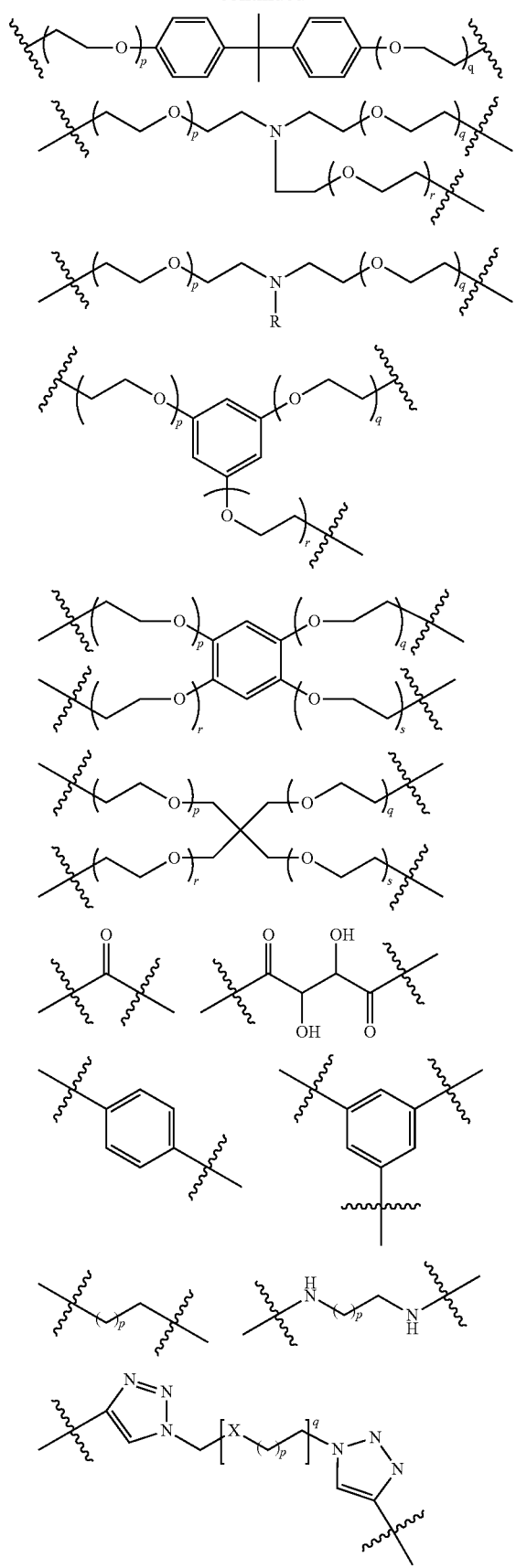
82
-continued
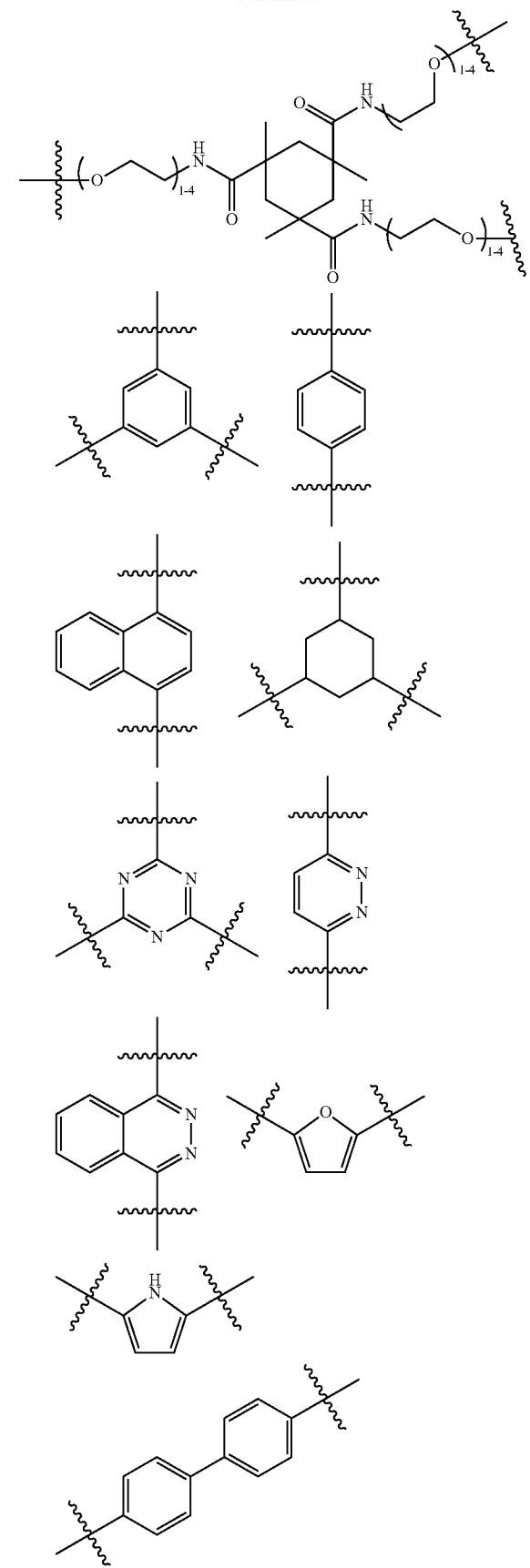

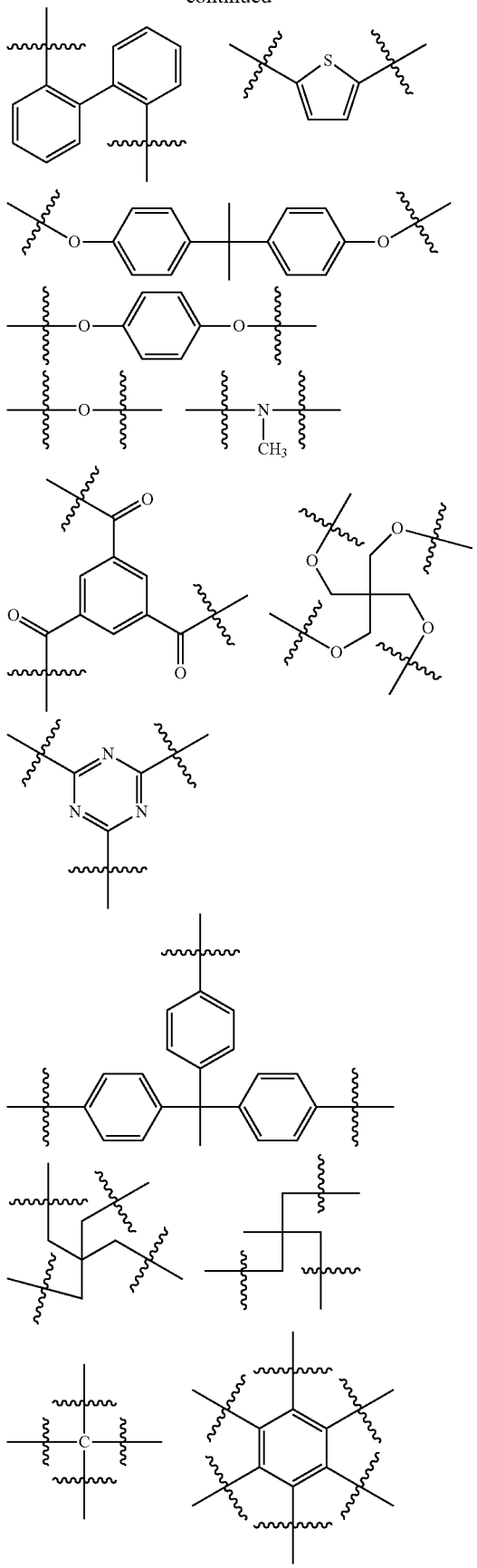
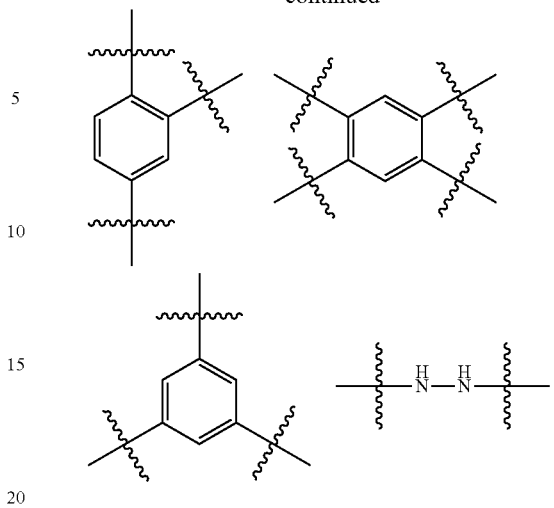

wherein the broken bonds (i.e., those having a wavy bond, $\xi$, through them) are points of connection to either an NHE binding compound or a linker moiety displaying an NHE binding compound, where said points of connection can be made using chemistries and functional groups known to the art of medicinal chemistry; and further wherein each p, q, r and s is an independently selected integer ranging from about 0 to about 48, preferably from about 0 to about 36, or from about 0 to about 24, or from about 0 to about 16. In some instances, each p, q, r and s can be an independently selected integer ranging from about 0 to 12. Additionally, R can be a substituent moiety generally selected from halide, hydroxyl, amine, thiol, ether, carbonyl, carboxyl, ester, amide, carbocyclic, heterocyclic, and moieties comprising combinations thereof.

In another approach, the core moiety is a dendrimer, defined as a repeatedly branched molecule (see, e.g., J. M. J. Fréchet, D. A. Tomalia, *Dendrimers and Other Dendritic Polymers*, John Wiley & Sons, Ltd. NY, N.Y., 2001) and represented in FIG. 17.

In this approach, the NHE-binding small molecule is attached through L to one, several or optionally all termini located at the periphery of the dendrimer. In another approach, a dendrimer building block named dendron, and illustrated above, is used as a core, wherein the NHE binding group is attached to one, several or optionally all termini located at the periphery of the dendron. The number of generations herein is typically between about 0 and about 6, and preferably between about 0 and about 3. (Generation is defined in, for example, J. M. J. Fréchet, D. A. Tomalia, *Dendrimers and Other Dendritic Polymers*, John Wiley & Sons, Ltd. NY, N.Y.) Dendrimer and/or dendron structures are well known in the art and include, for example, those shown in or illustrated by: (i) J. M. J. Fréchet, D. A. Tomalia, *Dendrimers and Other Dendritic Polymers*, John Wiley & Sons, Ltd. NY, N.Y.; (ii) George R Newkome, Charles N. Moorefield and Fritz Vogtle, *Dendrimers and Dendrons: Concepts, Syntheses, Applications*, VCH Verlagsgesellschaft Mbh; and, (iii) Boas, U., Christensen, J. B., Heegaard, P. M. H., *Dendrimers in Medicine and Biotechnology: New Molecular Tools*, Springer, 2006.

In yet another approach, the core moiety may be a polymer moiety or an oligomer moiety. The polymer or oligomer may, in each case, be independently considered and comprise repeat units consisting of a repeat moiety selected from alkyl (e.g., —CH$_2$—), substituted alkyl (e.g., —CHR—, wherein, for example, R is hydroxy), alkenyl, substituted alkenyl, alkynyl, substituted alkynyl, phenyl, aryl, heterocyclic, amine, ether, sulfide, disulfide, hydrazine, and any of the foregoing substituted with oxygen, sulfur, sulfonyl, phosphonyl, hydroxyl, alkoxyl, amine, thiol, ether, carbonyl, carboxyl, ester, amide, alkyl, alkenyl, alkynyl, aryl, heterocyclic, as well as moieties comprising combinations thereof. In still another approach, the core moiety comprises repeat units resulting from the polymerization of ethylenic monomers (e.g., such as those ethylenic monomers listed elsewhere herein below).

Preferred polymers for polymeric moieties useful in constructing substantially impermeable or substantially systemically non-bioavailable NHE-binding compounds that are multivalent, for use in the treatment various treatment methods disclosed herein, can be prepared by any suitable technique, such as by free radical polymerization, condensation polymerization, addition polymerization, ring-opening polymerization, and/or can be derived from naturally occurring polymers, such as saccharide polymers. Further, in some embodiments, any of these polymer moieties may be functionalized.

Examples of polysaccharides useful in preparation of such compounds include but are not limited to materials from vegetable or animal origin, including cellulose materials, hemicellulose, alkyl cellulose, hydroxyalkyl cellulose, carboxymethylcellulose, sulfoethylcellulose, starch, xylan, amylopectine, chondroitin, hyarulonate, heparin, guar, xanthan, mannan, galactomannan, chitin, and/or chitosan. More preferred, in at least some instances, are polymer moieties that do not degrade, or that do not degrade significantly, under the physiological conditions of the GI tract (such as, for example, carboxymethylcellulose, chitosan, and sulfoethylcellulose).

When free radical polymerization is used, the polymer moiety can be prepared from various classes of monomers including, for example, acrylic, methacrylic, styrenic, vinylic, and dienic, whose typical examples are given thereafter: styrene, substituted styrene, alkyl acrylate, substituted alkyl acrylate, alkyl methacrylate, substituted alkyl methacrylate, acrylonitrile, methacrylonitrile, acrylamide, methacrylamide, N-alkylacrylamide, N-alkylmethacrylamide, N,N-dialkylacrylamide, N,N-dialkylmethacrylamide, isoprene, butadiene, ethylene, vinyl acetate, and combinations thereof. Functionalized versions of these monomers may also be used and any of these monomers may be used with other monomers as co-monomers. For example, specific monomers or co-monomers that may be used in this disclosure include methyl methacrylate, ethyl methacrylate, propyl methacrylate (all isomers), butyl methacrylate (all isomers), 2-ethylhexyl methacrylate, isobomyl methacrylate, methacrylic acid, benzyl methacrylate, phenyl methacrylate, methacrylonitrile, α-methylstyrene, methyl acrylate, ethyl acrylate, propyl acrylate (all isomers), butyl acrylate (all isomers), 2-ethylhexyl acrylate, isobomyl acrylate, acrylic acid, benzyl acrylate, phenyl acrylate, acrylonitrile, styrene, glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N-n-butylmethacrylamide, N-methylolmethacrylamide, N-ethylolmethacrylamide, N-tert-butylacrylamide, N—N-butylacrylamide, N-methylolacrylamide, N-ethylolacrylamide, 4-acryloylmorpholine, vinyl benzoic acid (all isomers), diethylaminostyrene (all isomers), a-methylvinyl benzoic acid (all isomers), diethylamino α-methylstyrene (all isomers), p-vinylbenzene sulfonic acid, p-vinylbenzene sulfonic sodium salt, alkoxy and alkyl silane functional monomers, maleic anhydride, N-phenylmaleimide, N-butylmaleimide, butadiene, isoprene, chloroprene, ethylene, vinyl acetate, vinylformamide, allylamine, vinylpyridines (all isomers), fluorinated acrylate, methacrylates, and combinations thereof. Main chain heteroatom polymer moieties can also be used, including polyethyleneimine and polyethers such as polyethylene oxide and polypropylene oxide, as well as copolymers thereof.

In one particular embodiment, the polymer to which the NHE-binding small molecule, NHE, is attached or otherwise a part of is a polyol (e.g., a polymer having a repeat unit of, for example, a hydroxyl-substituted alkyl, such as —CH(OH)—). Polyols, such as mono- and disaccharides, with or without reducing or reducible end groups thereon, may be good candidates, for example, for installing additional functionality that could render the compound substantially impermeable.

In one particular embodiment, the NHE-binding small molecule, NHE, is attached at one or both ends of the polymer chain. More specifically, in yet another alternative approach to the polyvalent embodiment of the present disclosure, a macromolecule (e.g., a polymer or oligomer) having one of the following exemplary structures may be designed and constructed as described herein:

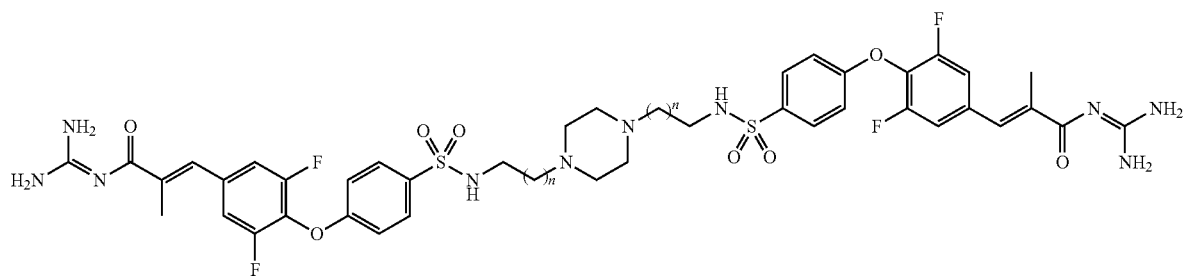

n = 1, 2, 3-10, or more

-continued
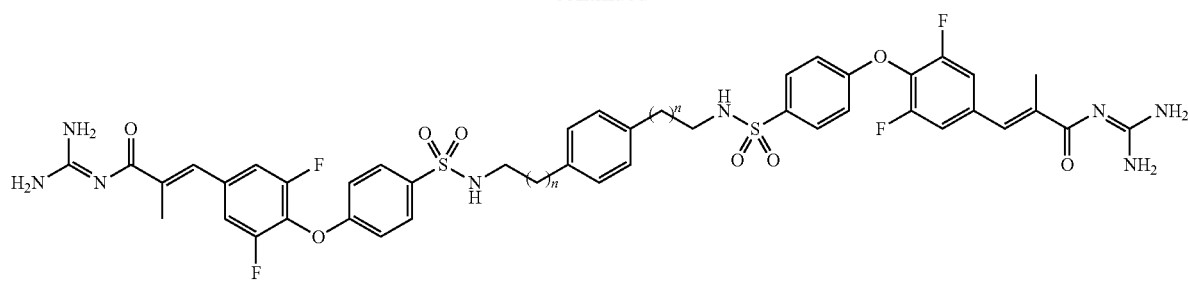
n = 0, 1, 2, 3-10, or more
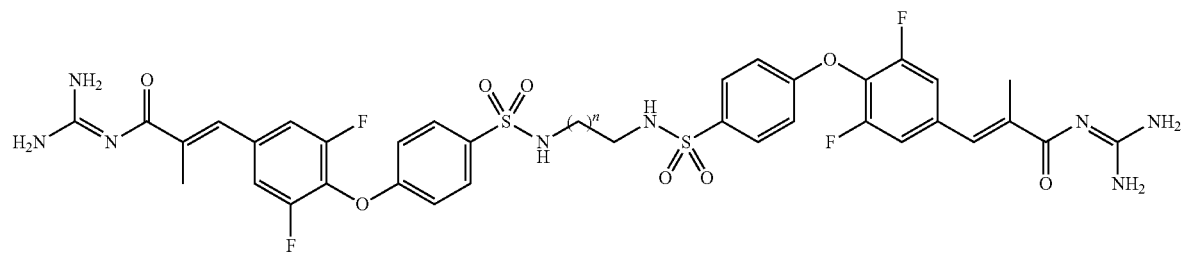
n = 1, 2, 3-10, or more
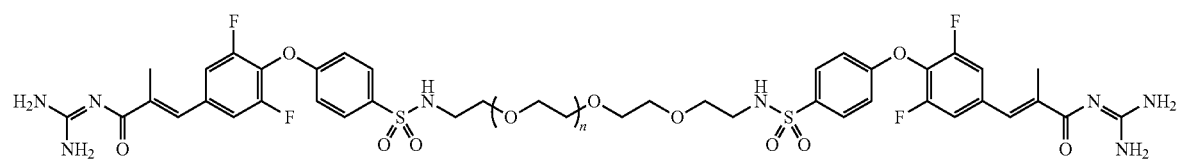
n = 0, 1, 2, 3-10, or more
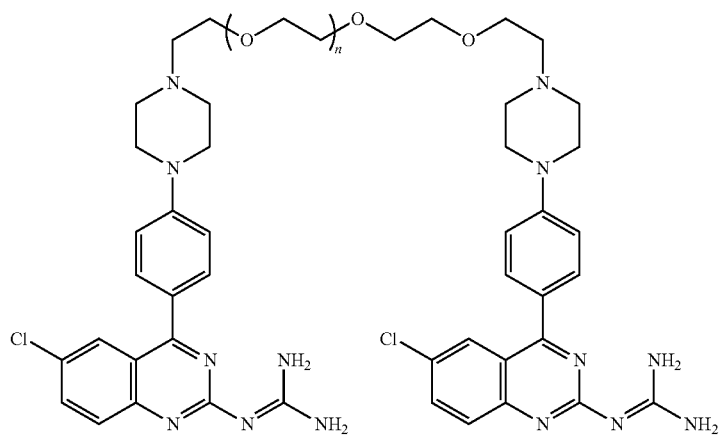
n = 0, 1, 2, 3-10, or more
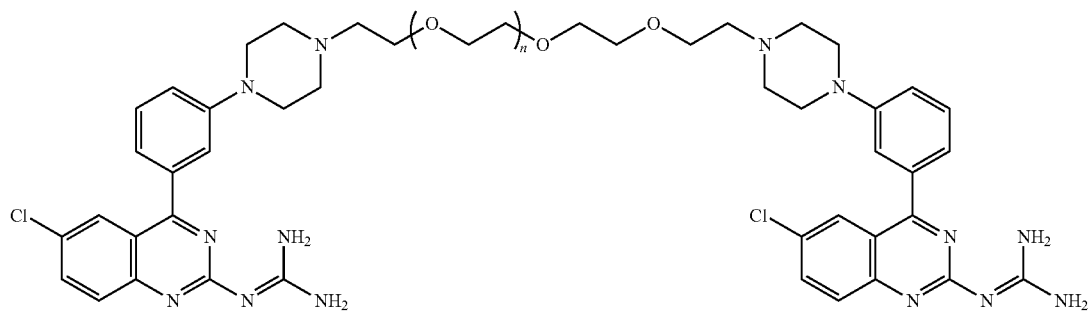
n = 0, 1, 2, 3-10, or more -continued
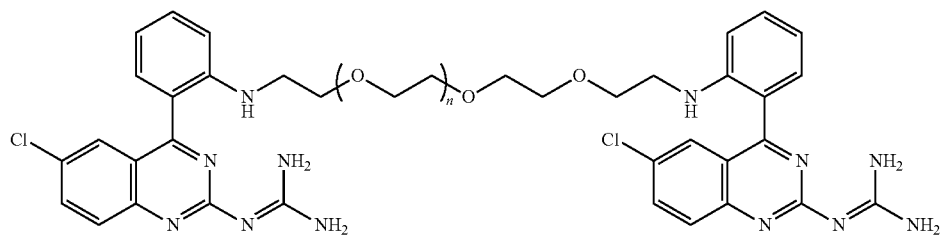
n = 0, 1, 2, 3-10, or more
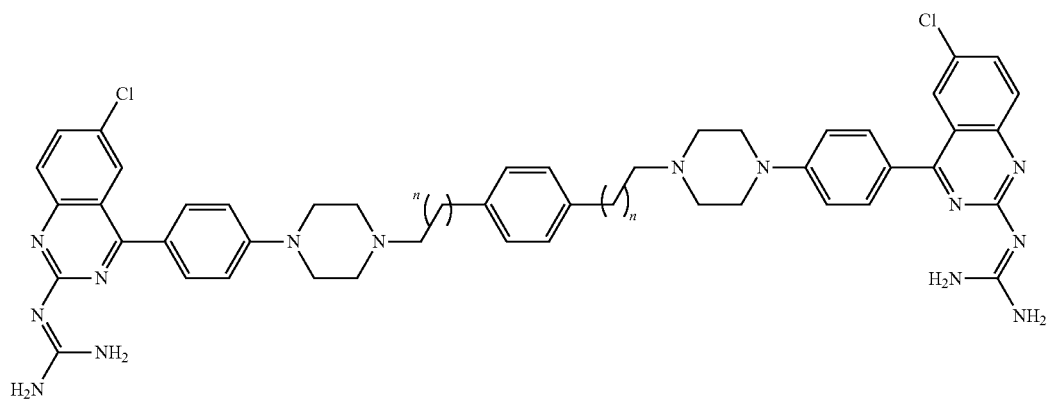
n = 0, 1, 2, 3-10, or more
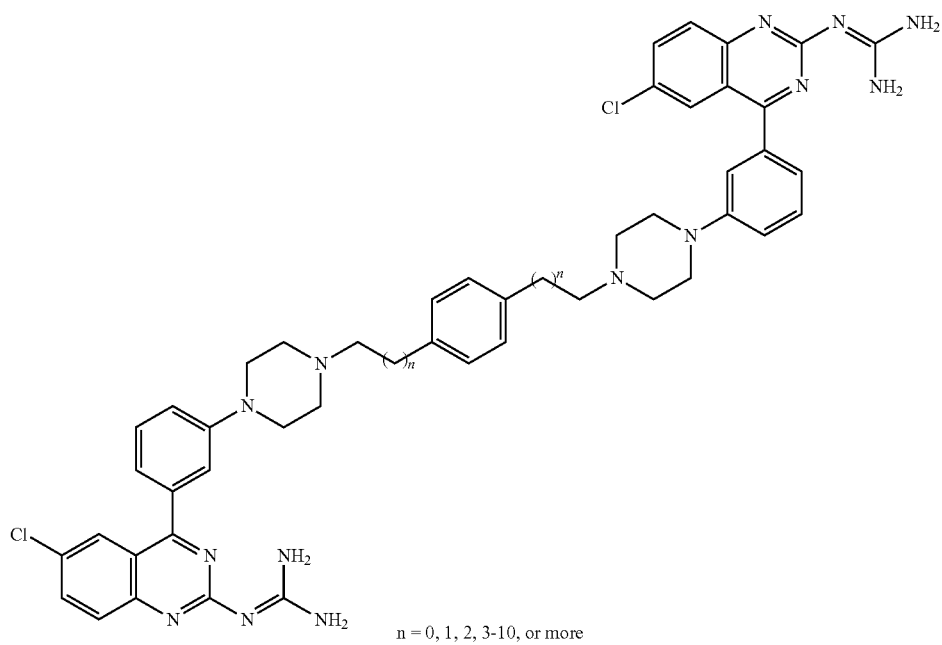
n = 0, 1, 2, 3-10, or more -continued
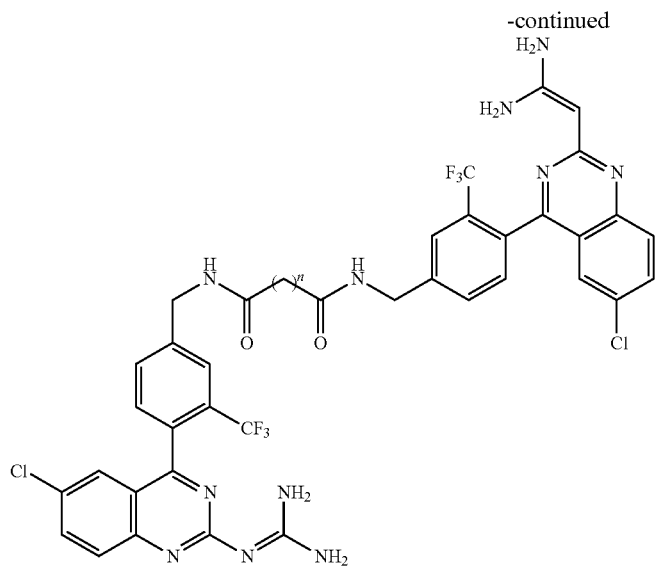
n = 0, 1, 2, 3-10, or more
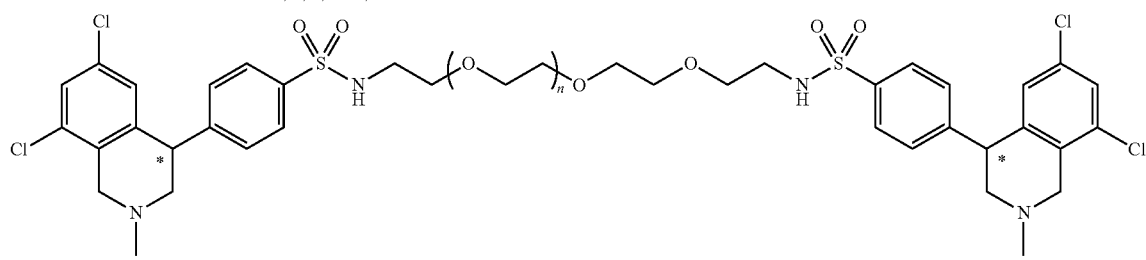
n = 0, 1, 2, 3, 4-10, or more
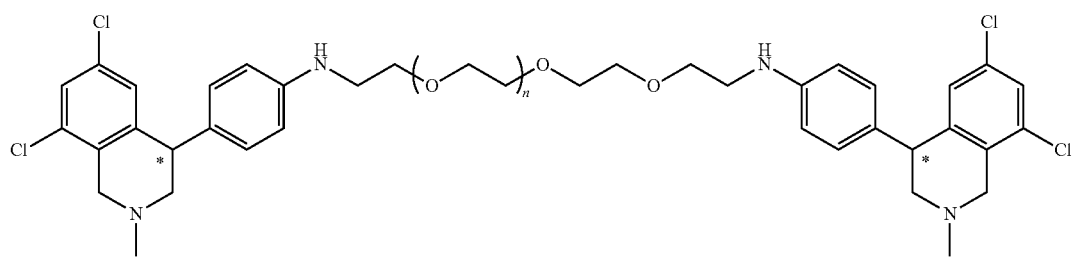
n = 0, 1, 2, 3, 4-10, or more
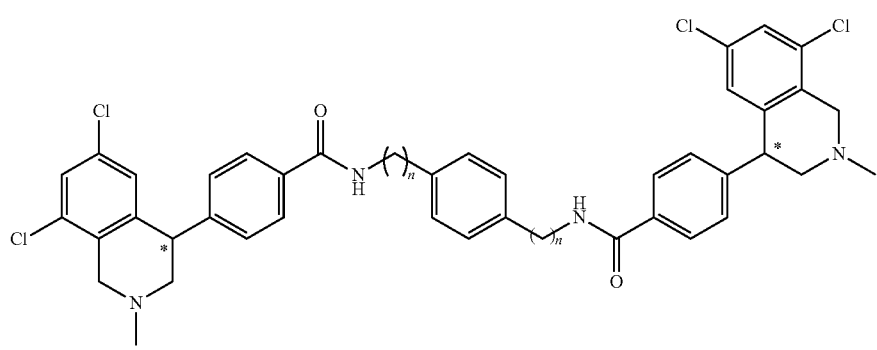
n = 0, 1, 2, 3, 4-10, or more -continued
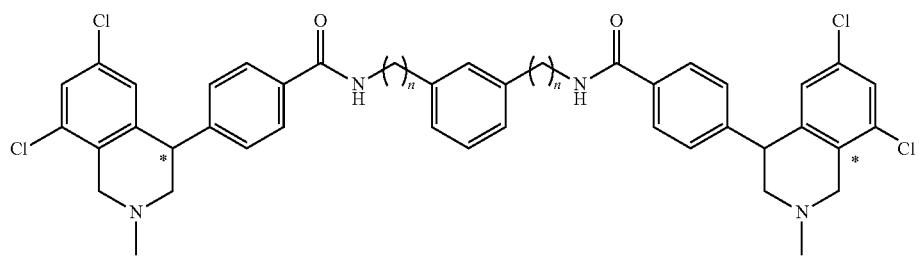
n = 0, 1, 2, 3, 4-10, or more
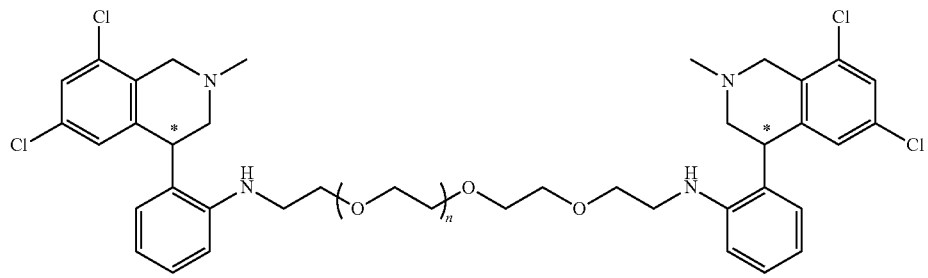
n = 0, 1, 2, 3, 4-10, or more
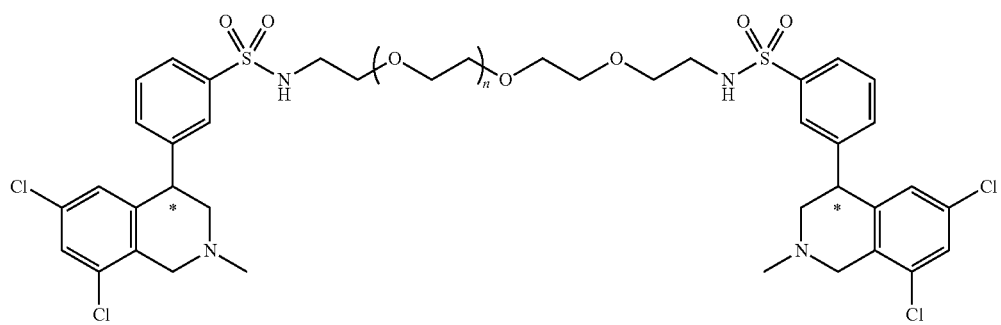
n = 0, 1, 2, 3, 4-10, or more
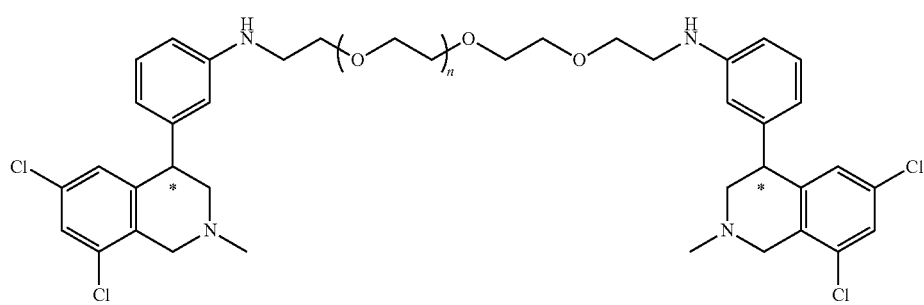
n = 0, 1, 2, 3, 4-10, or more
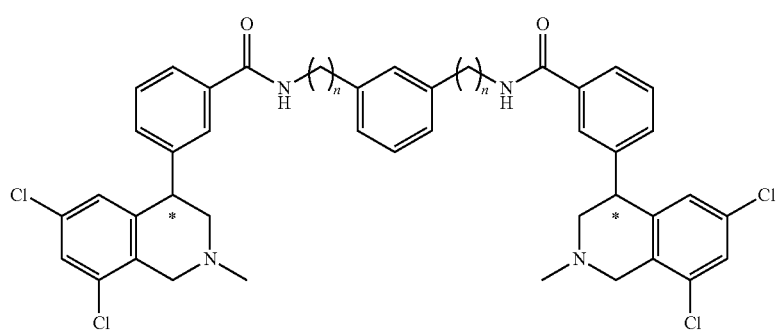
n = 0, 1, 2, 3, 4-10, or more

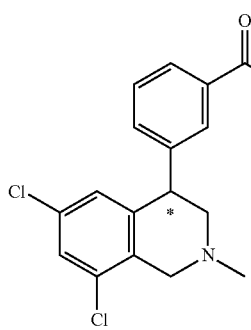
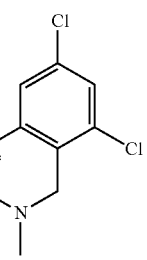

n = 0, 1, 2, 3, 4-10, or more

It is to be further noted that the repeat moiety in Formulas (XIIA) or (XIIB) generally encompasses repeating units of polymers and copolymers produced by methods referred to herein above.

It is to be noted that the various properties of the oligomers and polymers that form the core moiety as disclosed herein above may be optimized for a given use or application using experimental means and principles generally known in the art. For example, the overall molecular weight of the compounds or structures presented herein above may be selected so as to achieve non-absorbability, inhibition persistence and/or potency.

Additionally, with respect to those polymeric embodiments that encompass or include the compounds generally represented by the structure of Formula (I) herein, and/or those disclosed for example in the many patents and patent applications cited herein (see, e.g., U.S. Pat. No. 5,866,610; 6,399,824; 6,911,453; 6,703,405; 6,005,010; 6,887,870; 6,737,423; 7,326,705; 5,582,4691 (WO94/026709); U.S. Pat. No. 6,399,824 (WO02/024637); US 2004/0339001 (WO02/020496); US 2005/0020612 (WO03/055490); WO01/072742; CA 2387529 (WO01021582); CA 02241531 (WO97/024113); US 2005/0113396 (WO03/051866); US2005/0020612; US2005/0054705; US2008/0194621; US2007/0225323; US2004/0039001; US2004/0224965; US2005/0113396; US2007/0135383; US2007/0135385; US2005/0244367; US2007/0270414; and CA 2177007 (EP0744397), the entire contents of which are incorporated herein by reference for all relevant and consistent purposes), such as those wherein these compounds or structures are pendants off of a polymeric backbone or chain, the composition of the polymeric backbone or chain, as well as the overall size or molecular weight of the polymer, and/or the number of pendant molecules present thereon, may be selected according to various principles known in the art in view of the intended application or use.

With respect to the polymer composition of the NHE-binding compound, it is to be noted that a number of polymers can be used including, for example, synthetic and/or naturally occurring aliphatic, alicyclic, and/or aromatic polymers. In preferred embodiments, the polymer moiety is stable under physiological conditions of the GI tract. By "stable" it is meant that the polymer moiety does not degrade or does not degrade significantly or essentially does not degrade under the physiological conditions of the GI tract. For instance, at least about 90%, preferably at least about 95%, more preferably at least about 98%, and even more preferably at least about 99% of the polymer moiety remains un-degraded or intact after at least about 5 hours, at least about 12 hours, at least about 18 hours, at least about 24 hours, or at least about 48 hours of residence in a gastrointestinal tract. Stability in a gastrointestinal tract can be evaluated using gastrointestinal mimics, e.g., gastric mimics or intestinal mimics of the small intestine, which approximately model the physiological conditions at one or more locations therein.

Polymer moieties detailed herein for use as the core moiety can be hydrophobic, hydrophilic, amphiphilic, uncharged or non-ionic, negatively or positively charged, or a combination thereof. Additionally, the polymer architecture of the polymer moiety can be linear, grafted, comb, block, star and/or dendritic, preferably selected to produce desired solubility and/or stability characteristics as described above.

Additionally or alternatively, modifications may be made to NHE-binding small molecules that increase tPSA, thus contributing to the impermeability of the resulting compounds. Such modifications preferably include addition of di-anions, such as phosphonates, malonates, sulfonates and the like, and polyols such as carbohydrates and the like. Exemplary derivatives of NHEs with increased tPSA include but are not limited to the following:

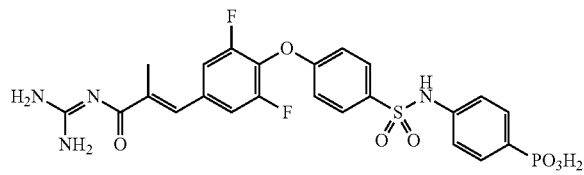

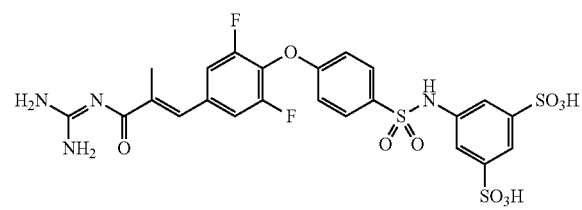

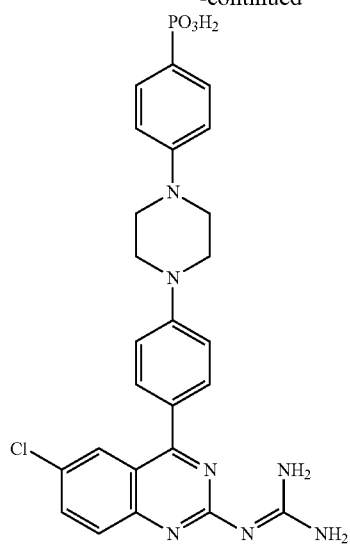
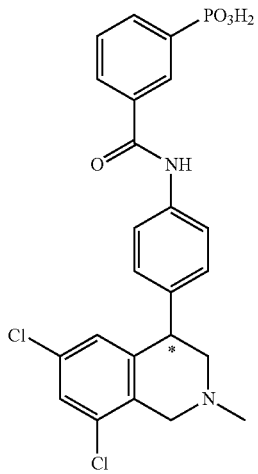
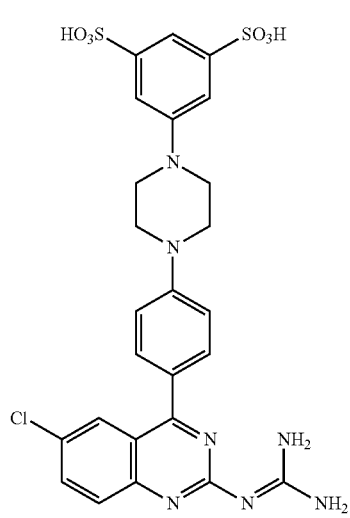
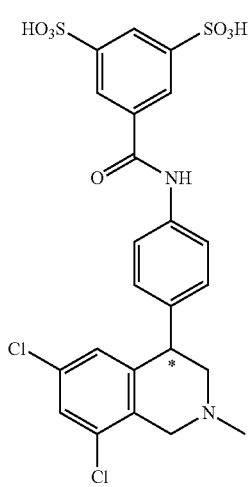
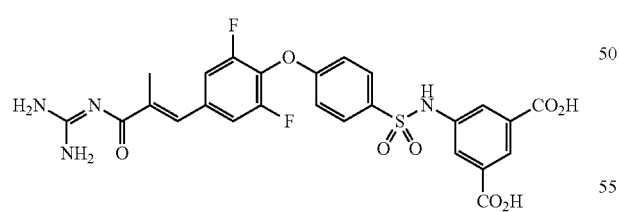
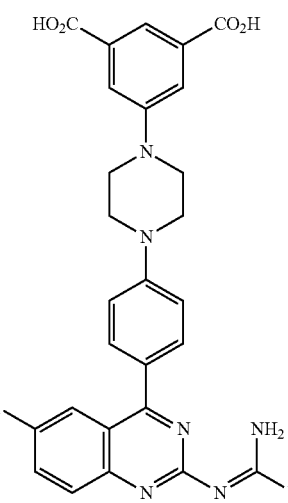

-continued

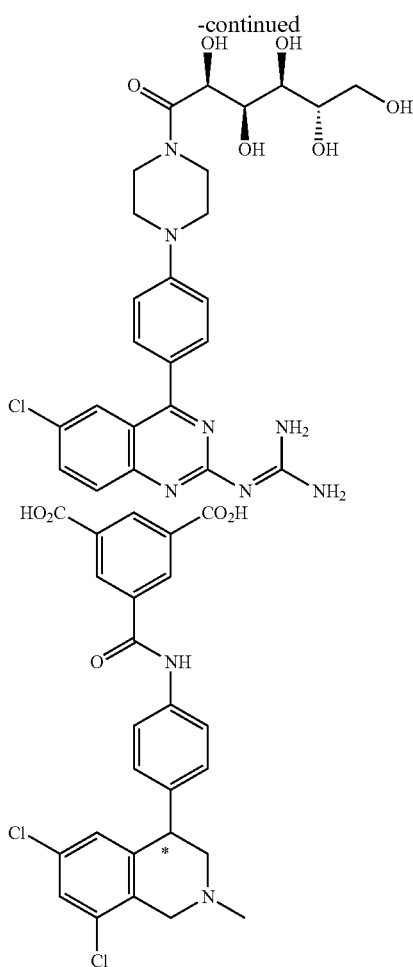

(ii). Exemplary Embodiments

In one or more particularly preferred embodiments of the present disclosure, the "NHE-Z" molecule is polyvalent; that is, the molecule contains two or more moieties that effectively acts to bind to and/or modulate NHE3 and also inhibit phosphate transport in the GI tract or kidneys. In such embodiments, the NHE-Z molecule may be selected, for example, from one of the following Formulas (IV), (V), (VI) or (VII):

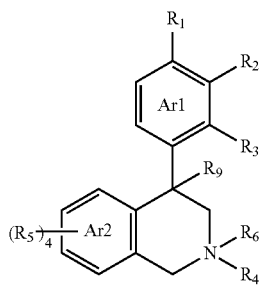
(IV)

wherein: each $R_1$, $R_2$, $R_3$, $R_5$ and $R_9$ are independently selected from H, halogen, —$NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H or L, provided at least one is L, wherein L is selected from the group consisting of substituted or unsubstituted hydrocarbyl, heterohydrocarbyl, polyalkylene glycol and polyols, and further wherein L links the repeat unit to at least one other repeat unit and/or at least one other Core moiety independently selected from substituted or unsubstituted hydrocarbyl, heterohydrocarbyl, polyalkylene glycol, polyols, polyamines, or polyacrylamides, of the polyvalent compound; $R_4$ is selected from H, $C_1$-$C_7$ alkyl or L, where L is as described above; $R_6$ is absent or selected from H and $C_1$-$C_7$ alkyl; and, Ar1 and Ar2 independently represent an aromatic ring, or alternatively a heteroaromatic ring wherein one or more of the carbon atoms therein is replaced with a N, O or S atom;

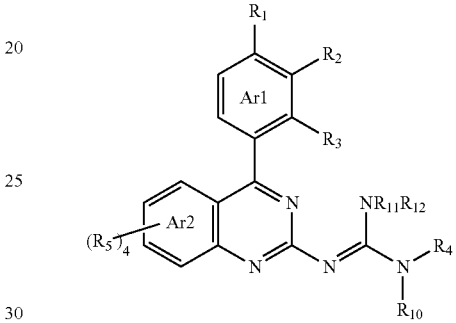
(V)

wherein: each $R_1$, $R_2$, $R_3$, and $R_5$ are optionally linked to the ring Ar1 by a heterocyclic linker, and further are independently selected from H, —$NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H or L, provided at least one is L, wherein L is selected from the group consisting of substituted or unsubstituted hydrocarbyl, heterohydrocarbyl, polyalkylene glycol and polyols, and further wherein L links the repeat unit to at least one other repeat unit and/or at least one other Core moiety independently selected from substituted or unsubstituted hydrocarbyl, heterohydrocarbyl, polyalkylene glycol, polyols, polyamines, or polyacrylamides, of the polyvalent compound; $R_4$ and $R_{12}$ are independently selected from H or L, where L is as defined above; $R_{10}$ and $R_{11}$, when presented, are independently selected from H and $C_1$-$C_7$ alkyl; and, Ar1 and Ar2 independently represent an aromatic ring, or alternatively a heteroaromatic ring wherein one or more of the carbon atoms therein is replaced with a N, O or S atom;

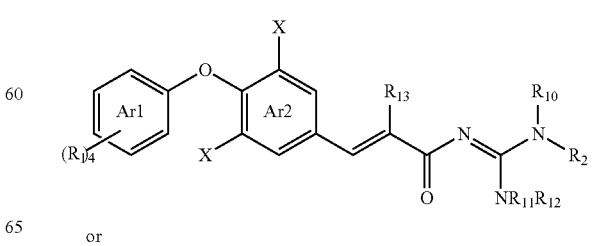
(VI)

or

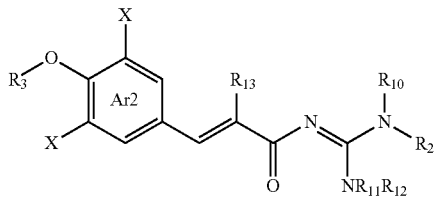

(VII)

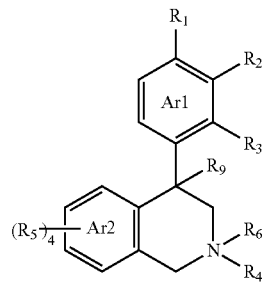

(IV)

wherein: each X is a halogen atom, which may be the same or different; $R_1$ is selected from —$SO_2$—$NR_7R_8$, —$NR_7(CO)R_8$, —$(CO)NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H or L, provided at least one is L, wherein L is selected from the group consisting of substituted or unsubstituted hydrocarbyl, heterohydrocarbyl, polyalkylene glycol and polyols, and further wherein L links the repeat unit to at least one other repeat unit and/or at least one other Core moiety independently selected from substituted or unsubstituted hydrocarbyl, heterohydrocarbyl, polyalkylene glycol, polyols, polyamines, or polyacrylamides, of the polyvalent compound; $R_3$ is selected from H or L, where L is as described above; $R_{13}$ is selected from substituted or unsubstituted $C_1$-$C_8$ alkyl; $R_2$ and $R_{12}$ are independently selected from H or L, wherein L is as described above; $R_{10}$ and $R_{11}$, when present, are independently selected from H and $C_1$-$C_7$ alkyl; Ar1 represents an aromatic ring, or alternatively a heteroaromatic ring wherein one or more of the carbon atoms therein is replaced with a N, O or S atom; and Ar2 represents an aromatic ring, or alternatively a heteroaromatic ring wherein one or more of the carbon atoms therein is replaced with a N, O or S atom.

In one particular embodiment for the structure of Formula (V), one of $R_1$, $R_2$ and $R_3$ is linked to the ring Ar1, and/or $R_5$ is linked to the ring Ar2, by a heterocyclic linker having the structure:

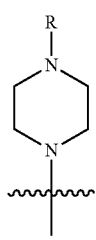

wherein R represents $R_1$, $R_2$, $R_3$, or $R_5$ bound thereto.

In one particular embodiment, the NHE-binding small molecule has the structure of Formula (IV):

or a stereoisomer, prodrug or pharmaceutically acceptable salt thereof, wherein: each $R_1$, $R_2$, $R_3$, $R_5$ and $R_9$ are independently selected from H, halogen, —$NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H or a bond linking the NHE-binding small molecule to L, provided at least one is a bond linking the NHE-binding small molecule to L; $R_4$ is selected from H, $C_1$-$C_7$ alkyl, or a bond linking the NHE-binding small molecule to L; $R_6$ is absent or selected from H and $C_1$-$C_7$ alkyl; and Ar1 and Ar2 independently represent an aromatic ring or a heteroaromatic ring.

In further particular embodiments of the above embodiment, the NHE-binding small molecule has the following structure:

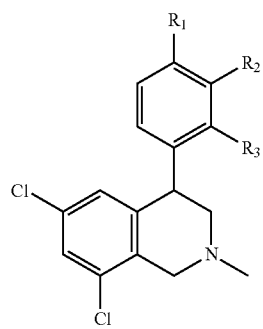

or a stereoisomer, prodrug or pharmaceutically acceptable salt thereof, wherein: each $R_1$, $R_2$ and $R_3$ are independently selected from H, halogen, —$NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H or a bond linking the NHE-binding small molecule to L, provided at least one is a bond linking the NHE-binding small molecule to L.

In one embodiment, the compound has the structure of Formula (X):

$$\text{Core} \text{-(-L-NHE)}_n \quad (X).$$

In further particular embodiments of the above embodiment, the NHE-binding small molecule has one of the following structures:

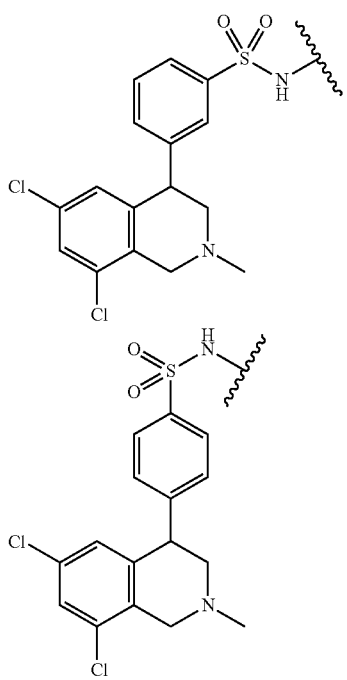

or a stereoisomer, prodrug or pharmaceutically acceptable salt thereof.

In further particular embodiments of the above embodiment, L is a polyalkylene glycol linker, such as a polyethylene glycol linker.

In further particular embodiments of the above embodiment, n is 2.

In further particular embodiments of the above embodiment, the Core has the following structure:

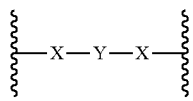

wherein: X is selected from the group consisting of a bond, —O—, —NH—, —S—, $C_{1-6}$alkylene, —NHC(=O)—, —C(=O)NH—, —NHC(=O)NH—, —SO$_2$NH—, and —NHSO$_2$—; Y is selected from the group consisting of a bond, optionally substituted $C_{1-8}$alkylene, optionally substituted aryl, optionally substituted heteroaryl, a polyethylene glycol linker, —(CH$_2$)$_{1-6}$O(CH$_2$)$_{1-6}$— and —(CH$_2$)$_{1-6}$NY$_1$(CH$_2$)$_{1-6}$—; and Y$_1$ is selected from the group consisting of hydrogen, optionally substituted $C_{1-8}$alkyl, optionally substituted aryl or optionally substituted heteroaryl.

In further particular embodiments of the above embodiment, the Core is selected from the group consisting of:

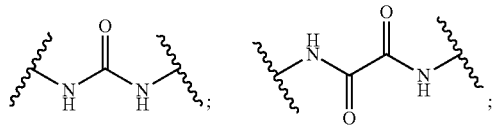

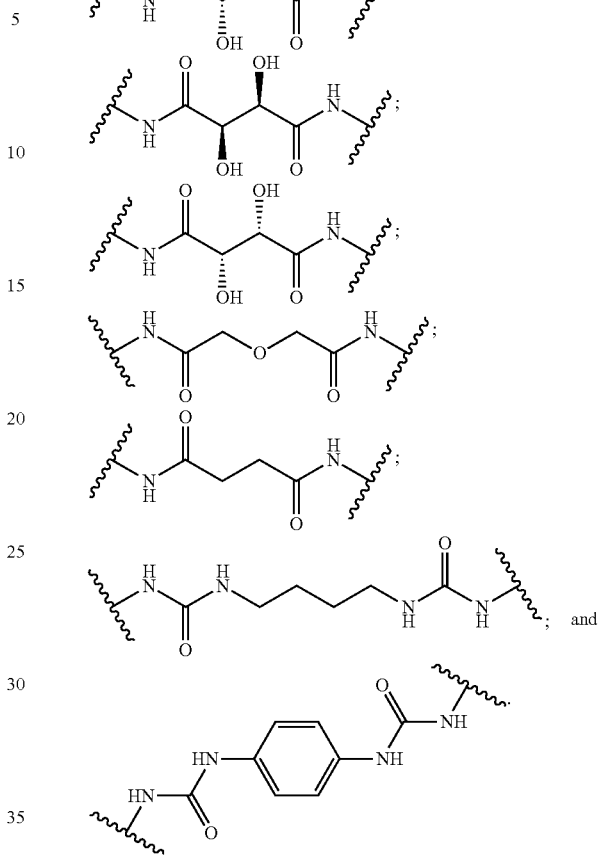

H. General Structure of Additional Exemplary Compounds

In one embodiment, the compounds of the present disclosure may be generally represented by Formula (I-H):

Core-(-L-NHE)      (I-H)

or a stereoisomer, prodrug or pharmaceutically acceptable salt thereof, wherein: (i) NHE represents a NHE-binding and/or modulating small molecule moiety as set forth below, (ii) n is an integer of 2 or more, (iii) Core is a Core moiety having two or more sites thereon for attachment to two or more NHE-binding small molecule moieties, and (iv) L is a bond or linker connecting the Core moiety to the two or more NHE-binding small molecule moieties, the resulting NHE-binding compound (i.e., a compound of Formula (I)) possessing overall physicochemical properties that render it substantially impermeable or substantially systemically non-bioavailable. The Core moiety may be bound to essentially any position on, or within, the NHE-binding small molecule moiety, provided that the installation thereof does not significantly adversely impact NHE-binding activity.

It is to be noted that, in the many structures illustrated herein, all of the various linkages or bonds will not be shown in every instance. For example, in one or more of the structures illustrated above, a bond or connection between the NHE-binding small molecule moiety and the Core moiety is not always shown. However, this should not be viewed in a limiting sense. Rather, it is to be understood that the NHE-binding small molecule moiety is bound or connected in some way (e.g., by a bond or linker of some kind) to the Core moiety, such that the resulting NHE-binding compound is suitable for use (i.e., substantially impermeable or substantially systemically non-bioavailable in the GI tract).

NHE-binding small molecule moieties suitable for use (i.e., suitable for modification or functionalization in accordance with the present disclosure) in the preparation of the substantially impermeable or substantially systemically non-bioavailable NHE-binding compounds of the present disclosure are disclosed in WO 2010/025856, the entire contents of which are incorporated herein by reference for all relevant and consistent purposes, and have the following structure of Formula (X-H):

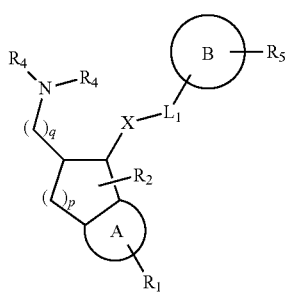

(X-H)

The variables in the structure are defined in WO 2010/025856, the details of which are incorporated herein by reference.

In more specific embodiments, the NHE-binding small molecule moiety has the following structure of Formula (XI-H):

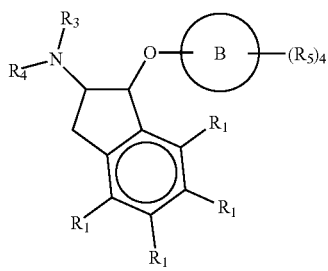

(XI-H)

wherein: B is selected from the group consisting of aryl and heterocyclyl; each $R_5$ is independently selected from the group consisting of hydrogen, halogen, optionally substituted $C_{1-4}$alkyl, optionally substituted $C_{1-4}$alkoxy, optionally substituted $C_{1-4}$thioalkyl, optionally substituted heterocyclyl, optionally substituted heterocyclylalkyl, optionally substituted aryl, optionally substituted heteroaryl, hydroxyl, oxo, cyano, nitro, —$NR_7R_8$, —$NR_7C(=O)R_8$, —$NR_7C(=O)OR_8$, —$NR_7C(=O)NR_8R_9$, —$NR_7SO_2R_8$, —$NR_7S(O)_2NR_8R_9$, —$C(=O)OR_7$, —$C(=O)R_7$, —$C(=O)NR_7R_8$, —$S(O)_{1-2}R_7$, and —$SO_2NR_7R_8$, wherein $R_7$, $R_8$, and $R_9$ are independently selected from the group consisting of hydrogen, $C_{1-4}$alkyl, or a bond linking the NHE-binding small molecule moiety to L, provided at least one is a bond linking the NHE-binding small molecule moiety to L; $R_3$ and $R_4$ are independently selected from the group consisting of hydrogen, optionally substituted $C_{1-4}$alkyl, optionally substituted cycloalkyl, optionally substituted cycloalkylalkyl, optionally substituted aryl, optionally substituted aralkyl, optionally substituted heterocyclyl and optionally substituted heteroaryl; or $R_3$ and $R_4$ form together with the nitrogen to which they are bonded an optionally substituted 4-8 membered heterocyclyl; and each $R_1$ is independently selected from the group consisting of hydrogen, halogen, optionally substituted $C_{1-6}$alkyl and optionally substituted $C_{1-6}$alkoxy.

In yet further more specific embodiments, the NHE-binding small molecule moiety has the following structure of Formula (XII-H):

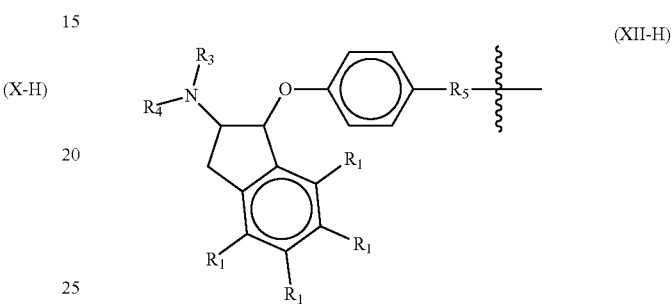

(XII-H)

wherein: each $R_3$ and $R_4$ are independently selected from the group consisting of hydrogen and optionally substituted $C_{1-4}$alkyl, or $R_3$ and $R_4$, taken together with the nitrogen to which they are bonded, form an optionally substituted 4-8 membered heterocyclyl; each $R_1$ is independently selected from the group consisting of hydrogen, halogen, $C_{1-6}$alkyl, and $C_{1-6}$haloalkyl; and $R_5$ is selected from the group consisting of —$SO_2$—$NR_7$— and —NHC(=O)NH—, wherein $R_7$ is hydrogen or $C_{1-4}$alkyl.

In various alternative embodiments, the NHE-binding small molecule moiety may be rendered substantially impermeable or substantially systemically non-bioavailable by forming a polymeric structure from multiple NHE-binding small molecule moieties, which may be the same or different, connected or bound by a series of linkers, L, which also may be the same or different, the compound having for example the structure of Formula (II-H):

(II-H)

wherein: NHE is as defined above; L is a bond or linker, as further defined elsewhere herein; and m is 0 or an integer of 1 or more. In this embodiment, the physicochemical properties, and in particular the molecular weight or polar surface area, of the NHE-binding small molecule moiety is modified (e.g., increased) by having a series of NHE-binding small molecule moieties linked together, in order to render them substantially impermeable or substantially systemically non-bioavailable.

In yet additional alternative embodiments, the polyvalent NHE-binding compound may be in oligomeric or polymeric form, wherein a backbone is bound (by means of a linker, for example) to multiple NHE-binding small molecule moieties. Such compounds may have, for example, the structures of Formulas (IIIA-H) or (IIIB-H):

(IIIA-H)

-continued

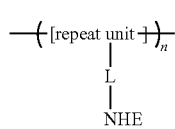
(IIIB-H)

wherein: NHE is as defined above; L is a bond or linker, as further defined elsewhere herein; and n is a non-zero integer (i.e., an integer of 1 or more). It is to be noted that the repeat unit in Formulas (IIIA-H) and (IIIB-H) generally encompasses repeating units of various polymeric embodiments, including linear, branched and dendritic structures, which may optionally be produced by methods referred to herein. In each polymeric, or more general polyvalent, embodiment, it is to be noted that each repeat unit may be the same or different, and may or may not be linked to the NHE-binding small molecule moiety by a linker, which in turn may be the same or different when present. In this regard it is to be noted that as used herein, "polyvalent" refers to a molecule that has multiple (e.g., 2, 4, 6, 8, 10 or more) NHE-binding small molecule moieties therein.

In the foregoing polyvalent embodiments, L may be a polyalkylene glycol linker, such as a polyethylene glycol linker; and/or the Core may have the following structure:

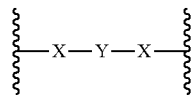

wherein: X is selected from the group consisting of a bond, —O—, —NH—, —S—, $C_{1-6}$alkylene, —NHC(=O)—, —C(=O)NH—, —NHC(=O)NH—, —SO$_2$NH—, and —NHSO$_2$—; Y is selected from the group consisting of a bond, optionally substituted $C_{1-8}$alkylene, optionally substituted aryl, optionally substituted heteroaryl, a polyethylene glycol linker, —(CH$_2$)$_{1-6}$O(CH$_2$)$_{1-6}$— and —(CH$_2$)$_{1-6}$NY$_1$(CH$_2$)$_{1-6}$—; and Y$_1$ is selected from the group consisting of hydrogen, optionally substituted $C_{1-8}$alkyl, optionally substituted aryl or optionally substituted heteroaryl. For example, in more specific embodiments, the Core may be selected, for example, from the group consisting of:

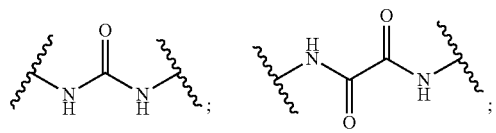

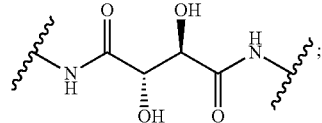

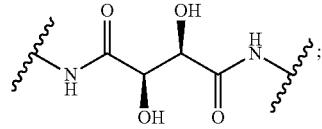

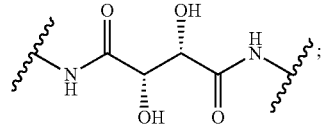

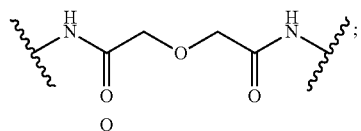;

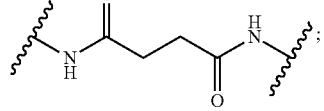;

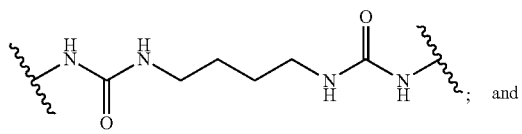; and

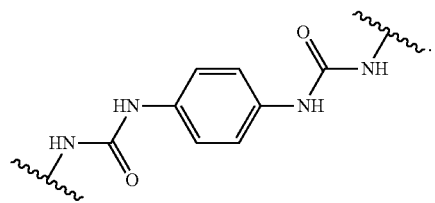.

In other more specific embodiments, the Core may be selected, for example, from the group consisting of:

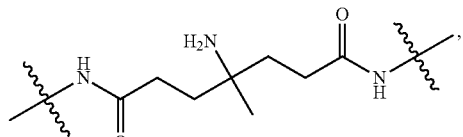,

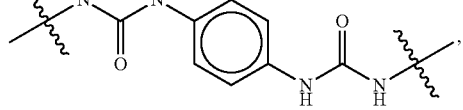,

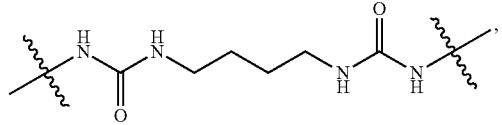,

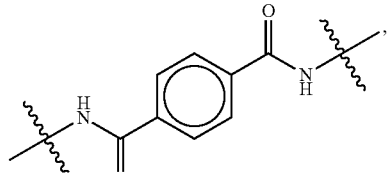,

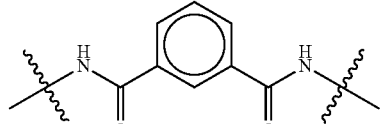,

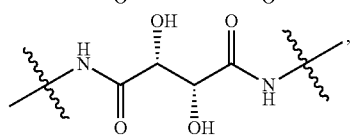,

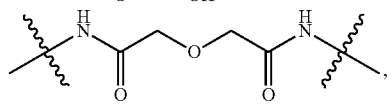,

-continued

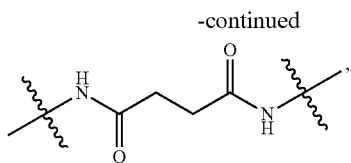

which may help avoid hydrophobic collapse (the intramolecular interaction of hydrophobic motifs that can occur when a hydrophobic molecule is exposed to an aqueous Research Reviews 1993, 13(3), 327-384). The core moiety illustrated below is also advantageous because it provides some rigidity to the molecule, allowing an increase in distance between the NHE-binding small molecule moieties while minimally increasing rotational degrees of freedom.

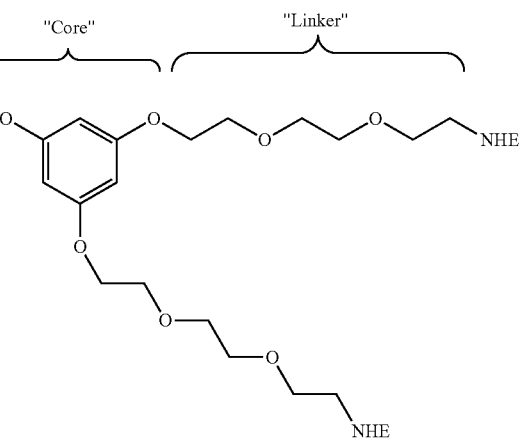

-continued

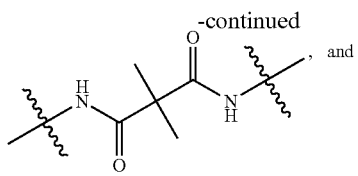
, and

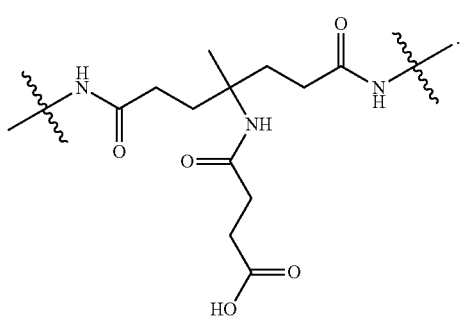

The above noted embodiments are further illustrated herein below. For example, the first representation below of an exemplary oligomer compound, wherein the various parts of the compound are identified, is intended to provide a broad context for the disclosure provided herein. It is to be noted that while each NHE-binding small molecule moiety in the structure below is the same, it is within the scope of this disclosure that each is independently selected and may be the same or different. In the illustration below, the linker moiety is a polyethylene glycol (PEG) motif. PEG derivatives are advantageous due in part to their aqueous solubility, environment (see, e.g., Wiley, R. A.; Rich, D. H. Medical In an alternative embodiment, wherein m=0, the structure may be, for example:

Within the polyvalent compounds utilized for treatments according to the present disclosure, n and m (when m is not zero) may be independently selected from the range of from about 1 to about 10, more preferably from about 1 to about 5, and even more preferably from about 1 to about 2. In alternative embodiments, however, n and m may be independently selected from the range of from about 1 to about 500, preferably from about 1 to about 300, more preferably from about 1 to about 100, and most preferably from about 1 to about 50. In these or other particular embodiments, E, n and m may be within the range of from about 1 to about 50, or from about 1 to about 20.

In designing and making the substantially impermeable or substantially systemically non-bioavailable NHE-binding compounds that may be utilized for the treatments detailed in the instant disclosure, it may in some cases be advantageous to first determine a likely point of attachment on a NHE-binding small molecule moiety, where a core or linker might be installed or attached before making a series of candidate multivalent or polyvalent compounds. This may be done by one skilled in the art via known methods by systematically installing functional groups, or functional groups displaying a fragment of the desired core or linker, onto various positions of the NHE-binding small molecule moiety and then testing these adducts to determine whether the modified compound still retains desired biological properties (e.g., NHE-binding activity). An understanding of the SAR of the compound also allows the design of cores and/or linkers that contribute positively to the activity of the resulting compounds.

Another aspect to be considered in the design of cores and linkers is the limiting or preventing of hydrophobic collapse. Compounds with extended hydrocarbon functionalities may collapse upon themselves in an intramolecular fashion, causing an increased enthalpic barrier for interaction with the desired biological target. Accordingly, when designing cores and linkers, these are preferably designed to be resistant to hydrophobic collapse. For example, conformational constraints such as rigid monocyclic, bicyclic or polycyclic rings can be installed in a core or linker to increase the rigidity of the structure. Unsaturated bonds, such as alkenes and alkynes, may also or alternatively be installed. Such modifications may ensure the NHE-binding compound is accessible for productive binding with its target. Furthermore, the hydrophilicity of the linkers may be improved by adding hydrogen bond donor or acceptor motifs, or ionic motifs such as amines that are protonated in the GI, or acids that are deprotonated. Such modifications will increase the hydrophilicity of the core or linker and help prevent hydrophobic collapse. Furthermore, such modifications will also contribute to the impermeability of the resulting compounds by increasing tPSA.

One skilled in the art may consider a variety of functional groups that will allow the facile and specific attachment of a NHE-binding small molecule moiety to a core or linker. These functional groups can include electrophiles, which can react with nucleophilic cores or linkers, and nucleophiles, which can react with electrophilic cores or linkers. NHE-binding small molecule moieties may be similarly derivatized with, for example, boronic acid groups which can then react with appropriate cores or linkers via palladium mediated cross-coupling reactions. The NHE-binding small molecule moiety may also contain olefins which can then react with appropriate cores or linkers via olefin metathesis chemistry, or alkynes or azides which can then react with appropriate cores or linkers via [2+3]cycloaddition.

It is to be noted that one skilled in the art can envision a number of core or linker moieties that may be functionalized with an appropriate electrophile or nucleophile. Shown below are a series of such compounds selected based on several design considerations, including solubility, steric effects, and their ability to confer, or be consistent with, favorable structure-activity relationships. In this regard it is to be further noted, however, that the structures provided below, and above, are for illustration purposes only, and therefore should not be viewed in a limiting sense.

Exemplary electrophilic and nucleophilic linker moieties include, but are not limited to, the linker moieties illustrated in the following:

Nucleophilic Linkers (for Use with Electrophilic NHEs)

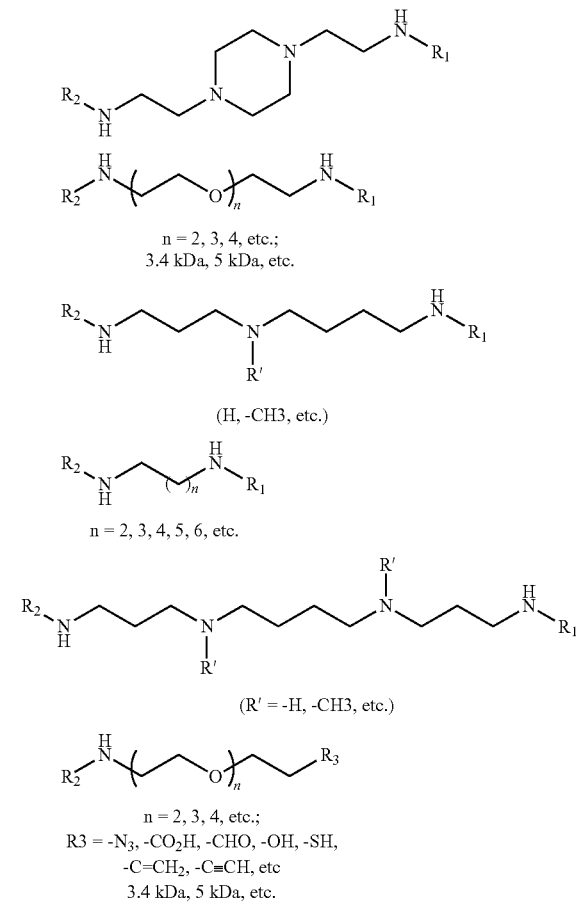

Electrophilic Linkers (for Use with Nucleophilic NHEs)

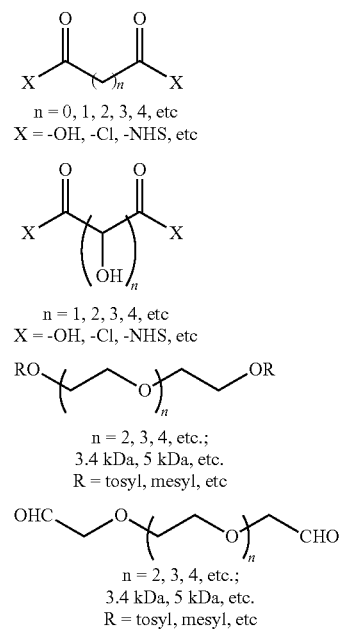

-continued

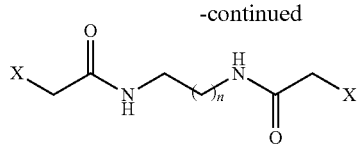

n = 2, 3, 4, 5, 6, etc.
X = -Cl, -Br, -OTs, etc.

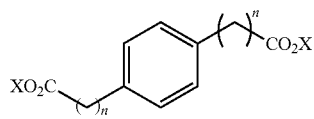

n = 1, 2, 3, etc.
X = -Cl, -NHS, OH, etc.

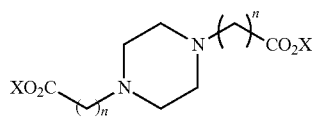

n = 1, 2, 3, etc.
X = -Cl, -NHS, OH, etc.

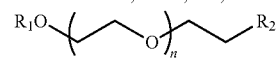

n = 2, 3, 4, etc.;
3.4 kDa, 5 kDa, etc.
$R_1$ = tosyl, mesyl, etc
$R_2$ = -$N_3$, -$CO_2H$, -CHO, -OH, -SH,
-C=$CH_2$, -C≡CH, etc The linking moiety, L, in each of the described embodiments (including embodiments in which a NHE-binding small molecule moiety is linked to a Core such as an atom, another small molecule, a polymer moiety, an oligomer moiety, or a non-repeating moiety) can be a chemical linker, such as a bond or other moiety, for example, comprising about 1 to about 200 atoms, or about 1 to about 100 atoms, or about 1 to about 50 atoms, that can be hydrophilic and/or hydrophobic. In one embodiment, the linking moiety can be a polymer moiety grafted onto a polymer backbone, for example, using living free radical polymerization approaches known in the art. Preferred L structures or moieties may also be selected from, for example, oligoethylene glycol, oligopeptide, oligoethyleneimine, oligotetramethylene glycol and oligocaprolactone.

As noted, the core moiety can be an atom, a small molecule, an oligomer, a dendrimer or a polymer moiety, in each case having one or more sites of attachment for L. For example, the core moiety can be a non-repeating moiety (considered as a whole including linking points to the NHE-binding small molecule moieties), selected for example from the group consisting of alkyl, phenyl, aryl, alkenyl, alkynyl, heterocyclic, amine, ether, sulfide, disulfide, hydrazine, and any of the foregoing substituted with oxygen, sulfur, sulfonyl, phosphonyl, hydroxyl, alkoxyl, amine, thiol, ether, carbonyl, carboxyl, ester, amide, alkyl, alkenyl, alkynyl, aryl, heterocyclic, and moieties comprising combinations thereof (in each permutation). A non-repeating moiety can include repeating units (e.g., methylene) within portions or segments thereof (e.g., within an alkyl segment), without having discrete repeat units that constitute the moiety as a whole (e.g., in the sense of a polymer or oligomer).

Exemplary core moieties include but are not limited to the core moieties illustrated in the Examples and ether moieties, ester moieties, sulfide moieties, disulfide moieties, amine moieties, aryl moieties, alkoxyl moieties, etc., such as, for example, the following:

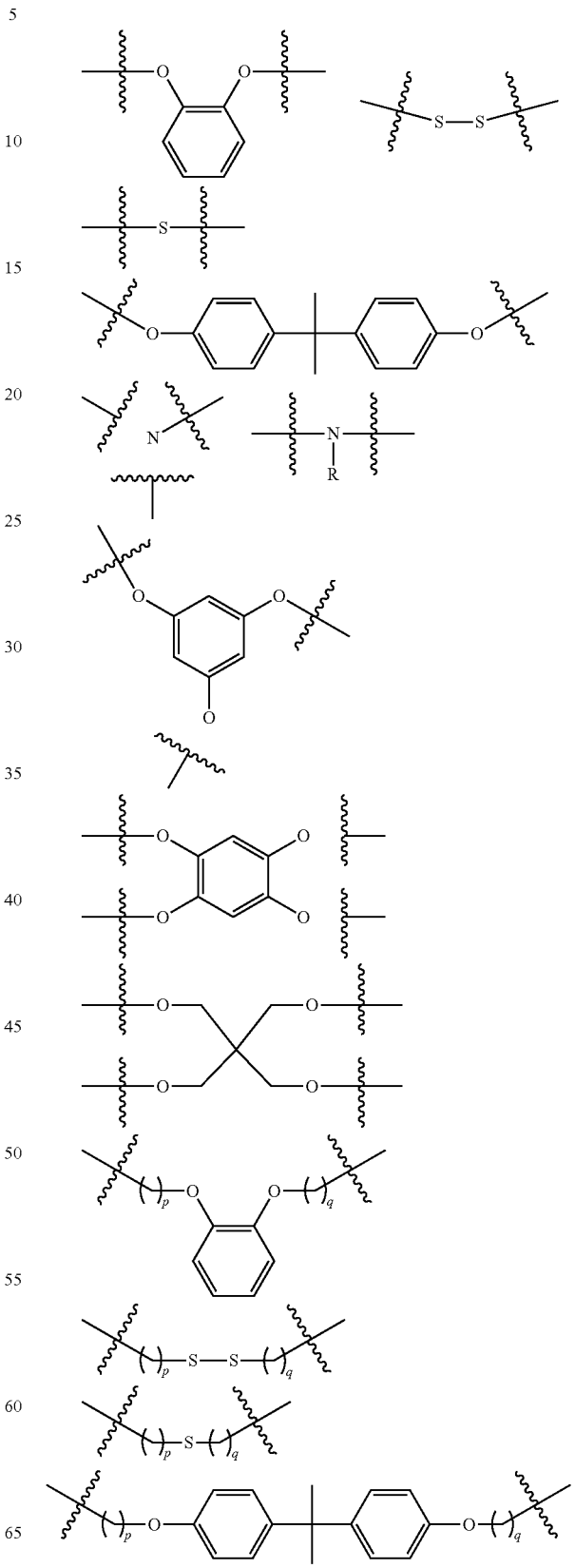

115
-continued
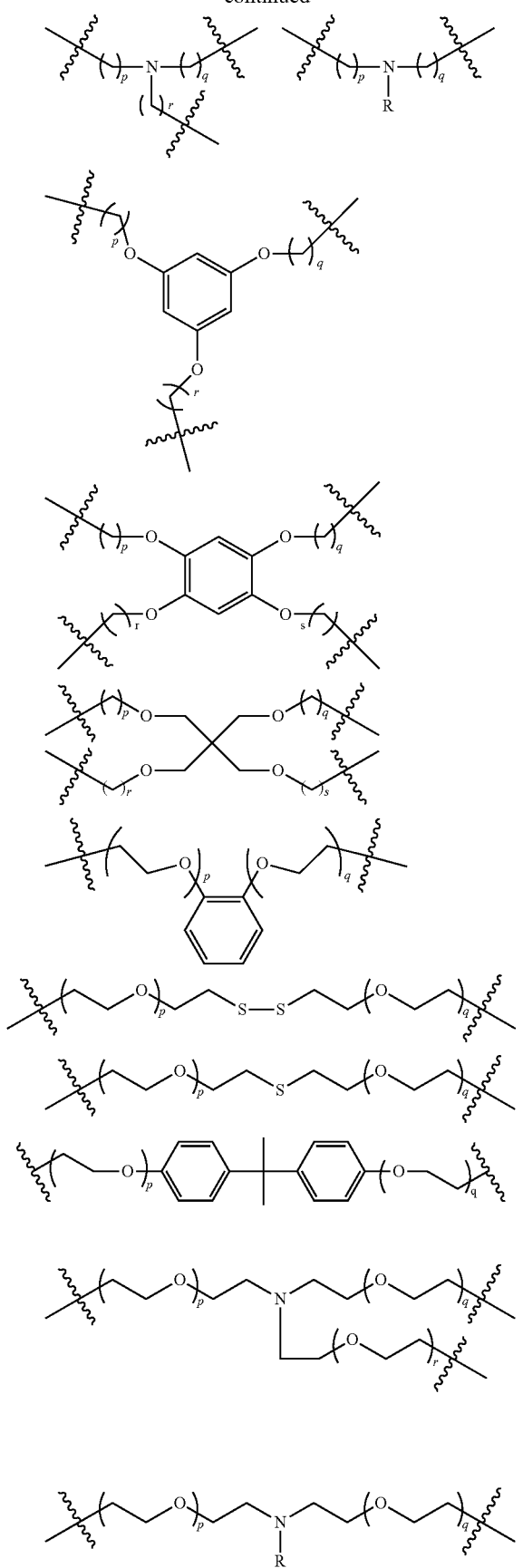
116
-continued
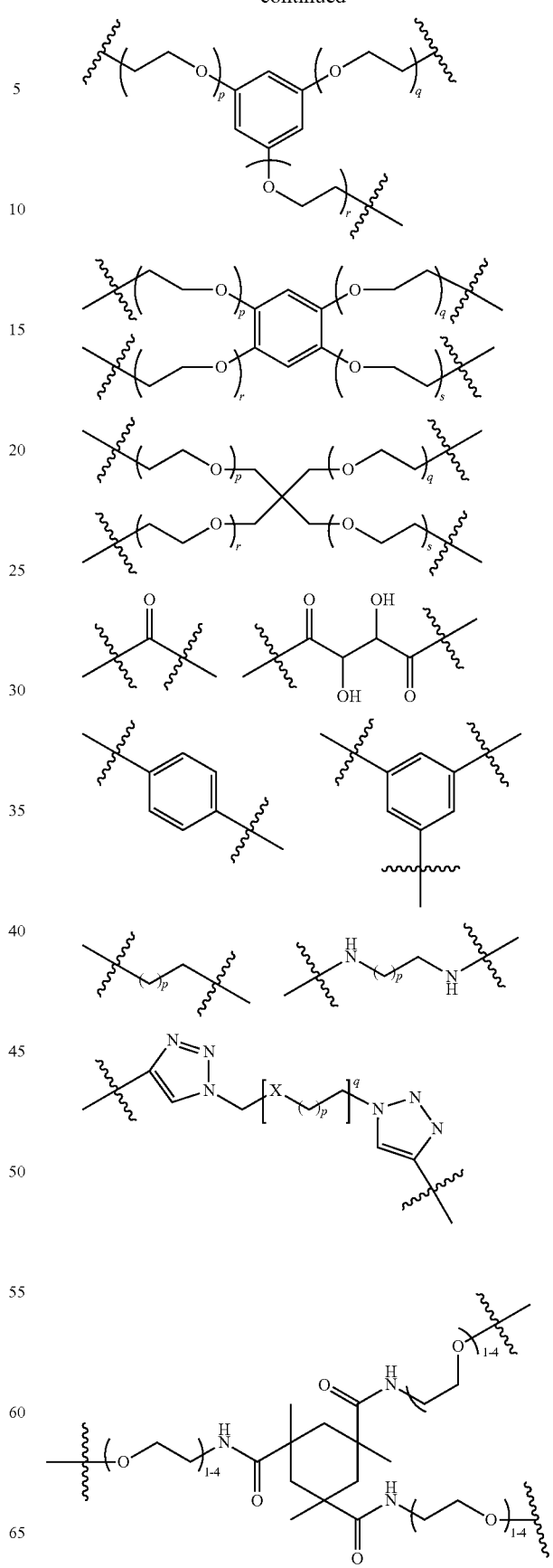

117
-continued
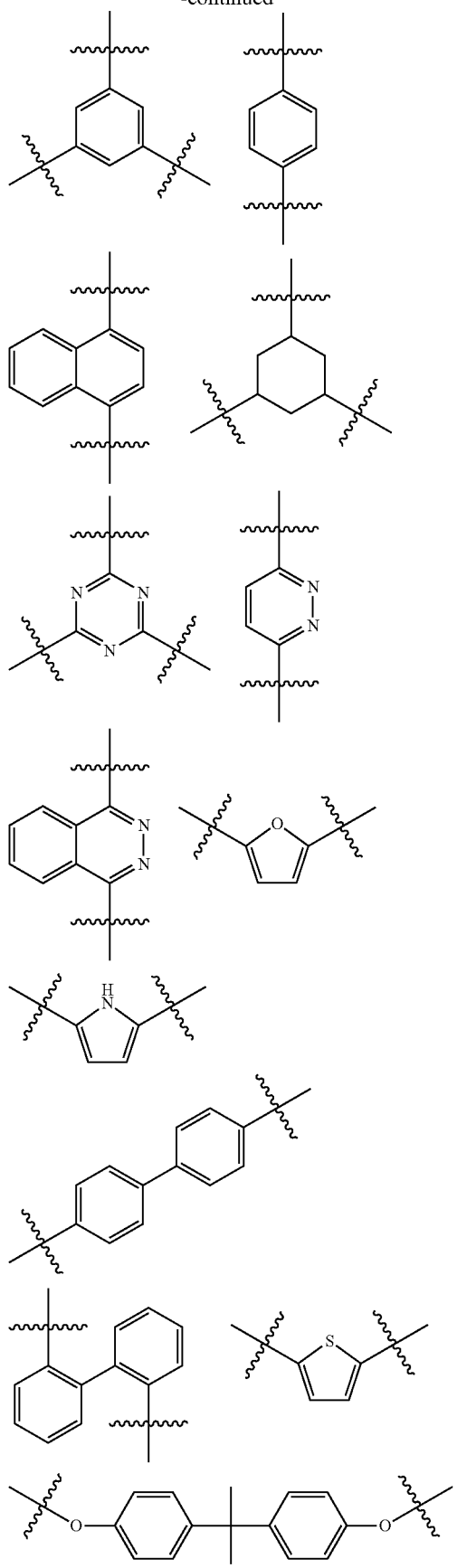
118
-continued
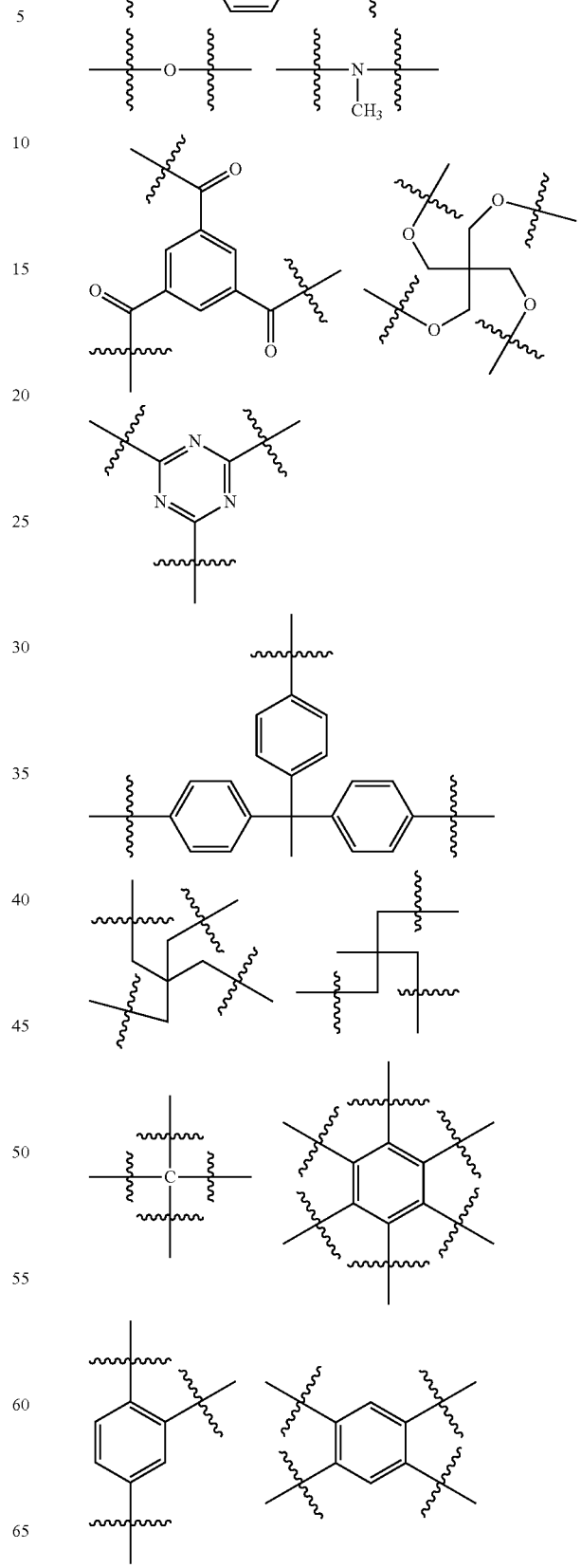

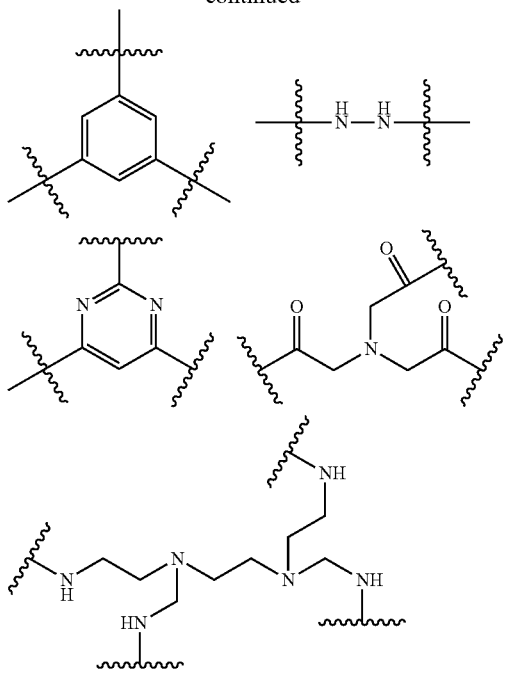

wherein the broken bonds (i.e., those having a wavy bond, ⁀, through them) are points of connection to either a NHE-binding small molecule moiety or a linker moiety displaying a NHE-binding small molecule moiety, where said points of connection can be made using chemistries and functional groups known to the art of medicinal chemistry; and further wherein each p, q, r and s is an independently selected integer ranging from about 0 to about 48, preferably from about 0 to about 36, or from about 0 to about 24, or from about 0 to about 16. In some instances, each p, q, r and s can be an independently selected integer ranging from about 0 to 12. Additionally, R can be a substituent moiety generally selected from halide, hydroxyl, amine, thiol, ether, carbonyl, carboxyl, ester, amide, carbocyclic, heterocyclic, and moieties comprising combinations thereof.

In another approach, the core moiety may be a dendrimer, defined as a repeatedly branched molecule (see, e.g., J. M. J. Fréchet, D. A. Tomalia, *Dendrimers and Other Dendritic Polymers*, John Wiley & Sons, Ltd. NY, N.Y., 2001) and schematically represented In FIG. 17.

In this approach, the NHE-binding small molecule moiety is attached through L to one, several or optionally all termini located at the periphery of the dendrimer. In another approach, a dendrimer building block named dendron, and illustrated above, is used as a core, wherein the NHE-binding small molecule moiety is attached to one, several or optionally all termini located at the periphery of the dendron. The number of generations herein is typically between about 0 and about 6, and preferably between about 0 and about 3. (Generation is defined in, for example, J. M. J. Fréchet, D. A. Tomalia, *Dendrimers and Other Dendritic Polymers*, John Wiley & Sons, Ltd. NY, N.Y.) Dendrimer and/or dendron structures are well known in the art and include, for example, those shown in or illustrated by: (i) J. M. J. Fréchet, D. A. Tomalia, *Dendrimers and Other Dendritic Polymers*, John Wiley & Sons, Ltd. NY, N.Y.; (ii) George R Newkome, Charles N. Moorefield and Fritz Vogtle, *Dendrimers and Dendrons: Concepts, Syntheses, Applications*, VCH Verlagsgesellschaft Mbh; and, (iii) Boas, U., Christensen, J. B., Heegaard, P. M. H., *Dendrimers in Medicine and Biotechnology: New Molecular Tools*, Springer, 2006.

In yet another approach, the core moiety may be a polymer moiety or an oligomer moiety. The polymer or oligomer may, in each case, be independently considered and comprise repeat units consisting of a repeat moiety selected from alkyl (e.g., —$CH_2$—), substituted alkyl (e.g., —CHR—, wherein, for example, R is hydroxy), alkenyl, substituted alkenyl, alkynyl, substituted alkynyl, phenyl, aryl, heterocyclic, amine, ether, sulfide, disulfide, hydrazine, and any of the foregoing substituted with oxygen, sulfur, sulfonyl, phosphonyl, hydroxyl, alkoxyl, amine, thiol, ether, carbonyl, carboxyl, ester, amide, alkyl, alkenyl, alkynyl, aryl, heterocyclic, as well as moieties comprising combinations thereof. In still another approach, the core moiety comprises repeat units resulting from the polymerization of ethylenic monomers (e.g., such as those ethylenic monomers listed elsewhere herein below).

Preferred polymers for polymeric moieties useful in constructing substantially impermeable or substantially systemically non-bioavailable NHE-binding compounds that are multivalent, for use in the treatment various treatment methods disclosed herein, can be prepared by any suitable technique, such as by free radical polymerization, condensation polymerization, addition polymerization, ring-opening polymerization, and/or can be derived from naturally occurring polymers, such as saccharide polymers. Further, in some embodiments, any of these polymer moieties may be functionalized.

Examples of polysaccharides useful in preparation of such compounds include but are not limited to materials from vegetable or animal origin, including cellulose materials, hemicellulose, alkyl cellulose, hydroxyalkyl cellulose, carboxymethylcellulose, sulfoethylcellulose, starch, xylan, amylopectine, chondroitin, hyarulonate, heparin, guar, xanthan, mannan, galactomannan, chitin, and/or chitosan. More preferred, in at least some instances, are polymer moieties that do not degrade, or that do not degrade significantly, under the physiological conditions of the GI tract (such as, for example, carboxymethylcellulose, chitosan, and sulfoethylcellulose).

When free radical polymerization is used, the polymer moiety can be prepared from various classes of monomers including, for example, acrylic, methacrylic, styrenic, vinylic, and dienic, whose typical examples are given thereafter: styrene, substituted styrene, alkyl acrylate, substituted alkyl acrylate, alkyl methacrylate, substituted alkyl methacrylate, acrylonitrile, methacrylonitrile, acrylamide, methacrylamide, N-alkylacrylamide, N-alkylmethacrylamide, N,N-dialkylacrylamide, N,N-dialkylmethacrylamide, isoprene, butadiene, ethylene, vinyl acetate, and combinations thereof. Functionalized versions of these monomers may also be used and any of these monomers may be used with other monomers as co-monomers. For example, specific monomers or co-monomers that may be used in this disclosure include methyl methacrylate, ethyl methacrylate, propyl methacrylate (all isomers), butyl methacrylate (all isomers), 2-ethylhexyl methacrylate, isobomyl methacrylate, methacrylic acid, benzyl methacrylate, phenyl methacrylate, methacrylonitrile, α-methylstyrene, methyl acrylate, ethyl acrylate, propyl acrylate (all isomers), butyl acrylate (all isomers), 2-ethylhexyl acrylate, isobomyl acrylate, acrylic acid, benzyl acrylate, phenyl acrylate, acrylonitrile, styrene, glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N-n-butylmethacrylamide, N-methylolmethacrylamide, N-ethylolmethacrylamide, N-tert-butylacrylamide, N-n-butylacrylamide, N-methylolacrylamide, N-ethylolacrylamide, 4-acryloylmorpholine, vinyl benzoic acid (all isomers), diethylaminostyrene (all isomers), a-methylvinyl benzoic acid (all isomers), diethylamino α-methylstyrene (all isomers), p-vinylbenzene sulfonic acid, p-vinylbenzene sulfonic sodium salt, alkoxy and alkyl silane functional monomers, maleic anhydride, N-phenylmaleimide, N-butylmaleimide, butadiene, isoprene, chloroprene, ethylene, vinyl acetate, vinylformamide, allylamine, vinylpyridines (all isomers), fluorinated acrylate, methacrylates, and combinations thereof. Main chain heteroatom polymer moieties can also be used, including polyethyleneimine and polyethers such as polyethylene oxide and polypropylene oxide, as well as copolymers thereof.

In one particular embodiment, the polymer to which the NHE-binding small molecule moiety is attached, or otherwise a part of, is a polyol (e.g., a polymer having a repeat unit of, for example, a hydroxyl-substituted alkyl, such as —CH(OH)—). Polyols, such as mono- and disaccharides, with or without reducing or reducible end groups thereon, may be good candidates, for example, for installing additional functionality that could render the compound substantially impermeable.

In one particular embodiment, the NHE-binding small molecule moiety is attached at one or both ends of the polymer chain. More specifically, in yet another alternative approach to the polyvalent embodiment of the present disclosure, a macromolecule (e.g., a polymer or oligomer) having one of the following exemplary structures (wherein is a NHE-binding small molecule moiety) may be designed and constructed as described herein:

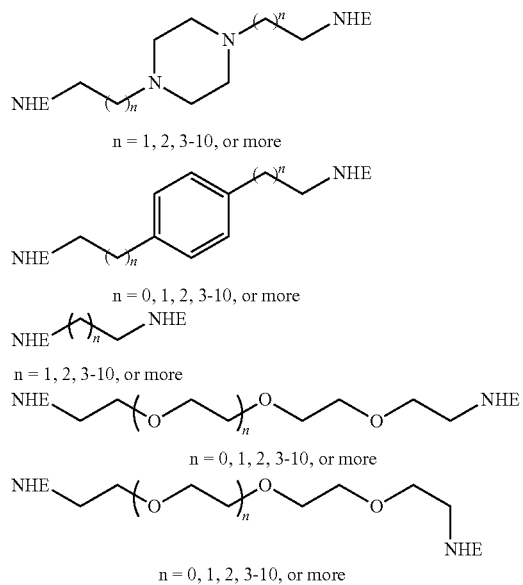

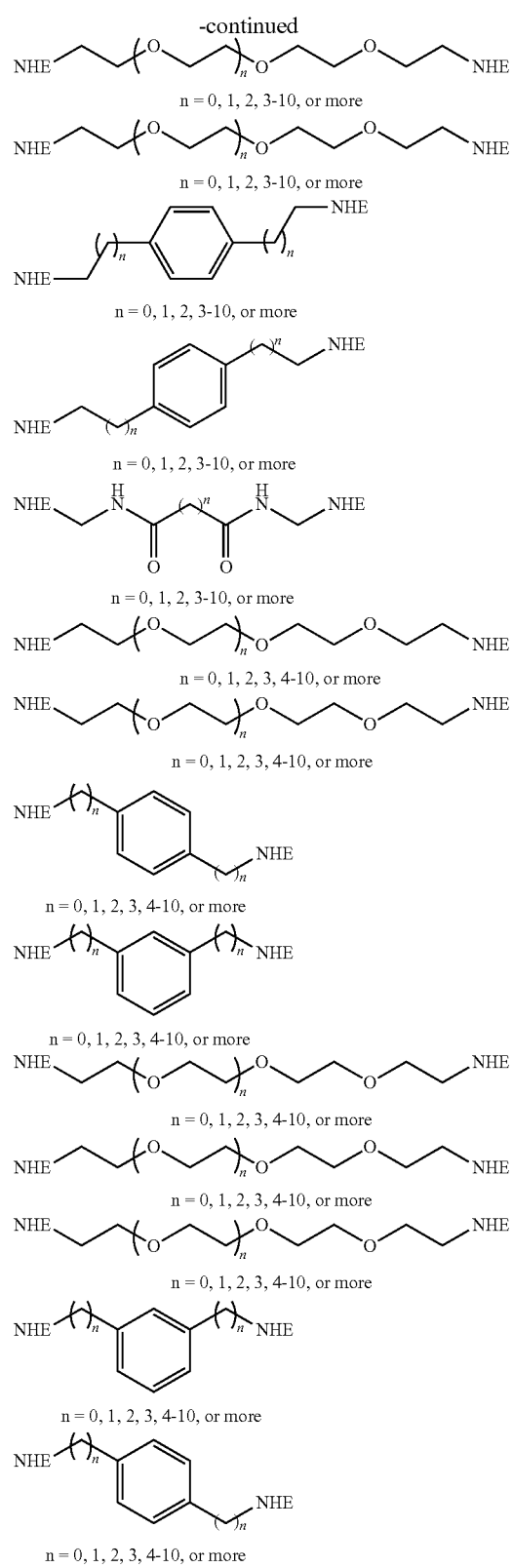

I. General Structure of Additional Exemplary Compounds

In one embodiment, a compound is provided having the structure of Formula (I-I):

Core—(L-NHE)$_3$     (I-I)

or a stereoisomer, prodrug or pharmaceutically acceptable salt thereof, wherein: (a) NHE is a NHE-binding small molecule moiety having the following structure of Formula (A-I):

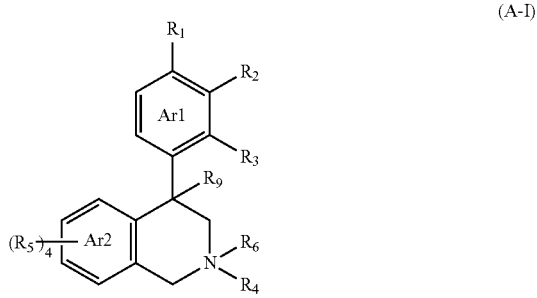

(A-I)

wherein: each $R_1$, $R_2$, $R_3$, $R_5$ and $R_9$ are independently selected from H, halogen, —$NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H, $C_{1-6}$alkyl, —$C_{1-6}$alkyl-OH or a bond linking the NHE-binding small molecule to L, provided at least one is a bond linking the NHE-binding small molecule to L; $R_4$ is selected from H, $C_1$-$C_7$ alkyl, or a bond linking the NHE-binding small molecule to L; $R_6$ is absent or selected from H and $C_1$-$C_7$ alkyl; and Ar1 and Ar2 independently represent an aromatic ring or a heteroaromatic ring; (b) Core is a Core moiety having the following structure of Formula (B-I):

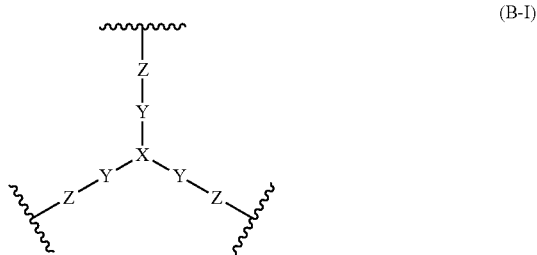

(B-I)

wherein: X is selected from $C(X_1)$, N and $N(C_{1-6}$alkyl); $X_1$ is selected from hydrogen, optionally substituted alkyl, —$NX_aX_b$, —$NO_2$, —$NX_c$—$C(=O)$—$NX_c$—$X_a$, —$C(=O)$ $NX_c$—$X_a$, —$NX_c$—$C(=O)$—$X_a$, —$NX_c$—$SO_2$—$X_a$, —$C(=O)$—$X_a$ and —$OX_a$; each $X_a$ and $X_b$ are independently selected from hydrogen, optionally substituted alkyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl and optionally substituted heteroarylalkyl; Y is $C_{1-6}$alkylene; Z is selected from —$NZ_a$—$C(=O)$—$NZ_a$—, —$C(=O)NZ_a$—, —$NZ_a$—$C(=O)$— and heteroaryl when X is $CX_1$; Z is selected from —$NZ_a$—$C(=O)$—$NZ_a$—, —$NZ_a$—$C(=O)$— and heteroaryl when X is N or $N(C_{1-6}$ alkyl); and each $X_c$ and $Z_a$ is independently selected from hydrogen and $C_{1-6}$alkyl; and (c) L is a bond or linker connecting the Core moiety to the NHE-binding small molecule moieties, the resulting NHE-binding compound (i.e., a compound of Formula (I)) possessing overall physicochemical properties that render it substantially impermeable or substantially systemically non-bioavailable. The Core moiety may be bound to essentially any position on, or within, the NHE-binding small molecule moiety, provided that the installation thereof does not significantly adversely impact activity.

In another embodiment, a compound is provided having the structure of Formula (II-I):

Core—(L-NHE)$_4$      (II-I)

or a stereoisomer, prodrug or pharmaceutically acceptable salt thereof, wherein: (a) NHE is a NHE-binding small molecule moiety having the structure of Formula (A-I):

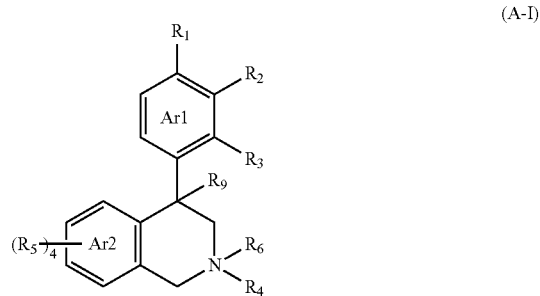

(A-I)

wherein: each $R_1$, $R_2$, $R_3$, $R_5$ and $R_9$ are independently selected from H, halogen, —$NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H, $C_{1-6}$alkyl, —$C_{1-6}$alkyl-OH or a bond linking the NHE-binding small molecule to L, provided at least one is a bond linking the NHE-binding small molecule to L; $R_4$ is selected from H, $C_1$-$C_7$ alkyl, or a bond linking the NHE-binding small molecule to L; $R_6$ is absent or selected from H and $C_1$-$C_7$ alkyl; and Ar1 and Ar2 independently represent an aromatic ring or a heteroaromatic ring; (b) Core is a Core moiety having the following structure of Formula (C-I):

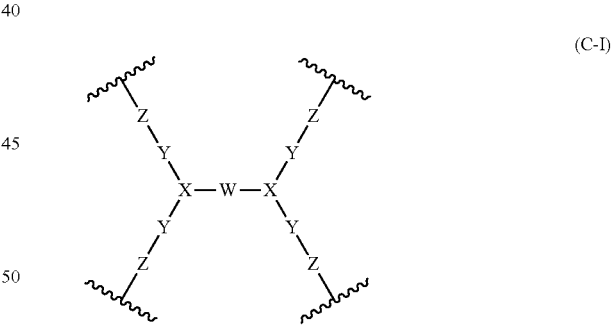

(C-I)

wherein: W is selected from alkylene, polyalkylene glycol, —$C(=O)$—NH-(alkylene)-NH—$C(=O)$—, —$C(=O)$—NH-(polyalkylene glycol)-NH—$C(=O)$—, —$C(=O)$-(alkylene)-$C(=O)$—, —$C(=O)$-(polyalkylene glycol)-C(=O)— and cycloalkyl; X is N; Y is $C_{1-6}$alkylene; Z is selected from —$NZ_a$—$C(=O)$—$NZ_a$—, —$C(=O)NZ_a$—, —$NZ_a$—$C(=O)$— and heteroaryl; each $Z_a$ is independently selected from hydrogen and $C_{1-6}$alkyl; and (c) L is a bond or linker connecting the Core moiety to the NHE-binding small molecules, the resulting NHE-binding compound (i.e., a compound of Formula (II-I)) possessing overall physicochemical properties that render it substantially impermeable or substantially systemically non-bioavailable. The Core moiety may be bound to essentially any position on, or within, the NHE-binding small molecule moiety, provided that the installation thereof does not significantly adversely impact activity.

It is to be noted that, in the structures illustrated herein, all of the various linkages or bonds will not be shown in every instance. For example, in one or more of the structures illustrated above, a bond or connection between the NHE-binding small molecule moiety and the Core moiety is not always shown. However, this should not be viewed in a limiting sense. Rather, it is to be understood that the NHE-binding small molecule moiety is bound or connected in some way (e.g., by a bond or linker of some kind) to the Core moiety, such that the resulting NHE-binding compound is suitable for use (i.e., substantially impermeable or substantially systemically non-bioavailable in the GI tract).

The above noted embodiments are further illustrated herein below. For example, the first representation below of an exemplary oligomer compound, wherein the various parts of the compound are identified, is intended to provide a broad context for the disclosure provided herein. It is to be noted that while each NHE-binding small molecule moiety in the structure below is the same, it is within the scope of this disclosure that each is independently selected and may be the same or different. In the illustration below, the linker moiety is a polyethylene glycol (PEG) motif. PEG derivatives are advantageous due in part to their aqueous solubility, which may help avoid hydrophobic collapse (the intramolecular interaction of hydrophobic motifs that can occur when a hydrophobic molecule is exposed to an aqueous environment (see, e.g., Wiley, R. A.; Rich, D. H. Medical Research Reviews 1993, 13(3), 327-384). The core moiety illustrated below is also advantageous because it provides some rigidity to the molecule, allowing an increase in distance between the NHE-binding small molecule moieties while minimally increasing rotational degrees of freedom.

standing of the SAR of the compound also allows the design of cores and/or linkers that contribute positively to the activity of the resulting compounds.

Another aspect to be considered in the design of cores and linkers is the limiting or preventing of hydrophobic collapse. Compounds with extended hydrocarbon functionalities may collapse upon themselves in an intramolecular fashion, causing an increased enthalpic barrier for interaction with the desired biological target. Accordingly, when designing cores and linkers, these are preferably designed to be resistant to hydrophobic collapse. For example, conformational constraints such as rigid monocyclic, bicyclic or polycyclic rings can be installed in a core or linker to increase the rigidity of the structure. Unsaturated bonds, such as alkenes and alkynes, may also or alternatively be installed. Such modifications may ensure the NHE-binding compound is accessible for productive binding with its target. Furthermore, the hydrophilicity of the linkers may be improved by adding hydrogen bond donor or acceptor motifs, or ionic motifs such as amines that are protonated in the GI, or acids that are deprotonated. Such modifications will increase the hydrophilicity of the core or linker and help prevent hydrophobic collapse. Furthermore, such modifications will also contribute to the impermeability of the resulting compounds by increasing tPSA.

It is understood that any embodiment of the compounds of the present invention, as set forth above, and any specific substituent set forth herein in such compounds, as set forth above, may be independently combined with other embodiments and/or substituents of such compounds to form embodiments of the inventions not specifically set forth above. In addition, in the event that a list of substituents is listed for any particular substituent in a particular embodiment and/or claim, it is understood that each individual substituent may be deleted from the particular embodiment

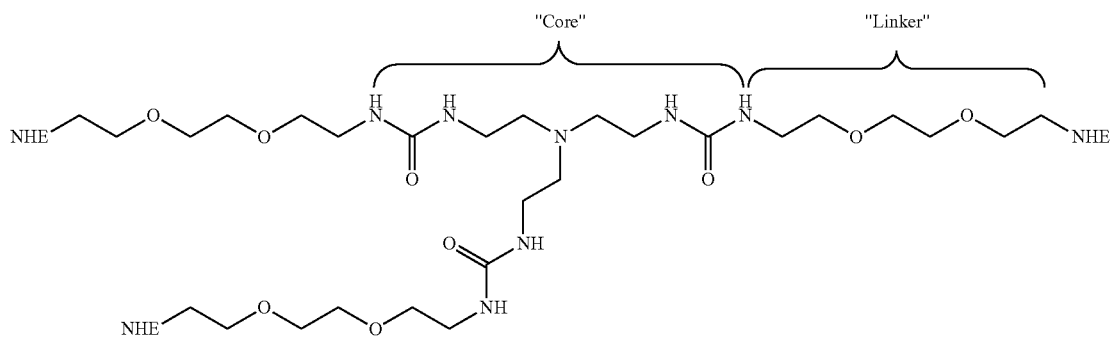

In designing and making the substantially impermeable or substantially systemically non-bioavailable NHE-binding compounds that may be utilized for the treatments detailed in the instant disclosure, it may in some cases be advantageous to first determine a likely point of attachment on a NHE-binding small molecule moiety, where a core or linker might be installed or attached before making a series of candidate multivalent or polyvalent compounds. This may be done by one skilled in the art via known methods by systematically installing functional groups, or functional groups displaying a fragment of the desired core or linker, onto various positions of the NHE-binding small molecule moiety and then testing these adducts to determine whether the modified compound still retains desired biological properties (e.g., inhibition of phosphate transport). An underand/or claim and that the remaining list of substituents will be considered to be within the scope of the invention. Furthermore, it is understood that in the present description, combinations of substituents and/or variables of the depicted formulae are permissible only if such contributions result in stable compounds.

III. Substantially Systemically Bioavailable Compounds

A. Physical and Performance Properties of Compounds

Certain of the compounds described herein are designed to be substantially active in systemic tissues, including the tissues of the kidney, upon administration via any route including enteral administration. For enteral administration, including oral delivery, certain of these compounds are substantially permeable to the epithelium of the gastrointestinal tract, including the epithelium of the oral cavity, esophagus, stomach, small intestine, and/or large intestine. The term "gastrointestinal lumen" is used interchangeably herein with the term "lumen," to refer to the space or cavity within a gastrointestinal tract (GI tract, which can also be referred to as the gut), delimited by the apical membrane of GI epithelial cells of the subject. In some embodiments, the compounds are substantially absorbed through the layer of epithelial cells of the GI tract (also known as the GI epithelium). "Gastrointestinal mucosa" refers to the layer(s) of cells separating the gastrointestinal lumen from the rest of the body and includes gastric and intestinal mucosa, such as the mucosa of the small intestine. A "gastrointestinal epithelial cell" or a "gut epithelial cell" as used herein refers to any epithelial cell on the surface of the gastrointestinal mucosa that faces the lumen of the gastrointestinal tract, including, for example, an epithelial cell of the stomach, an intestinal epithelial cell, a colonic epithelial cell, and the like.

"Substantially systemically bioavailable" and/or "substantially permeable" as used herein (as well as variations thereof) generally include situations in which a statistically significant amount, and in some embodiments essentially all of the compound of the present disclosure, enters the bloodstream or systemic tissues via the gastrointestinal lumen. For example, in accordance with one or more embodiments of the present disclosure, preferably at least about 60%, about 70%, about 75%, about 80%, about 85%, about 90%, about 95%, about 96%, about 97%, about 98%, about 99%, or even about 99.5%, of the compound enters the bloodstream or systemic tissues via the gastrointestinal lumen. In such cases, localization to the bloodstream or systemic tissues refers to increasing the net movement of a compound across a gastrointestinal layer of epithelial cells, for example, by way of both transcellular and paracellular transport, as well as by active and/or passive transport. The compound in such embodiments permeates a layer of gastrointestinal epithelial cells in transcellular transport, for example, through an apical membrane of an epithelial cell of the small intestine. The compound in these embodiments may also permeate through the "tight junctions" in paracellular transport between gastrointestinal epithelial cells lining the lumen.

In this regard it is to be further noted, however, that in alternative embodiments "substantially permeable" or "substantially systemically bioavailable" provides or allows for some limited retention in the GI tract to occur (e.g., some detectable amount of absorption, such as for example less than about 0.1%, 0.5%, 1% or less than about 30%, 20%, 10%, 5%, etc., the range of retention being for example between about 1% and 30%, or 5% and 20%, etc.).

In this regard it is to be further noted, that in certain embodiments, due to the substantial permeability and/or substantial systemic bioavailability of the compounds of the present invention, no greater than about 50%, 60%, 70%, 80%, 90%, or 95% of a compound of the invention is recoverable from the feces over, for example, a 24, 36, 48, 60, 72, 84, or 96 hour period following (e.g., enteral) administration to a subject in need thereof. In some embodiments, less than about 40%, 30%, 20%, or less than about 10%, or less than about 5%, of the amount of compound administered is present or recoverable in the subject's feces. In this respect, it is understood that a recovered compound can include the sum of the parent compound and its metabolites derived from the parent compound, e.g., by means of hydrolysis, conjugation, reduction, oxidation, N-alkylation, glucuronidation, acetylation, methylation, sulfation, phosphorylation, or any other modification that adds atoms to or removes atoms from the parent compound, wherein the metabolites are generated via the action of any enzyme or exposure to any physiological environment including, pH, temperature, pressure, or interactions with foodstuffs as they exist in the digestive milieu.

Measurement of fecal recovery of compound and metabolites can be carried out using standard methodology. For example, a compound can be administered enterally (e.g., orally) at a suitable dose (e.g., 10 mg/kg) and feces are then collected at predetermined times after dosing (e.g., 24 hours, 36 hours, 48 hours, 60 hours, 72 hours, 96 hours). Parent compound and metabolites can be extracted with organic solvent and analyzed quantitatively using mass spectrometry. A mass balance analysis of the parent compound and metabolites (including, parent=M, metabolite 1 [M+16], and metabolite 2 [M+32]) can be used to determine the percent recovery in the feces.

(i) $C_{max}$ and $IC_{50}$

In some embodiments, the substantially systemically bioavailable compounds detailed herein, when administered either alone or in combination with one or more additional pharmaceutically active compounds or agents to a subject in need thereof, exhibit a maximum concentration detected in the serum, defined as $C_{max}$, that is about the same as or greater than the phosphate ion (Pi) transport or uptake inhibitory concentration $IC_{50}$ of the compound. In some embodiments, for instance, the $C_{max}$ is about or at least about 5%, 10%, 20%, 30%, 40%, 50%, 60%, 70%, 80%, 90%, 100%, 200%, 300%, 400%, 500% or greater than the $IC_{50}$ for inhibiting Pi transport or uptake. In some embodiments, the $C_{max}$ is about 1, 1.5, 2, 2.5, 3, 4, 5, 6, 7, 8, 9, 10, 20, 30, 40, 50, 60, 70, 80, 90, or 100× (100 times) the $IC_{50}$ for inhibiting Pi transport or uptake.

Additionally, or alternatively, it is also to be noted that, in various embodiments of the present disclosure, one or more of compounds detailed herein, when administered to a subject in need thereof, may have a ratio of $C_{max}$:$IC_{50}$ (for inhibiting Pi transport or uptake), wherein $C_{max}$ and $IC_{50}$ are expressed in terms of the same units, of at about or at least about 1, 1.5, 2, 2.5, 3, 4, 5, 6, 7, 8, 9, 10, 20, 30, 40, 50, 60, 70, 80, 90, or 100, or a range in between about 1-100, 1-50, or 1-10.

Additionally, or alternatively, it is also to be noted that, in various embodiments of the present disclosure, one or more of the compounds detailed herein, when administered (e.g., enterally) either alone or in combination with one or more additional pharmaceutically active compounds or agents to a subject in need thereof, may have a $C_{max}$ of about or greater than about 10 ng/ml, about 12.5 ng/ml, about 15 ng/ml, about 17.5 ng/ml, about 20 ng/ml, about 30 ng/ml, about 40 ng/ml, about 50 ng/ml, about 60 ng/ml, about 70 ng/ml, about 80 ng/ml, about 90 ng/ml, about 100 ng/ml, or about 200 ng/ml, the $C_{max}$ being for example within the range of about 10 ng/ml to about 200 ng/ml, 10 ng/ml to about 100 ng/ml, or about 10 ng/ml to about 50 ng/ml.

B. Exemplary Substantially Systemically Bioavailable Compounds

Generally, the present disclosure encompasses essentially any small molecule, which may be monovalent or polyvalent, that binds to, interacts with, and/or modulates NHE3, and has activity as a phosphate transport inhibitor, including small molecules that are substantially permeable or substantially systemically bioavailable upon administration via the gastrointestinal tract or other route, and including known NHE-binding and NHE-inhibitor compounds. Certain embodiments thus include compounds that are generally represented by the "NHE" moiety, as described elsewhere herein (e.g., supra), wherein NHE is a NHE-binding small molecule.

Small molecules suitable for use (i.e., suitable for use as substantially bioavailable compounds) include those illustrated below.

In view of the foregoing, in one particular embodiment, the following small molecule, disclosed in U.S. Patent Application No. 2005/0054705, the entire content of which (and in particular the text of pages 1-2 therein) is incorporated herein by reference for all relevant and consistent purposes, may be suitable for use as a substantially systemically bioavailable NHE-binding compound.

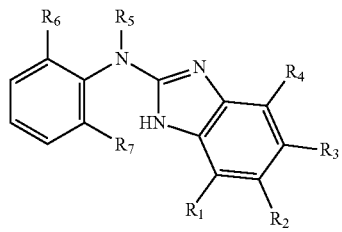

The variables in the structure are defined in the cited patent application, the details of which are incorporated herein by reference. In one particularly preferred embodiment, $R_6$ and $R_7$ are a halogen (e.g., Cl), $R_5$ is lower alkyl (e.g., $CH_3$), and $R_1$-$R_4$ are H, the compound having for example the structure:

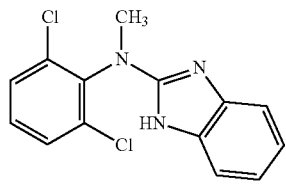 [SMILES: CN(c1nc2ccccc2[nH]1)c1c(Cl)cccc1Cl]

In yet another particular embodiment, the following small molecule, disclosed in Canadian Patent Application No. 2,241,531 (or International Patent Publication No. WO 97/24113), the entire content of which (and in particular pages 1-2 therein) is incorporated herein for all relevant and consistent purposes, may be suitable for use as a substantially systemically bioavailable NHE-binding compound.

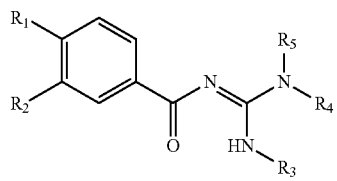

The variables in the structure are defined in the cited patent application, the details of which are incorporated herein by reference.

In yet another particular embodiment, the following small molecule, disclosed in Canadian Patent Application No. 2,241,531 (or International Patent Publication No. WO 97/24113), the entire content of which (and in particular page 49 therein) is incorporated herein for all relevant and consistent purposes, may be suitable for use as a substantially systemically bioavailable NHE-binding compound.

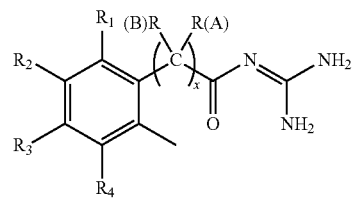

The variables in the structure are defined in the cited patent application, the details of which are incorporated herein by reference.

In yet another particular embodiment, the following small molecule, disclosed in Canadian Patent Application No. 2,241,531 (or International Patent Publication No. WO 97/24113), the entire content of which (and in particular pages 118-120 and 175-177 therein) is incorporated herein for all relevant and consistent purposes, may be suitable for use as a substantially systemically bioavailable NHE-binding compound.

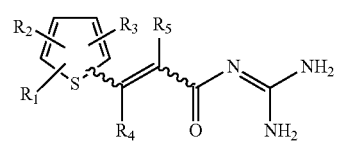

The variables in the structure are defined in the cited patent application, the details of which are incorporated herein by reference.

In yet another particular embodiment, the following small molecule, disclosed in Canadian Patent Application No. 2,241,531 (or International Patent Publication No. WO 97/24113), the entire content of which (and in particular pages 129-131 therein) is incorporated herein for all relevant and consistent purposes, may be suitable for use as a substantially systemically bioavailable NHE-binding compound.

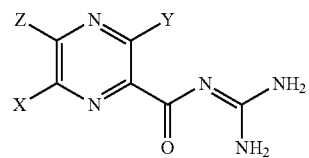

The variables in the structure are defined in the cited patent application, the details of which are incorporated herein by reference. (In this regard it is to be noted that the substituent Z within the structure illustrated above is not to be confused with the moiety Z that, in accordance with the present disclosure, can be attached to the NHE-binding small molecule in order effective render the resulting "NHE-Z" molecule substantially impermeable.).

In yet another particular embodiment, the following small molecule, disclosed in Canadian Patent Application No. 2,241,531 (or International Patent Publication No. WO 97/24113), the entire content of which (and in particular pages 127-129 therein) is incorporated herein for all relevant and consistent purposes, may be suitable for use as a substantially systemically bioavailable NHE-binding compound.

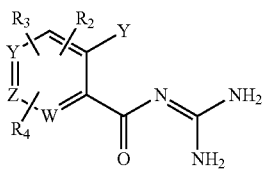

The variables in the structure are defined in the cited patent application, the details of which are incorporated herein by reference. (In this regard it is to be noted that Z within the ring of the structure illustrated above is not to be confused with the moiety Z that, in accordance with the present disclosure, can be attached to the NHE-binding small molecule in order effective render the resulting "NHE-Z" molecule substantially impermeable.)

In yet another particular embodiment, the following small molecule, disclosed in Canadian Patent Application No. 2,241,531 (or International Patent Publication No. WO 97/24113), the entire content of which (and in particular pages 134-137 therein) is incorporated herein for all relevant and consistent purposes, may be suitable for use as a substantially systemically bioavailable NHE-binding compound.

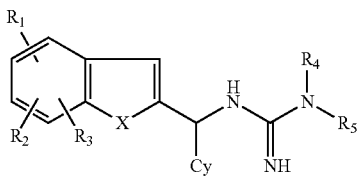

The variables in the structure are defined in the cited patent application, the details of which are incorporated herein by reference.

In yet another particular embodiment, the following small molecule, disclosed in Canadian Patent Application No. 2,241,531 (or International Patent Publication No. WO 97/24113), the entire content of which (and in particular pages 31-32 and 137-139 therein) is incorporated herein for all relevant and consistent purposes, may be suitable for use as a substantially systemically bioavailable NHE-binding compound.

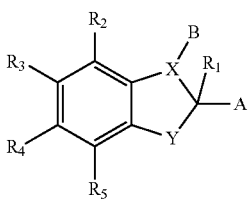

The variables in the structure are defined in the cited patent application, the details of which are incorporated herein by reference.

In yet another particular embodiment, the following small molecule, disclosed in Canadian Patent Application No. 2,241,531 (or International Patent Publication No. WO 97/24113), the entire content of which (and in particular pages 37-45 therein) is incorporated herein for all relevant and consistent purposes, may be suitable for use as a substantially systemically bioavailable NHE-binding compound.

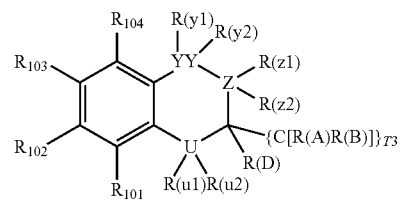

The variables in the structure are defined in the cited patent application, the details of which are incorporated herein by reference. (In this regard it is to be noted that Z within the ring structure illustrated above is not to be confused with the moiety Z that, in accordance with the present disclosure, can be attached to the NHE-binding small molecule in order effective render the resulting "NHE-Z" molecule substantially impermeable.)

In yet another particular embodiment, the following small molecule, disclosed in Canadian Patent Application No. 2,241,531 (or International Patent Publication No. WO 97/24113), the entire content of which (and in particular pages 100-102 therein) is incorporated herein for all relevant and consistent purposes, may be suitable for use as a substantially systemically bioavailable NHE-binding compound.

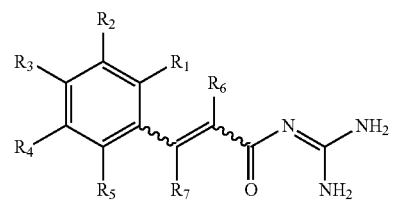

The variables in the structure are defined in the cited patent application, the details of which are incorporated herein by reference (wherein, in particular, the wavy bonds indicate variable length, or a variable number of atoms, therein).

In yet another particular embodiment, the following small molecule, disclosed in Canadian Patent Application No. 2,241,531 (or International Patent Publication No. WO 97/24113), the entire content of which (and in particular pages 90-91 therein) is incorporated herein for all relevant and consistent purposes, may be suitable for use as a substantially systemically bioavailable NHE-binding compound.

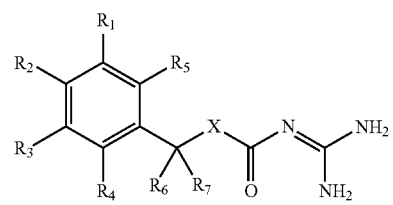

The variables in the structure are defined in the cited patent application, the details of which are incorporated herein by reference.

In yet another particular embodiment, the following small molecule, disclosed in U.S. Pat. No. 5,900,436 (or EP 0822182 B1), the entire contents of which (and in particular column 1, lines 10-55 therein) are incorporated herein by reference for all relevant and consistent purposes, may be suitable for use as a substantially systemically bioavailable NHE-binding compound.

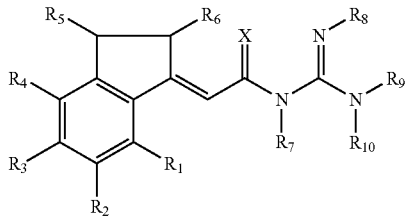

The variables in the structures are defined in the cited patents, the details of which are incorporated herein by reference.

In yet another particular embodiment, the following small molecule, disclosed in Canadian Patent Application No. 2,241,531 (or International Patent Publication No. WO 97/24113), the entire content of which (and in particular pages 35-47 therein) is incorporated herein for all relevant and consistent purposes, may be suitable for use as a substantially systemically bioavailable NHE-binding compound.

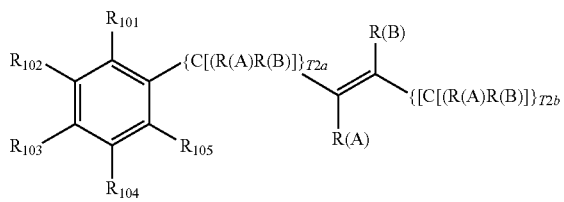

The variables in the structure are defined in the cited patent application, the details of which are incorporated herein by reference.

In yet another particular embodiment, the following small molecule, disclosed in Canadian Patent Application No. 2,241,531 (or International Patent Publication No. WO 97/24113), the entire content of which (and in particular pages 154-155 therein) is incorporated herein for all relevant and consistent purposes, may be suitable for use as a substantially systemically bioavailable NHE-binding compound.

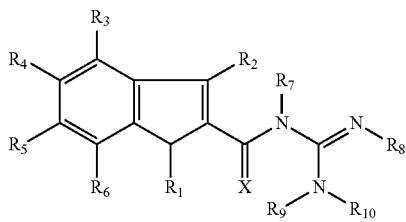

The variables in the structure are defined in the cited patent application, the details of which are incorporated herein by reference.

In yet another particular embodiment, the following small molecule, disclosed in Canadian Patent Application No. 2,241,531 (or International Patent Publication No. WO 97/24113), the entire content of which (and in particular pages 132-133 therein) is incorporated herein for all relevant and consistent purposes, may be suitable for use as a substantially systemically bioavailable NHE-binding compound.

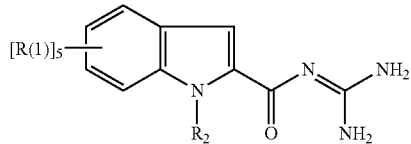

The variables in the structure are defined in the cited patent application, the details of which are incorporated herein by reference.

In yet another particular embodiment, the following small molecule, disclosed in Canadian Patent Application No. 2,241,531 (or International Patent Publication No. WO 97/24113), the entire content of which (and in particular pages 58-65 AND 141-148 therein) is incorporated herein for all relevant and consistent purposes, may be suitable for use as a substantially systemically bioavailable NHE-binding compound.

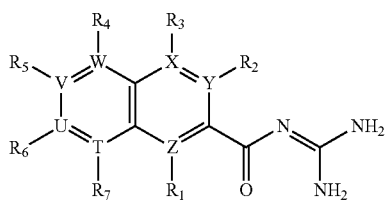

The variables in the structure are defined in the cited patent application, the details of which are incorporated herein by reference. (In this regard it is to be noted that Z within the ring structure illustrated above is not to be confused with the moiety Z that, in accordance with the present disclosure, can be attached to the NHE-binding small molecule in order effective render the resulting "NHE-Z" molecule substantially impermeable.)

In yet another particular embodiment, the following small molecule, disclosed in U.S. Pat. Nos. 6,911,453 and 6,703,405, the entire contents of which (and in particular the text of columns 1-7 and 46 of U.S. Pat. No. 6,911,453 and columns 14-15 of U.S. Pat. No. 6,703,405) are incorporated herein by reference for all relevant and consistent purposes, may be suitable for use as a substantially systemically bioavailable NHE-binding compound.

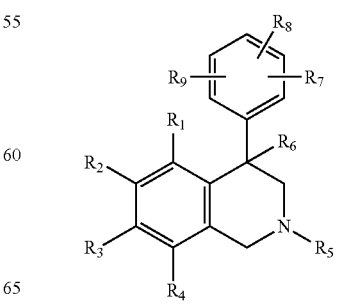

The variables in the structure are defined in the cited patents, the details of which are incorporated herein by reference. A particularly preferred small molecule falling within the above-noted structure is further illustrated below (see, e.g., Example 1 of the U.S. Pat. No. 6,911,453 patent, the entire contents of which are specifically incorporated herein by reference):

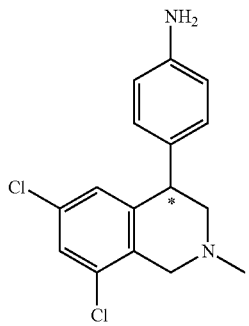 [SMILES: CN1Cc2c(Cl)cc(Cl)cc2C(c2ccc(N)cc2)C1]

In yet another particular embodiment, the following small molecules, disclosed in U.S. Patent Publication Nos. 2004/0039001, 2004/0224965, 2005/0113396 and 2005/0020612, the entire contents of which are incorporated herein by reference for all relevant and consistent purposes, may be suitable for use as a substantially systemically bioavailable NHE-binding compound).

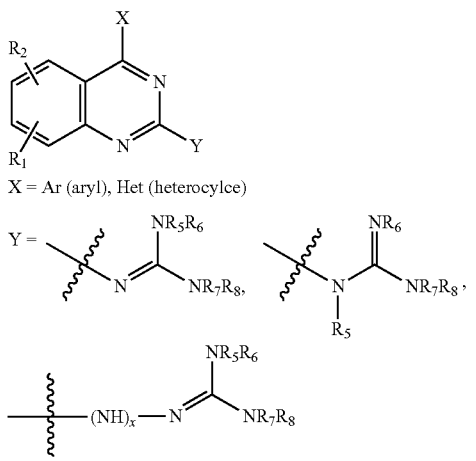

The variables in the structures are defined above and/or in one or more of the cited patent applications, the details of which are incorporated herein by reference, and/or as illustrated above (wherein the broken bonds indicate a point of attachment for the Y moiety to the fused heterocyclic ring). In particular, in various embodiments the combination of X and Y may be as follows:

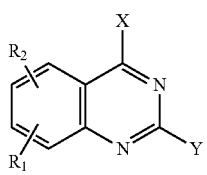

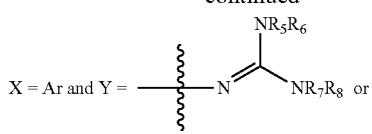

(see, e.g., US 2004/0039001, p. 1 therein)

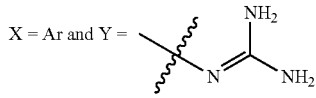

(see, e.g., US 2004/0224965, p. 1 therein)

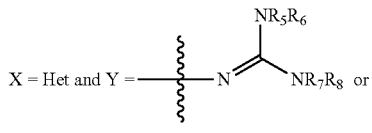

(see, e.g., US 2005/0113396, p. 1 therein)

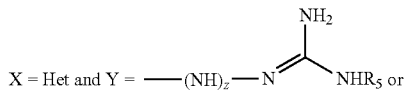

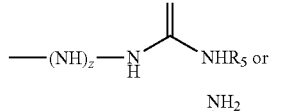

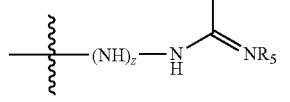

(see, e.g., US 2005/00020612, p. 1 therein)

In a particularly preferred embodiment of the above-noted structure, the small molecule has the general structure:

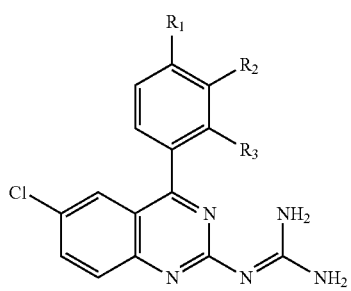

wherein $R_1$, $R_2$ and $R_3$ may be the same or different, but are preferably different, and are independently selected from H, NR'R" (wherein R' and R" are independently selected from H and hydrocarbyl, such as lower alkyl, as defined elsewhere herein) and the structure:

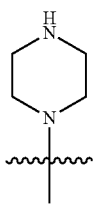

In a more particularly preferred embodiment of the above structure, a small molecule falling within the above-noted structure is further illustrated below (see, e.g., compound I1 on p. 5 of the 2005/0020612 patent application, the entire contents of which are specifically incorporated herein by reference):

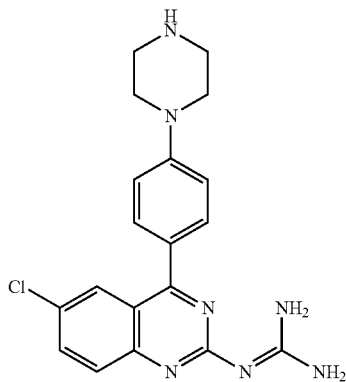 [SMILES: NC(N)=Nc1nc(-c2ccc(N3CCNCC3)cc2)c2cc(Cl)ccc2n1]

In another particularly preferred embodiment, the following small molecule, disclosed in U.S. Pat. No. 6,399,824, the entire content of which (and in particular the text of Example 1 therein) is incorporated herein by reference for all relevant and consistent purposes, may be suitable for use as a substantially systemically bioavailable NHE-binding compound.

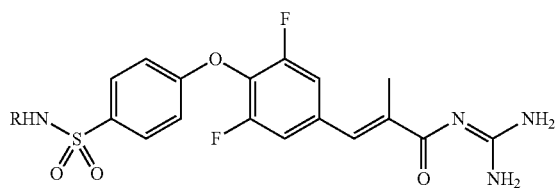

In the structure, R may be preferably selected from H and $(CH_3)_2NCH_2CH_2$—, with H being particularly preferred in various embodiments.

In yet another particular embodiment, the following small molecule, disclosed in U.S. Pat. No. 6,005,010 (and in particular columns 1-3 therein), and/or U.S. Pat. No. 6,166,002 (and in particular columns 1-3 therein), the entire contents of which are incorporated herein by reference for all relevant and consistent purposes, may be suitable for use as a substantially systemically bioavailable NHE-binding compound.

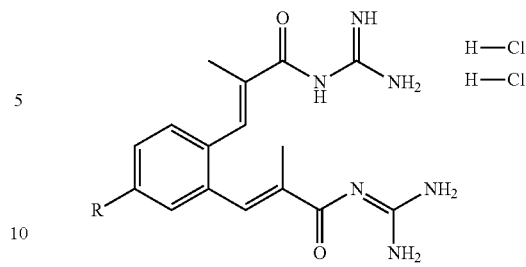

The variable ("R") in the structure is defined in the cited patent application, the details of which are incorporated herein by reference.

In another embodiment, the NHE-binding small molecules suitable for use as substantially systemically bioavailable compounds are disclosed in WO 2010/025856, the entire contents of which are incorporated herein by reference for all relevant and consistent purposes, and have the following structure.

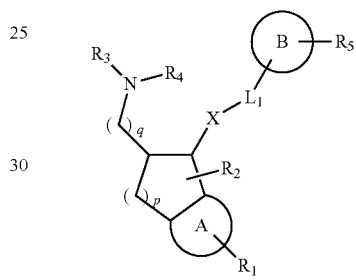

The variables in the structure are defined in WO 2010/025856, the details of which are incorporated herein by reference.

In yet another particularly preferred embodiment, the following small molecule, disclosed in U.S. Patent Application No. 2008/0194621, the entire content of which (and in particular the text of Example 1 therein) is incorporated herein by reference for all relevant and consistent purposes, may be suitable for use as a substantially systemically bioavailable NHE-binding compound.

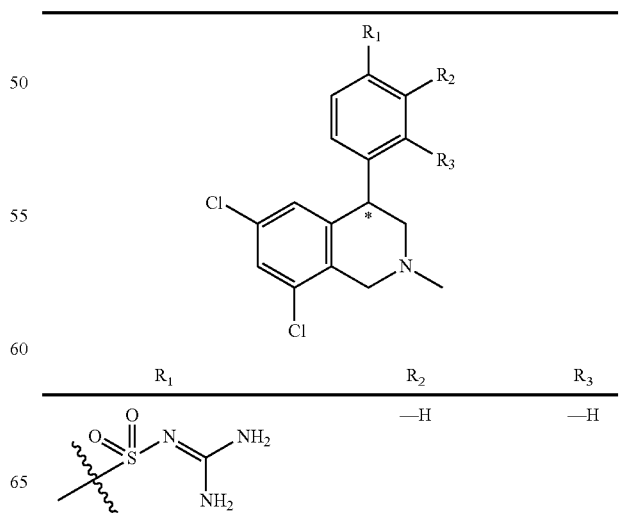

-continued

| R₁ | R₂ | R₃ |
|---|---|---|
| —NH2 | —H | —H |
| —H | (sulfonyl guanidine group) | —H |
| —H | —NH2 | —H |
| —H | —H | —NH2 |

The variables ("R₁", "R₂ and "R₃") in the structure are as defined above, and/or as defined in the cited patent application, the details of which are incorporated herein by reference.

In yet another particularly preferred embodiment, the following small molecule, disclosed in U.S. Patent Application No. 2007/0225323, the entire content of which (and in particular the text of Example 36 therein) is incorporated herein by reference for all relevant and consistent purposes, may be suitable for use as a substantially systemically bioavailable NHE-binding compound.

In yet another particularly preferred embodiment, the following small molecule, disclosed in U.S. Pat. No. 6,911,453, the entire content of which (and in particular the text of Example 35 therein) is incorporated herein by reference for all relevant and consistent purposes, may be suitable for use as a substantially systemically bioavailable NHE-binding compound.

In one particularly preferred embodiment of the present disclosure, the small molecule may be selected from the group consisting of:

SAR218034

In some embodiments, the substantially systemically bioavailable NHE-binding and/or modulating compound is selected from one or more of the following:

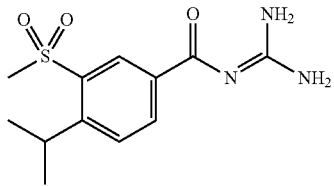

Cariporide

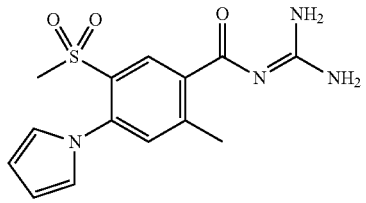

Eniporide

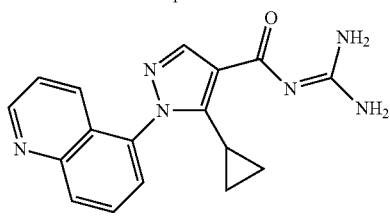

Zoniporide

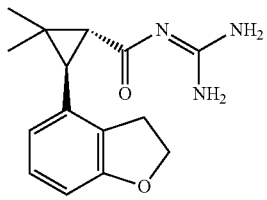

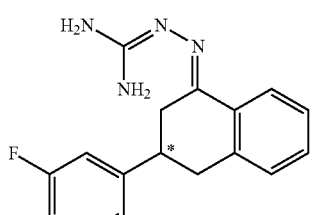

S-3226

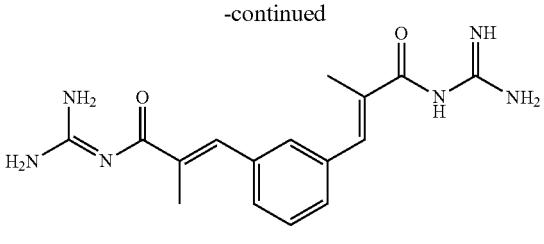

S-2120

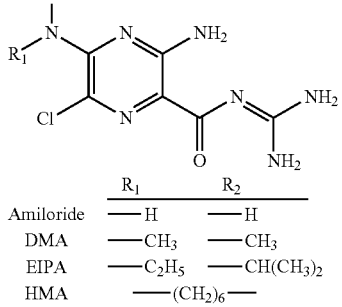

| | $R_1$ | $R_2$ |
|---|---|---|
| Amiloride | —H | —H |
| DMA | —$CH_3$ | —$CH_3$ |
| EIPA | —$C_2H_5$ | —$CH(CH_3)_2$ |
| HMA | —$(CH_2)_6$— | |

IV. Pharmaceutical Compositions and Methods of Treatment

For the purposes of administration, the compounds of the present invention may be administered to a patient or subject as a raw chemical or may be formulated as pharmaceutical compositions. Pharmaceutical compositions of the present invention generally comprise a compound of the invention and a pharmaceutically acceptable carrier, diluent, or excipient. The compound is present in the composition in an amount which is effective to treat a particular disease or condition of interest, as described herein, and preferably with acceptable toxicity to the subject. The activity of compound(s) can be determined by one skilled in the art, for example, as described in the Examples below. Appropriate concentrations and dosages can be readily determined by one skilled in the art.

A compound or composition of the invention may be used in a method for treating essentially any disease or other condition in a subject which would benefit from phosphate uptake inhibition in the gastrointestinal tract and/or kidneys.

For example, by way of explanation, but not limitation, kidney damage reduces the production and activity of renal 1-alpha hydroxylase, leading to lower 1,25-dihydroxy vitamin D. Decreased vitamin D levels limit gastrointestinal calcium absorption, leading to a decline in serum calcium levels. The combination of lower 1,25-dihydroxy vitamin D and lower serum calcium levels synergistically stimulate parathyroid tissue to produce and secrete PTH. A loss of nephrons also impairs Pi excretion, but serum P levels are actively defended by the actions of PTH and FGF-23, and by higher serum P levels, which considerably enhance urinary $PO_4$ excretion. However, tubular actions of PTH and FGF-23 cannot maintain serum P levels in the face of continual nephron loss. Once renal insufficiency progresses to the loss of about 40-50% of renal function, the decrease in the amount of functioning renal tissue does not allow excretion of the full amount of ingested phosphate required to maintain homeostasis. As a result, hyperphosphatemia develops. In addition, a rise in serum P levels impedes renal 1-alpha hydroxylase activity, further suppressing activated vitamin D levels, and further stimulating PTH, leading to secondary hyperparathyroidism (sHPTH).

T-162559

Phosphorus imbalance, however, does not necessarily equate with hyperphosphatemia. Rather, the vast majority of CKD patients not yet on dialysis are normophosphatemic but their phosphorus balance is positive with the excess phosphorus being disposed in the vasculature in the form of ectopic calcification, e.g. intima-localized vascular calcification. Clinically, patients with CKD have elevated levels of FGF-23 that are significantly associated with deteriorating renal function and with decreased calcitriol levels, and it has been hypothesized that the synthesis of FGF-23 is induced by the presence of excess P in the body consecutive to renal failure.

Furthermore, an unrecognized effect on cardiovascular disease is post-prandial phosphatemia, i.e. serum P excursion secondary to meal intake. Further still, studies have investigated the acute effect of phosphorus loading on endothelial function in vitro and in vivo. Exposing bovine aortic endothelial cells to a phosphorus load increased production of reactive oxygen species and decreased nitric oxide, a known vasodilator agent. In the acute P loading study in healthy volunteers described above, it was found that the flow mediated dilation correlated inversely with postprandial serum P (Shuto et al., 2009b, *J. Am. Soc. Nephrol.*, v. 20, no. 7, p. 1504-1512).

Accordingly, in certain embodiments, a compound or composition of the invention can be used in a method selected from one or more of the following: a method for treating hyperphosphatemia, optionally postprandial hyperphosphatemia; a method for treating a renal disease (e.g., chronic kidney disease (CKD), end stage renal disease (ESRD)); a method for reducing serum creatinine levels; a method for treating proteinuria; a method for delaying time to renal replacement therapy (RRT) such as dialysis; a method for reducing FGF23 levels; a method for reducing the hyperphosphatemic effect of active vitamin D; a method for attenuating hyperparathyroidism such as secondary hyperparathyroidism; a method for reducing serum parathyroid hormone (PTH or iPTH); a method for reducing inderdialytic weight gain (IDWG); a method for improving endothelial dysfunction optionally induced by postprandial serum phosphate; a method for reducing vascular calcification or attenuating intima-localized vascular calcification; a method for reducing urinary phosphorus (e.g., enterally administering a GI-acting, substantially systemically non-bioavailable compound); a method for increasing urinary phosphorus (e.g., administering a substantially systemically bioavailable compound, administering a substantially systemically non-bioavailable compound via a route other than enteral administration); a method for normalizing serum phosphorus levels; a method for reducing phosphate burden in an elderly patient; a method for decreasing dietary phosphate uptake; a method for reducing postprandial calcium absorption; a method for reducing renal hypertrophy; a method for reducing heart hypertrophy; and a method for treating obstructive sleep apnea.

In some embodiments, the invention provides the use of a compound or composition for treating hyperphosphatemia, optionally postprandial hyperphosphatemia; treating a renal disease (e.g., chronic kidney disease (CKD), end stage renal disease (ESRD)); reducing serum creatinine levels; treating proteinuria; delaying time to renal replacement therapy (RRT) such as dialysis; reducing FGF23 levels; for reducing the hyperphosphatemic effect of active vitamin D; attenuating hyperparathyroidism such as secondary hyperparathyroidism; reducing serum parathyroid hormone (PTH or iPTH); reducing inderdialytic weight gain (IDWG); improving endothelial dysfunction optionally induced by postprandial serum phosphate; reducing vascular calcification or attenuating intima-localized vascular calcification; reducing urinary phosphorus (e.g., enterally administering a GI-acting, substantially systemically non-bioavailable compound); increasing urinary phosphorus (e.g., administering a substantially systemically bioavailable compound, administering a substantially systemically non-bioavailable compound via a route other than enteral administration); normalizing serum phosphorus levels; reducing phosphate burden in an elderly patient; decreasing dietary phosphate uptake; reducing postprandial calcium absorption; reducing renal hypertrophy; reducing heart hypertrophy; and treating obstructive sleep apnea.

In some embodiments, the invention provides the use of a compound or composition in the manufacture of a medicament for: treating hyperphosphatemia, optionally postprandial hyperphosphatemia; treating a renal disease (e.g., chronic kidney disease (CKD), end stage renal disease (ESRD)); reducing serum creatinine levels; treating proteinuria; delaying time to renal replacement therapy (RRT) such as dialysis; reducing FGF23 levels; for reducing the hyperphosphatemic effect of active vitamin D; attenuating hyperparathyroidism such as secondary hyperparathyroidism; reducing serum parathyroid hormone (PTH or iPTH); reducing inderdialytic weight gain (IDWG); improving endothelial dysfunction optionally induced by postprandial serum phosphate; reducing vascular calcification or attenuating intima-localized vascular calcification; reducing urinary phosphorus (e.g., enterally administering a GI-acting, substantially systemically non-bioavailable compound); increasing urinary phosphorus (e.g., administering a substantially systemically bioavailable compound, administering a substantially systemically non-bioavailable compound via a route other than enteral administration); normalizing serum phosphorus levels; reducing phosphate burden in an elderly patient; decreasing dietary phosphate uptake; reducing postprandial calcium absorption; reducing renal hypertrophy; reducing heart hypertrophy; and treating obstructive sleep apnea.

In some embodiments, the invention provides a pharmaceutical composition comprising a compound or composition for: treating hyperphosphatemia, optionally postprandial hyperphosphatemia; treating a renal disease (e.g., chronic kidney disease (CKD), end stage renal disease (ESRD)); reducing serum creatinine levels; treating proteinuria; delaying time to renal replacement therapy (RRT) such as dialysis; reducing FGF23 levels; for reducing the hyperphosphatemic effect of active vitamin D; attenuating hyperparathyroidism such as secondary hyperparathyroidism; reducing serum parathyroid hormone (PTH or iPTH); reducing inderdialytic weight gain (IDWG); improving endothelial dysfunction optionally induced by postprandial serum phosphate; reducing vascular calcification or attenuating intima-localized vascular calcification; reducing urinary phosphorus (e.g., enterally administering a GI-acting, substantially systemically non-bioavailable compound); increasing urinary phosphorus (e.g., administering a substantially systemically bioavailable compound, administering a substantially systemically non-bioavailable compound via a route other than enteral administration); normalizing serum phosphorus levels; reducing phosphate burden in an elderly patient; decreasing dietary phosphate uptake; reducing postprandial calcium absorption; reducing renal hypertrophy; reducing heart hypertrophy; and treating obstructive sleep apnea.

Hyperphosphatemia refers to a condition in which there is an elevated level of phosphate in the blood. Average serum phosphorus mass in a human adult typically range from about 2.5-4.5 mg/dL (about 0.81-1.45 mmol/L). Levels are often about 50% higher in infants and about 30% higher in children because of growth hormone effects. Hence, certain methods include treating an adult human patient having hyperphosphatemia, where the patient has serum phosphorus mass of about or at least about 4.5, 4.6, 4.7, 4.8, 4.9, 5.0, 5.1, 5.2, 5.3, 5.4, or 5.5 mg/dL. In some aspects, the treatment reduces serum phosphate concentrations or levels in a hyperphosphatemic subject to about 150%, 145%, 140%, 135%, 130%, 125%, 120%, 115%, 110%, 105%, or 100% (normalized) of the normal serum phosphate levels (e.g., 2.5-4.5 mg/dL or 0.81-1.45 mmol/L for an adult). In some aspects, the treatment regimen results in and/or includes monitoring phosphate levels so that they remain within the range of about 2.5-4.5 mg/dL (about 0.81-1.45 mmol/L). Also included are methods of treating a child or adolescent human patient, where the patient has serum phosphorus mass of about or at least about 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or 8.0 mg/dL. As noted herein, in these and related embodiments, administration of a compound or composition described herein may reduce serum phosphorus mass in the subject by about or at least about 5%, 10%, 20%, 30%, 40%, 50%, 60%, 70%, 80%, 90%, 100%, 200% or more.

Certain embodiments relate to methods of treating chronic kidney disease (CKD), a condition characterized by the progressive loss of renal function. Common causes of CKD include diabetes mellitus, hypertension, and glomerulonephritis. Hence, certain methods include treating a subject with CKD, where the subject optionally also has one or more of the foregoing conditions.

In some aspects, a subject is classified as having CKD if they have a glomerular filtration rate (GFR) of less than 60 mL/min/1.73 m$^2$ for about 3 months, whether or not they also present with kidney damage. Certain methods thus include treating a subject with a GFR (e.g., an initial GFR, prior to treatment) of about or less than about 60, 55, 50, 45, 40, 30, 35, 20, 25, 20, 15, or 10 mL/min/1.73 m$^2$ or so. In certain embodiments, administration of a compound or composition described herein may result in an increase in GFR of about or at least about 5%, 10%, 20%, 30%, 40%, 50%, 60%, 70%, 80%, 90%, 100%, 200% or more.

CKD is most often characterized according to the stage of disease: Stage 1, Stage 2, Stage, 3, Stage 4, and Stage 5. Stage 1 CKD includes subjects with kidney damage and a normal or relatively high GFR of about or greater than about 90 mL/min/1.73 m$^2$. Stage 2 CKD includes subjects with kidney damage and a GFR of about 60-89 mL/min/1.73 m$^2$. Stage 3 CKD includes subjects with kidney damage and a GFR of about 30-59 mL/min/1.73 m$^2$. Stage 4 CKD includes subjects with kidney damage and a GFR of about 15-29 mL/min/1.73 m$^2$. Stage 5 CKD includes subjects with established kidney failure and a GFR of less than about 15 mL/min/1.73 m$^2$. Stage 5 CKD is also referred to as end-stage renal disease (ESRD). Accordingly, in certain methods, a subject has Stage 1, 2, 3, 4, or 5, CKD and one or more of its associated clinical characteristics (e.g., defined GFR, kidney damage). In some embodiments, the subject has ESRD and any one or more of its associated clinical characteristics, as described herein and known in the art.

CKD can be characterized according to the affected parts of the kidney. For instance, in certain aspects, CKD includes vascular-associated CKD, including large vessel disease such as bilateral renal artery stenosis, and small vessel disease such as ischemic nephropathy, hemolytic-uremic syndrome and vasculitis. In certain aspects, CKD includes glomerular-associated CKD, including primary glomerular disease such as focal segmental glomerulosclerosis and IgA nephritis, and secondary Glomerular diseases such as diabetic nephropathy and lupus nephritis. Also included is tubulointerstitial-associated CKD, including polycystic kidney disease, drug and toxin-induced chronic tubulointerstitial nephritis, and reflux nephropathy. Certain subjects being treated for CKD may thus have one or more foregoing CKD-associated characteristics.

Certain aspects relate to methods of treating a subject with kidney damage or one or more symptoms/clinical signs of kidney damage. Examples of kidney damage (e.g., CKD-associated kidney damage) and its related symptoms include pathological abnormalities and markers of damage, including abnormalities identified in blood testing (e.g., high blood or serum levels of creatinine, creatinine clearance), urine testing (e.g., proteinuria), and/or imaging studies.

Creatinine is a break-down product of creatine phosphate in muscle, and provides an easily-measured and useful indicator of renal health. Normal human reference ranges for blood or serum creatinine range from about 0.5 to 1.0 mg/dL (about 45-90 µmol/l) for women and about 0.7 to 1.2 mg/dL (about 60-110 µmol/L) for men. Hence, certain subjects for treatment according to the methods described herein (e.g., initially, prior to treatment) may have blood or serum creatine levels that are about or greater than about 1.0, 1.1, 1.2, 1.3, 1.4, 1.5, 1.6, 1.7, 1.8, 1.9, 2.0 mg/dL. In these and related embodiments, administration of a compound or composition described herein may reduce overall blood or serum creatinine levels in a subject by about or at least about 5%, 10%, 20%, 30%, 40%, 50%, 60%, 70%, 80%, 90%, 100%, or 200% or more.

Creatinine clearance rate ($C_{Cr}$ or CrCl) refers to the volume of blood plasma that is cleared of creatinine per unit time; it is measured by comparing the levels of creatinine in blood relative to urine over a period of time (e.g., 24 hours). Creatine clearance is often measured as milliliters/minute (ml/min) or as a function of body mass (ml/min/kg). Depending on the test performed, normal values range from about 97-137 ml/min for males and about 88-128 ml/min for females. Reduced creatinine clearance provides a useful sign of kidney damage. Hence, certain male subjects for treatment according to the methods described herein (e.g., initially, prior to treatment) may have a $C_{Cr}$ of about or less than about 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50 or less. Certain female subjects for treatment according to the methods described herein (e.g., initially, prior to treatment) may have a $C_{Cr}$ of about or less than about 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 47, 46, 45, 44, 43, 42, 41, 40 or less. In some embodiments, administration of a compound or composition described herein may maintain or increase the $C_{Cr}$ in a subject by about or at least about 5%, 10%, 20%, 30%, 40%, 50%, 60%, 70%, 80%, 90%, 100%, or 200% or more.

Proteinuria refers to a condition of excess protein in the urine. It is associated with variety of disease conditions including kidney damage. Proteinuria is often characterized as a urine protein/creatinine ratio of greater than about 45 mg/mmol, or in specific tests an albumin/creatinine ratio of greater than about 30 mg/mmol Certain subjects for treatment according to the methods provided herein (e.g., prior to treatment) have proteinuria, alone or in combination with CKD or other kidney damage, including subjects with a urine protein/creatinine ratio of about or greater than about 45, 50, 55, 60, 65, 70, 75, 80, 85, 90, 95, 100, 105, 110, 115, or 120 mg/mmol and/or a urine albumin/creatinine ratio of about or greater than about 30, 35, 40, 50, 55, 60, 65, 70, 75, 80, 85, 90, 95, 100, 105, 110, 115, or 120 mg/mmol. In these and related embodiments, administration of a compound or composition described herein may treat proteinuria, for instance, by reducing the urine protein/creatinine ratio and/or the urine albumin/creatinine ratio by about or at least about 5%, 10%, 20%, 30%, 40%, 50%, 60%, 70%, 80%, 90%, 100%, or 200% or more.

CKD is associated with a variety of clinical symptoms. Examples include high blood pressure (hypertension), urea accumulation, hyperkalemia, anemia, hyperphosphatemia, hypocalcemia, metabolic acidosis, and atherosclerosis. Thus, in certain methods, a subject with CKD may also have or be at risk for having one or more of the foregoing clinical symptoms. In specific aspects, the subject with CKD has or is at risk for having hyperphosphatemia, as described herein.

Renal replacement therapy (RRT) relates to the various life-supporting treatments for renal failure, including those initiated in the later stages of CKD and ESRD. Examples of RRT include dialysis, hemodialysis, hemofiltration, and renal transplantation. In certain embodiments, a subject for treatment according to the methods provided herein is about to undergo, is undergoing, or has undergone one or more types of RRT. In some embodiments, the subject is not yet undergoing RRT, and administration of a compound described herein delays the time to initiating RRT (e.g., relative to an untreated state) by about or at least about 1, 2, 3, 4, 5, 6, 7, 8, 9, 10, 11, 12 weeks, or by about or at least about 1, 2, 3, 4, 5, 6, 7, 8, 9, 10, 11, 12 months, or by about or at least about 1, 2, 3, 4, 5, 6, 7, 8, 9, 10, 11, 12 years or more.

Fibroblast growth factor 23 (FGF23) regulates phosphorus and vitamin D metabolism. It also promotes phosphaturia and decreases production of calcitriol. Increased FGF23 levels associate with mortality, left ventricular hypertrophy (or left ventricular mass index), myocardial performance, endothelial dysfunction, and progression of CKD. Indeed, FGF23 levels increase progressively in early CKD, presumably as a physiological adaptation to maintain normal serum phosphate levels or normal phosphorus balance. FGF23 levels might also contribute directly to tissue injury in the heart, vessels, and kidneys. Certain embodiments thus relate to the treatment of subjects having increased FGF23 levels in blood or serum (see, e.g., Kirkpantur et al., *Nephrol Dial Transplant.* 26:1346-54, 2011), including subjects with CKD and subjects undergoing dialysis/hemodialysis. In some aspects, administration of a compound or composition described herein reduces the logarithm of FGF23 levels in blood or serum by about or at least about 5%, 10%, 20%, 30%, 40%, 50%, 60%, 70%, 80%, 90%, 100%, or 200% or more.

Vitamin D stimulates, inter alia, the absorption of phosphate ions in the small intestine. Hence, excess levels or activity of Vitamin D can lead to increased phosphate levels and hyperphosphatemia. Certain embodiments thus relate to methods for reducing the hyperphosphatemic effect of active vitamin D, for instance, in a subject having elevated levels or activity of Vitamin D. In some aspects, the subject has Vitamin D toxicity due to over-ingestion of Vitamin D.

Hyperparathyroidism is a disorder in which the parathyroid glands produce too much parathyroid hormone (PTH). Secondary hyperparathyroidism is characterized by the excessive secretion of PTH in response to hypocalcemia and associated hypertrophy of the parathyroid glands. CKD is the most common cause of secondary hyperparathyroidism, generally because the kidneys fail to convert sufficient vitamin D into its active form and to excrete sufficient phosphate. Insoluble calcium phosphate forms in the body and thus removes calcium from the circulation, leading to hypocalcemia. The parathyroid glands then further increase the secretion of PTH in an attempt to increase serum calcium levels. Certain subjects for treatment according to the methods provided herein may thus present (e.g., initially, prior to treatment) with hyperparathyroidism and/or increased PTH levels, optionally in combination with CKD, hyperphosphatemia, hypocalcemia, or other condition or symptom described herein. In some aspects, administration of a compound or composition described herein may reduce hyperparathyroidism including secondary hyperparathyroidism in a subject in need thereof. In some aspects, administration of a compound or composition described herein may reduce PTH levels by about or at least about 5%, 10%, 20%, 30%, 40%, 50%, 60%, 70%, 80%, 90%, 100%, or 200% or more, for instance, by reducing serum phosphate levels and the associated formation of insoluble calcium phosphate, increasing available calcium, and thereby reducing the hypocalcemia-induced production of PTH.

In certain embodiments, the administration of a compound described herein, for instance, a dual-active compound that inhibits both transport of Pi and NHE3-mediated antiport of sodium and hydrogen ions, can provide multiple therapeutic effects to a subject with CKD. In some instances, the administration of a dual-active compound reduces the logarithm of FGF23 levels and serum parathyroid hormone (PTH) levels by about or at least about 5%, 10%, 20%, 30%, 40%, 50%, 60%, 70%, 80%, 90%, 100%, or 200% or more relative to an untreated state, reduces blood pressure, and reduces proteinuria by at least about 5%, 10%, 20%, 30%, 40%, 50%, 60%, 70%, 80%, 90%, 100%, or 200% or more relative to an untreated state.

In particular embodiments, the administration of a compound described herein, for instance, a dual-active compound that inhibits both transport of Pi and NHE3-mediated antiport of sodium and hydrogen ions, can provide multiple therapeutic effects to a subject with ESRD (or Stage 5 CKD). In specific instances, the administration of a dual-active compound reduces serum phosphate concentrations or levels by about or at least about 5%, 10%, 20%, 30%, 40%, 50%, 60%, 70%, 80%, 90%, 100%, or 200% or more relative to an untreated state, and reduces inderdialytic weight gain (IDWG) by about or at least about 5%, 10%, 20%, 30%, 40%, 50%, 60%, 70%, 80%, 90%, 100%, or 200% or more relative to an untreated state. IDWG is an easily measurable parameter that is routinely assessed before, during, or after dialysis (see Sarkar et al., *Semin Dial.* 19:429-33, 2006).

Hyperphosphatemia can lead to endothelial dysfunction in both healthy subjects and those with kidney disease, independently of vascular calcification (see, e.g., Di Marco et al., *Kidney International.* 83:213-222, 2013). Management of serum phosphate level by dietary phosphate restriction or phosphate binders can prevent such subjects from developing cardiovascular disease. Studies have also shown that dietary phosphate restriction can improve aortic endothelial dysfunction (e.g., in CKD with hyperphosphatemia) by increasing the activatory phosphorylation of endothelial nitric oxide synthase and Akt (see, e.g., Van et al., *J Clin Biochem Nutr.* 51:27-32, 2012). Certain subjects for treatment according to the methods provided herein may have or be at risk for having endothelial dysfunction, optionally combined with hyperphosphatemia, kidney disease, or any other condition described herein. By reducing postprandial or dietary phosphate uptake, alone or in combination with dietary phosphate restriction, administration of a compound or composition described herein may reduce the risk of developing endothelial dysfunction, or may improve already-existing endothelial dysfunction, including endothelial dysfunction induced by postprandial serum phosphate.

Hyperphosphatemia is a primary inducer of vascular calcification (see Giachelli, *Kidney Int.* 75:890-897, 2009). Calcium phosphate deposition, mostly in the form of apatite, is the hallmark of vascular calcification and can occur in the blood vessels, myocardium, and cardiac valves. Together with passive deposition of calcium-phosphate in extra-skeletal tissues, inorganic phosphate can also induce arterial calcification directly through "ossification" of the tunica media in the vasculature. Moreover, vascular smooth muscle cells respond to elevated phosphate levels by undergoing an osteochondrogenic phenotype change and mineralizing their extracellular matrix through a mechanism requiring sodium-dependent phosphate cotransporters.

Intimal calcification is usually found in atherosclerotic lesions. Medial calcification is commonly observed in age-associated arteriosclerosis and diabetes, and is the major form of calcification observed in ESRD. Indeed, extensive calcification of the arterial wall and soft tissues is a frequent feature of patients with CKD, including those with ESRD. In valves, calcification is a defining feature of aortic valve stenosis, and occurs in both the leaflets and ring, predominantly at sites of inflammation and mechanical stress. These mechanical changes are associated with increased arterial pulse wave velocity and pulse pressure, and lead to impaired arterial distensibility, increased afterload favoring left ventricular hypertrophy, and compromised coronary perfusion (see Guerin et al., *Circulation.* 103:987-992, 2001). Both intimal and medial calcifications may thus contribute to the morbidity and mortality associated with cardiovascular disease, and are likely to be major contributors to the significant increase in cardiovascular mortality risk observed in CKD and ESRD patients. Control of serum phosphate may thus reduce the formation of calcium/phosphate products and thereby reduce vascular calcification. Accordingly, certain of the subjects for treatment according to the methods provided herein may have or be at risk for developing vascular calcification, including intimal and/or medial calcification, optionally combined with any of hyperphosphatemia, CKD, and ESRD. In some embodiments, administration of a compound or composition described herein reduces the risk of developing or reduces the formation or levels of vascular calcification in a subject in need thereof. In particular embodiments, administration of a compound or composition described herein may reduce vascular calcification by about or at least about 5%, 10%, 20%, 30%, 40%, 50%, 60%, 70%, 80%, 90%, 100%, or 200% or more, for example, relative to an untreated state.

Elderly patients can be especially susceptible to increased phosphate. For instance, dietary and genetic manipulation studies provide in vivo evidence that phosphate toxicity accelerates the aging process and suggest a novel role for phosphate in mammalian aging (see, e.g., Ohnishi and Razzaque, *FASEB J.* 24:3562-71, 2010). These studies show that excess phosphate associates with many signs of premature aging, including kyphosis, uncoordinated movement, hypogonadism, infertility, skeletal muscle wasting, emphysema, and osteopenia, as well as generalized atrophy of the skin, intestine, thymus, and spleen. Certain embodiments thus relate to reducing phosphate burden in an elderly patient, for instance, to reduce any one or more signs of premature aging, comprising administering to the elderly patient a compound described herein. In some instances, an elderly patient is about or at least about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more years of age.

Hypertrophy refers to the increase in the volume of an organ or tissue due to the enlargement of its component cells. Hyperphosphatemia associates with myocardial hypertrophy including left ventricular hypertrophy (see Neves et al., *Kidney Int.* 66:2237-44, 2004; and Achinger and Ayus, *Am Soc Nephrol.* 17(12 Suppl 3):S255-61, 2006) and compensatory renal hypertrophy including glomerular hypertrophy, the latter being often-observed in CKD. Certain subjects for treatment according to the methods provided herein may have (e.g., initially, prior to treatment) myocardial hypertrophy, renal hypertrophy, or both, alone or in combination with CKD or kidney damage. In some embodiments, administration of a compound described herein may reduce myocardial hypertrophy and/or renal hypertrophy by about or at least about 5%, 10%, 20%, 30%, 40%, 50%, 60%, 70%, 80%, 90%, 100%, 200% or more relative to an untreated state.

Sleep apnea is a sleep disorder characterized by abnormal pauses in breathing or abnormally low breathing during sleep. Pauses in breathing are referred to as apneas, and low-breathing events are referred to as hypopneas. These events can last from seconds to minutes, and may occur numerous times in an hour (e.g., >30 times an hour). The apnea-hypoapnea index (AHI) is calculated as the total number of apneas or hypoapneas divided by the hours of sleep. Mild, moderate, and severe sleep apnea are defined respectively as AHI 5-14, 15-29 and ≥30 events/hour. Obstructive sleep apnea (OSA) is the most common type of sleep apnea. In OSA, breathing is obstructed upon collapse of the walls of soft tissue in the airway, which occurs as the muscle tone of the body ordinarily relaxes during sleep. Chronic severe OSA can lead to hypoxemia (low blood oxygen), sleep deprivation, and other complications, including cardiovascular complications. Moreover, a high prevalence of CKD is present in severe OSA patients, including those without hypertension or diabetes. Significantly positive correlations are also found between severity of OSA and renal function impairment (see Chou et al., *Nephrol. Dial. Transplant.* 0:1-6, 2011). Moreover, acute hypoxia is associated with proteinuria, a sign of kidney damage or dysfunction (see Luks et al., *J Am Soc Nephrol.* 19:2262-2271, 2008). OSA and hypoxia thus associate with kidney dysfunction and OSA is considered a stand-alone risk factor for CKD (Chou et al., supra). Accordingly, certain subjects for treatment according to the methods provided herein may have OSA, alone or in combination with CKD or other symptoms of kidney damage. Administration of a compound or composition described herein to a subject with OSA may reduce the AHI by about or at least about 5%, 10%, 20%, 30%, 40%, 50%, 60%, 70%, 80% or more.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

In certain embodiments, a typical dosage of the substantially impermeable or substantially systemically non-bioavailable, compound may be between about 0.2 mg per day and about 2 g per day, or between about 1 mg and about 1 g per day, or between about 5 mg and about 500 mg, or between about 10 mg and about 250 mg per day, which is administered to a subject in need of treatment.

The frequency of administration of the compounds and compositions described herein may vary from once-a-day (QD) to twice-a-day (BID) or thrice-a-day (TID), etc., the precise frequency of administration varying with, for example, the patient's condition, the dosage, etc.

Compounds of the invention, or pharmaceutically acceptable derivatives thereof, may also be administered simultaneously with, prior to, or after administration of one or more other therapeutic or biologically active agents, dietary supplements, or any combination thereof. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

For example, in certain embodiments, the additional biologically active agent included in a pharmaceutical composition (or method) of the invention is selected, for example, from vitamin $D_2$ (ergocalciferol), vitamin $D_3$ (cholecalciferol), active vitamin D (calcitriol) and active vitamin D analogs (e.g. doxercalciferol, paricalcitol).

In other specific embodiments, the additional biologically active agent included in a pharmaceutical composition (or method) of the invention is a phosphate binder, such as sevelamer (e.g., Renvela® (sevelamer carbonate), Renagel® (sevelamer hydrochloride)), lanthanum carbonate (e.g., Fosrenol®), calcium carbonate (e.g., Calcichew®, Titralac®), calcium acetate (e.g. PhosLo®, Phosex®), calcium acetate/magnesium carbonate (e.g., Renepho®, Osva-Ren®), MCI-196, ferric citrate (e.g., Zerenex™), magnesium iron hydroxycarbonate (e.g., Fermagate™), aluminum hydroxide (e.g., Alucaps®, Basaljel®), APS1585, SBR-759, PA-21, and the like.

In some aspects, the compounds may act synergistically with phosphate binders by providing a higher efficacy than the sum of the efficacy of the transport inhibitor and that of a phosphate binder administered alone. Without wishing to be bound by theory, it is believed that the synergy results from the distinct mechanisms of action of a phosphate transport inhibitor and a phosphate binder. More specifically, a phosphate transport inhibitor blocks the epithelial inward transport of phosphate ions whereas phosphate binders sequester free phosphate ions in the lumen of the intestine.

The efficacy of a phosphate binder, as measured by its in vivo binding capacity (mole of phosphate ions bound per gram of binder) is essentially dictated by: i) the density of binding sites (i.e., amine groups in Renvela® (sevelamer), a polymeric amine material; or multivalent cations such calcium or lanthanum in PhosLo® (Calcium acetate) or Fosrenol (lanthanum carbonate)); and ii) the affinity of said binding sites for phosphate ions. Notably only a fraction of the binding sites are available for phosphate binding in vivo as other anions, such as bile acids and fatty acids, compete for the binding sites and therefore lower efficacy. Bound phosphate ions are in equilibrium with free phosphate in the intestinal lumen and are themselves subject to intense pumping from phosphate transport proteins lining up the epithelia. Experiments have shown that the efficacy of phosphate intestinal uptake is remarkably high, exceeding 95% of the phosphate presented to the epithelia. It is believed that the active transport of phosphate contributes to lower the luminal free phosphate concentration and therefore to drive the binding equilibrium of a phosphate binder to lower binding capacity. It is also believed that by reducing the phosphate intestinal transport using a phosphate transport inhibitor, one restores a higher in vivo binding capacity of phosphate sequestering agents. The synergistic effect is thought to be even more pronounced when the contribution of active phosphate transport is increased as a result of, e.g. vitamin D treatment, an agent promoting NaPi2b expression.

In some embodiments, the additional biologically active agent is an inhibitor of the intestinal sodium-dependent phosphate transporter (NaPi2b inhibitor). Examples of NaPi2b inhibitors can be found, for instance, in International Application Nos. PCT/US2011/043267; PCT/US2011/043261; PCT/US2011/043232; PCT/US2011/043266; and PCT/US2011/043263; and U.S. Pat. No. 8,134,015, each of which is incorporated by reference in its entirety.

In certain embodiments, the additionally biologically active agent is niacin or nicotinamide.

It is understood that in the present description, combinations of substituents and/or variables of the depicted formulae are permissible only if such contributions result in stable or reasonably stable compounds.

It will also be appreciated by those skilled in the art that in the process described herein the functional groups of intermediate compounds may need to be protected by suitable protecting groups. Such functional groups include hydroxy, amino, mercapto, and carboxylic acid. Suitable protecting groups for hydroxy include trialkylsilyl or diaryalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

Furthermore, all compounds of the invention which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

DEFINITIONS AND TERMINOLOGY

"Amino" refers to the —$NH_2$ radical.
"Aminocarbonyl" refers to the —C(=O)$NH_2$ radical.
"Carboxy" refers to the —$CO_2$H radical. "Carboxylate" refers to a salt or ester thereof.
"Cyano" refers to the —CN radical.
"Hydroxy" or "hydroxyl" refers to the —OH radical.
"Imino" refers to the =NH radical.
"Nitro" refers to the —$NO_2$ radical.
"Oxo" or "carbonyl" refers to the =O radical.
"Thioxo" refers to the =S radical.
"Guanidinyl" (or "guanidine") refers to the —NHC(=NH)$NH_2$ radical.
"Amidinyl" (or "amidine") refers to the —C(=NH)$NH_2$ radical.
"Phosphate" refers to the —OP(=O)(OH)$_2$ radical.
"Phosphonate" refers to the —P(=O)(OH)$_2$ radical.
"Phosphinate" refers to the —PH(=O)OH radical, wherein each $R^a$ is independently an alkyl group as defined herein.
"Sulfate" refers to the —OS(=O)$_2$OH radical.
"Sulfonate" or "hydroxysulfonyl" refers to the —S(=O)$_2$OH radical.
"Sulfinate" refers to the —S(=O)OH radical.
"Sulfonyl" refers to a moiety comprising a —$SO_2$— group. For example, "alkysulfonyl" or "alkylsulfone" refers to the —$SO_2$—$R^a$ group, wherein $R^a$ is an alkyl group as defined herein.
"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_{1-12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butyryl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —$OR_a$ where $R_a$ is an alkyl radical as defined above containing one to twelve carbon atoms. Unless stated otherwise specifically in the specification, an alkoxy group may be optionally substituted.

"Alkylamino" refers to a radical of the formula —$NHR_a$ or —$NR_aR_a$ where each $R_a$ is, independently, an alkyl radical as defined above containing one to twelve carbon atoms. Unless stated otherwise specifically in the specification, an alkylamino group may be optionally substituted.

"Thioalkyl" refers to a radical of the formula —$SR_a$ where $R_a$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl and the like. Unless stated otherwise specifically in the specification, an aralkyl group may be optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]

heptanyl, and the like. Unless otherwise stated specifically in the specification, a cycloalkyl group may be optionally substituted.

"Cycloalkylalkyl" refers to a radical of the formula —$R_bR_d$ where $R_d$ is an alkylene chain as defined above and $R_g$ is a cycloalkyl radical as defined above. Unless stated otherwise specifically in the specification, a cycloalkylalkyl group may be optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —$R_bR_e$ where $R_b$ is an alkylene chain as defined above and $R_e$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —$R_bR_f$ where $R_b$ is an alkylene chain as defined above and $R_f$ is a heteroaryl radical as defined above. Unless stated otherwise specifically in the specification, a heteroarylalkyl group may be optionally substituted.

The term "substituted" used herein means any of the above groups (i.e., alkyl, alkylene, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, carboxyl groups, phosphate groups, sulfate groups, alkoxy groups, and ester groups; a sulfur atom in groups such as thiol groups, thioalkyl groups, sulfinate groups, sulfone groups, sulfonyl groups, and sulfoxide groups; a phosphorus atom in groups such as phosphinate groups and phosphonate groups; a nitrogen atom in groups such as guanidine groups, amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$, —$(CH_2CH_2O)_{1-10}R_g$, —$(CH_2CH_2O)_{2-10}R_g$, —$(OCH_2CH_2)_{1-10}R_g$ and —$(OCH_2CH_2)_{2-10}R_g$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. The above non-hydrogen groups are generally referred to herein as "substituents" or "non-hydrogen substituents". In addition, each of the foregoing substituents may also be optionally substituted with one or more of the above substituents.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight, length, or other unit described herein.

The term "activate" refers to the application of physical, chemical, or biochemical conditions, substances or processes that a receptor (e.g., pore receptor) to structurally change in a way that allows passage of ions, molecules, or other substances.

The term "active state" refers to the state or condition of a receptor in its non-resting condition.

"Efflux" refers to the movement or flux of ions, molecules, or other substances from an intracellular space to an extracellular space.

"Enteral" or "enteric" administration refers to administration via the gastrointestinal tract, including oral, sublingual, sublabial, buccal, and rectal administration, and including administration via a gastric or duodenal feeding tube.

The term "inactive state" refers to the state of a receptor in its original endogenous state, that is, its resting state.

The term "modulating" includes "increasing" or "enhancing," as well as "decreasing" or "reducing," typically in a statistically significant or a physiologically significant amount as compared to a control. An "increased" or "enhanced" amount is typically a "statistically significant" amount, and may include an increase that is about 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.4, 3.6, 3.8, 4.0, 4.2, 4.3, 4.4, 4.6, 4.8, 5, 6, 7, 8, 9, 10, 15, 20, 30, 40, 50 or more times (e.g., 100, 200, 500, 1000 times) (including all integers and decimal points and ranges in between and above 1, e.g., 5.5, 5.6, 5.7. 5.8, etc.) the amount produced by a control (e.g., the absence or lesser amount of a compound, a different compound or treatment), or the amount of an earlier time-point (e.g., prior to treatment with a compound). A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease (including all integers and decimal points and ranges in between) in the amount or activity produced by a control (e.g., the absence or lesser amount of a compound, a different compound or treatment), or the amount of an earlier time-point (e.g., prior to treatment with a compound).

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., *Design of Prodrugs* (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event or circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

"Stable compound" and "stable structure" are meant to indicate a compound that is sufficiently robust to survive isolation to a useful degree of purity from a reaction mixture, and formulation into an efficacious therapeutic agent.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

"Substantially" or "essentially" includes nearly totally or completely, for instance, 80%, 85%, 90%, 95%, 96%, 97%, 98%, 99% or greater of some given quantity.

The term "secondary" refers to a condition or state that can occur with another disease state, condition, or treatment, can follow on from another disease state, condition, or treatment, or can result from another disease state, condition or treatment. The term also refers to situations where a disease state, condition, or treatment can play only a minor role in creating symptoms or a response in a patient's final diseased state, symptoms or condition.

"Subjects" or "patients" (the terms are used interchangeably herein) in need of treatment with a compound of the present disclosure include, for instance, subjects "in need of phosphate lowering." Included are mammals with diseases and/or conditions described herein, particularly diseases and/or conditions that can be treated with the compounds of the invention, with or without other active agents, to achieve a beneficial therapeutic and/or prophylactic result. A beneficial outcome includes a decrease in the severity of symptoms or delay in the onset of symptoms, modulation of one or more indications described herein (e.g., reduced phosphate ion levels in serum or blood of patients with or at risk for hyperphosphatemia, increased fecal output of phosphate ions in patients with or at risk for hyperphosphatemia), increased longevity, and/or more rapid or more complete resolution of the disease or condition.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

A "therapeutically effective amount" or "effective amount" includes an amount of a compound of the invention which, when administered to a mammal, preferably a human, is sufficient to inhibit or otherwise reduce the transport of phosphate ions from the gastrointestinal lumen, increase fecal output of phosphate ions, reduce serum levels of phosphate ions, treat hyperphosphatemia in the mammal, preferably a human, and/or treat any one or more other conditions described herein. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

EXAMPLES

The following Examples, provided for purposes of illustration, not limitation, illustrate various methods of making compounds of this invention. It is understood that one skilled in the art may be able to make these compounds by similar methods or by combining other methods known to one skilled in the art. It is also understood that one skilled in the art would be able to make, in a similar manner as described below, other compounds of the invention not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Advanced Organic Chemistry: Reactions, Mechanisms, and Structure, 5th edition (Wiley, December 2000)) or prepared as described herein.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diaryalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

Furthermore, all compounds of the invention which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

Example 1

Cell-Based Activity of NHE3 Inhibition and Inhibition of Intestinal of Sodium and Phosphate Absorption The compounds in Table E1, or pharmaceutically acceptable salts thereof, below were tested in a cell-based assay of NHE3 inhibition under prompt conditions (prompt inhibition). These compounds were also tested for the ability to inhibit sodium and phosphate absorption in the intestinal lumen of rats.

TABLE E1
| Cmpd. # | Structure |
|---|---|
| 1 | 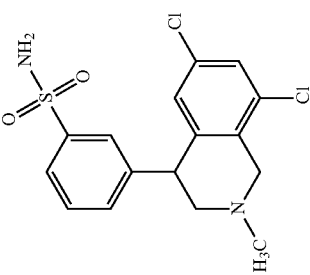 |
| 2 | 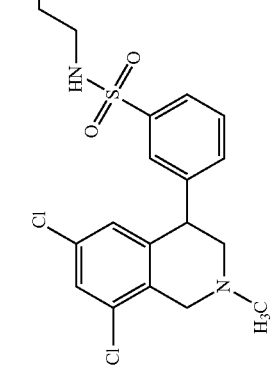 |
| 3 | 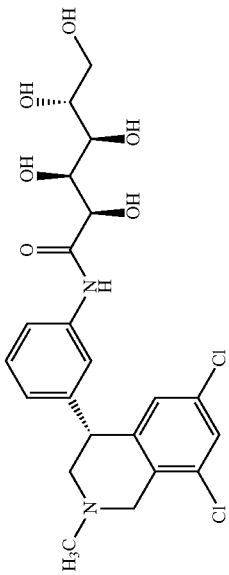 |

TABLE E1-continued

| Cmpd. # | Structure |
|---|---|
| 4 | (chemical structure) |
| 5 | (chemical structure) |

TABLE E1-continued

| Cmpd. # | Structure |
|---|---|
| 6 | (chemical structure) |
| 7 | (chemical structure) |
| 8 | (chemical structure) |

TABLE E1-continued

| Cmpd. # | Structure |
|---|---|
| 9 | (chemical structure) |
| 10 | (chemical structure) |

TABLE E1-continued
| Cmpd. # | Structure |
|---|---|
| 11 | 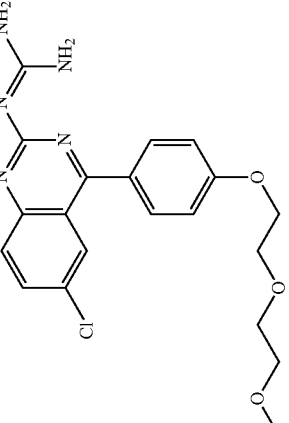 |
| 12 | 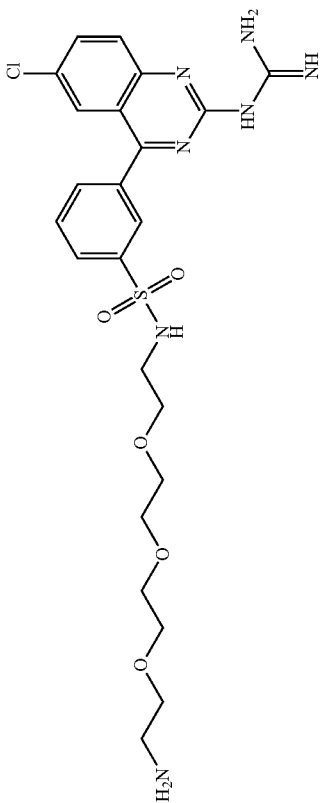 |

TABLE E1-continued
| Cmpd. # | Structure |
|---|---|
| 13 | 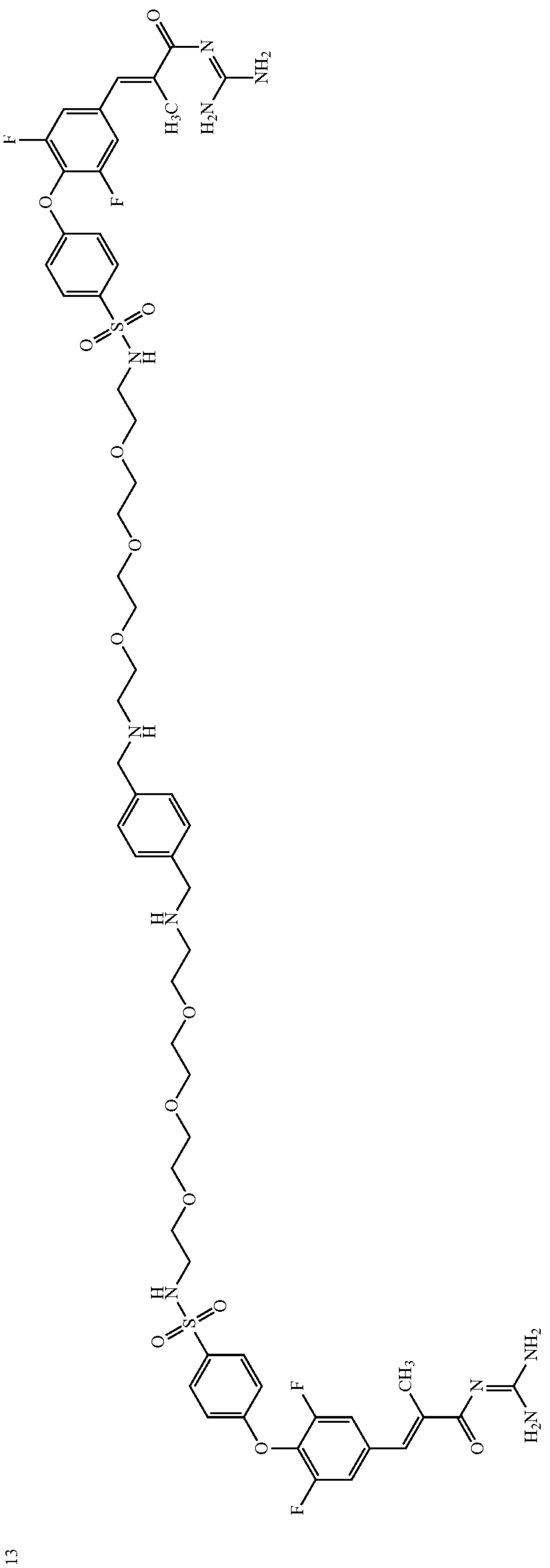 |
| 14 | 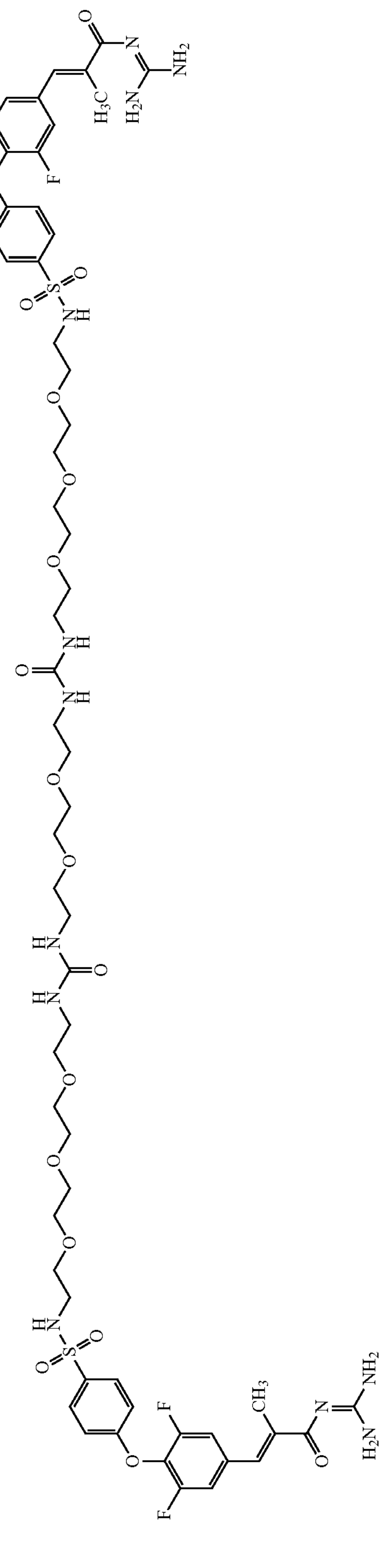 |

TABLE E1-continued

| Cmpd. # | Structure |
|---|---|
| 15 | 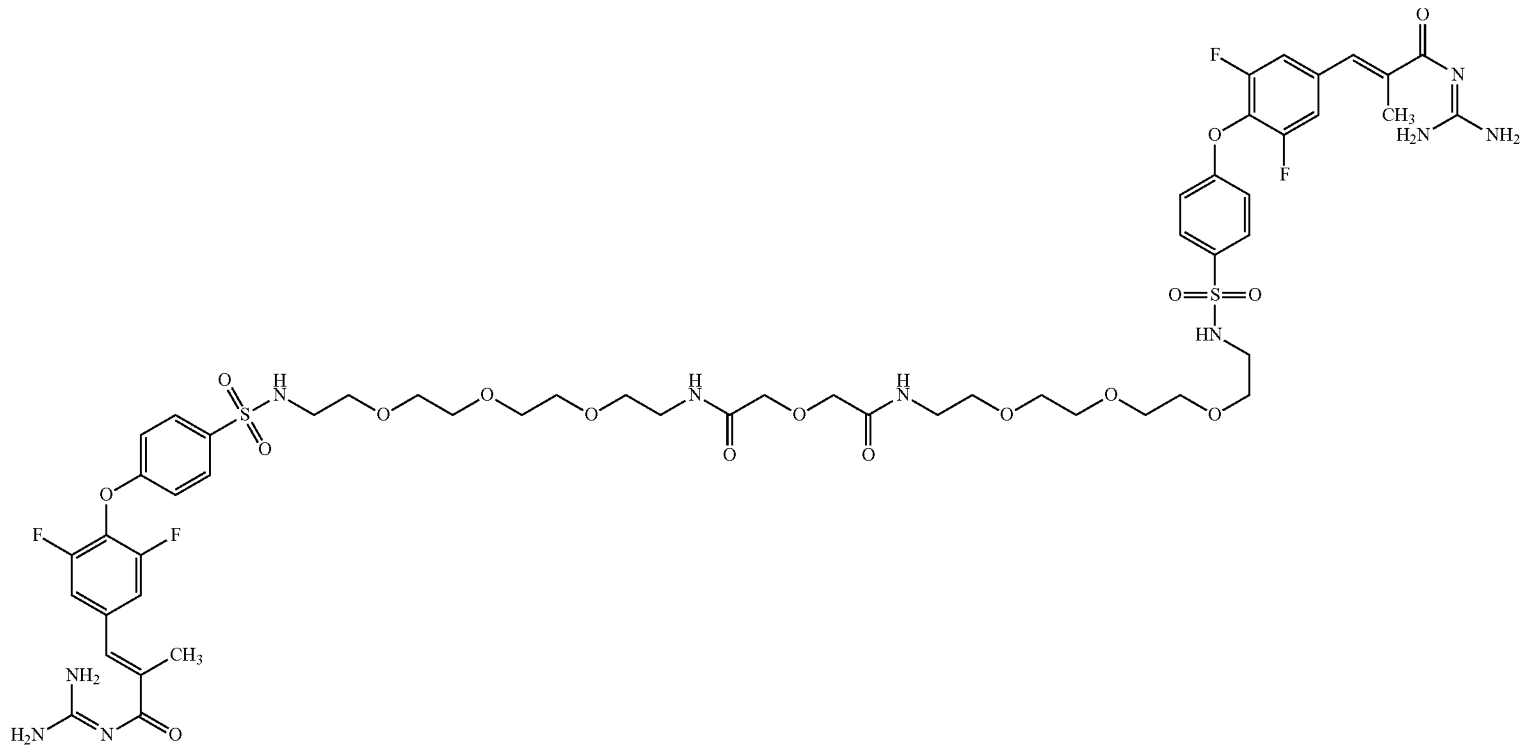 [SMILES: C/C(=C\c1cc(F)c(Oc2ccc(S(=O)(=O)NCCOCCOCCOCCNC(=O)COCC(=O)NCCOCCOCCOCCNS(=O)(=O)c3ccc(Oc4c(F)cc(/C=C(\C)C(=O)N=C(N)N)cc4F)cc3)cc2)c(F)c1)C(=O)N=C(N)N] |

TABLE E1-continued
| Cmpd. # | Structure |
|---|---|
| 16 | 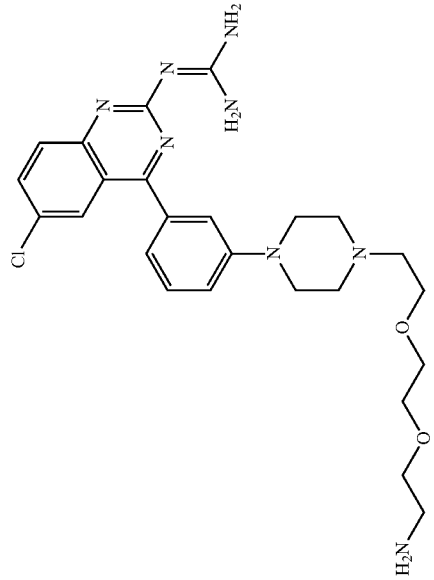 |

TABLE E1-continued
| Cmpd. # | Structure |
|---|---|
| 17 | 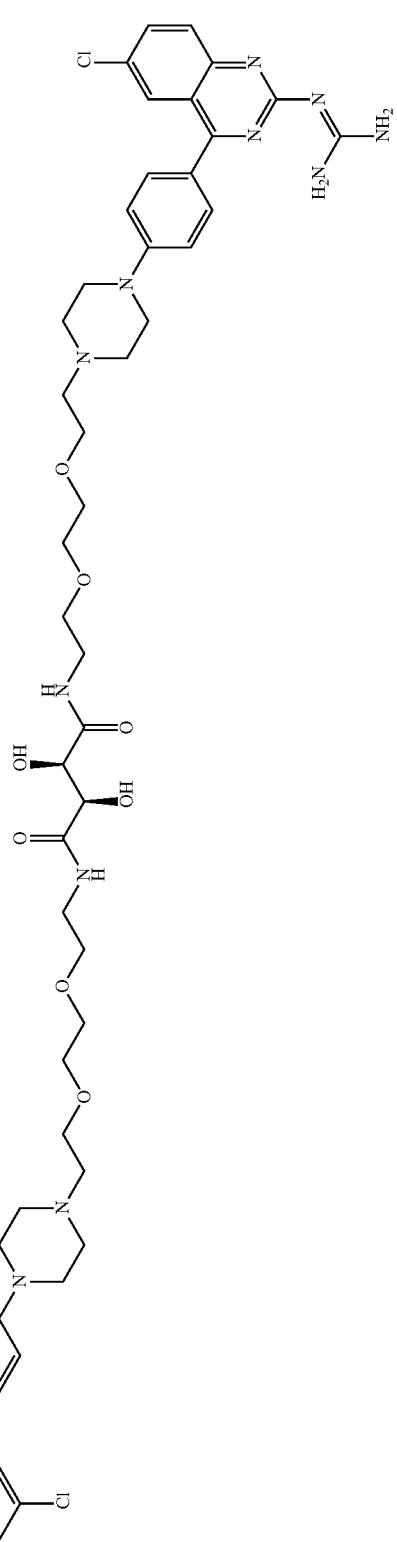 |
| 18 | 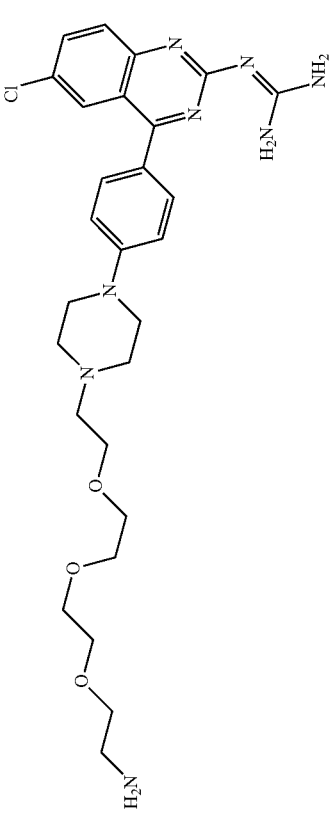 |

TABLE E1-continued

| Cmpd. # | Structure |
|---|---|
| 19 | 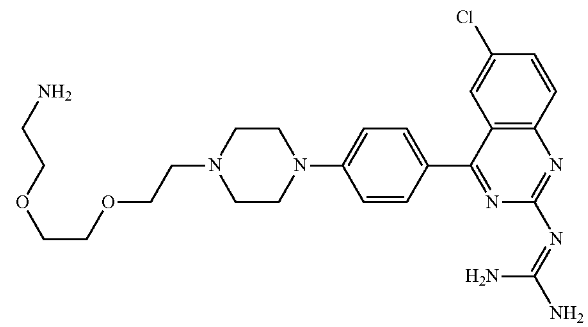 [SMILES: NCCOCCOCCN1CCN(c2ccc(-c3nc(N=C(N)N)nc4ccc(Cl)cc34)cc2)CC1] |
| 20 | 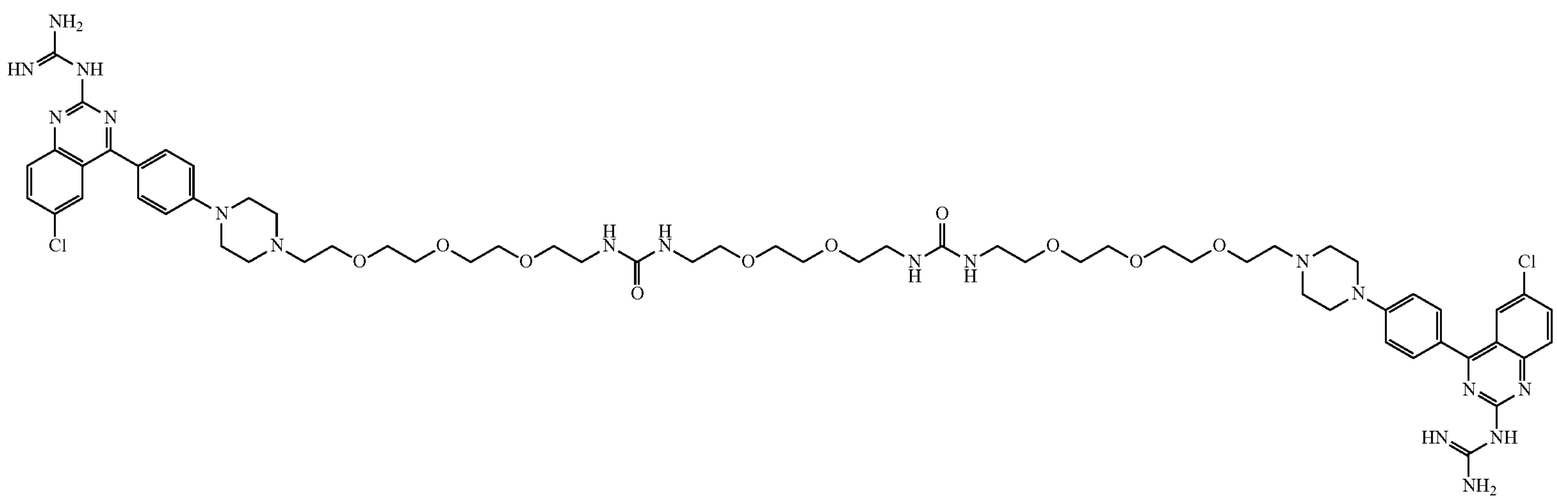 [SMILES: N=C(N)Nc1nc(-c2ccc(N3CCN(CCOCCOCCOCCNC(=O)NCCOCCOCCNC(=O)NCCOCCOCCOCCN4CCN(c5ccc(-c6nc(NC(=N)N)nc7ccc(Cl)cc67)cc5)CC4)CC3)cc2)c2cc(Cl)ccc2n1] |

TABLE E1-continued

| Cmpd. # | Structure |
|---|---|
| 21 | (chemical structure) |
| 22 | (chemical structure) |
| 23 | (chemical structure) |

TABLE E1-continued

| Cmpd. # | Structure |
|---|---|
| 24 | 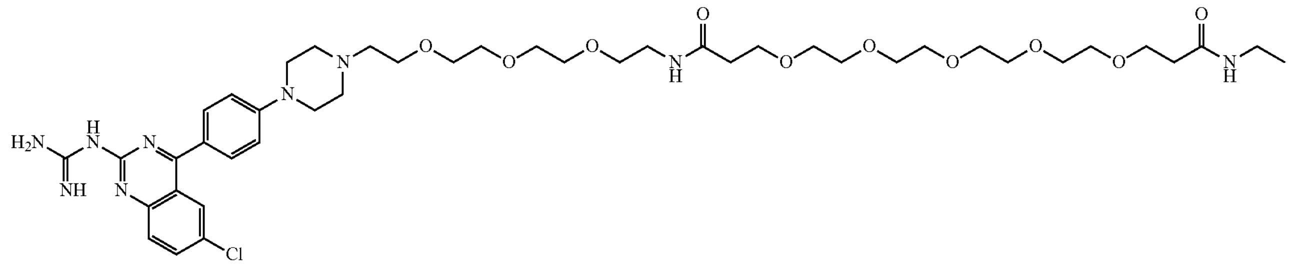 |

TABLE E1-continued

| Cmpd. # | Structure |
|---|---|
| 25 | 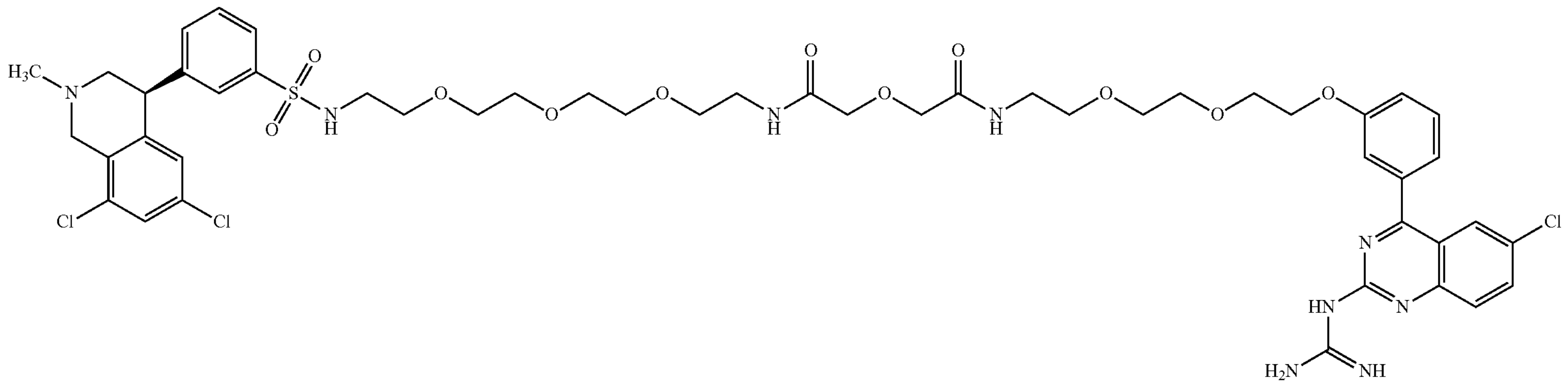 [SMILES: CN1Cc2c(Cl)cc(Cl)cc2[C@H](c2cccc(S(=O)(=O)NCCOCCOCCOCCNC(=O)COCC(=O)NCCOCCOCCOc3cccc(-c4nc(NC(=N)N)nc5ccc(Cl)cc45)c3)c2)C1] |
| 26 | 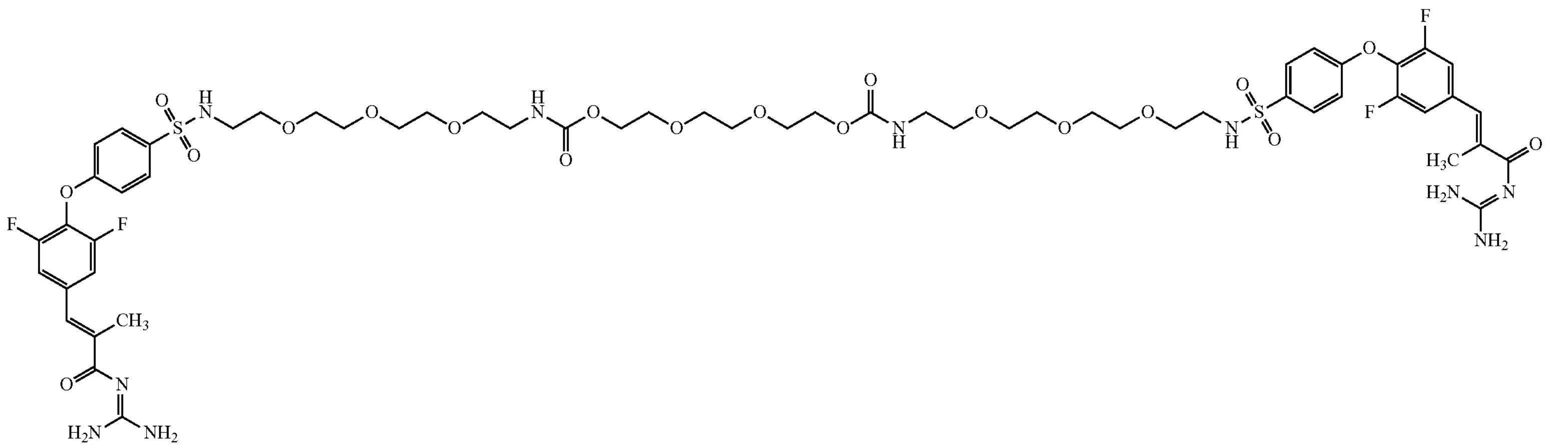 [SMILES: C/C(=C\c1cc(F)c(Oc2ccc(S(=O)(=O)NCCOCCOCCOCCNC(=O)OCCOCCOCCOC(=O)NCCOCCOCCOCCNS(=O)(=O)c3ccc(Oc4c(F)cc(/C=C(\C)C(=O)N=C(N)N)cc4F)cc3)cc2)c(F)c1)C(=O)N=C(N)N] |

TABLE E1-continued

| Cmpd. # | Structure |
|---|---|
| 27 | (chemical structure) |
| 28 | (chemical structure) |

TABLE E1-continued
| Cmpd. # | Structure |
|---|---|
| 29 | 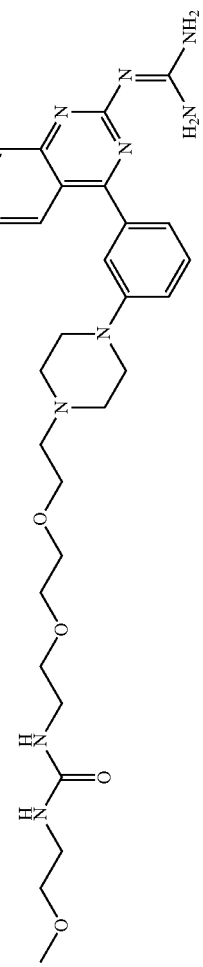 |

TABLE E1-continued

| Cmpd. # | Structure |
|---|---|
| 30 | (structure) |
| 31 | (structure) |

TABLE E1-continued
| Cmpd. # | Structure |
|---|---|
| 32 | 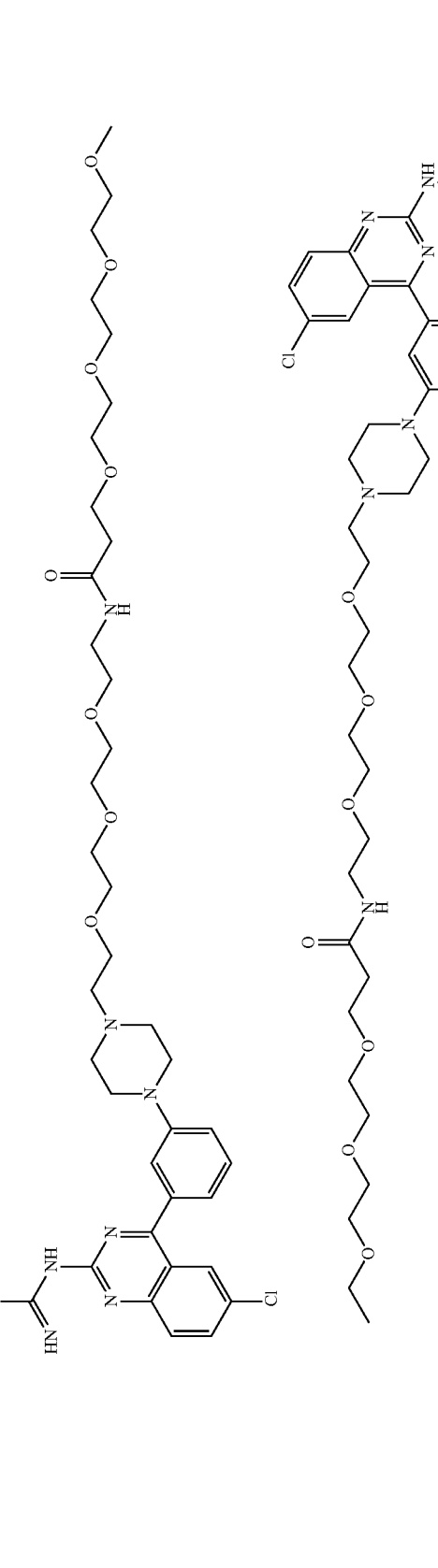 |
| 33 | 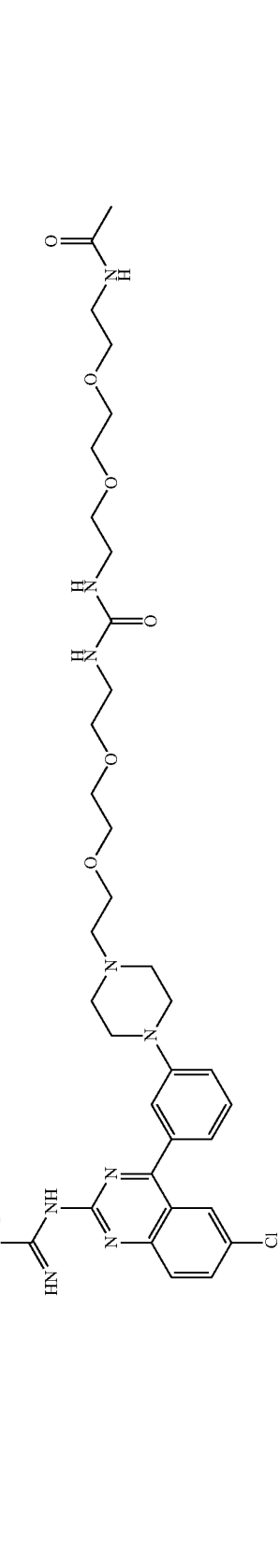 |

TABLE E1-continued
| Cmpd. # | Structure |
|---|---|
| 34 | 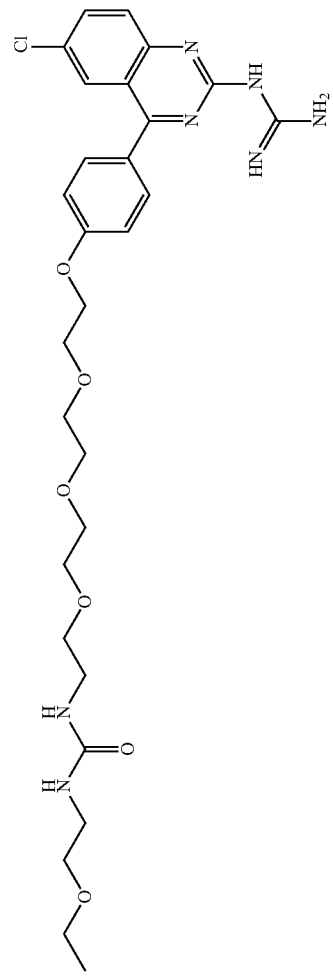 |

TABLE E1-continued
| Cmpd. # | Structure |
|---|---|
| 35 | 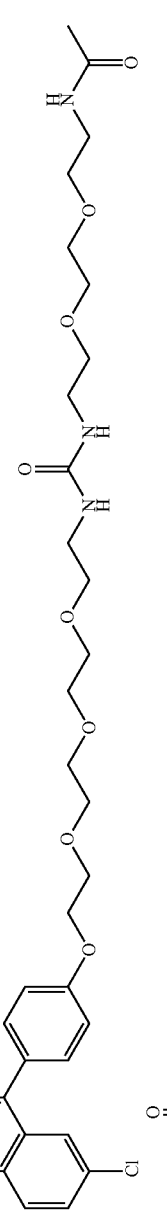 |
| 36 | 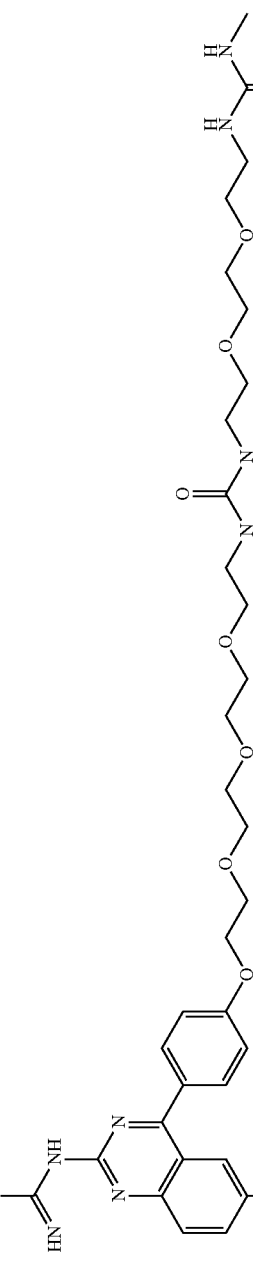 |

TABLE E1-continued

| Cmpd. # | Structure |
|---|---|
| 37 | (6-chloro-4-{4-[2-(2-{2-[2-(3-butylureido)ethoxy]ethoxy}ethoxy)ethoxy]phenyl}quinazolin-2-yl)guanidine-linked PEG-urea structure |
| 38 | 2-{2-[2-(4-{6-chloro-2-guanidinoquinazolin-4-yl}phenoxy)ethoxy]ethoxy}ethylamine structure |
| — | trans-2-piperidinyl-indanyl 4-sulfamoylphenyl ether structure |

TABLE E1-continued
| Cmpd. # | Structure |
|---|---|
| 39 | 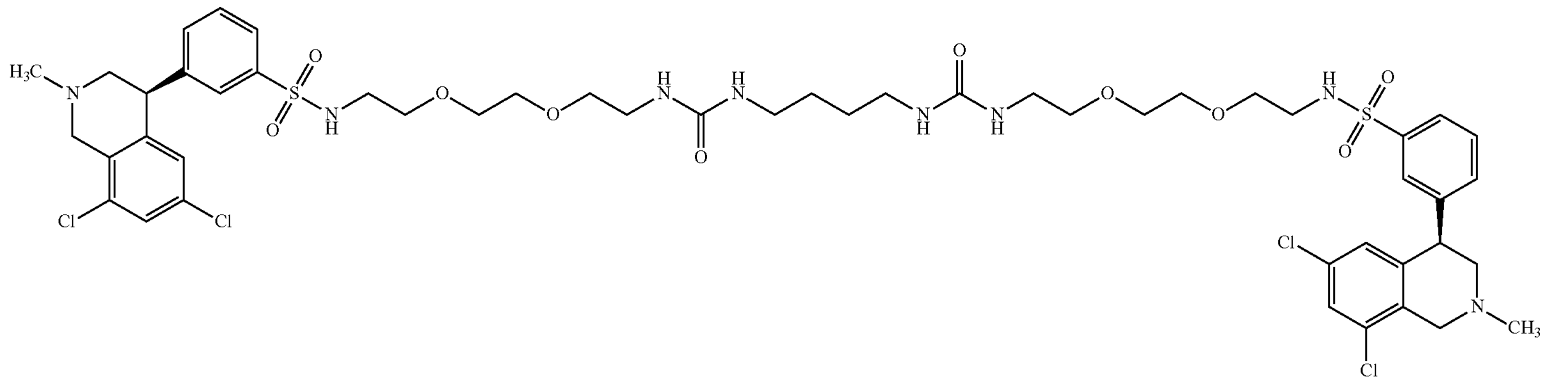 |
| 40 | 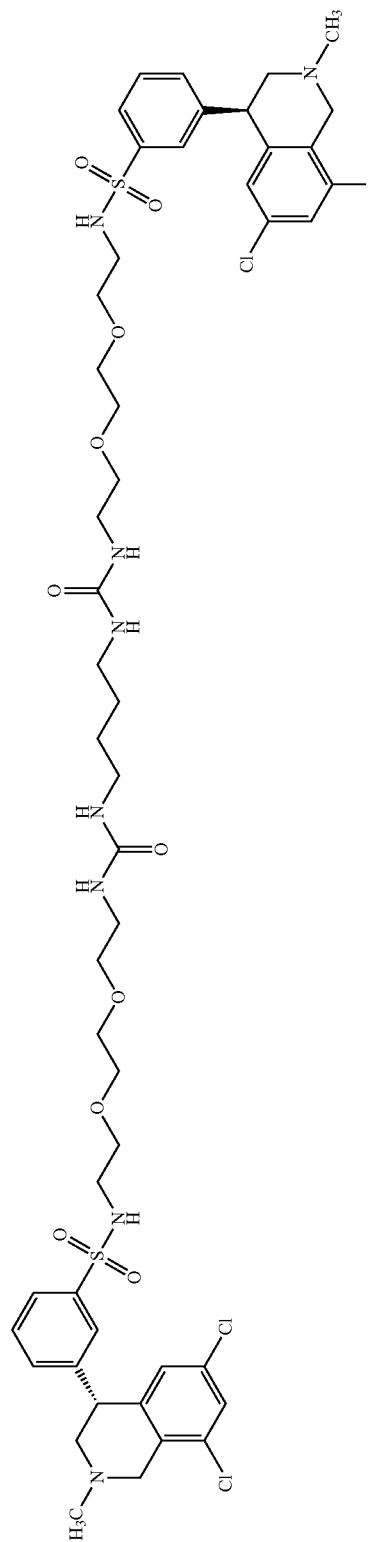 |

TABLE E1-continued

| Cmpd. # | Structure |
|---|---|
| 41 | (chemical structure) |
| 42 | (chemical structure) |

TABLE E1-continued

| Cmpd. # | Structure |
|---|---|
| 43 | (chemical structures) |

TABLE E1-continued

| Cmpd. # | Structure |
|---|---|
| 44 | 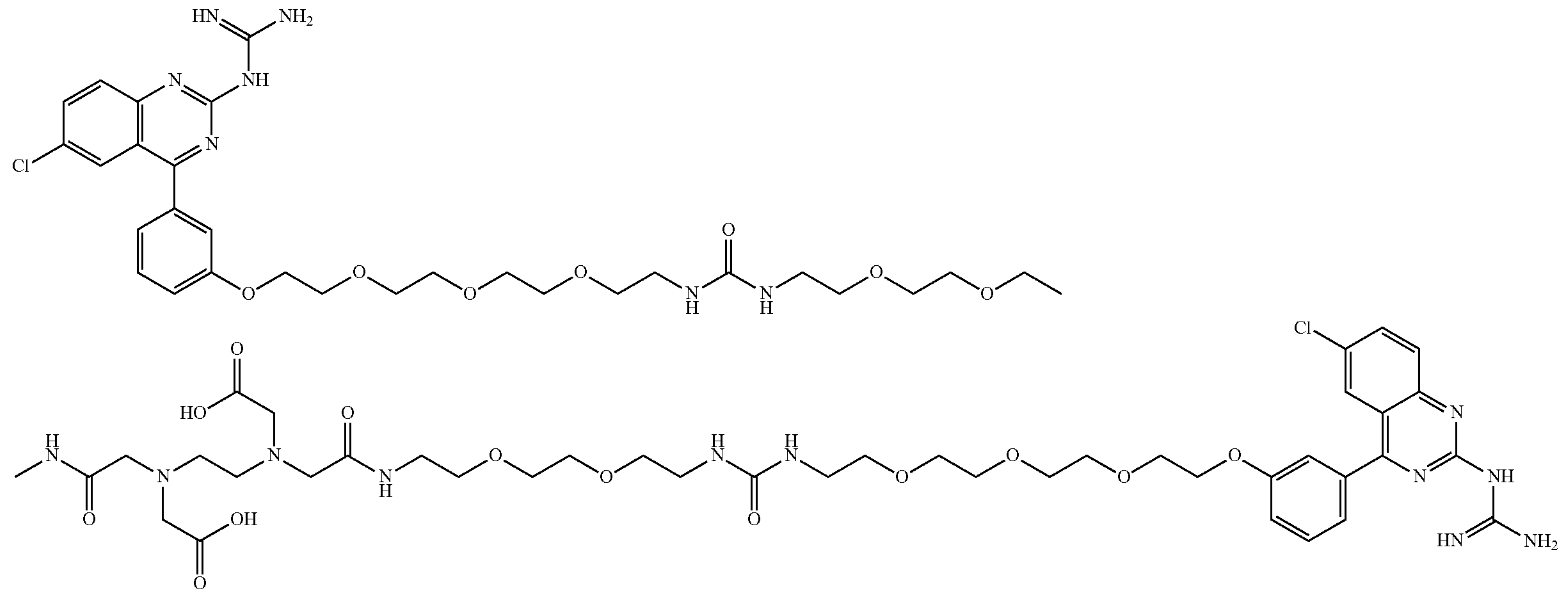 |
| 45 | 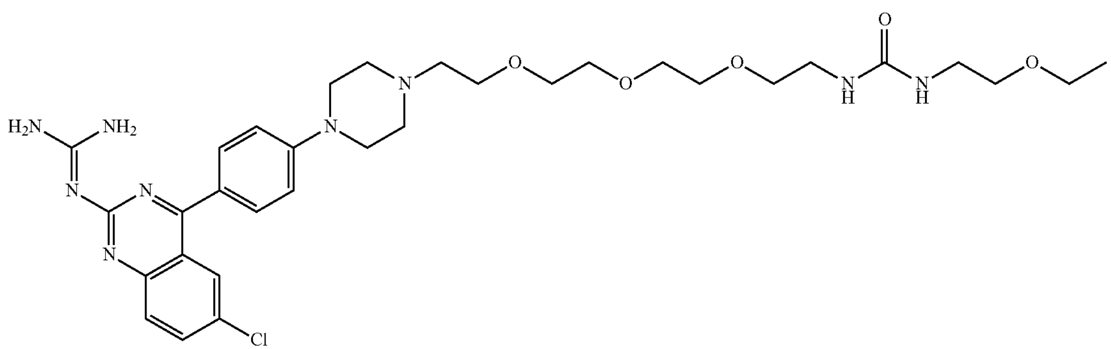 |

TABLE E1-continued
| Cmpd. # | Structure |
|---|---|
| 46 | 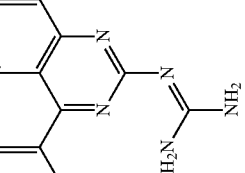 |

| Cmpd. # | Structure |
|---|---|
| 47 | 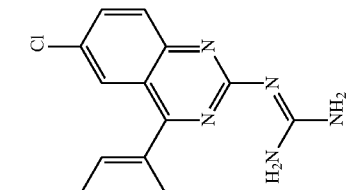 |

TABLE E1-continued

| Cmpd. # | Structure |
|---|---|
| 48 | 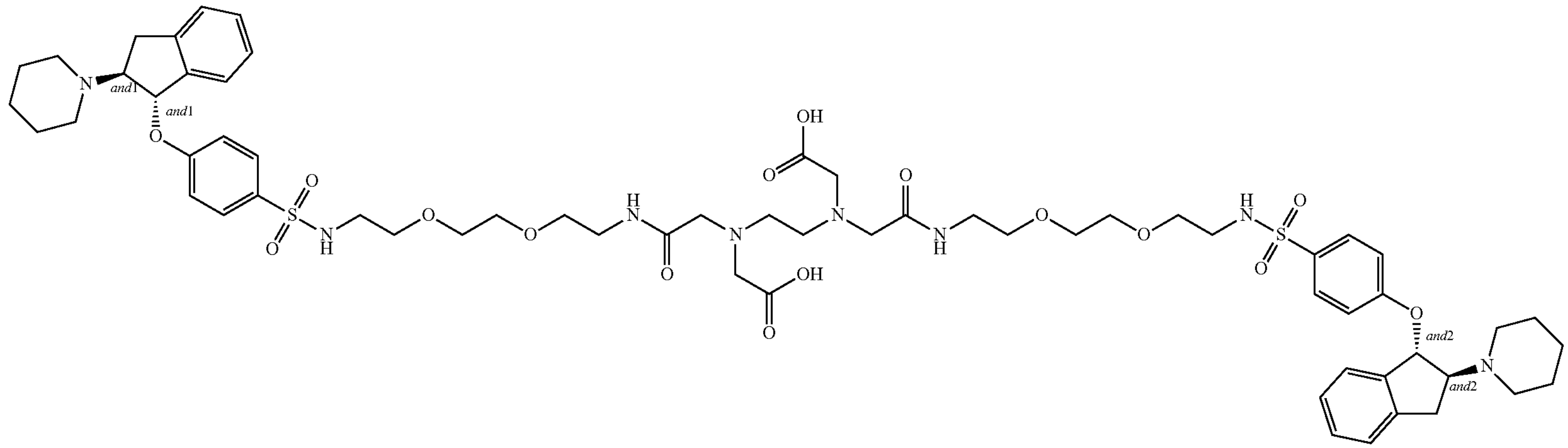 [SMILES: O=C(O)CN(CCN(CC(=O)O)CC(=O)NCCOCCOCCNS(=O)(=O)c1ccc(O[C@H]2c3ccccc3C[C@@H]2N2CCCCC2)cc1)CC(=O)NCCOCCOCCNS(=O)(=O)c1ccc(O[C@H]2c3ccccc3C[C@@H]2N2CCCCC2)cc1] |
| 49 | 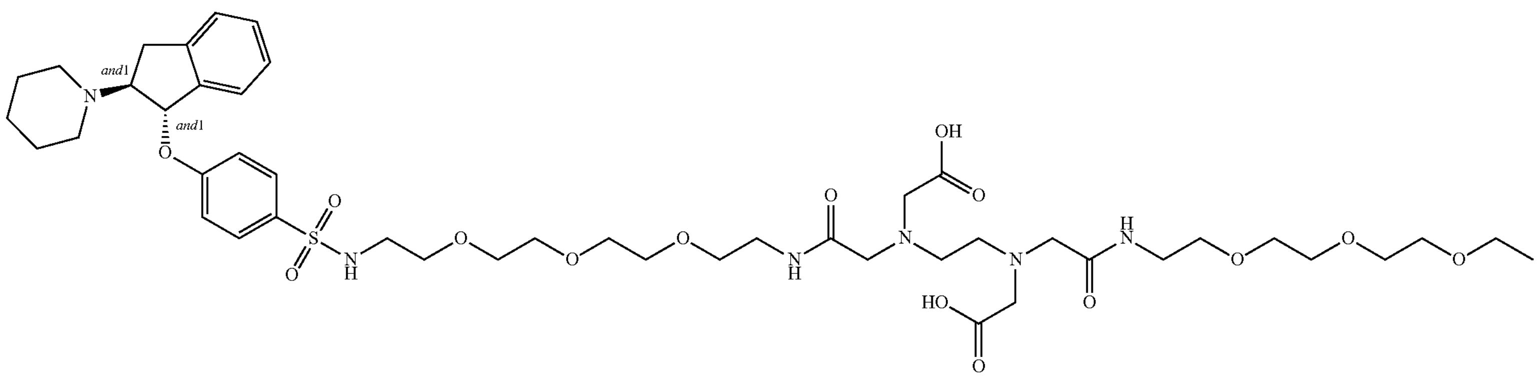 |

TABLE E1-continued
| Cmpd. # | Structure |
|---|---|
| 50 | 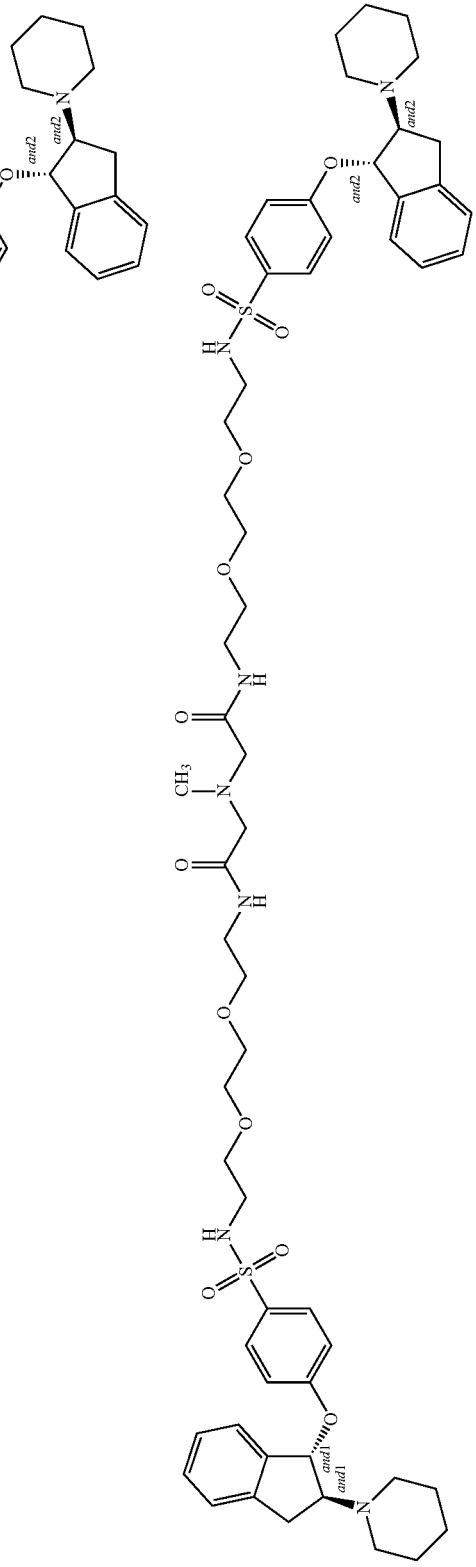 |
| 51 | 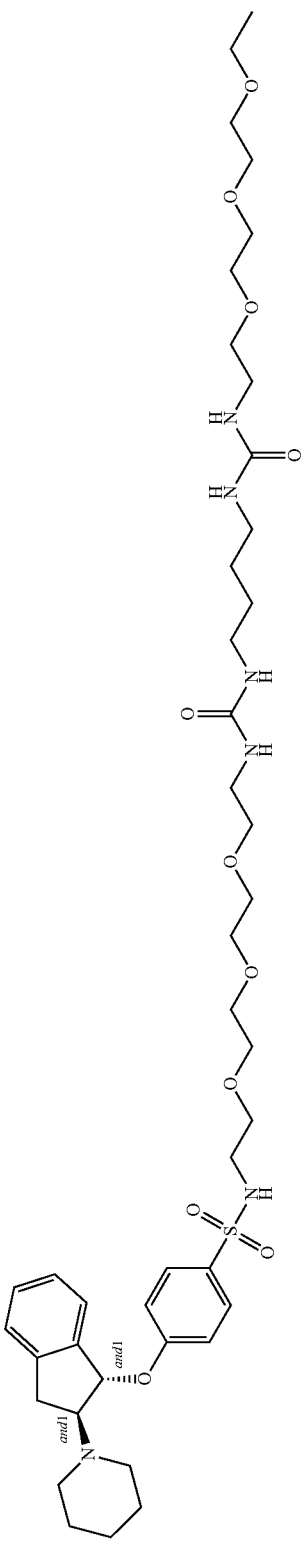 |

TABLE E1-continued
| Cmpd. # | Structure |
|---|---|
| 52 | 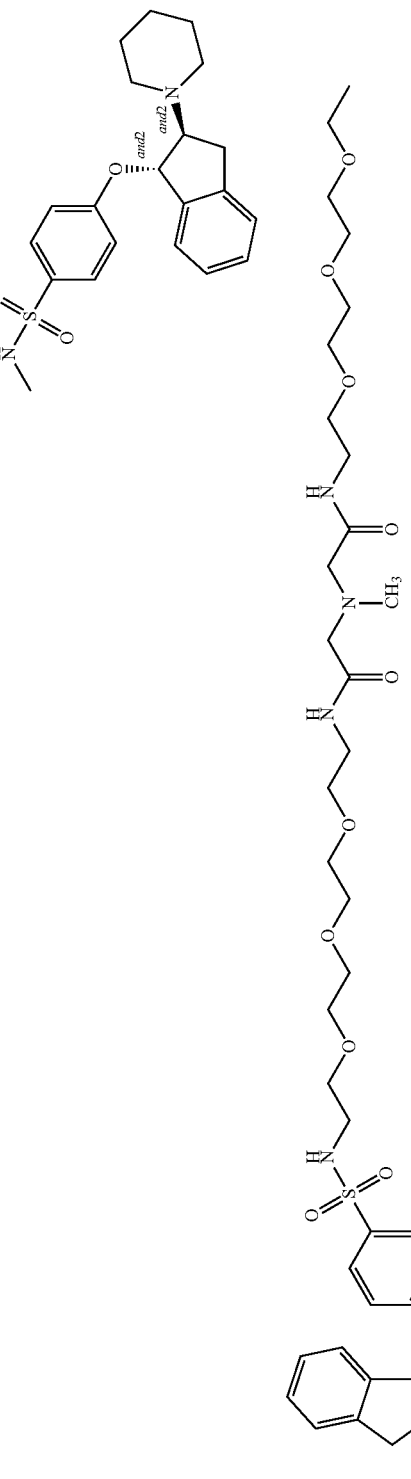 |

TABLE E1-continued
| Cmpd. # | Structure |
|---|---|
| 53 | 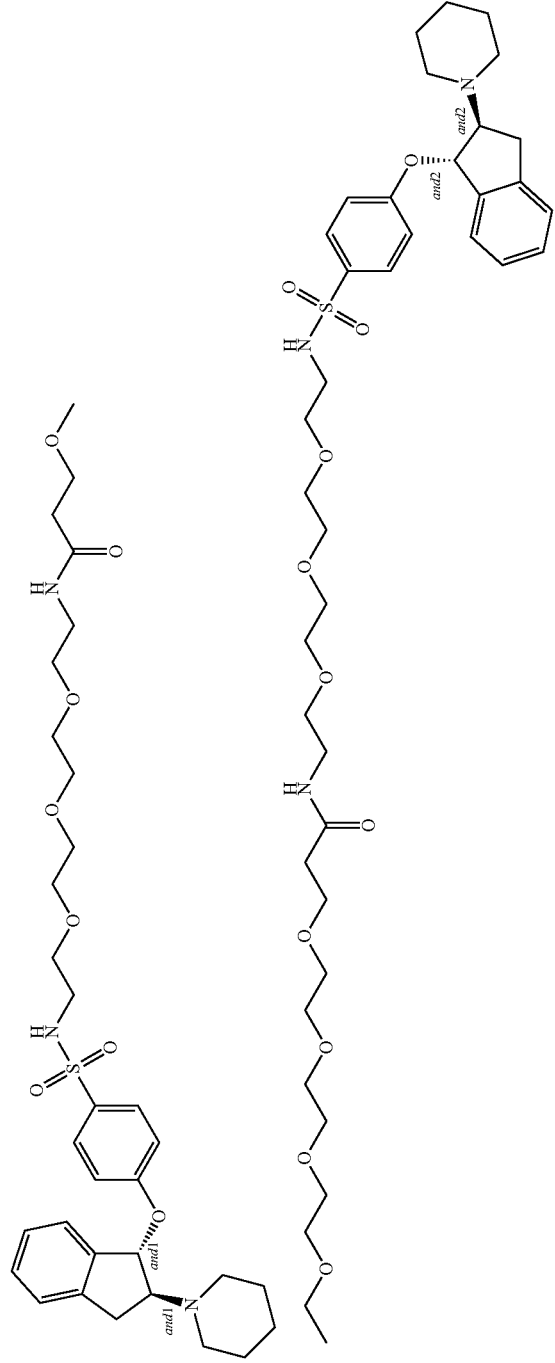 |
| 54 | 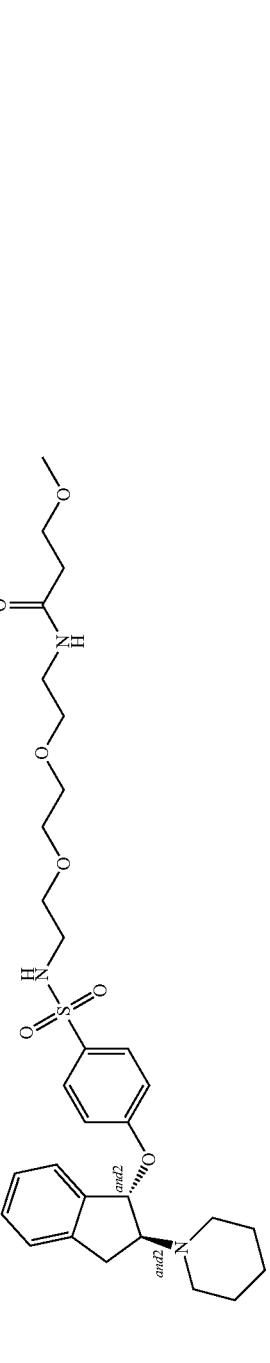 |

TABLE E1-continued
| Cmpd. # | Structure |
|---|---|
| 55 | 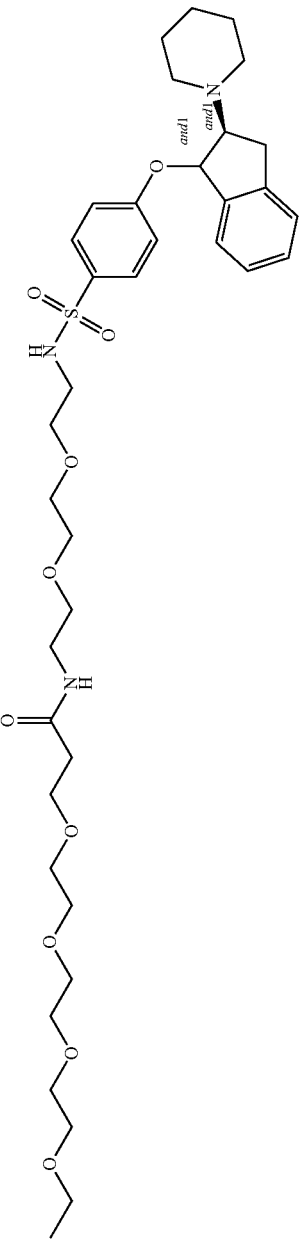 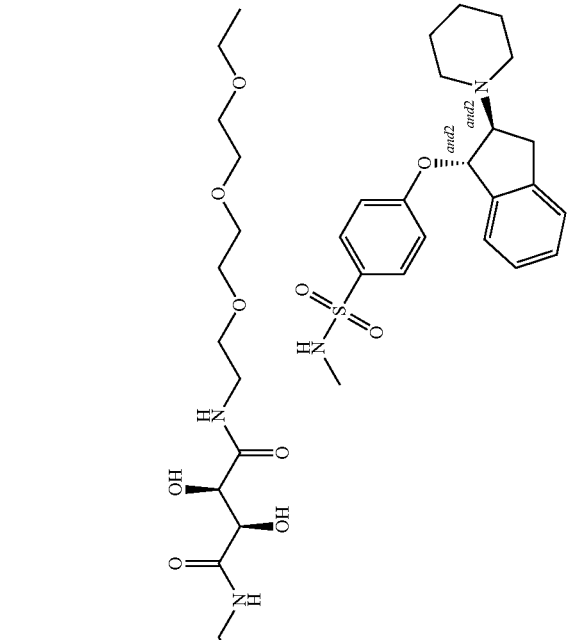 |

TABLE E1-continued
| Cmpd. # | Structure |
|---|---|
| 56 | 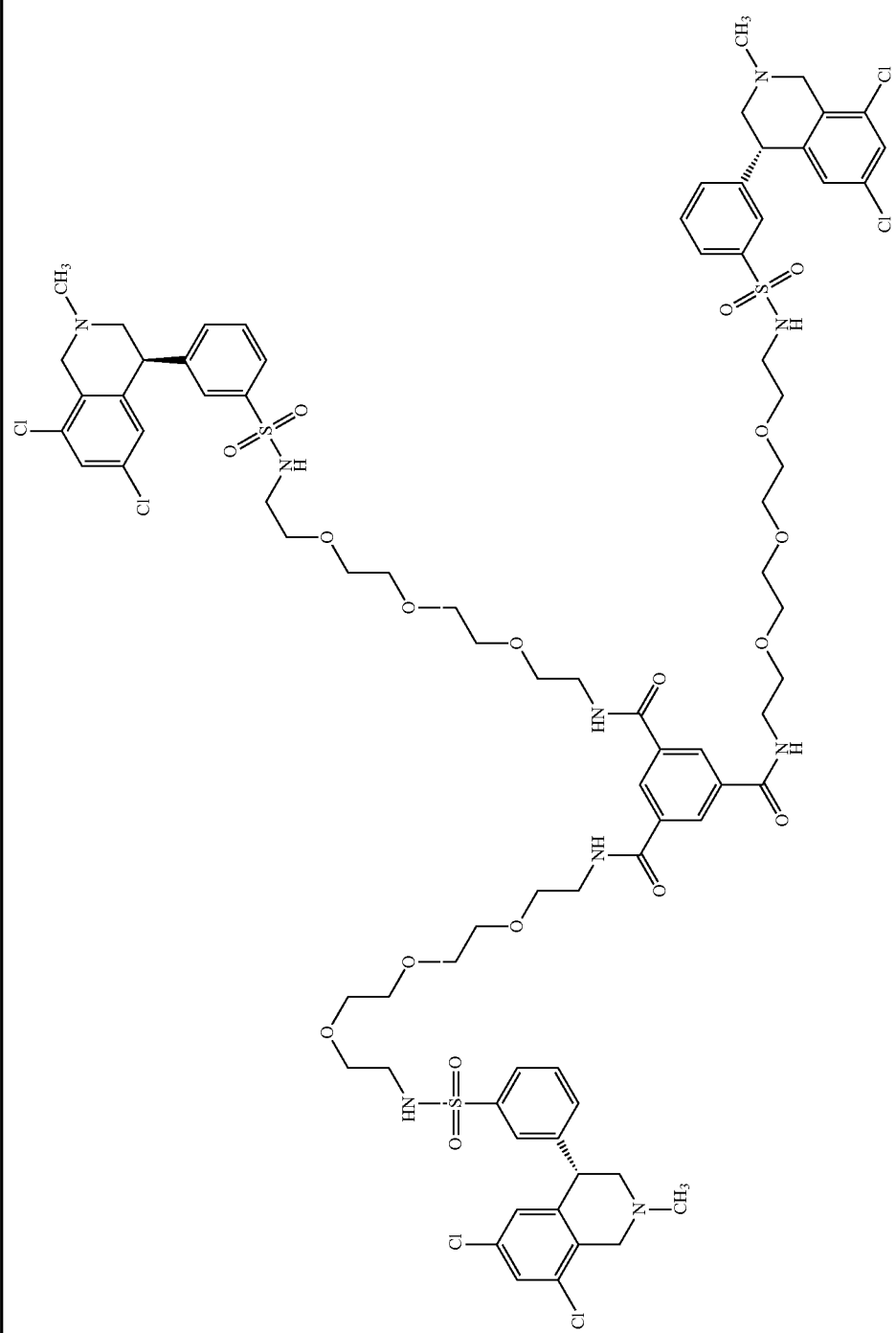 |

TABLE E1-continued
| Cmpd. # | Structure |
|---|---|
| 57 | 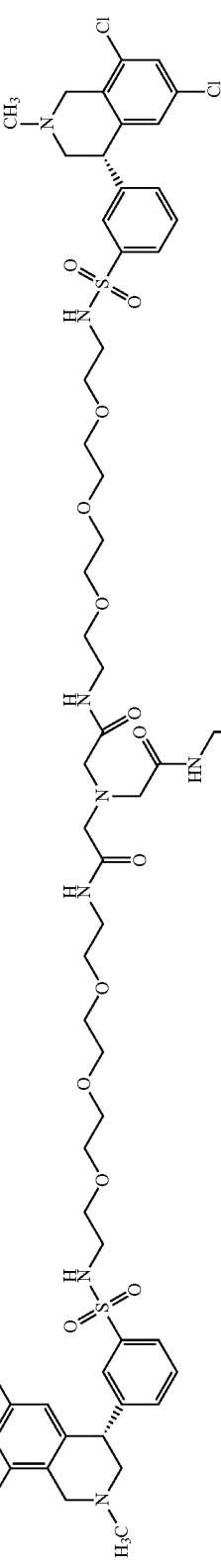 |

TABLE E1-continued

| Cmpd. # | Structure |
|---|---|
| 58 | ![Structure of compound 58: (S)-5,8-dichloro-2-methyl-1,2,3,4-tetrahydroisoquinoline substituted at the 4-position with a phenyl ring bearing a sulfonamide linked to a triethylene glycol monomethyl ether chain] |

TABLE E1-continued
| Cmpd. # | Structure |
|---|---|
|  |  |

TABLE E1-continued
| Cmpd. # | Structure |
|---|---|
| 59 | 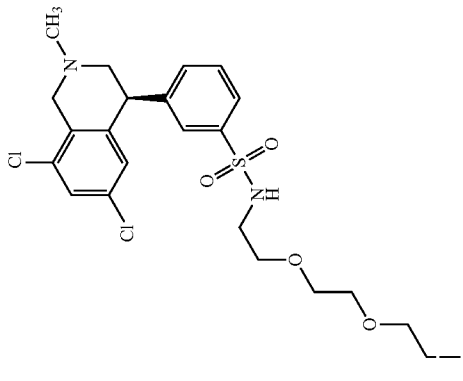 |

TABLE E1-continued

| Cmpd. # | Structure |
|---|---|
| 60 | 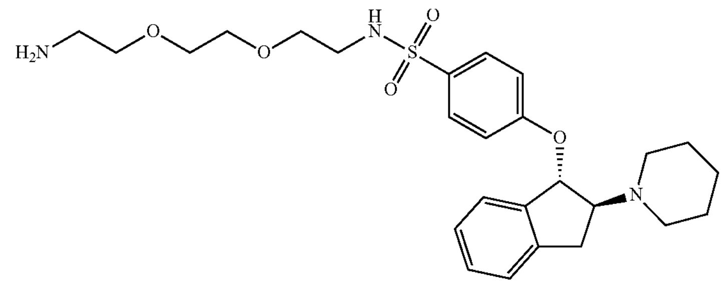 [SMILES: NCCOCCOCCNS(=O)(=O)c1ccc(O[C@H]2c3ccccc3C[C@@H]2N2CCCCC2)cc1] |
| 61 | 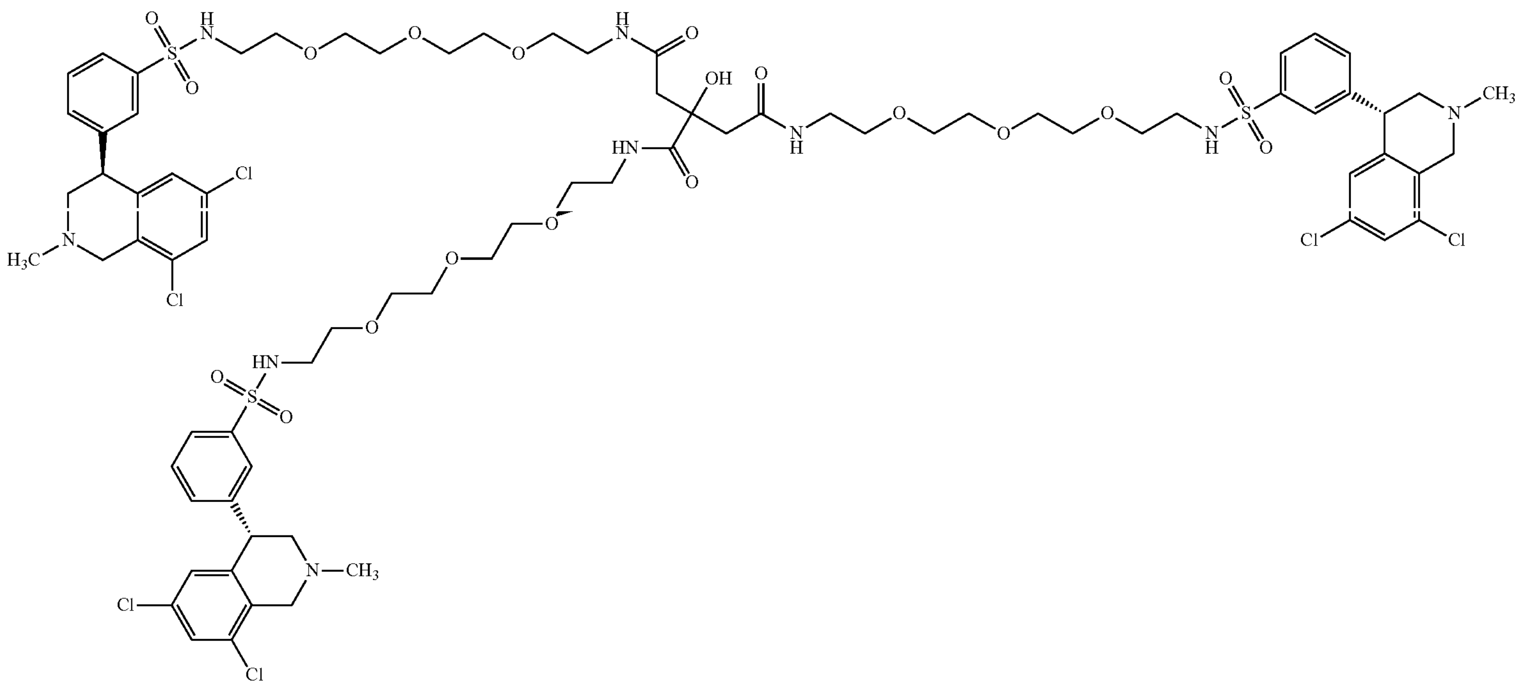 |

| Cmpd. # | Structure |
|---|---|
| 62 | 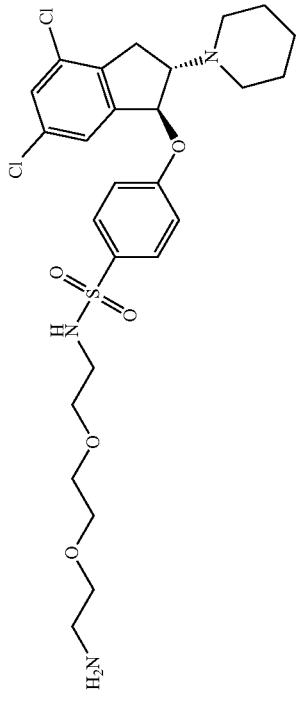 |
| 63 | 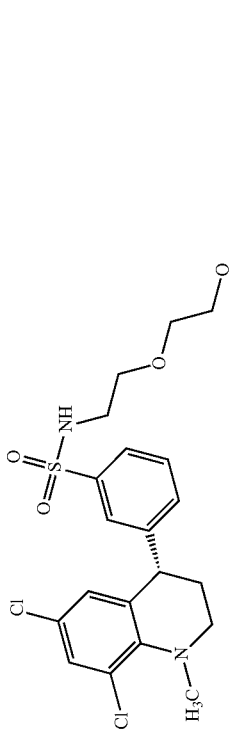 |

| Cmpd. # | Structure |
|---|---|
|  | 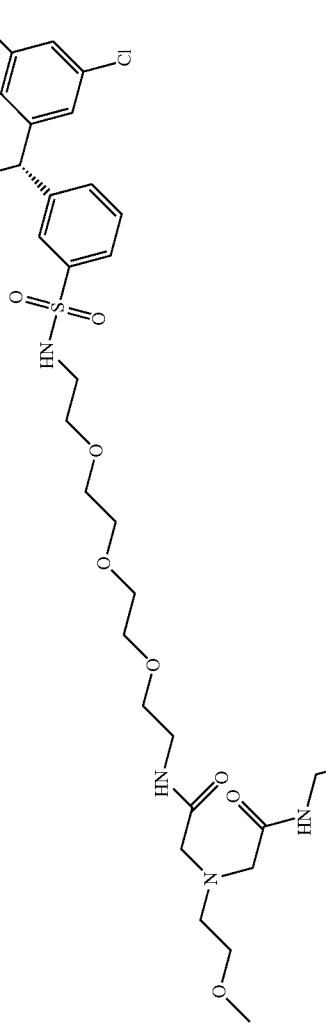 |

TABLE E1-continued
| Cmpd. # | Structure |
|---|---|
| 64 | 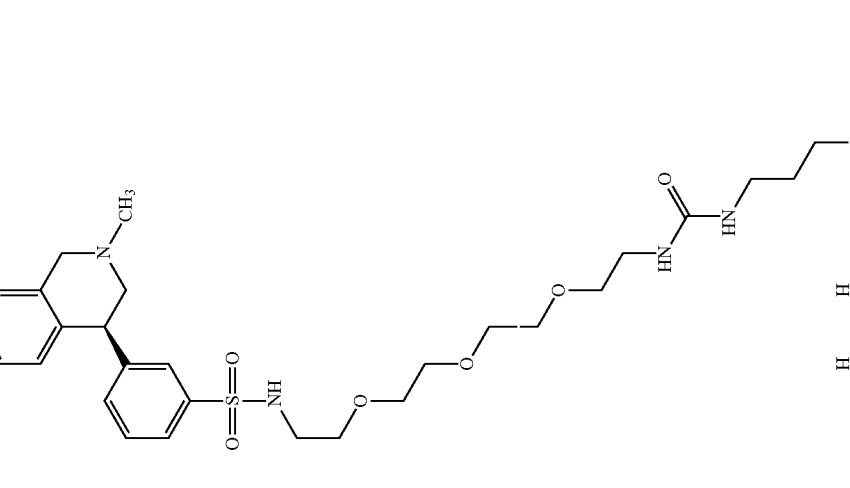 |

| Cmpd. # | Structure |
|---|---|
| 65 | 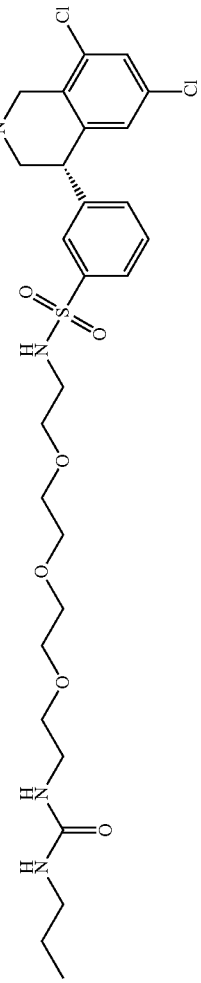 |

TABLE E1-continued

| Cmpd. # | Structure |
|---|---|
| 66 | 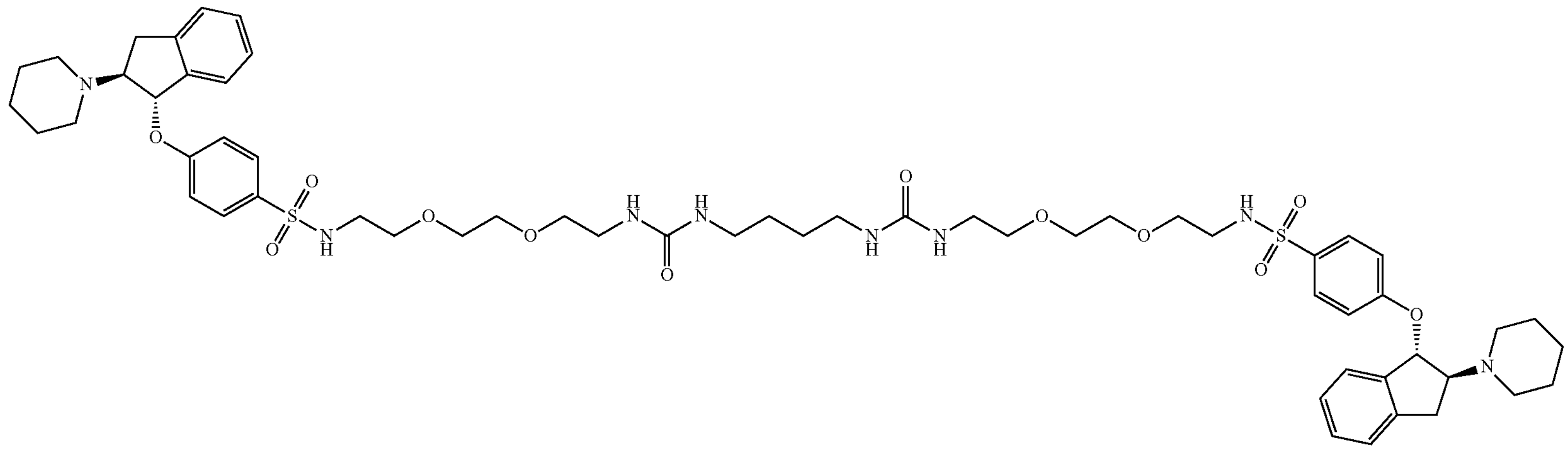 [SMILES: O=C(NCCCCNC(=O)NCCOCCOCCNS(=O)(=O)c1ccc(O[C@H]2c3ccccc3C[C@@H]2N2CCCCC2)cc1)NCCOCCOCCNS(=O)(=O)c1ccc(O[C@H]2c3ccccc3C[C@@H]2N2CCCCC2)cc1] |
| 67 | 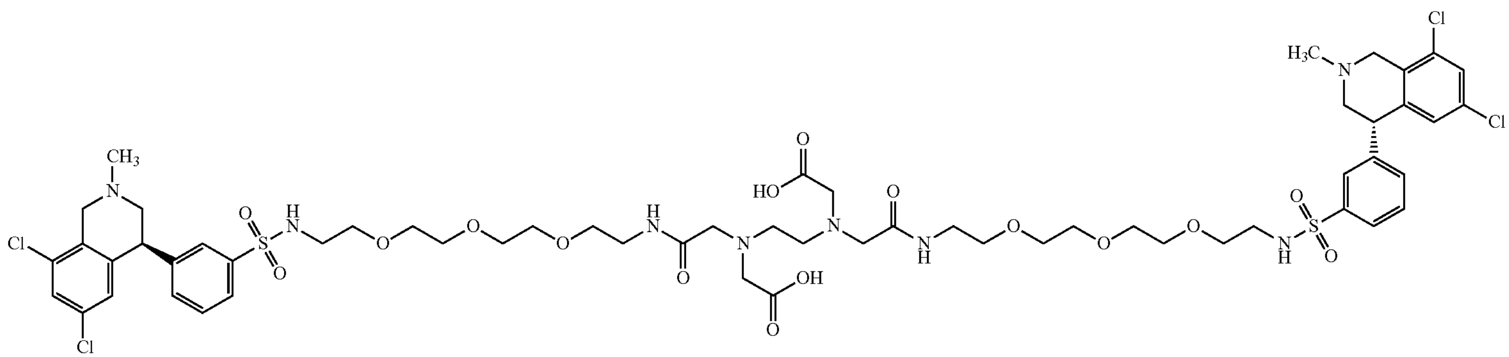 [SMILES: CN1Cc2c(Cl)cc(Cl)cc2[C@H](c2cccc(S(=O)(=O)NCCOCCOCCOCCNC(=O)CN(CCN(CC(=O)O)CC(=O)NCCOCCOCCOCCNS(=O)(=O)c3cccc([C@@H]4CN(C)Cc5c(Cl)cc(Cl)cc54)c3)CC(=O)O)c2)C1] |

TABLE E1-continued

| Cmpd. # | Structure |
|---|---|
| 68 | 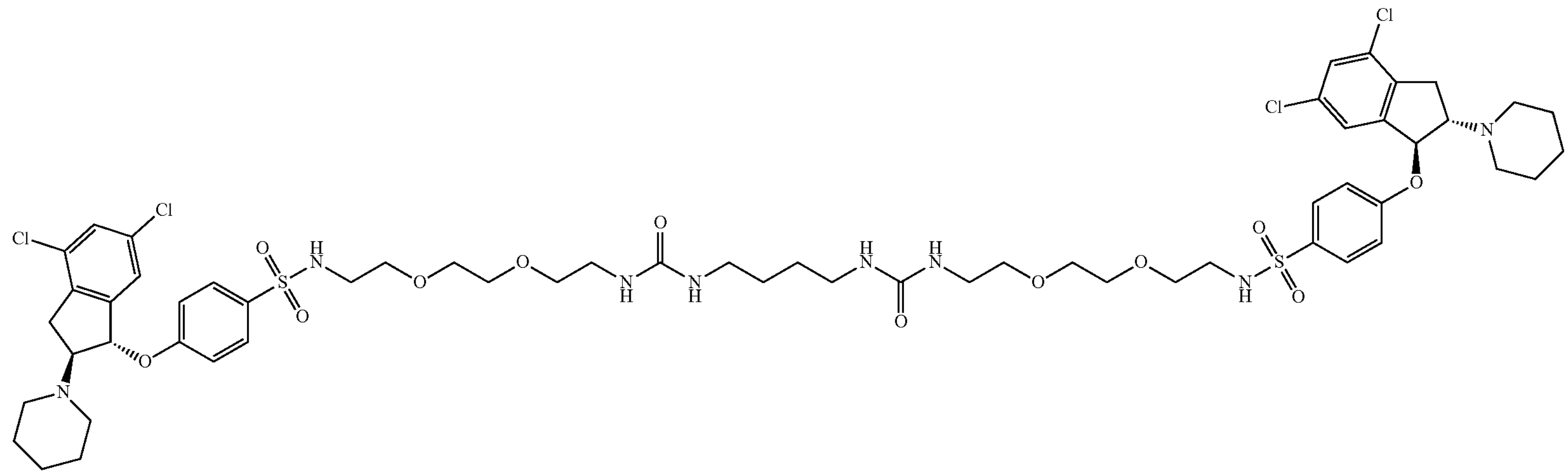 [SMILES: O=C(NCCCCNC(=O)NCCOCCOCCNS(=O)(=O)c1ccc(O[C@H]2c3cc(Cl)cc(Cl)c3C[C@@H]2N2CCCCC2)cc1)NCCOCCOCCNS(=O)(=O)c1ccc(O[C@H]2c3cc(Cl)cc(Cl)c3C[C@@H]2N2CCCCC2)cc1] |
| 69 | 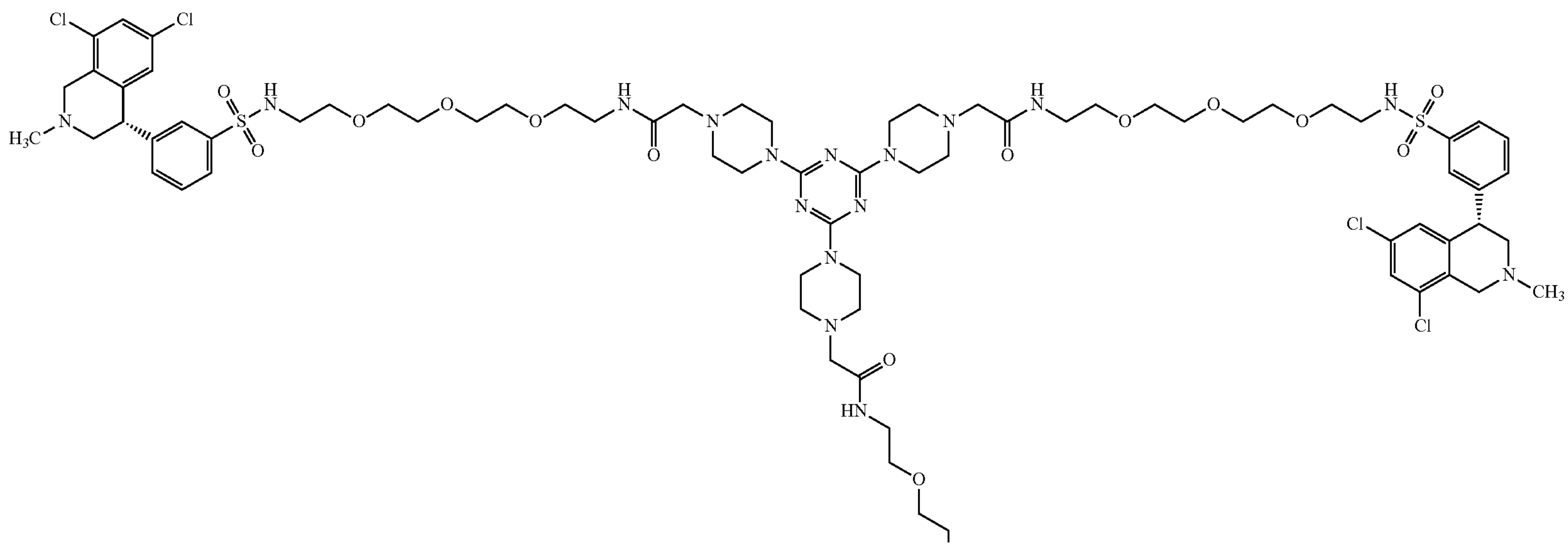 |

| Cmpd. # | Structure |
|---|---|
| 70 | *(chemical structure)* |

TABLE E1-continued

| Cmpd. # | Structure |
|---|---|
| 71 | 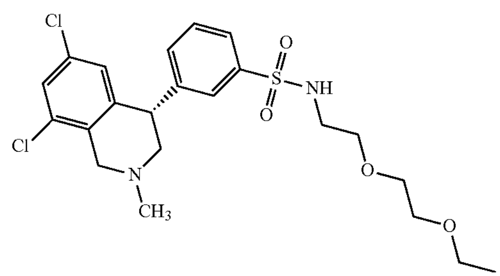 |

TABLE E1-continued
| Cmpd. # | Structure |
|---|---|
| 72 | 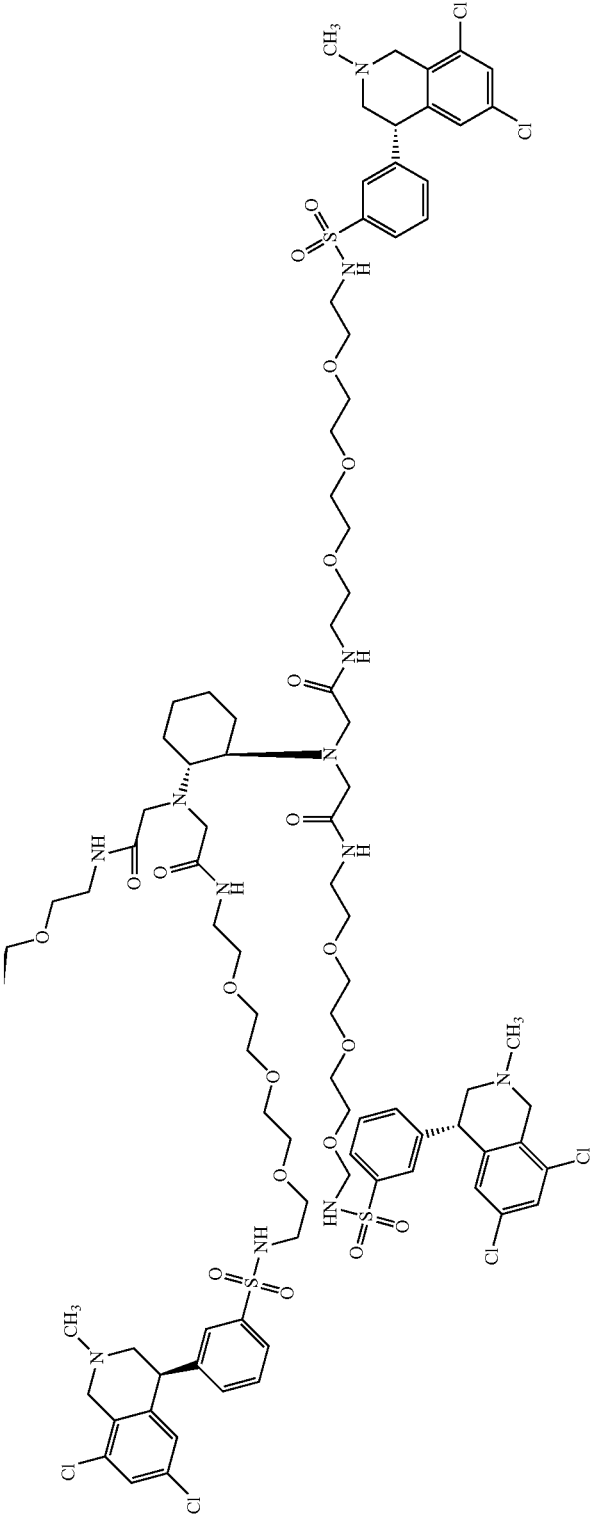 |

TABLE E1-continued
| Cmpd. # | Structure |
|---|---|
| 73 | 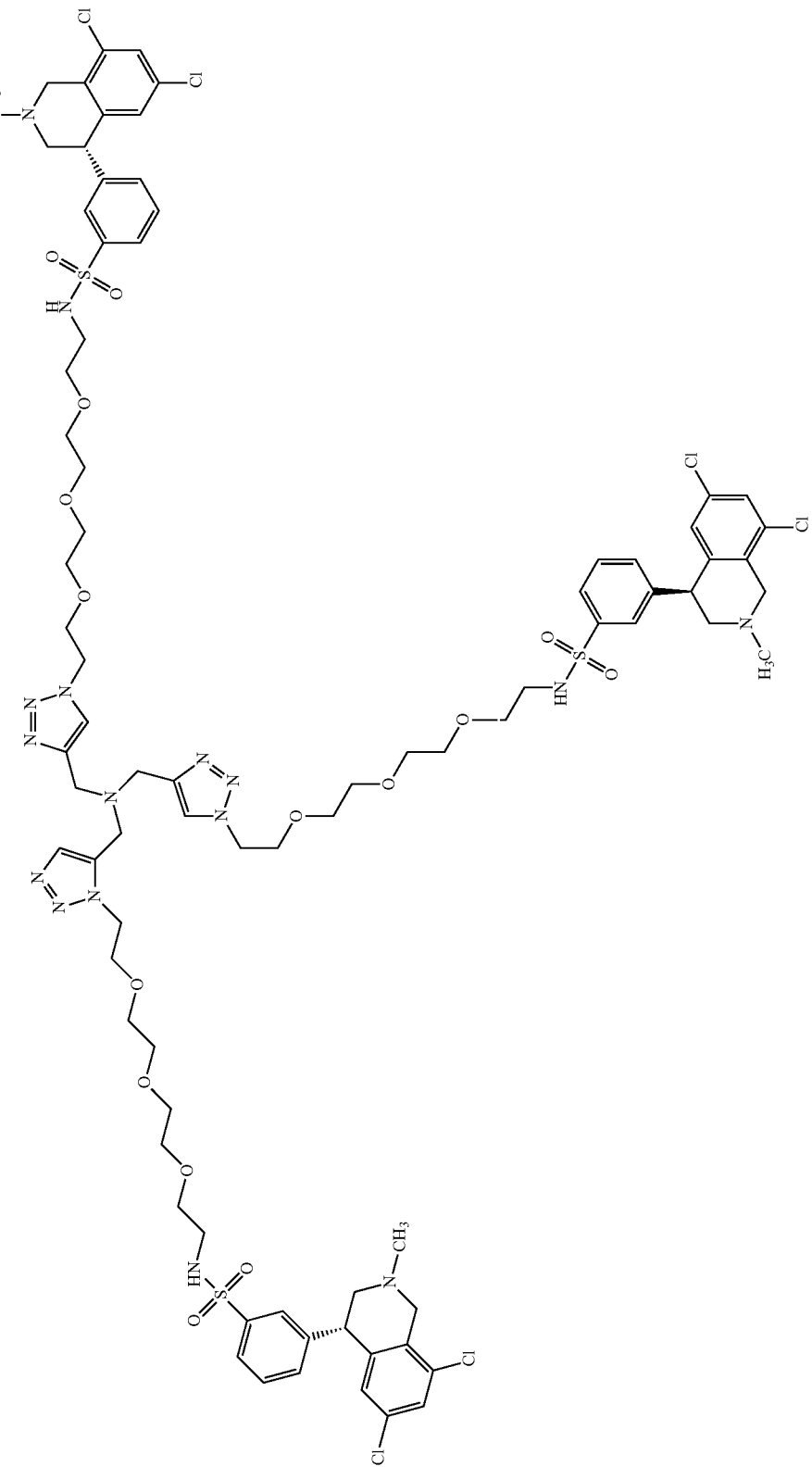 |

TABLE E1-continued
| Cmpd. # | Structure |
|---|---|
| 74 | 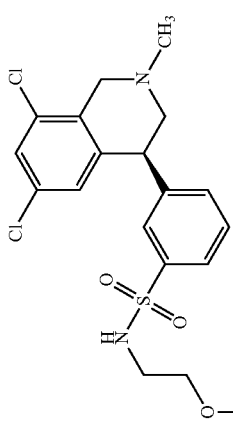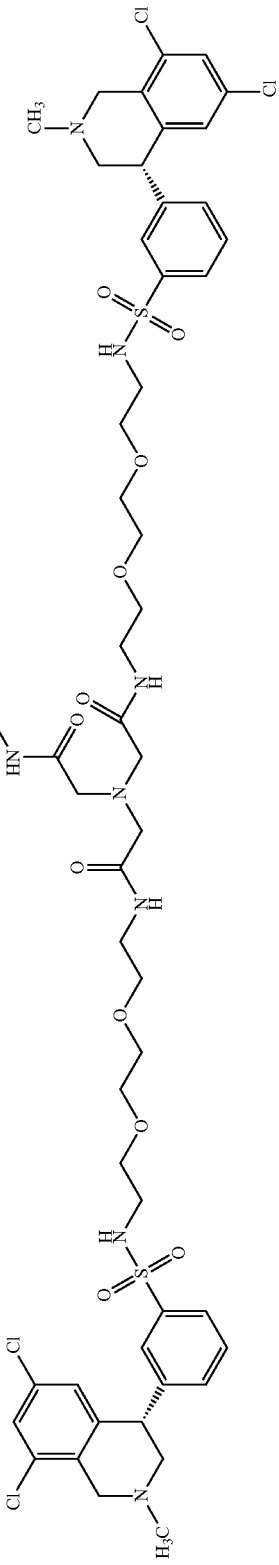 |

TABLE E1-continued
| Cmpd. # | Structure |
|---|---|
| 75 | 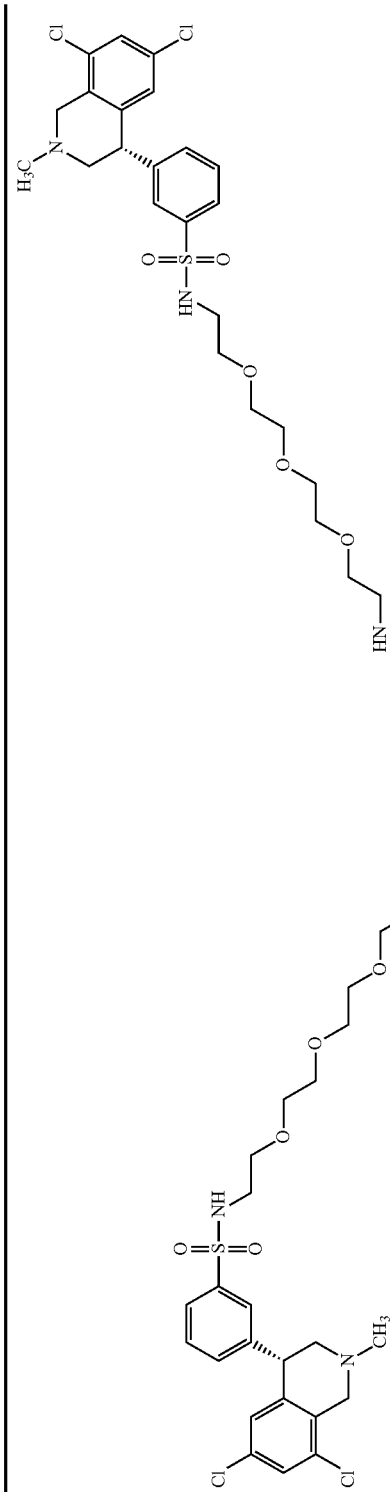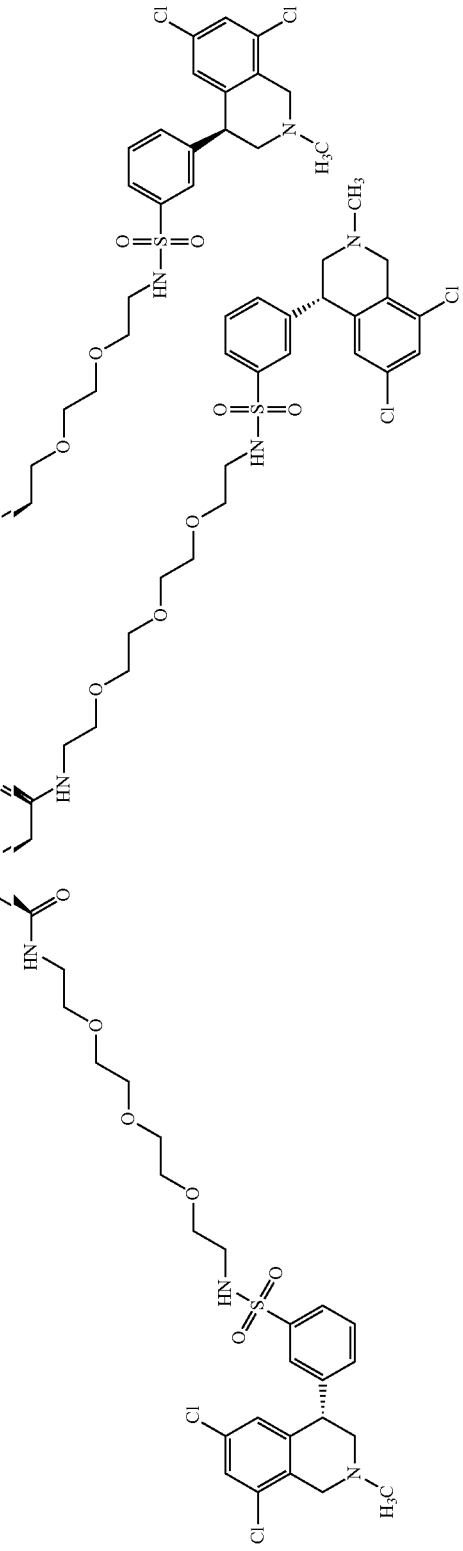 |

TABLE E1-continued
| Cmpd. # | Structure |
|---|---|
| 76 | 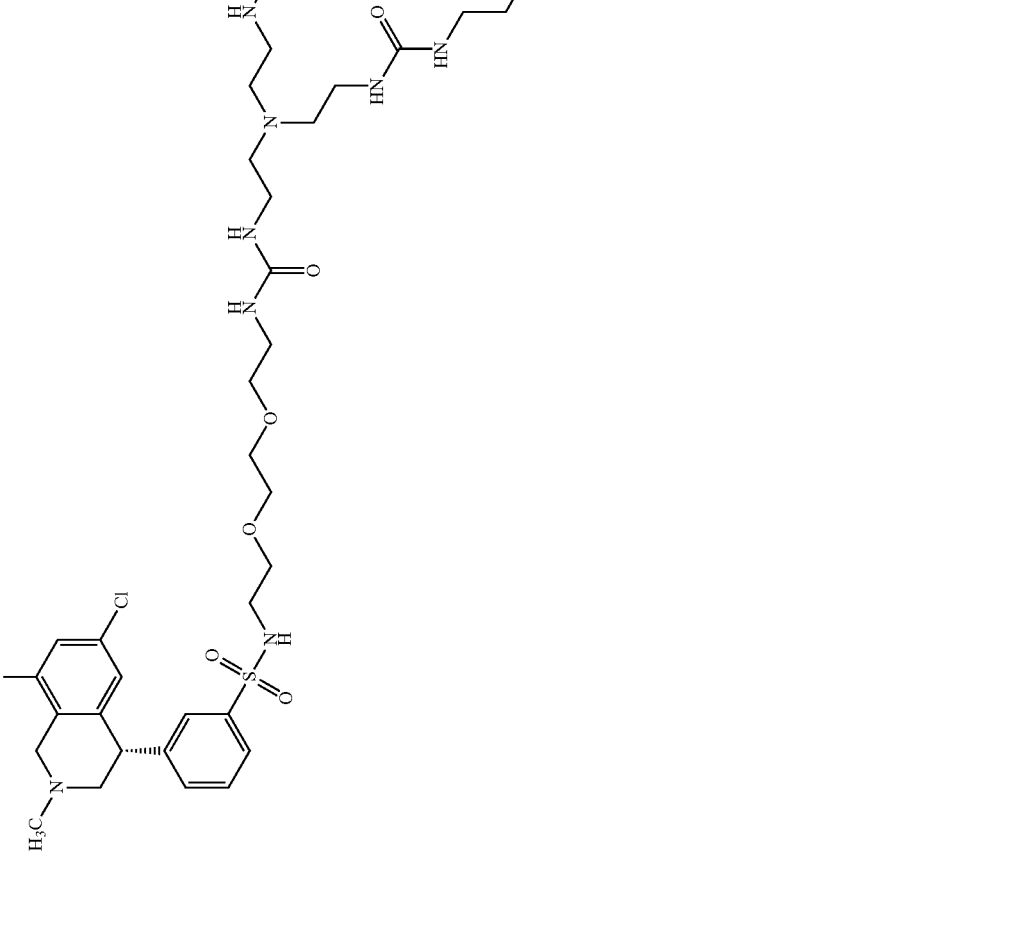 |

TABLE E1-continued
| Cmpd. # | Structure |
|---|---|
| 77 | 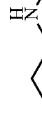 |
| 78 | 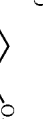 |

TABLE E1-continued
| Cmpd. # | Structure |
|---|---|
| 79 | 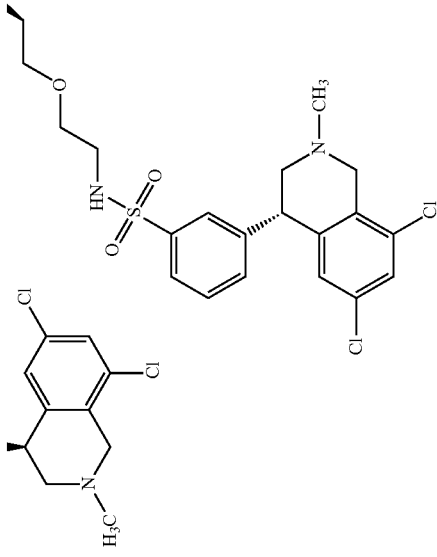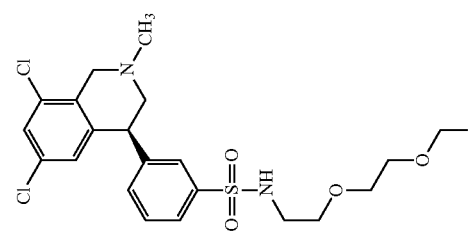 |

TABLE E1-continued
| Cmpd. # | Structure |
|---|---|
|  | 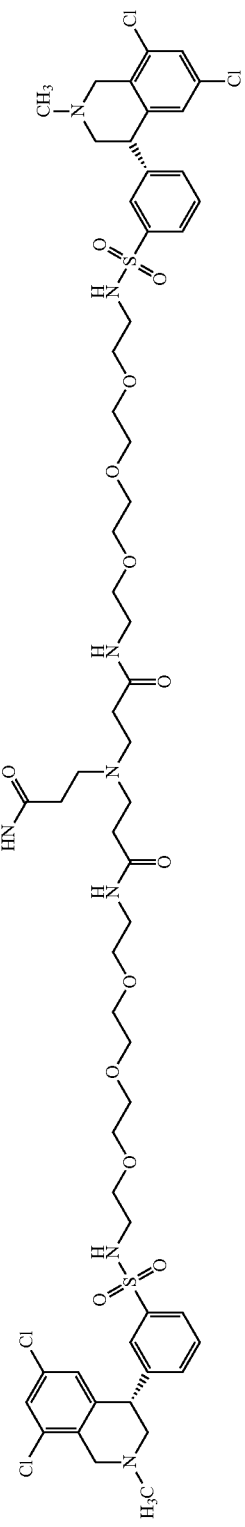 |
| 80 | 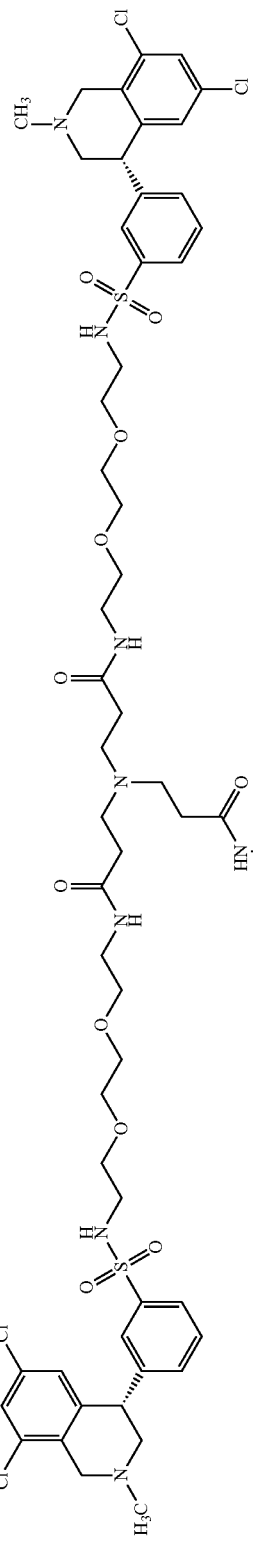 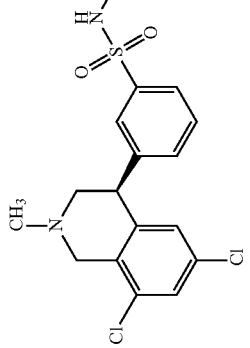 |

TABLE E1-continued
| Cmpd. # | Structure |
|---|---|
| 81 | 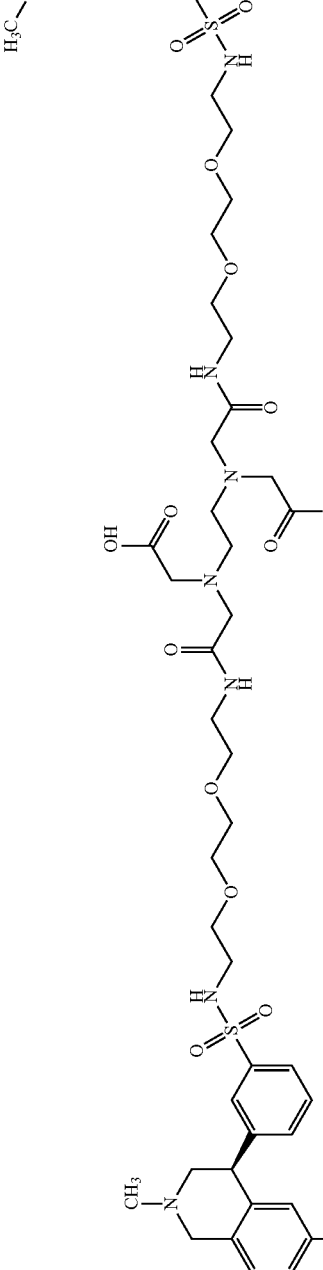 |
| 82 | 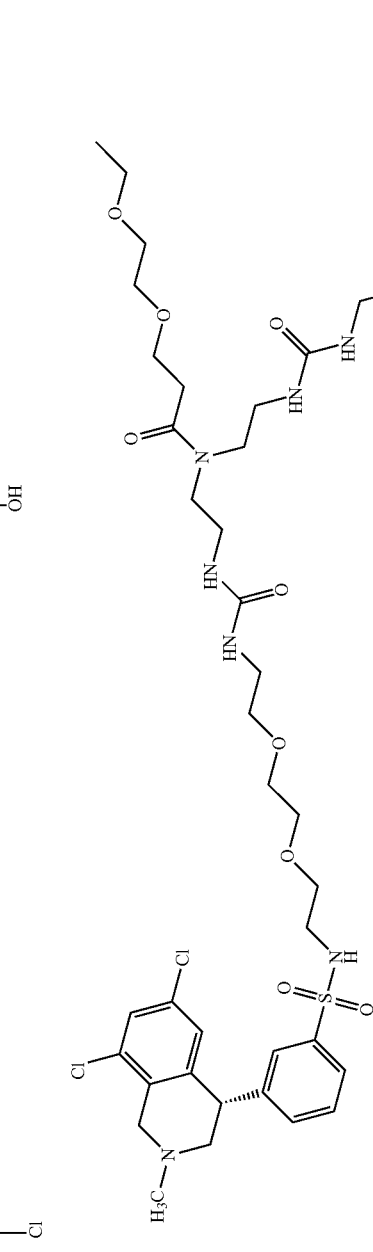 |

TABLE E1-continued
| Cmpd. # | Structure |
|---|---|
| | 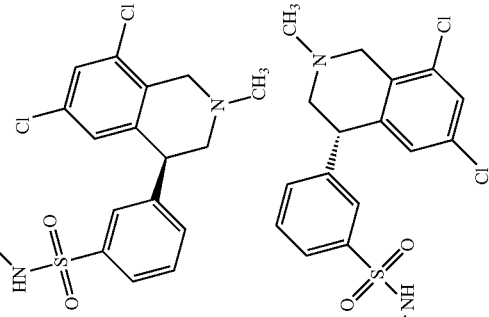 |

TABLE E1-continued
| Cmpd. # | Structure |
|---|---|
| 83 | 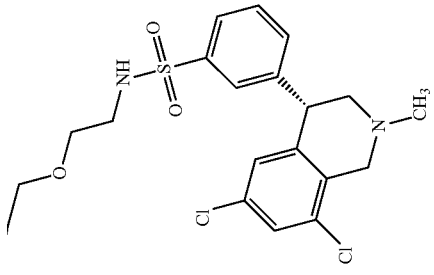 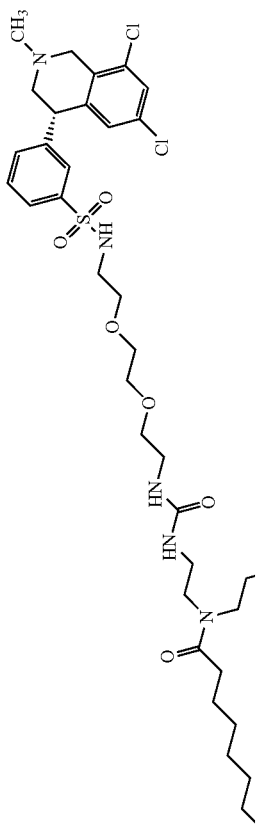 |

TABLE E1-continued
| Cmpd. # | Structure |
|---|---|
| 84 | 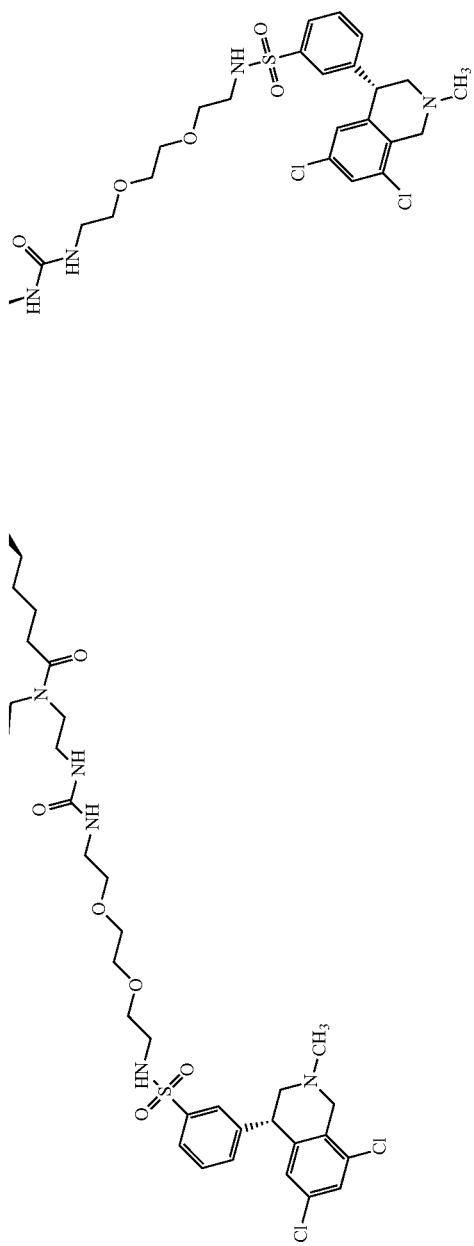 |

TABLE E1-continued
| Cmpd. # | Structure |
|---|---|
| 85 | 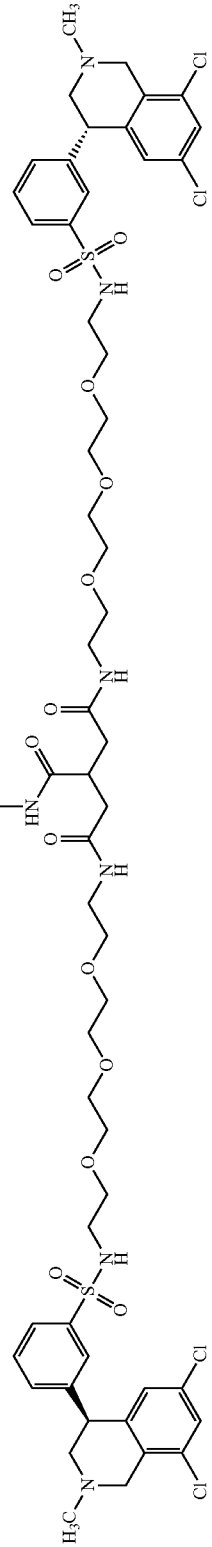 |

TABLE E1-continued
| Cmpd. # | Structure |
|---|---|
| 86 | 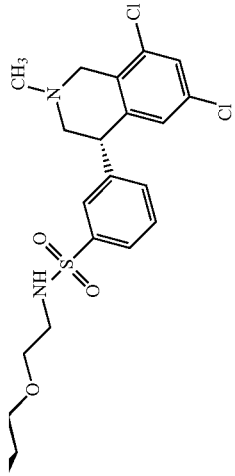 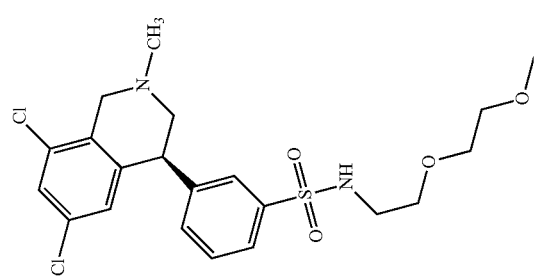 |

TABLE E1-continued
| Cmpd. # | Structure |
|---|---|
| | 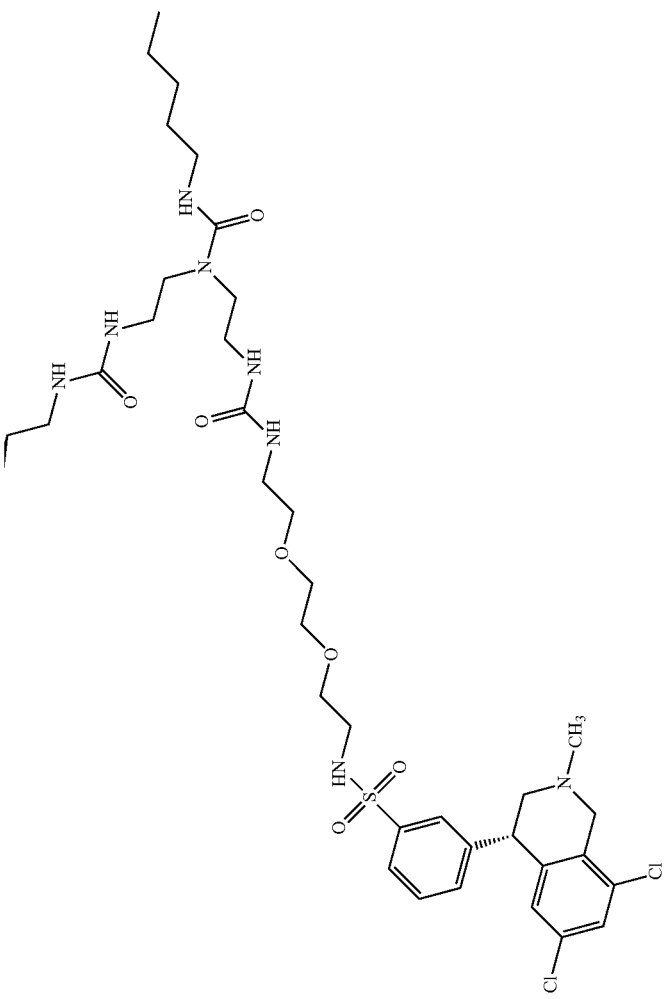 |

TABLE E1-continued

| Cmpd. # | Structure |
|---|---|
| | |

TABLE E1-continued
| Cmpd. # | Structure |
|---|---|
| 87 | 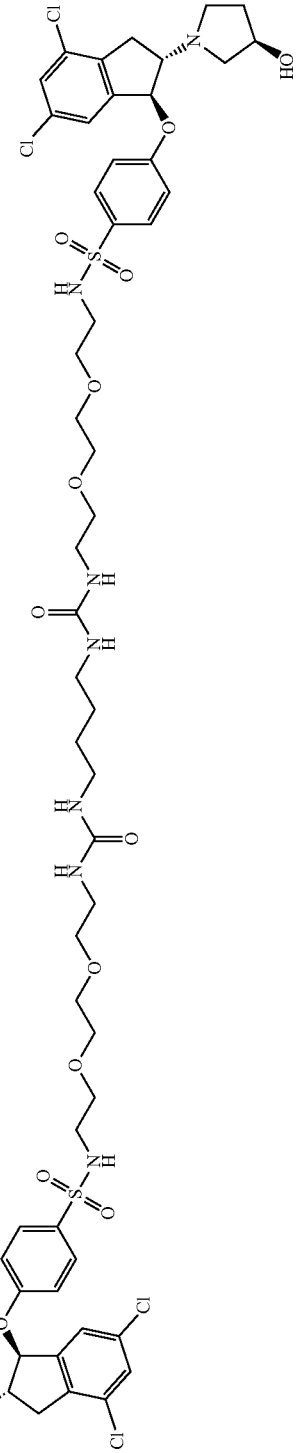 |
| 88 | 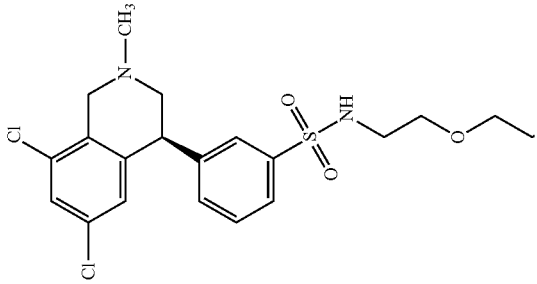 |

TABLE E1-continued

| Cmpd. # | Structure |
|---|---|
| 89 | 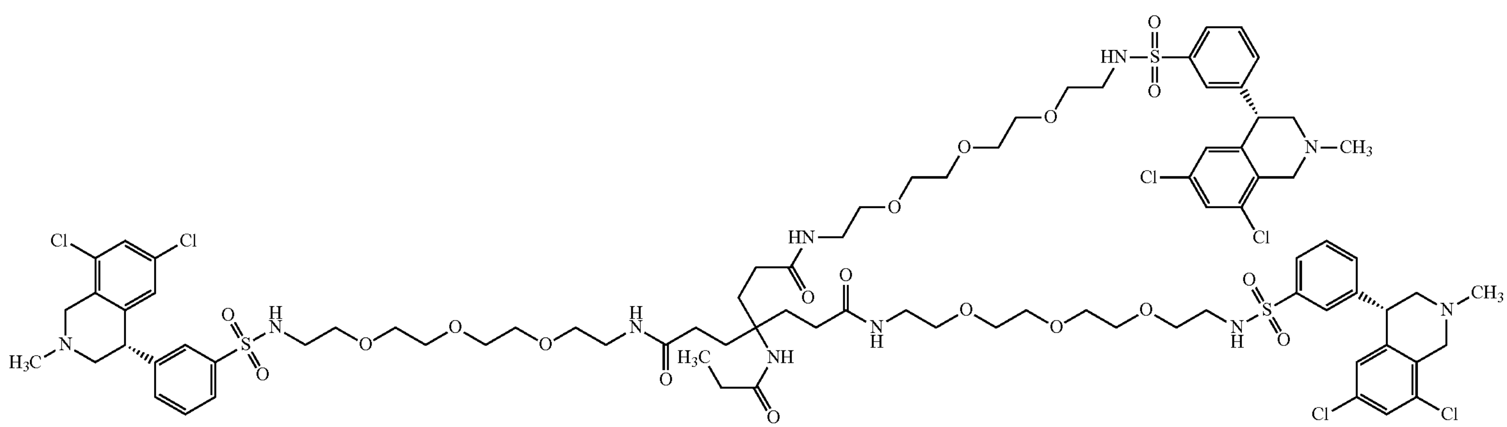 |

TABLE E1-continued
| Cmpd. # | Structure |
|---|---|
| 90 | 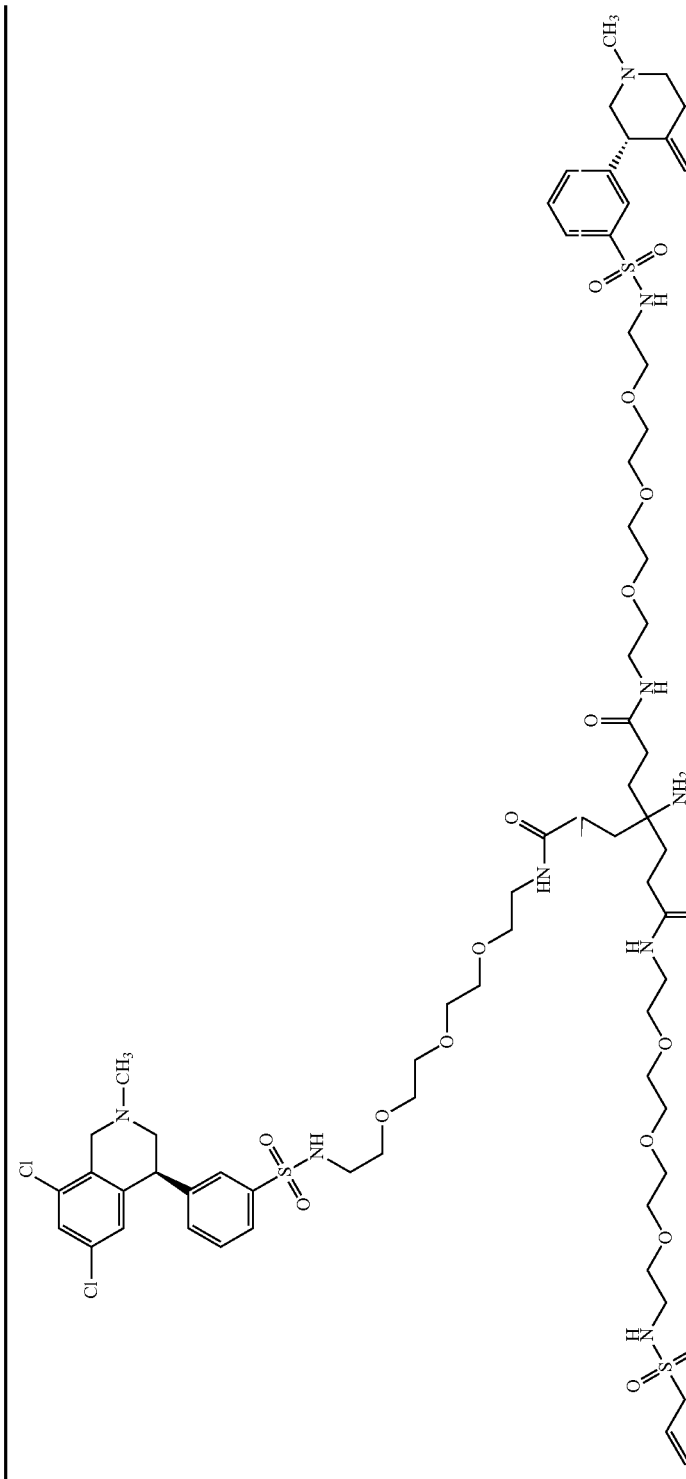 |

TABLE E1-continued
| Cmpd. # | Structure |
|---|---|
| 91 | 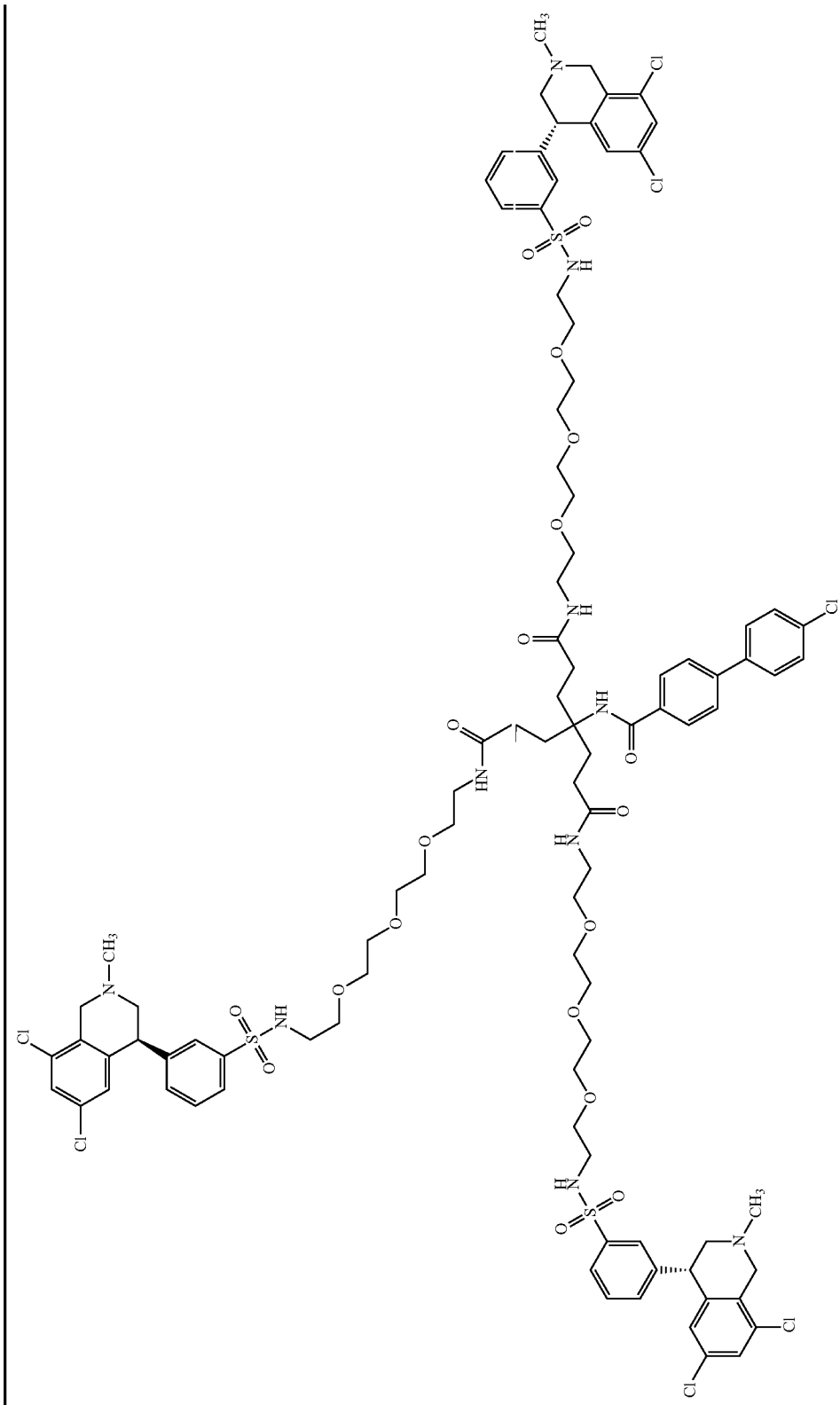 |

TABLE E1-continued

| Cmpd. # | Structure |
|---|---|
| 92 | 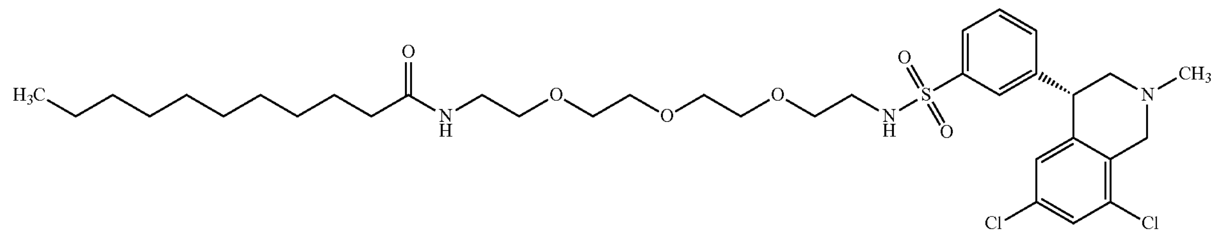 [SMILES: CCCCCCCCCCC(=O)NCCOCCOCCOCCNS(=O)(=O)c1cccc([C@@H]2CN(C)Cc3c(Cl)cc(Cl)cc32)c1] |
| 93 | 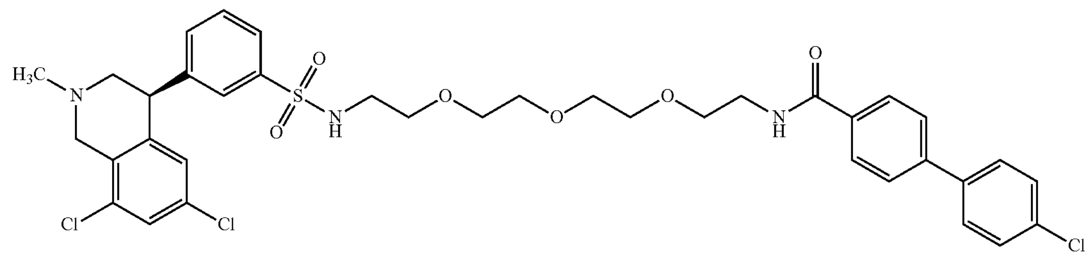 [SMILES: CN1Cc2c(Cl)cc(Cl)cc2[C@H](c2cccc(S(=O)(=O)NCCOCCOCCOCCNC(=O)c3ccc(-c4ccc(Cl)cc4)cc3)c2)C1] |
| 94 | 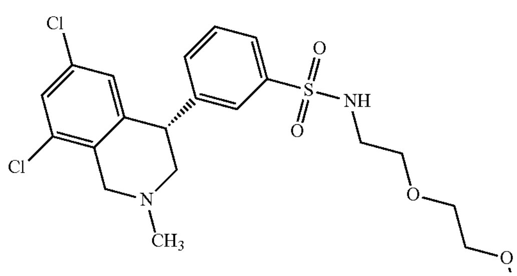 |

TABLE E1-continued
| Cmpd. # | Structure |
|---|---|
|  | 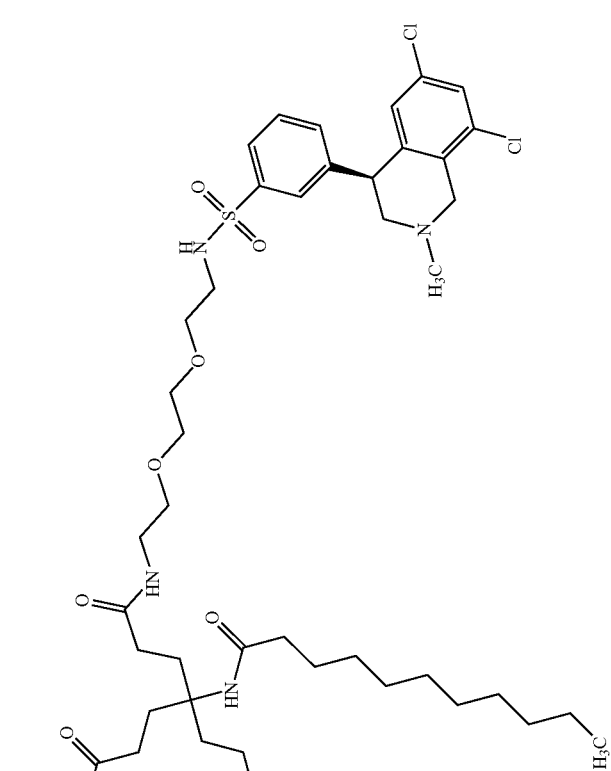 |

TABLE E1-continued
| Cmpd. # | Structure |
|---|---|
| 95 | 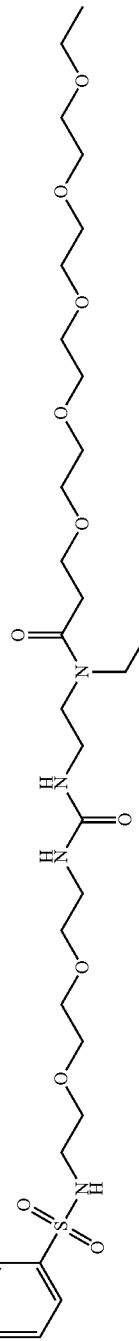 |

TABLE E1-continued

| Cmpd. # | Structure |
|---|---|
| | |

TABLE E1-continued
| Cmpd. # | Structure |
|---|---|
| 96 | 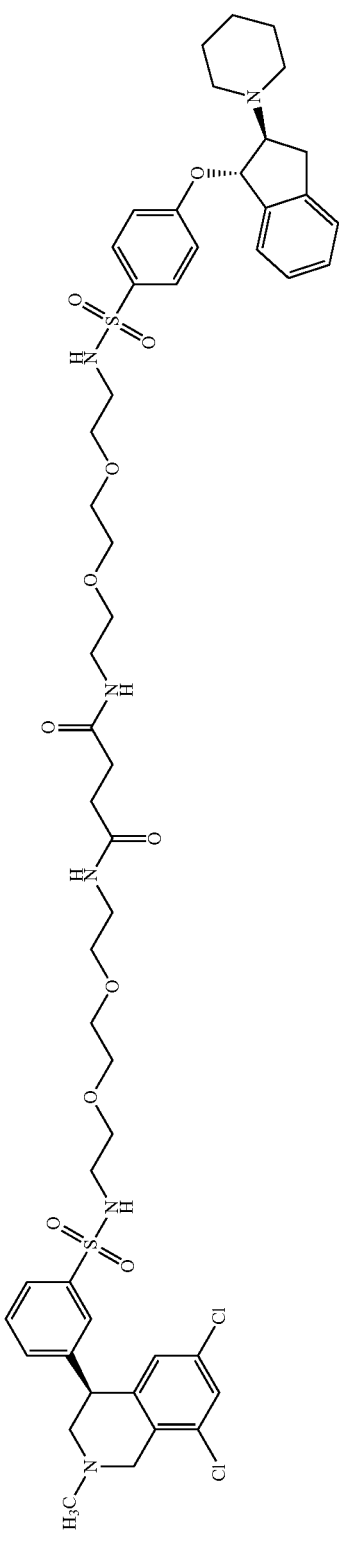 |
| 97 | 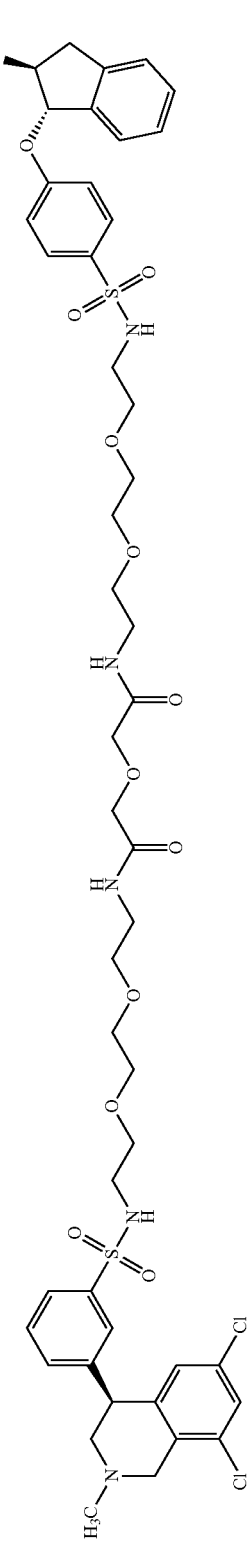 |

TABLE E1-continued
| Cmpd. # | Structure |
|---|---|
| 98 | 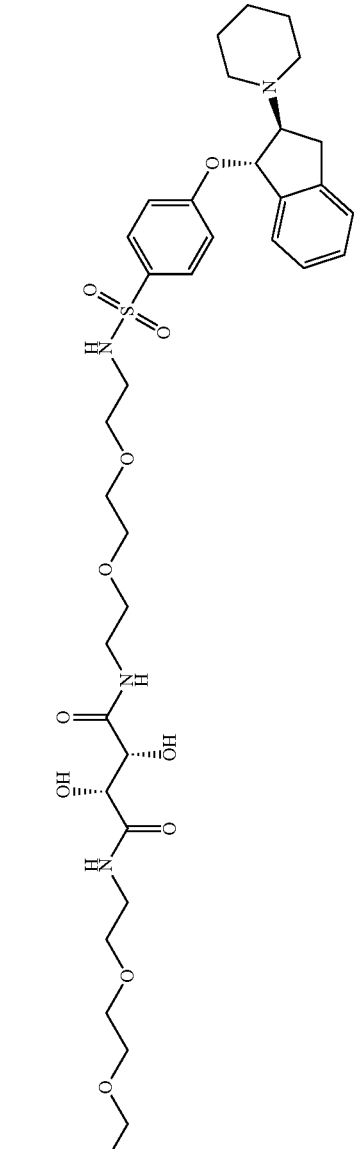 |
| 99 | 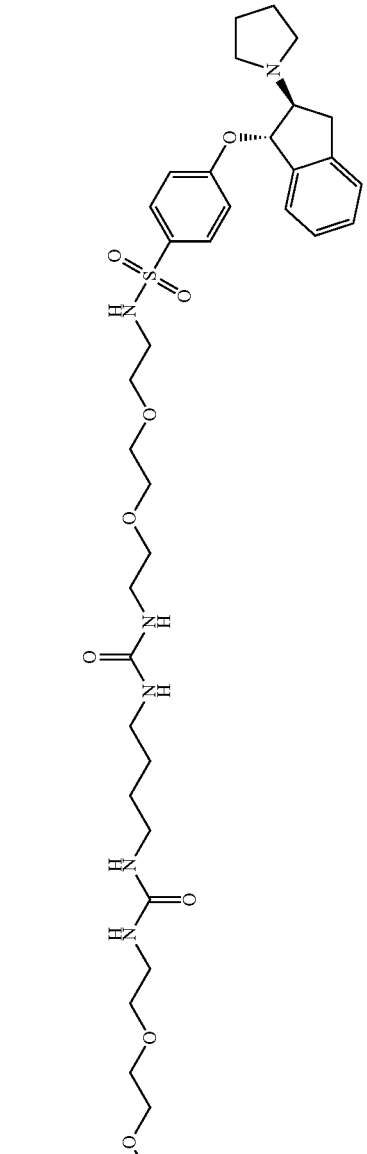 |

TABLE E1-continued

| Cmpd. # | Structure |
|---|---|
| 100 | 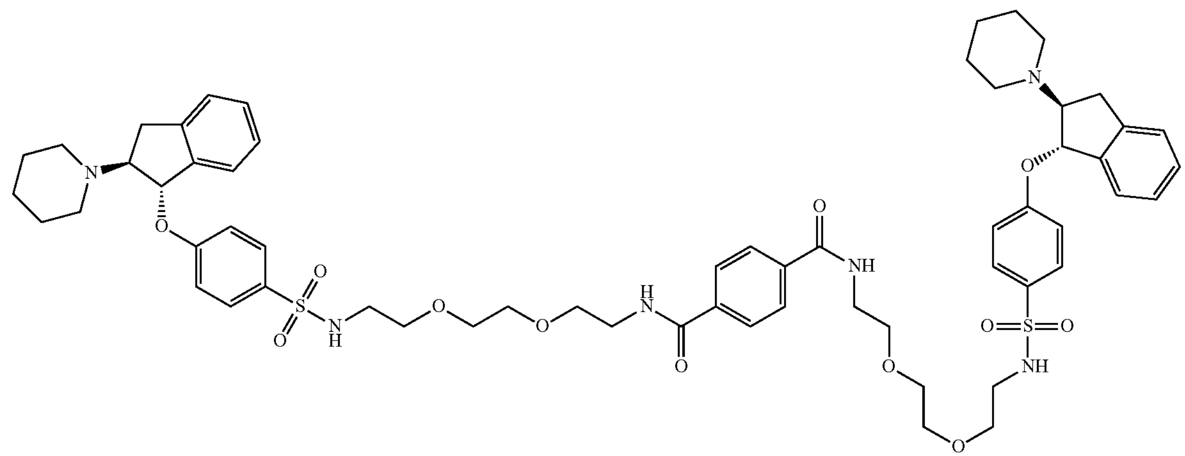 [SMILES: O=C(NCCOCCOCCNS(=O)(=O)c1ccc(O[C@H]2c3ccccc3C[C@@H]2N2CCCCC2)cc1)c1ccc(C(=O)NCCOCCOCCNS(=O)(=O)c2ccc(O[C@H]3c4ccccc4C[C@@H]3N3CCCCC3)cc2)cc1] |
| 101 | 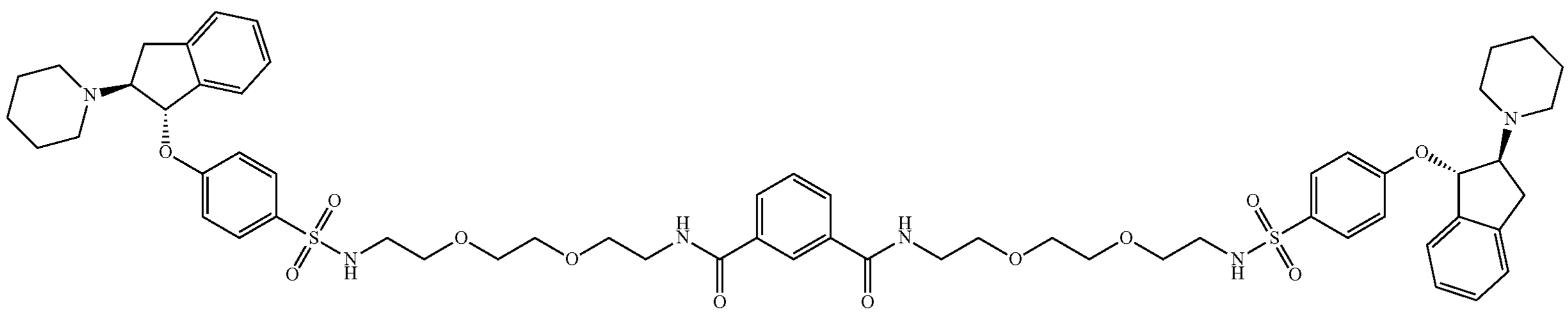 [SMILES: O=C(NCCOCCOCCNS(=O)(=O)c1ccc(O[C@H]2c3ccccc3C[C@@H]2N2CCCCC2)cc1)c1cccc(C(=O)NCCOCCOCCNS(=O)(=O)c2ccc(O[C@H]3c4ccccc4C[C@@H]3N3CCCCC3)cc2)c1] |
| 102 | 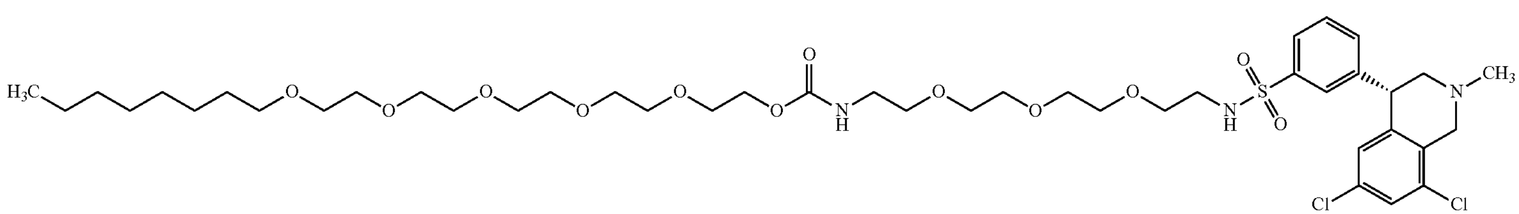 [SMILES: CCCCCCCCOCCOCCOCCOCCOCCOC(=O)NCCOCCOCCOCCNS(=O)(=O)c1cccc([C@@H]2CN(C)Cc3c(Cl)cc(Cl)cc32)c1] |

TABLE E1-continued
| Cmpd. # | Structure |
|---|---|
| 103 | 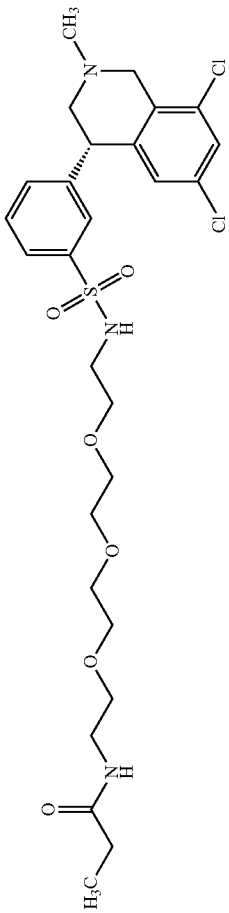 |
| 104 | 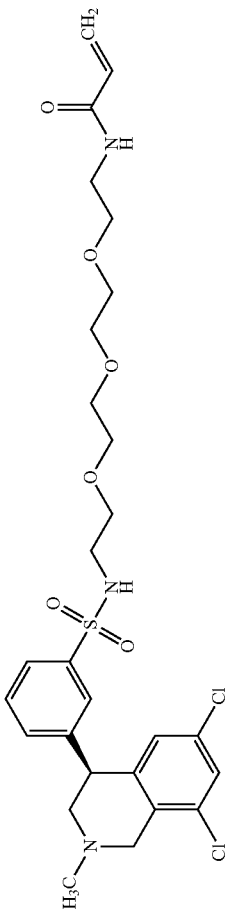 |
| 105 | 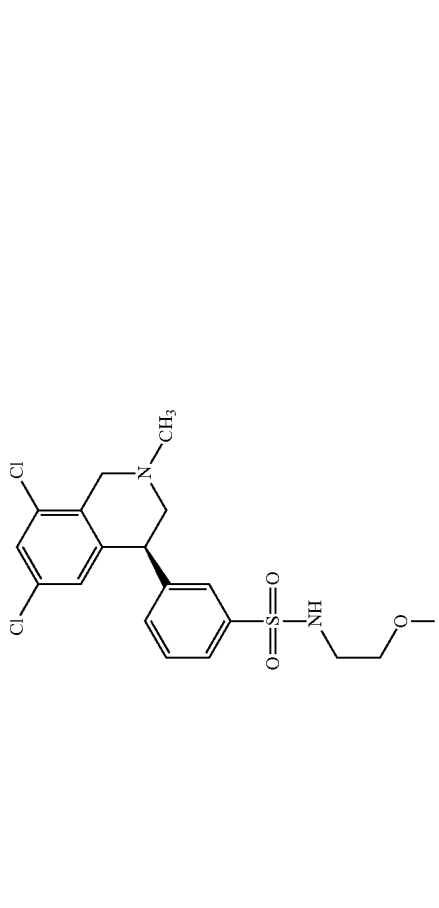 |

| Cmpd. # | Structure |
|---|---|
| 106 | 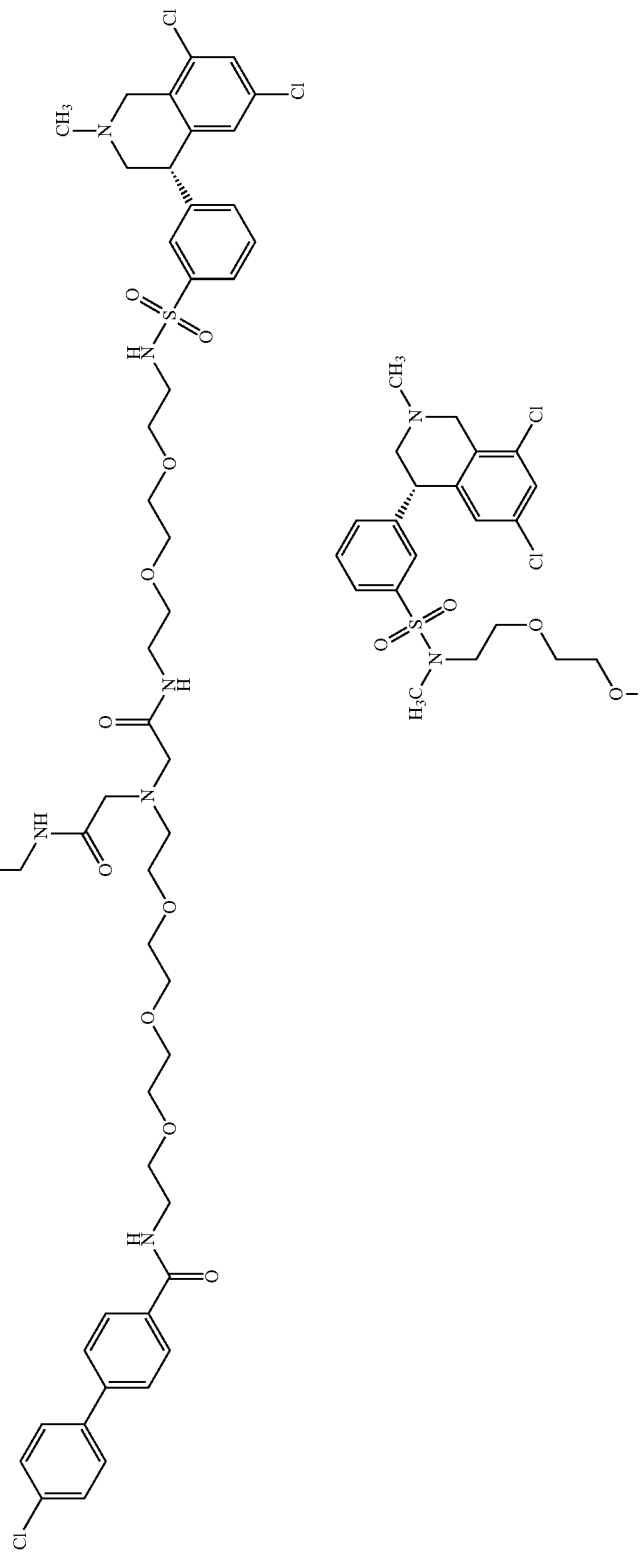 |

TABLE E1-continued
| Cmpd. # | Structure |
|---|---|
| 107 | 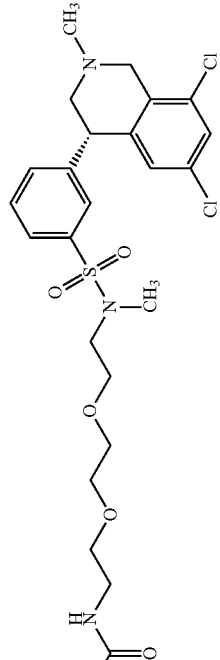 |

TABLE E1-continued
| Cmpd. # | Structure |
|---|---|
| 315 | 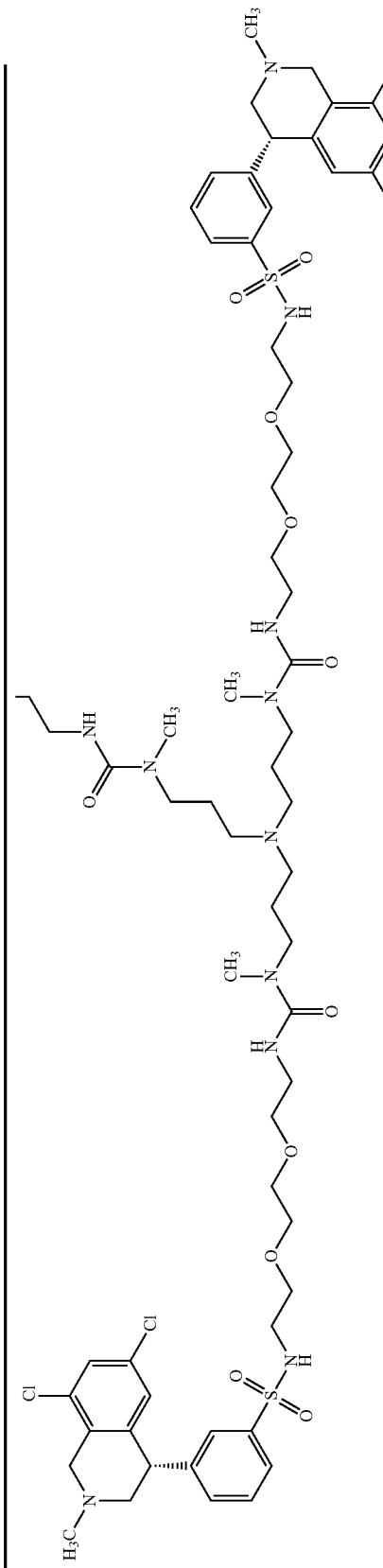 |
| 316 | 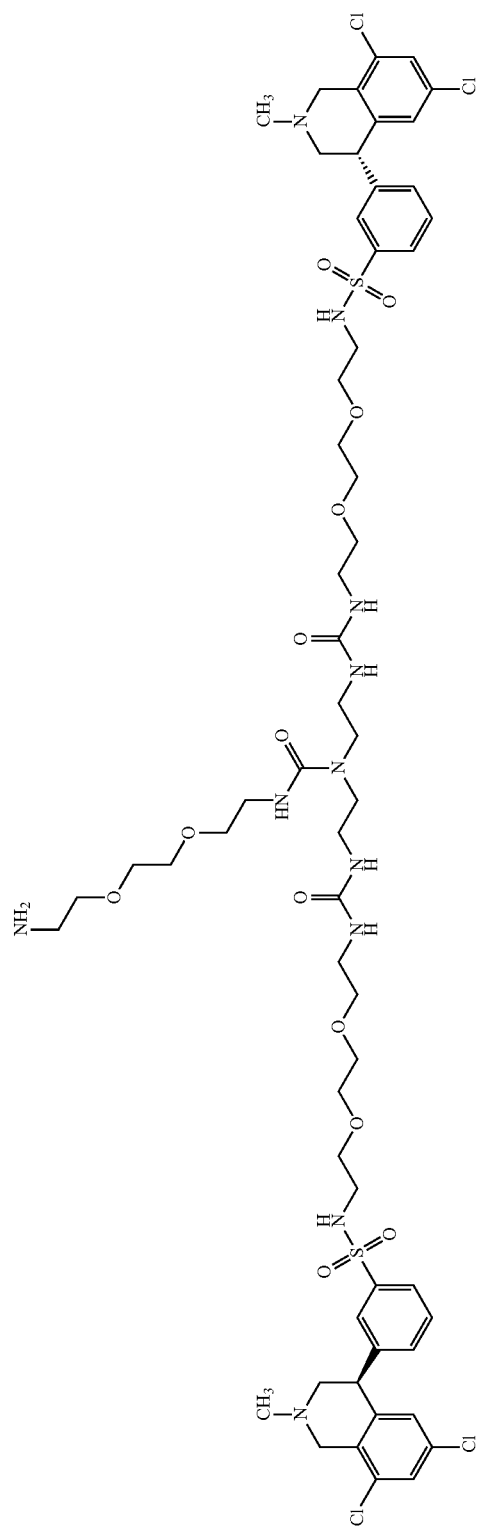 |

TABLE E1-continued

| Cmpd. # | Structure |
|---|---|
| 109 | |

TABLE E1-continued
| Cmpd. # | Structure |
|---|---|
| 110 | 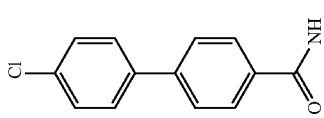 |

TABLE E1-continued

| Cmpd. # | Structure |
|---|---|
| 111 | 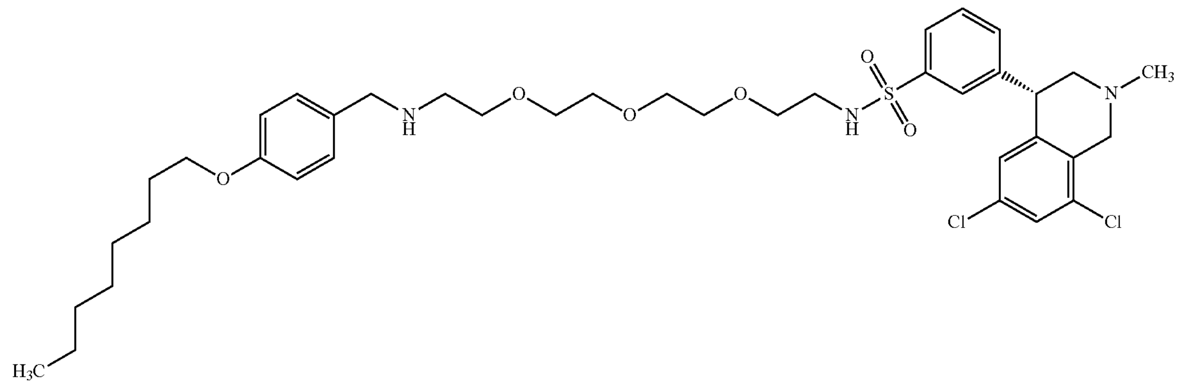 [SMILES: CCCCCCCCOc1ccc(CNCCOCCOCCOCCNS(=O)(=O)c2cccc([C@@H]3CN(C)Cc4c(Cl)cc(Cl)cc43)c2)cc1] |
| 112 | 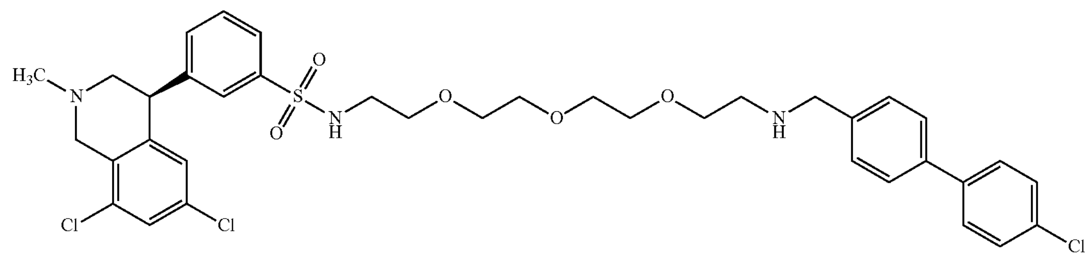 [SMILES: CN1Cc2c(Cl)cc(Cl)cc2[C@H](c2cccc(S(=O)(=O)NCCOCCOCCOCCNCc3ccc(-c4ccc(Cl)cc4)cc3)c2)C1] |

TABLE E1-continued
| Cmpd. # | Structure |
|---|---|
| 113 | 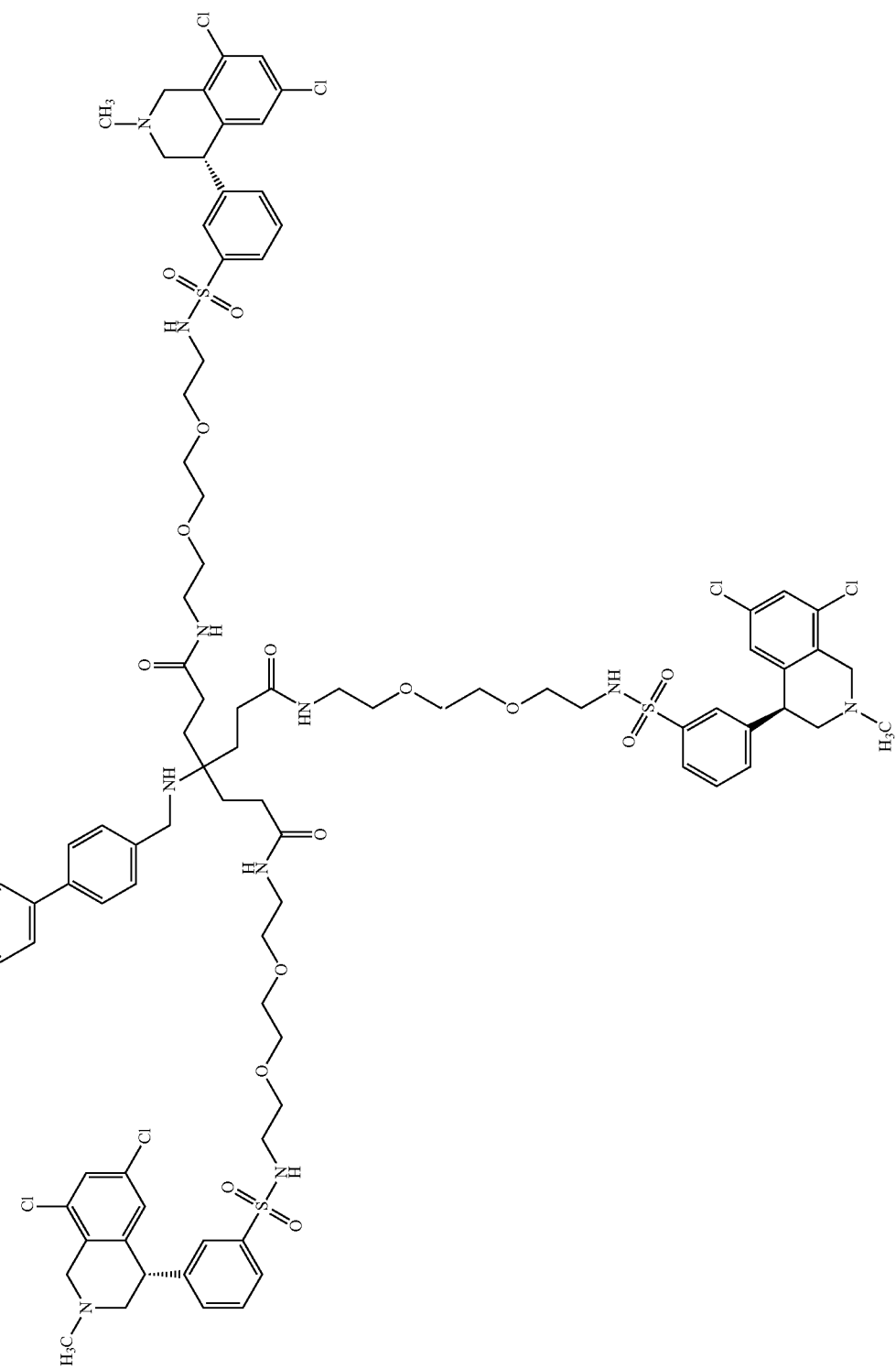 |

TABLE E1-continued
| Cmpd. # | Structure |
|---|---|
| 114 | 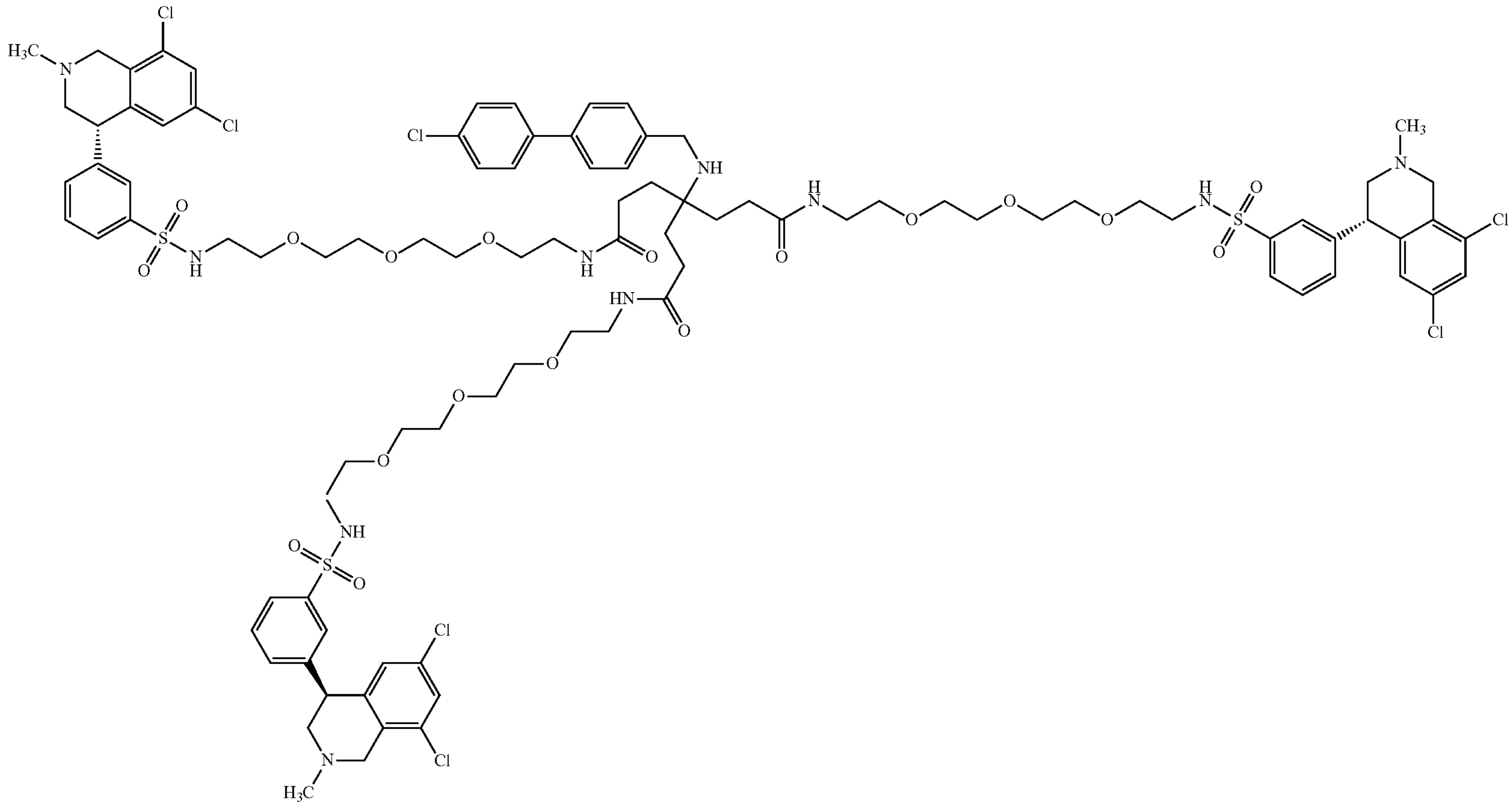 [SMILES: CN1Cc2c(Cl)cc(Cl)cc2[C@H](c2cccc(S(=O)(=O)NCCOCCOCCOCCNC(=O)CCC(CCC(=O)NCCOCCOCCOCCNS(=O)(=O)c3cccc([C@@H]4CN(C)Cc5c(Cl)cc(Cl)cc54)c3)(CCC(=O)NCCOCCOCCOCCNS(=O)(=O)c3cccc([C@@H]4CN(C)Cc5c(Cl)cc(Cl)cc54)c3)NCc3ccc(-c4ccc(Cl)cc4)cc3)c2)C1] |

TABLE E1-continued
| Cmpd. # | Structure |
|---|---|
| 115 | 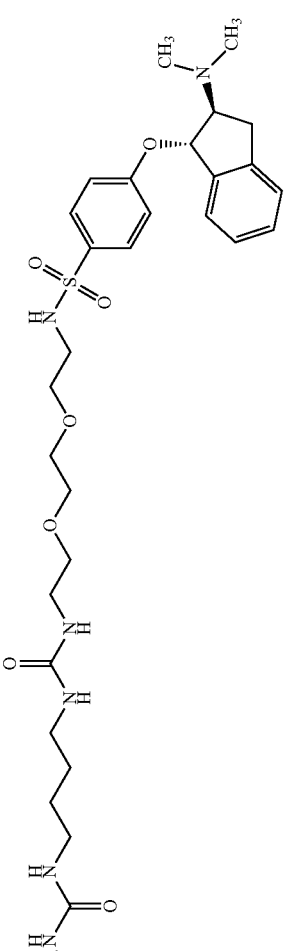 |
| 116 | 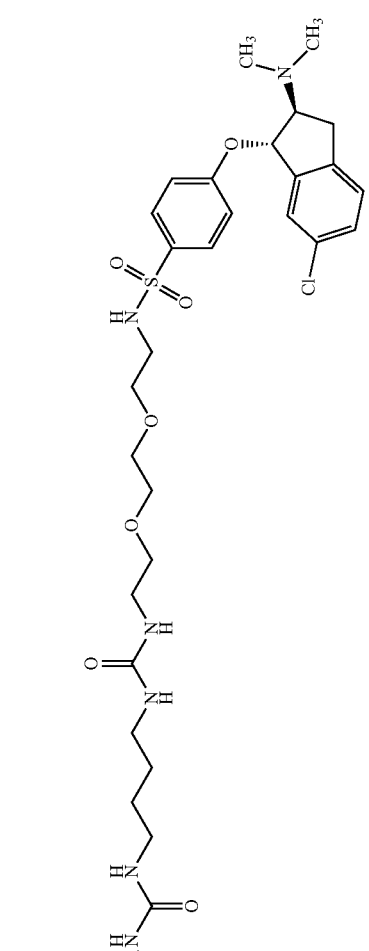 |

TABLE E1-continued
| Cmpd. # | Structure |
|---|---|
| 117 | 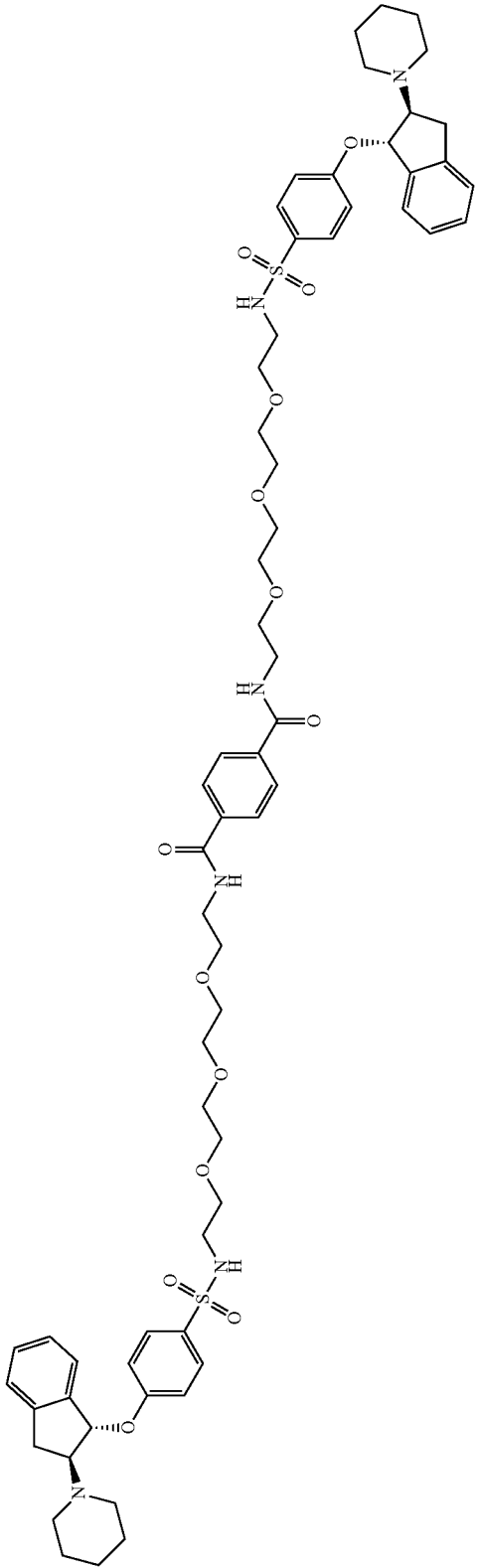 |

TABLE E1-continued
| Cmpd. # | Structure |
|---|---|
| 118 | 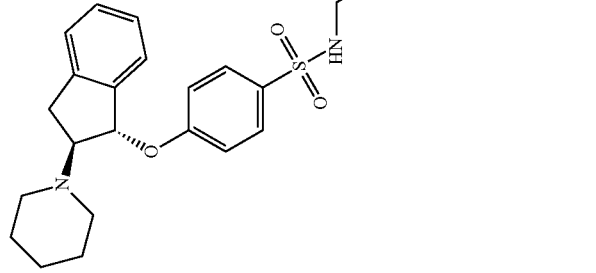 |
| 119 | 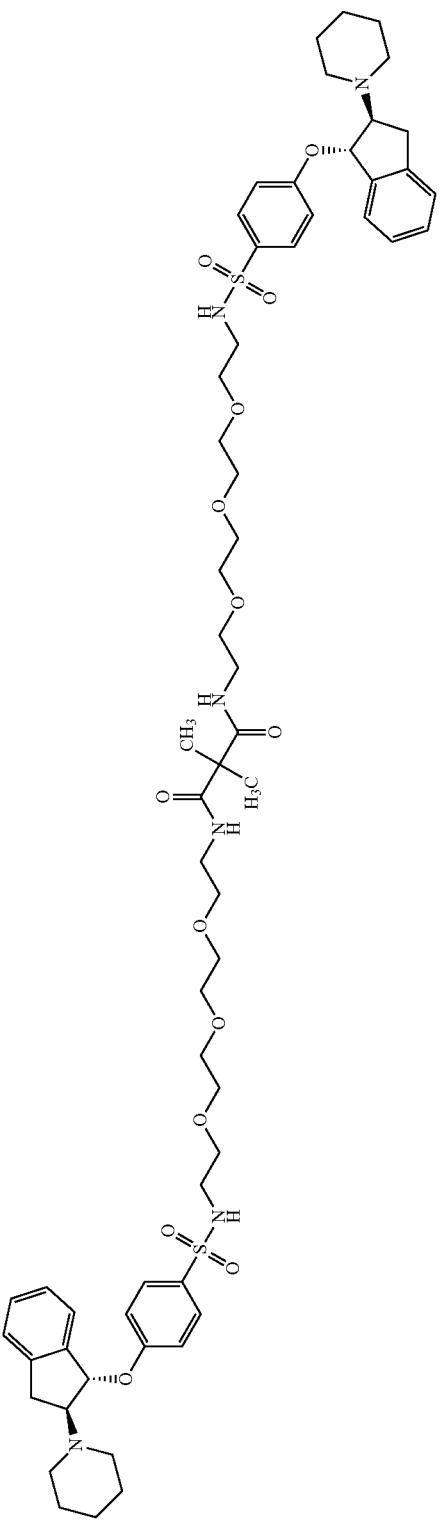 |

TABLE E1-continued
| Cmpd. # | Structure |
|---|---|
| 120 | 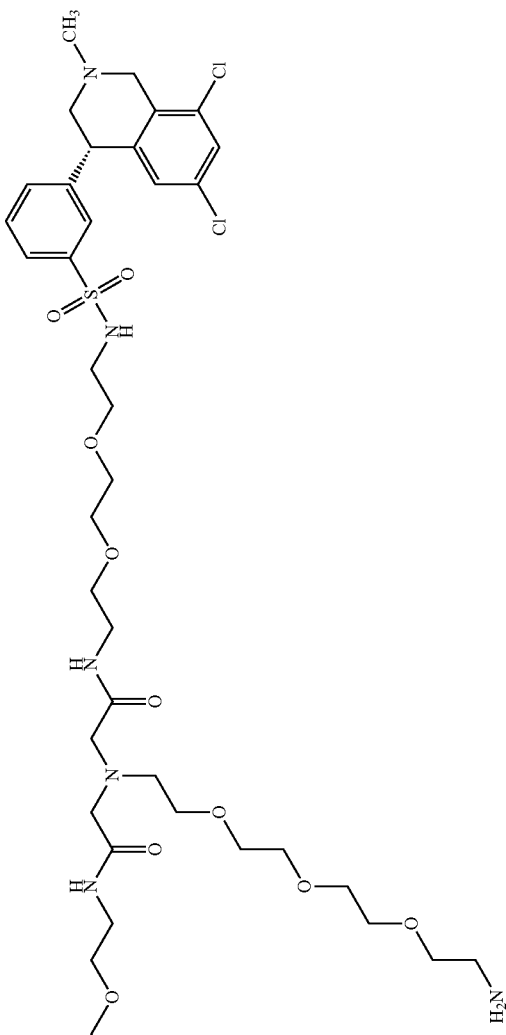 |
| 121 | 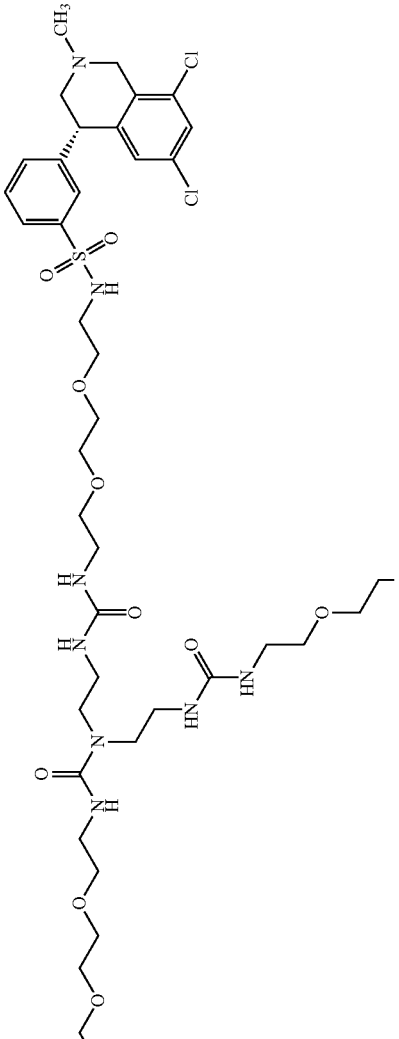 |

TABLE E1-continued
| Cmpd. # | Structure |
|---|---|
| 122 | 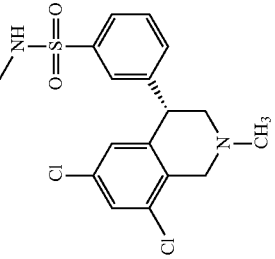 |

TABLE E1-continued

| Cmpd. # | Structure |
|---|---|
| 123 | 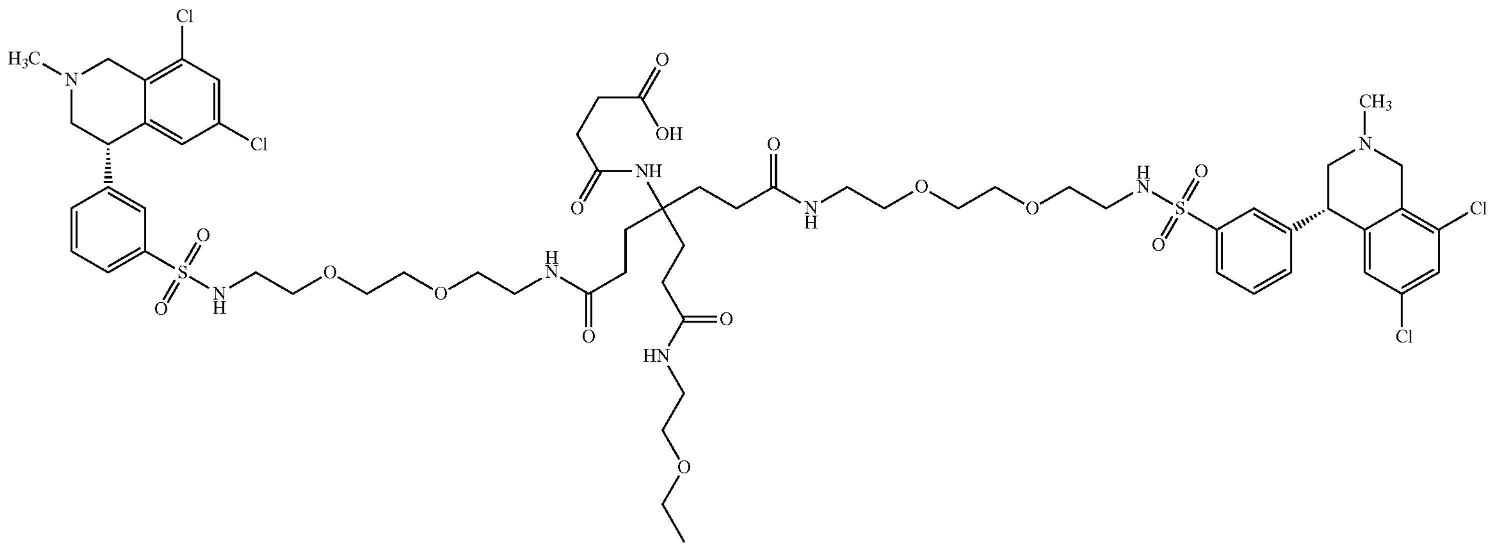 |

TABLE E1-continued
| Cmpd. # | Structure |
|---|---|
| 124 | 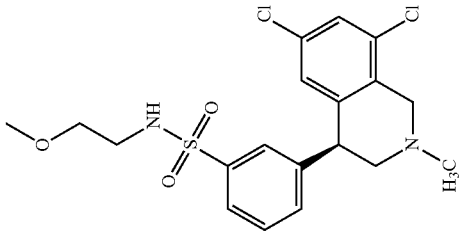 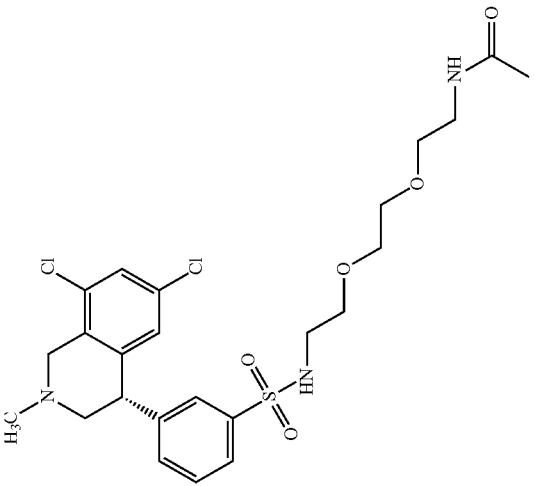 |

TABLE E1-continued

| Cmpd. # | Structure |
|---|---|
| 125 | 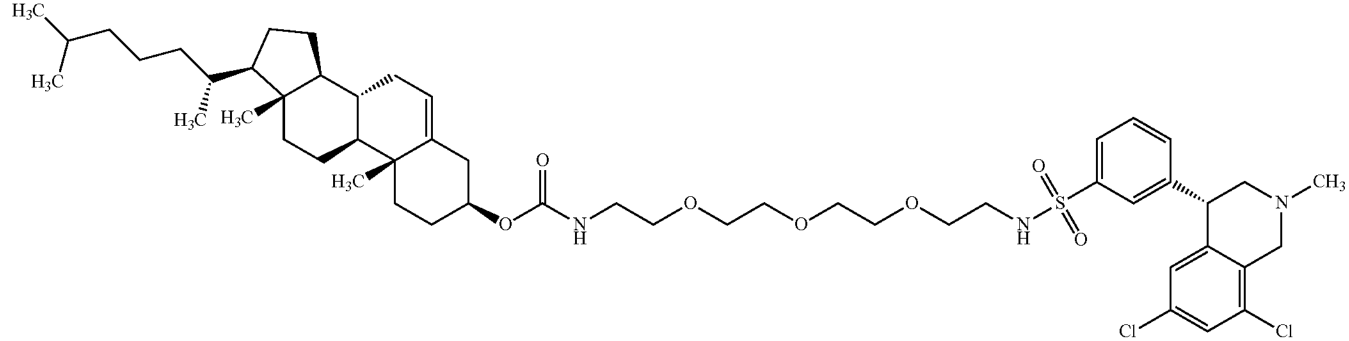 [SMILES: CC(C)CCC[C@@H](C)[C@H]1CC[C@H]2[C@@H]3CC=C4C[C@@H](OC(=O)NCCOCCOCCOCCNS(=O)(=O)c5cccc([C@@H]6CN(C)Cc7c(Cl)cc(Cl)cc76)c5)CC[C@]4(C)[C@H]3CC[C@]12C] |
| 126 | 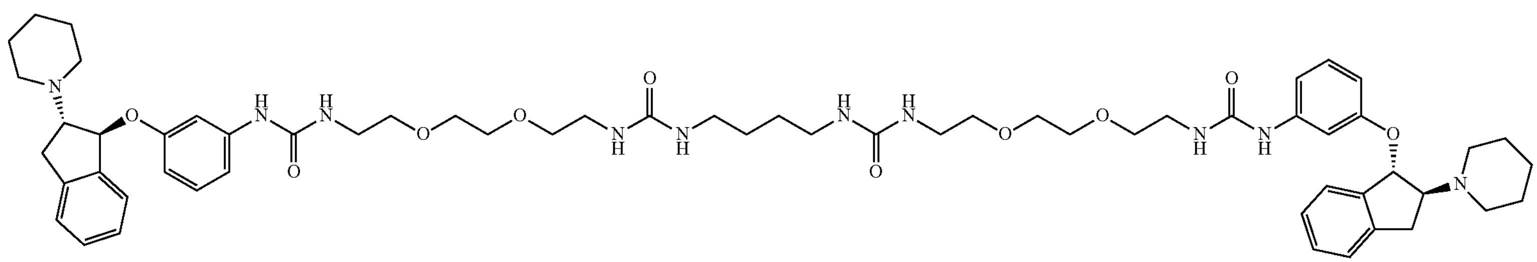 [SMILES: O=C(NCCCCNC(=O)NCCOCCOCCNC(=O)Nc1cccc(O[C@H]2c3ccccc3C[C@@H]2N2CCCCC2)c1)NCCOCCOCCNC(=O)Nc1cccc(O[C@H]2c3ccccc3C[C@@H]2N2CCCCC2)c1] |

TABLE E1-continued

| Cmpd. # | Structure |
|---|---|
| 127 | (chemical structure) |
| 128 | (chemical structure) |

TABLE E1-continued
| Cmpd. # | Structure |
|---|---|
| 129 | 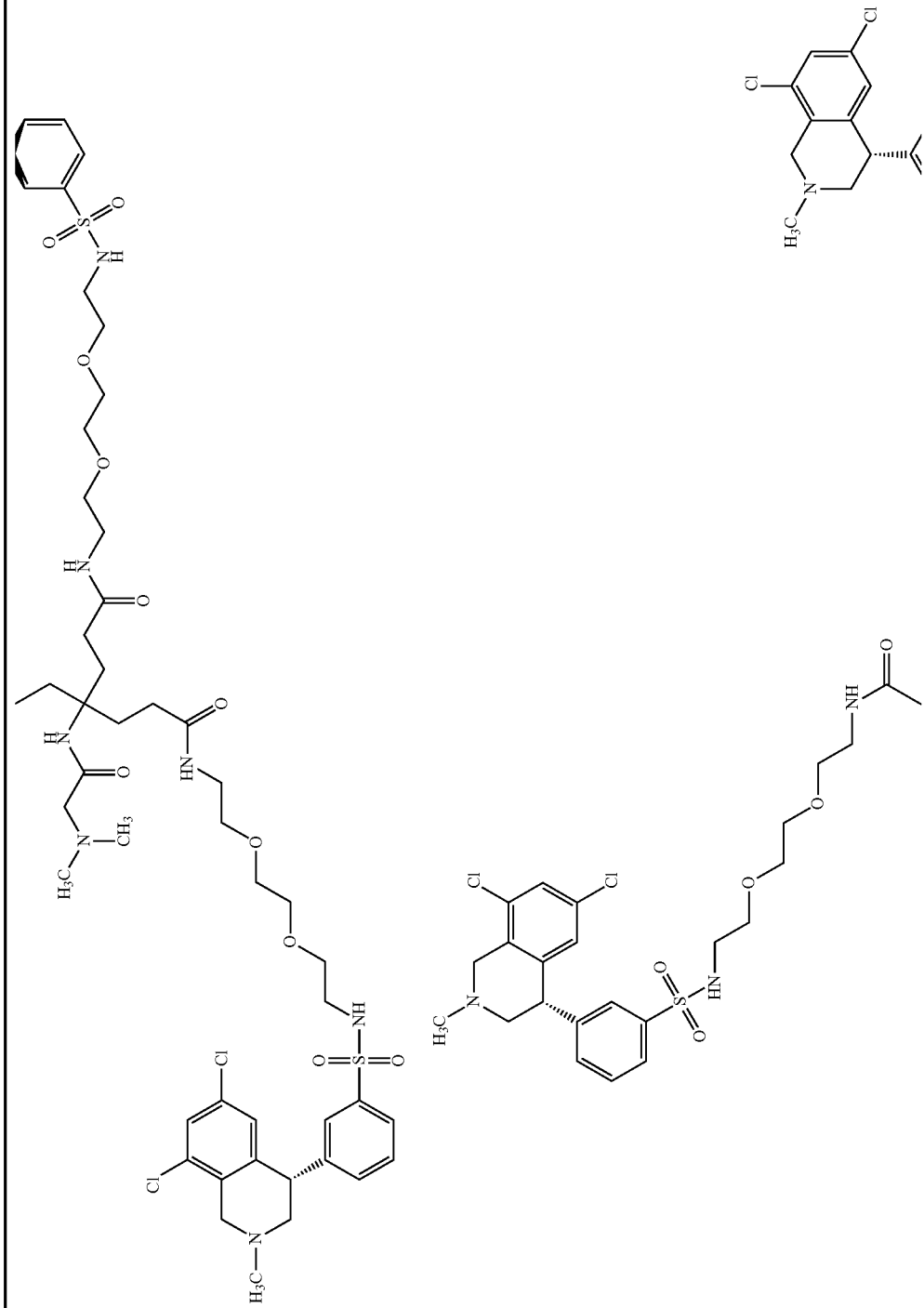 |

TABLE E1-continued
| Cmpd. # | Structure |
|---|---|
| 130 | 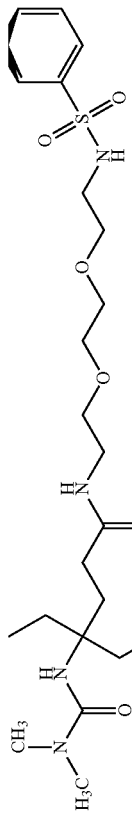 |

TABLE E1-continued
| Cmpd. # | Structure |
|---|---|
| 131 | 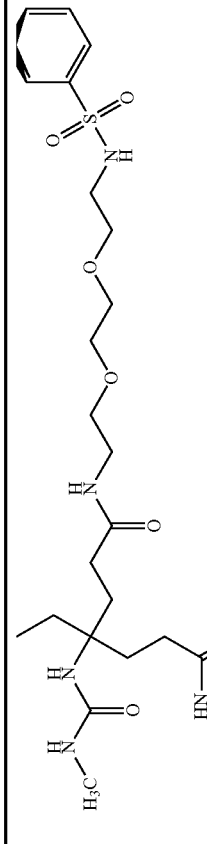 |

TABLE E1-continued
| Cmpd. # | Structure |
|---|---|
| 132 | 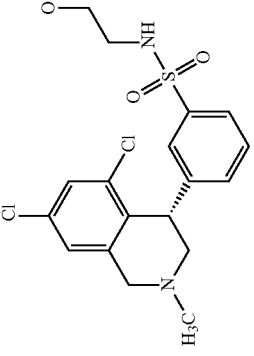 |

TABLE E1-continued
| Cmpd. # | Structure |
|---|---|
| 133 | 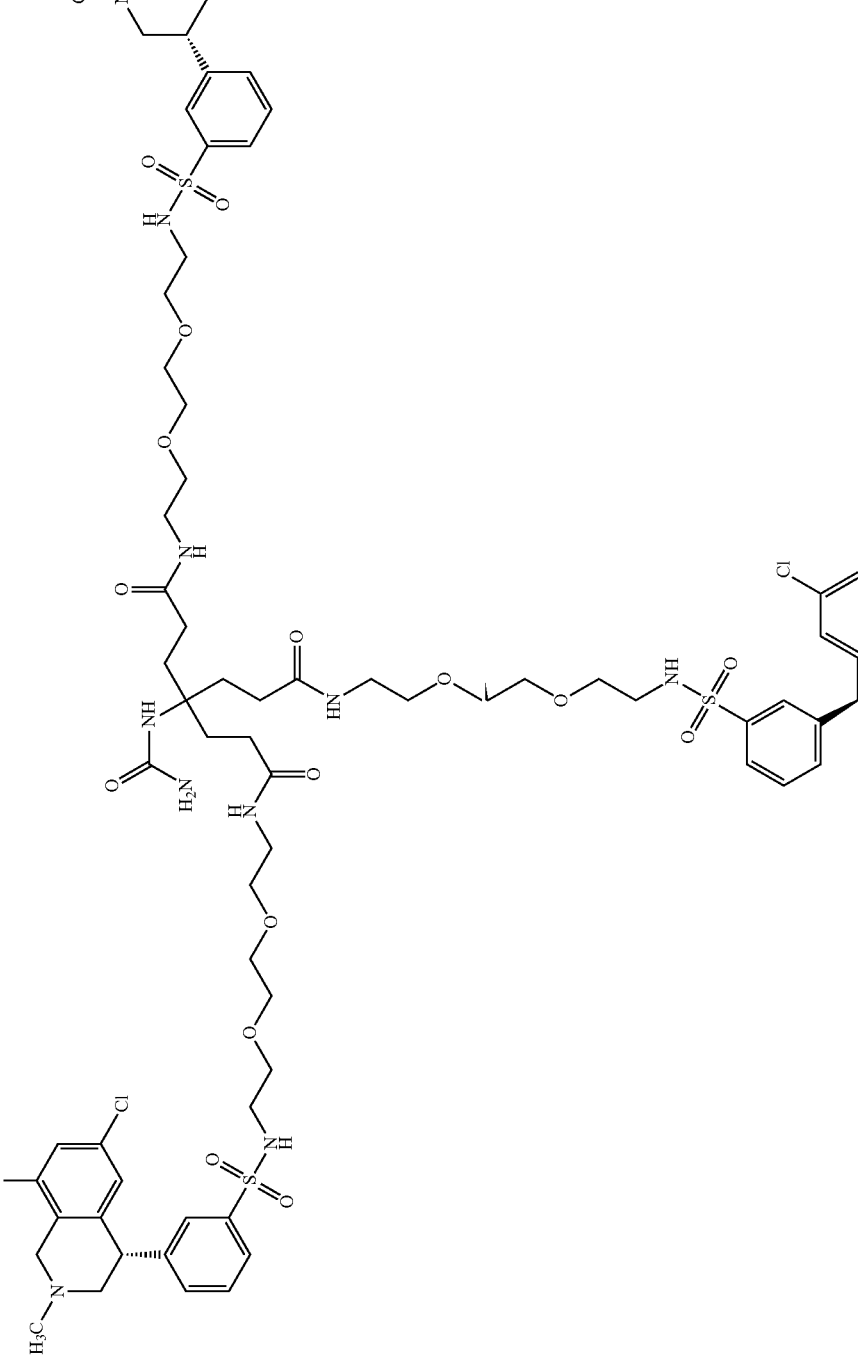 |

TABLE E1-continued
| Cmpd. # | Structure |
|---|---|
| 134 | 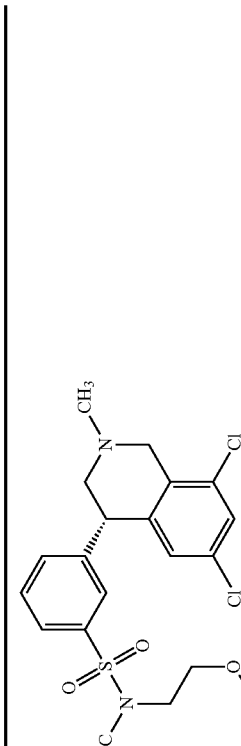 |

TABLE E1-continued
| Cmpd. # | Structure |
|---|---|
| 135 | 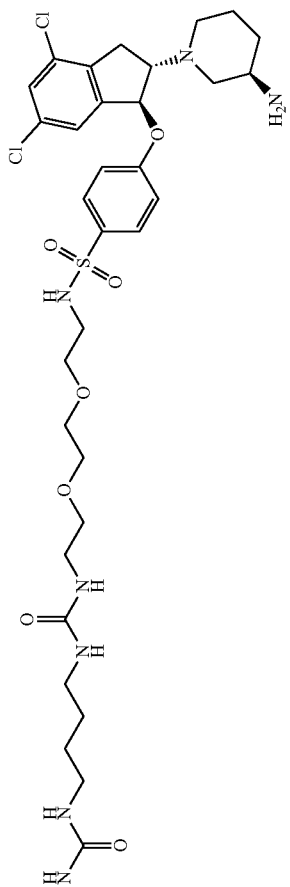 |
| 136 | 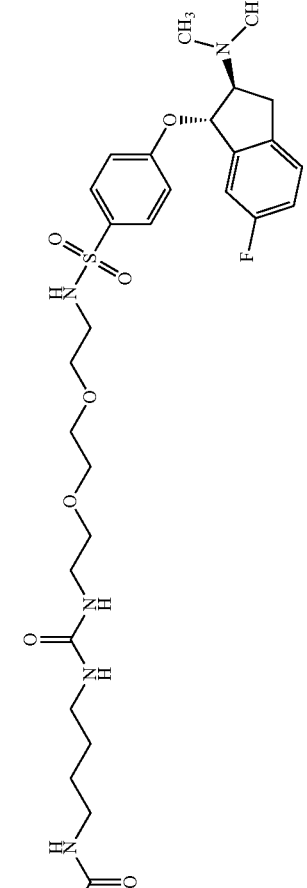 |

TABLE E1-continued
| Cmpd. # | Structure |
|---|---|
| 137 | 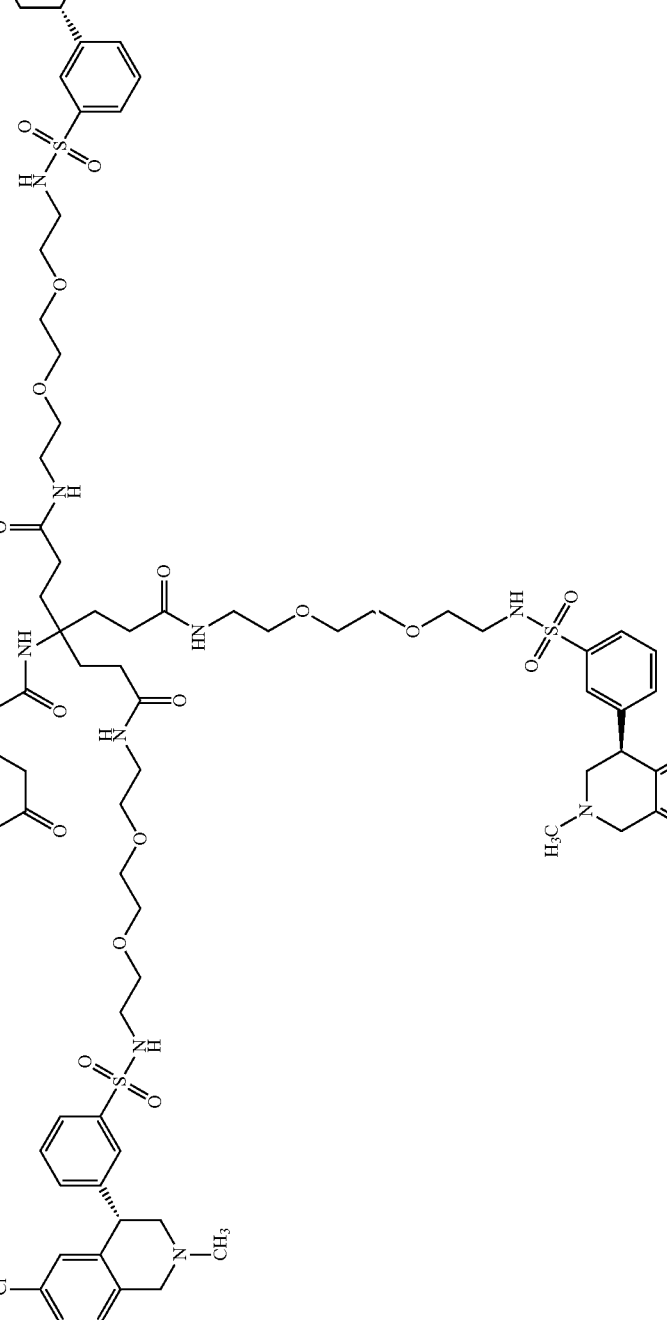 |

US 10,272,079 B2
| Cmpd. # | Structure |
|---|---|
| 138 | 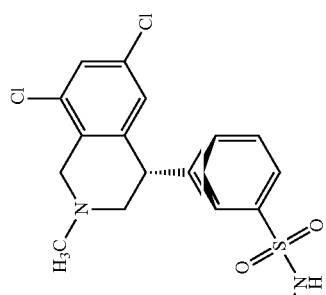 |

TABLE E1-continued
| Cmpd. # | Structure |
|---|---|
| 139 | 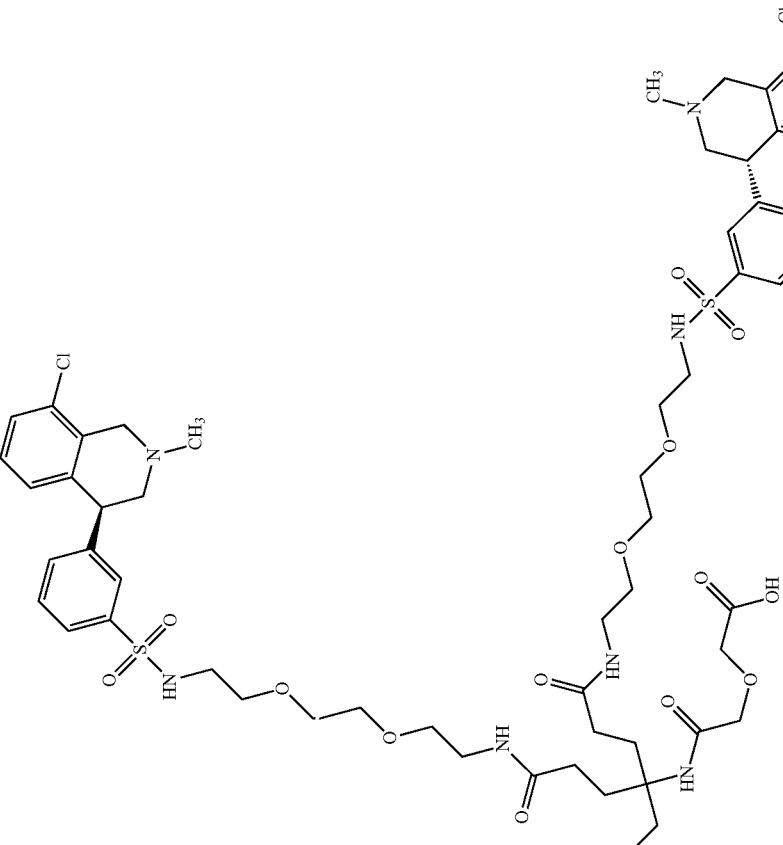 |

TABLE E1-continued

| Cmpd. # | Structure |
|---|---|
| 140 | (chemical structure) |
| 141 | (chemical structure) |

TABLE E1-continued
| Cmpd. # | Structure |
|---|---|
| 142 | 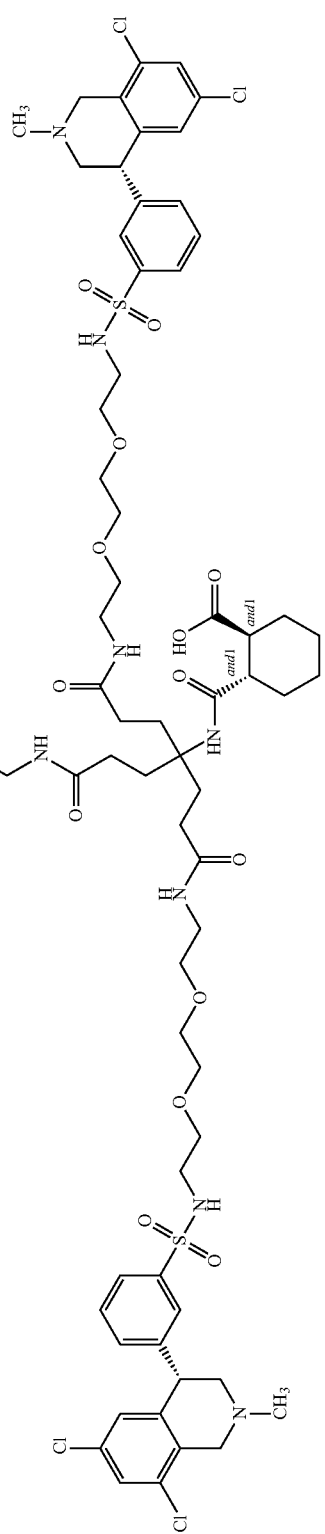 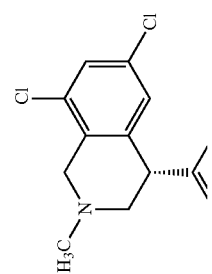 |

TABLE E1-continued
| Cmpd. # | Structure |
|---|---|
| 143 | 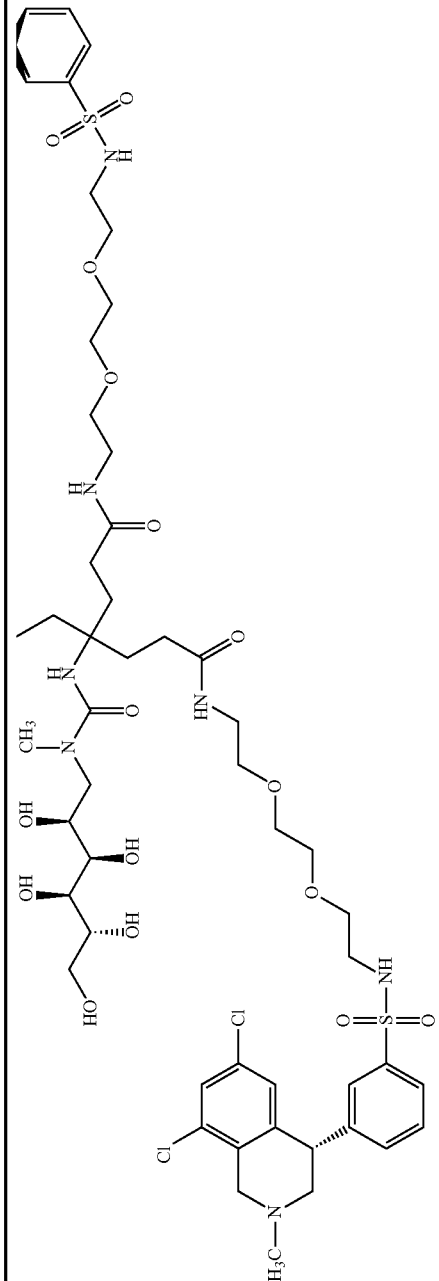 |

TABLE E1-continued
| Cmpd. # | Structure |
|---|---|
| | 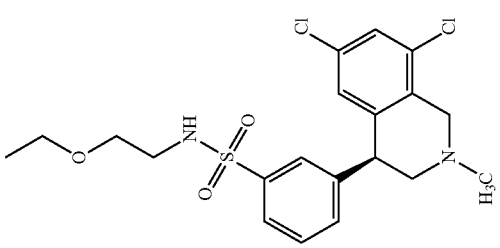 |

TABLE E1-continued
| Cmpd. # | Structure |
|---|---|
| 144 | 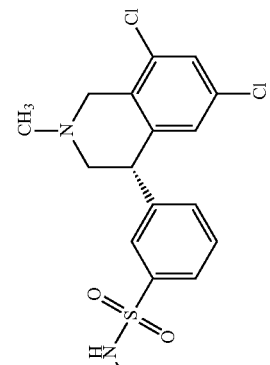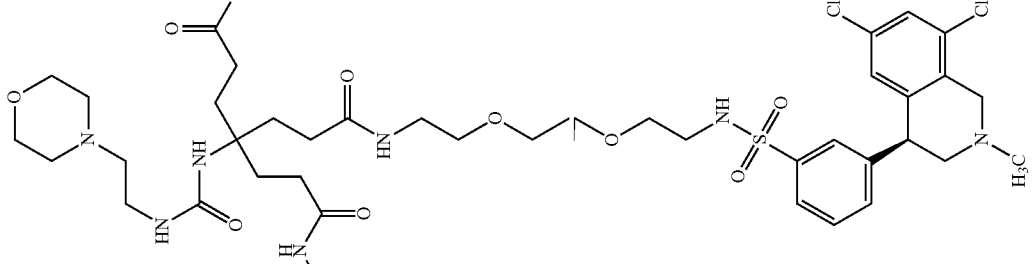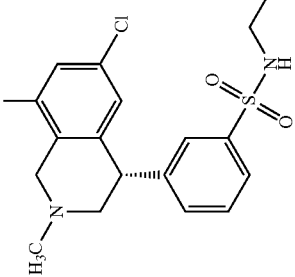 |

TABLE E1-continued
| Cmpd. # | Structure |
|---|---|
| 145 | 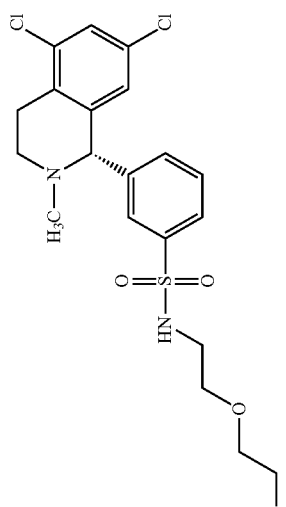 |

TABLE E1-continued
| Cmpd. # | Structure |
|---|---|
| | 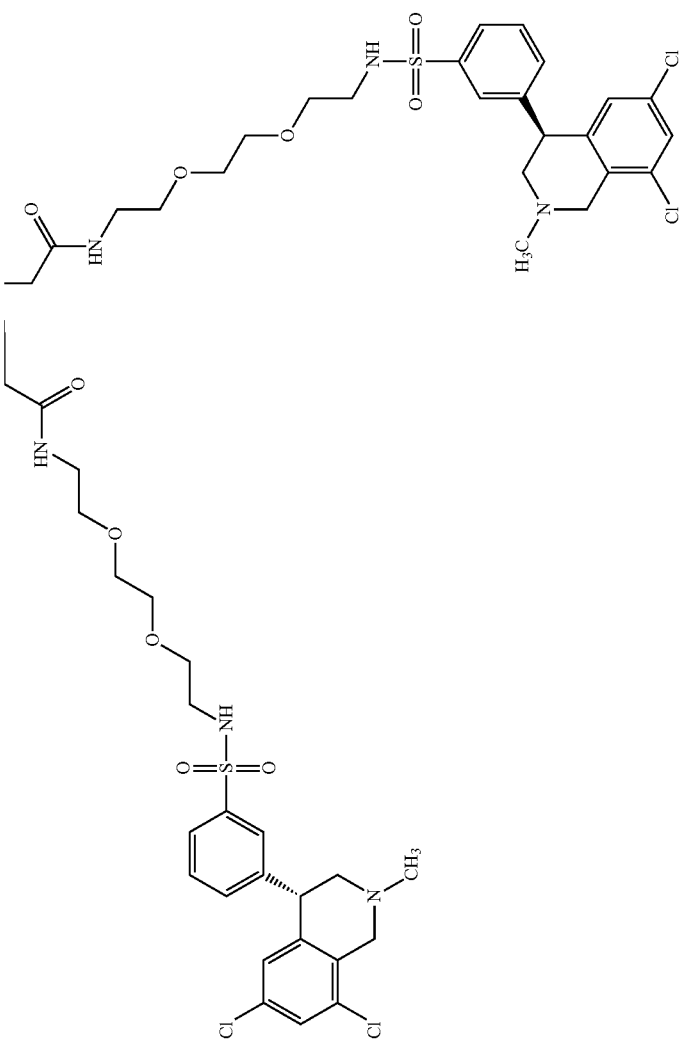 |

| Cmpd. # | Structure |
|---|---|
| 146 | 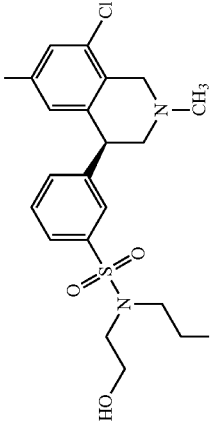 |

TABLE E1-continued
| Cmpd. # | Structure |
|---|---|
| 147 | 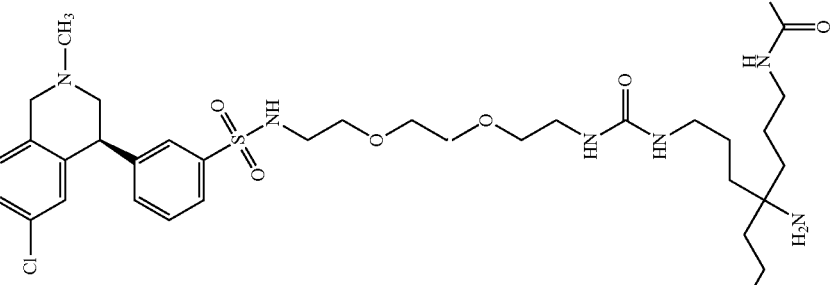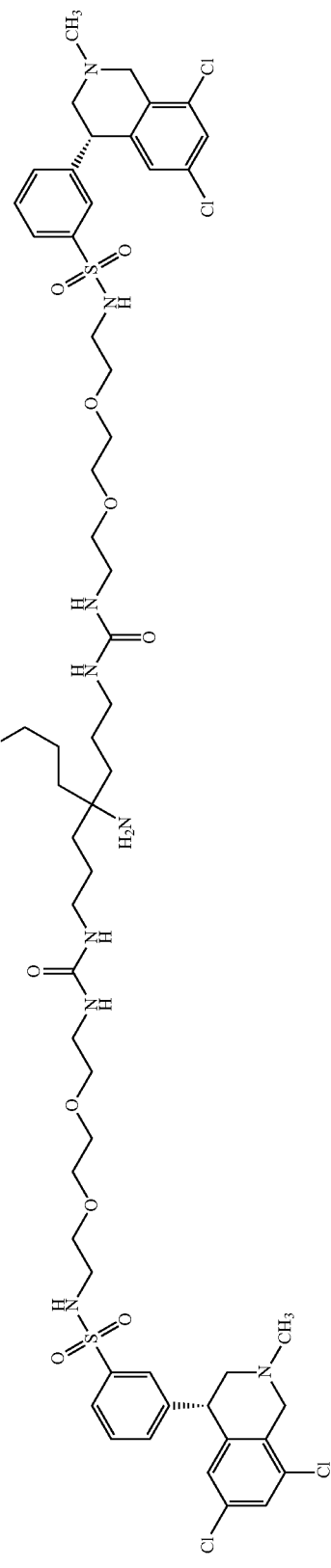 |

TABLE E1-continued

| Cmpd. # | Structure |
|---|---|
| 148 | 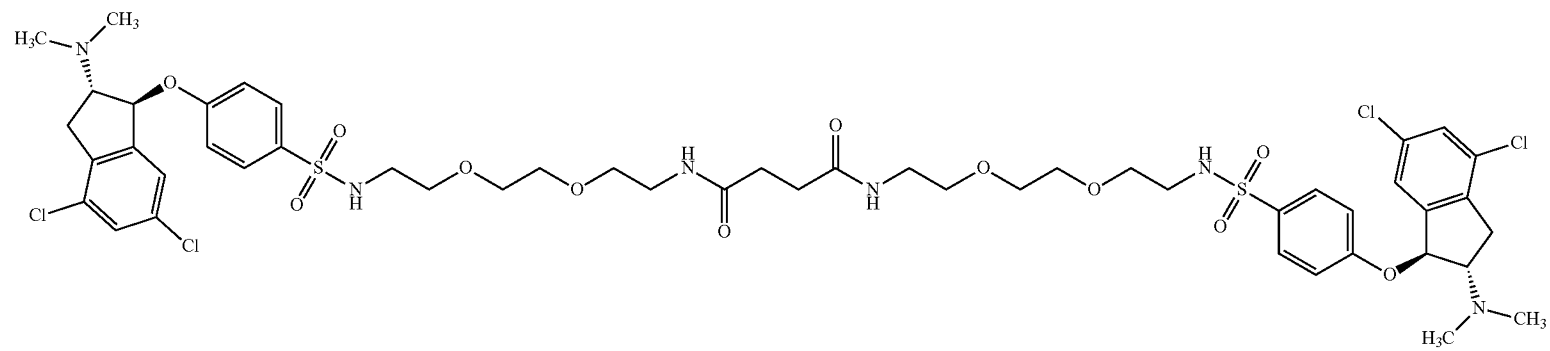 |
| 149 | 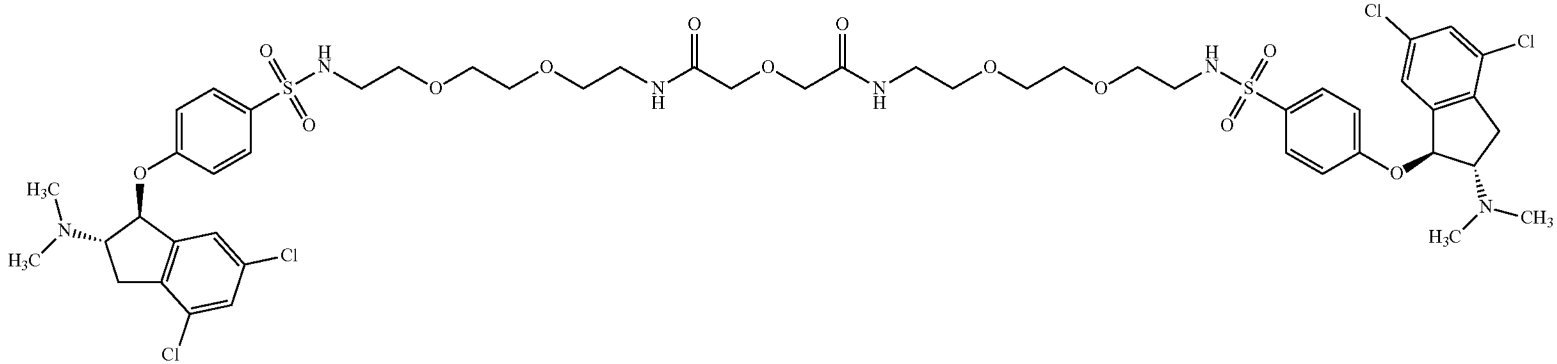 |

TABLE E1-continued
| Cmpd. # | Structure |
|---|---|
| 150 | 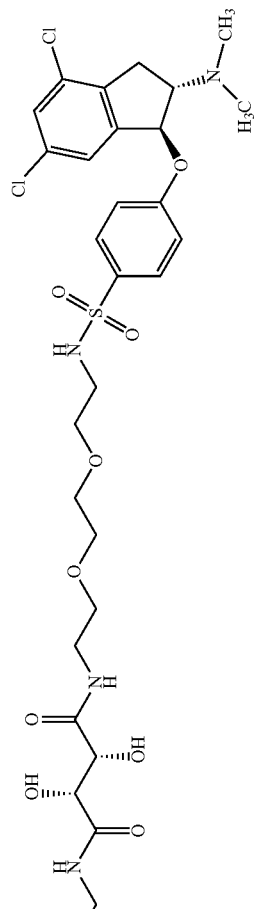 |
| 151 | 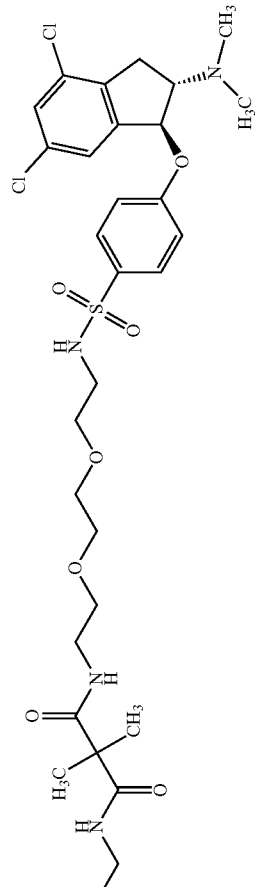 |

TABLE E1-continued
| Cmpd. # | Structure |
|---|---|
| 152 | 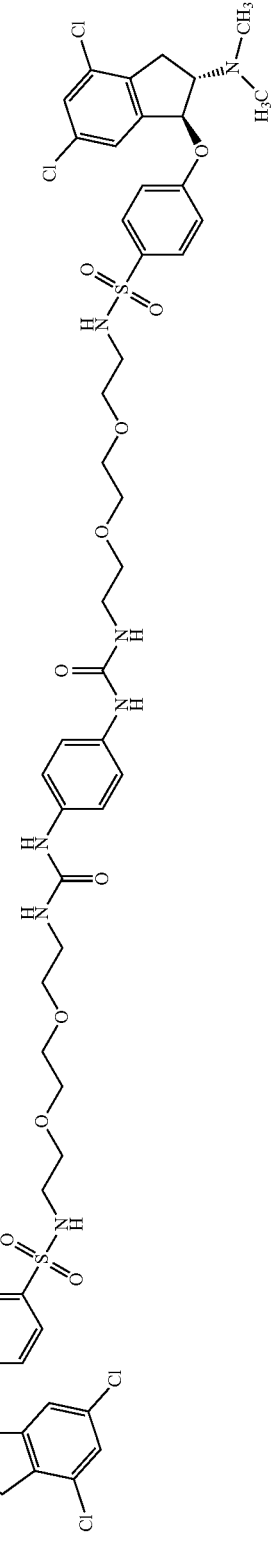 |
| 153 | 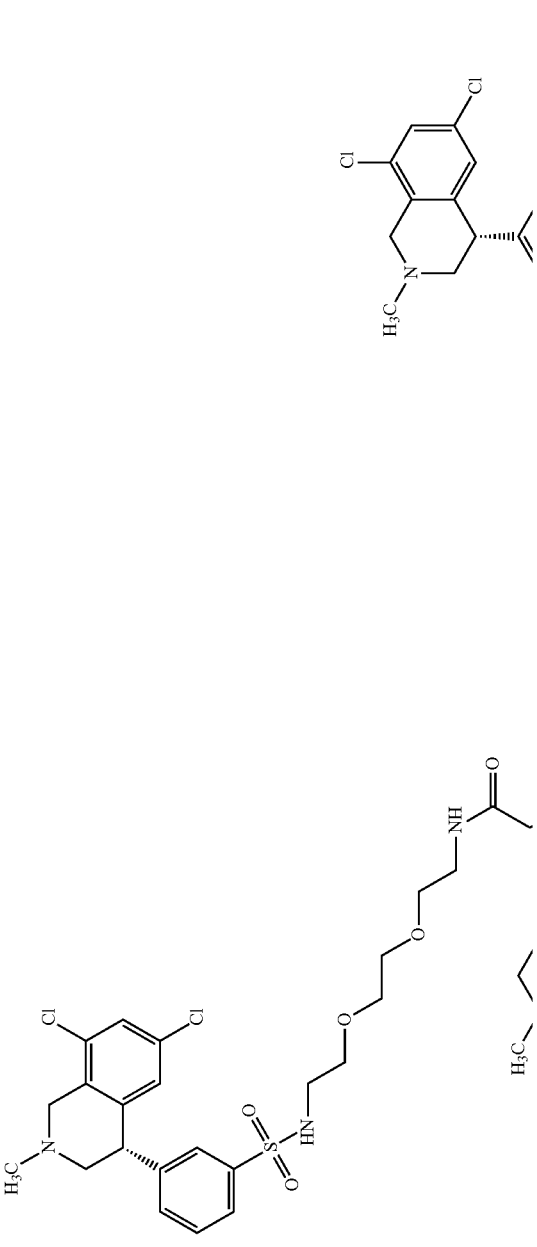 |

TABLE E1-continued
| Cmpd. # | Structure |
|---|---|
| | 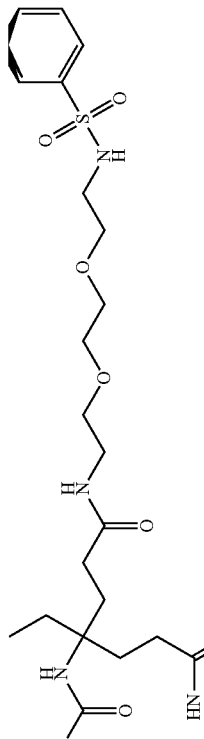 |
| 154 | 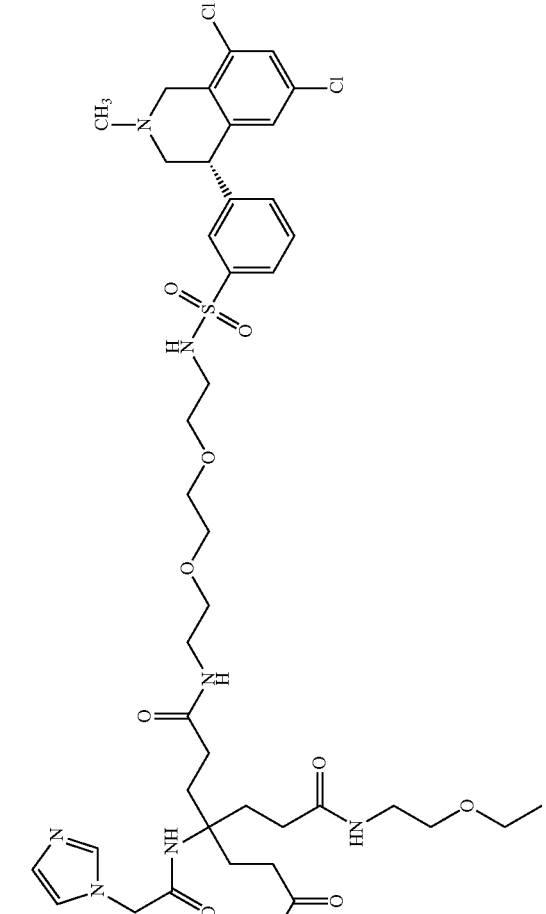 |

TABLE E1-continued
| Cmpd. # | Structure |
|---|---|
| 155 | 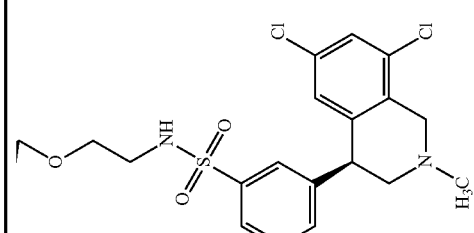 |

TABLE E1-continued
| Cmpd. # | Structure |
|---|---|
| 156 | 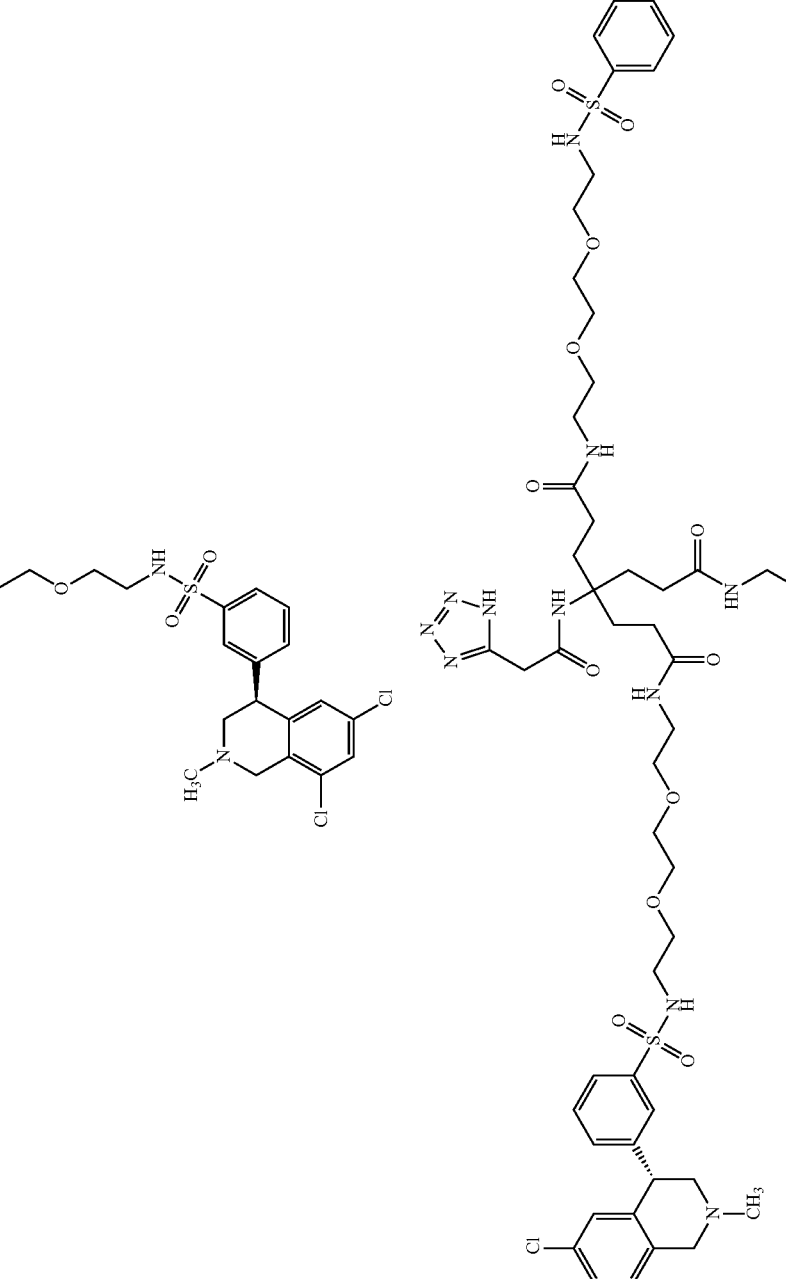 |

TABLE E1-continued
| Cmpd. # | Structure |
|---|---|
| 157 | 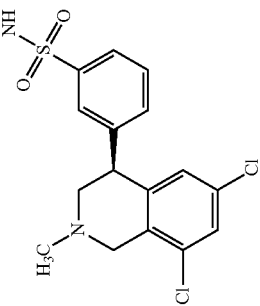 |

TABLE E1-continued
| Cmpd. # | Structure |
|---|---|
| 158 | 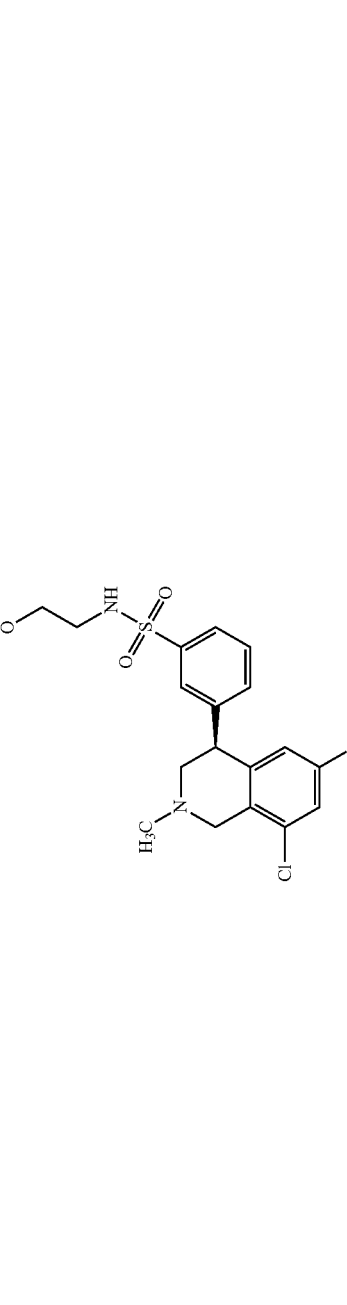 |

TABLE E1-continued
| Cmpd. # | Structure |
|---|---|
| 159 | 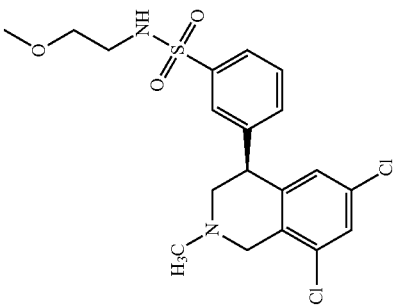 |

TABLE E1-continued
| Cmpd. # | Structure |
|---|---|
| 401 | 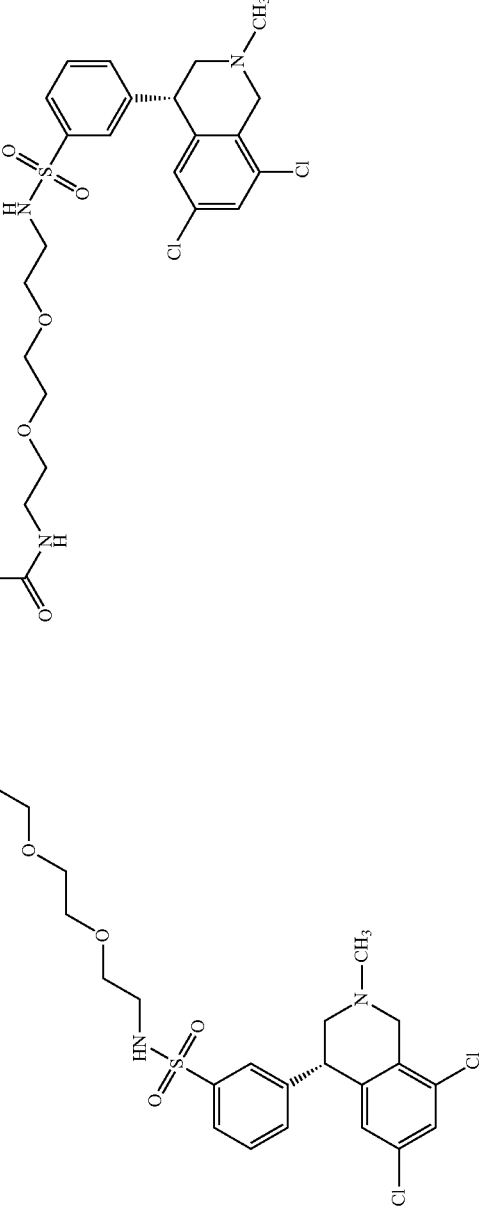 |
| 402 | 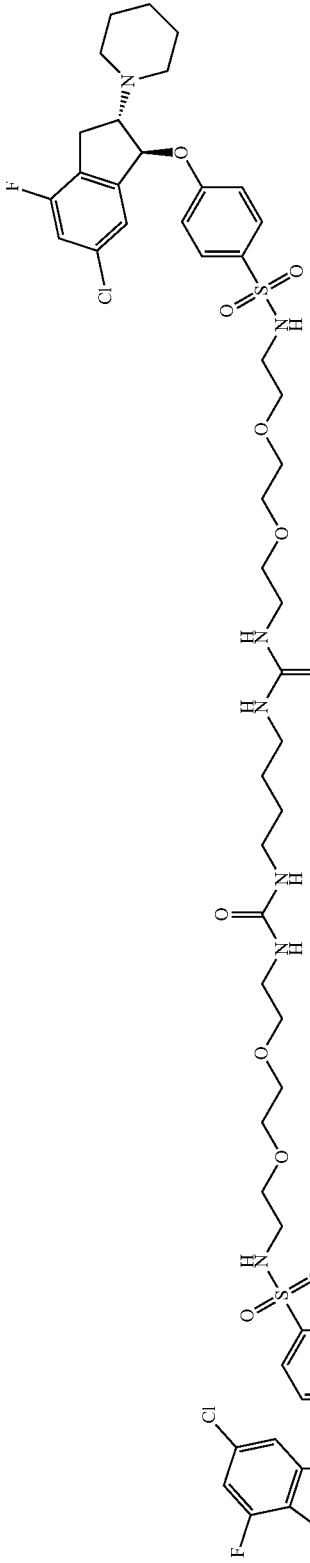 |

TABLE E1-continued
| Cmpd. # | Structure |
|---|---|
| 161 | 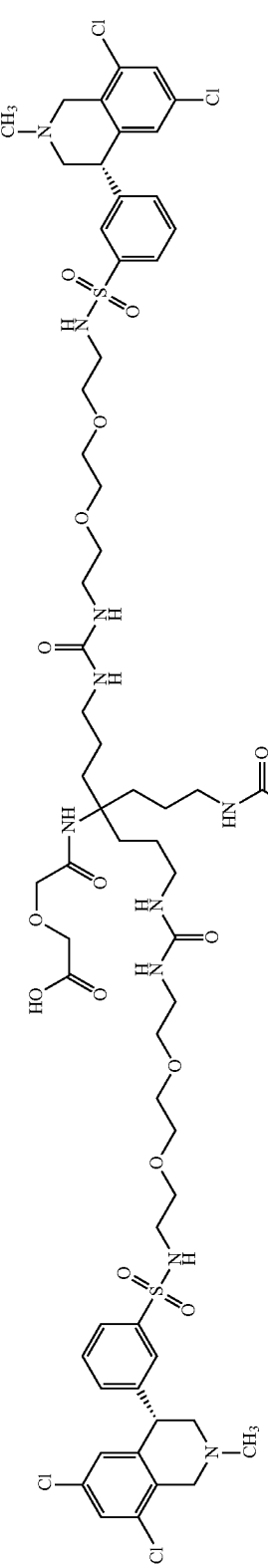 |

TABLE E1-continued
| Cmpd. # | Structure |
|---|---|
| 162 | 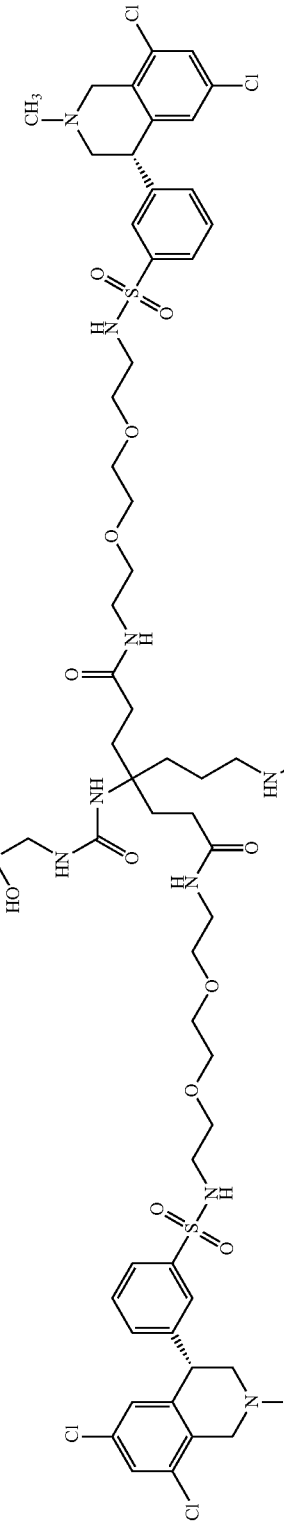 |

TABLE E1-continued
| Cmpd. # | Structure |
|---|---|
| 163 | 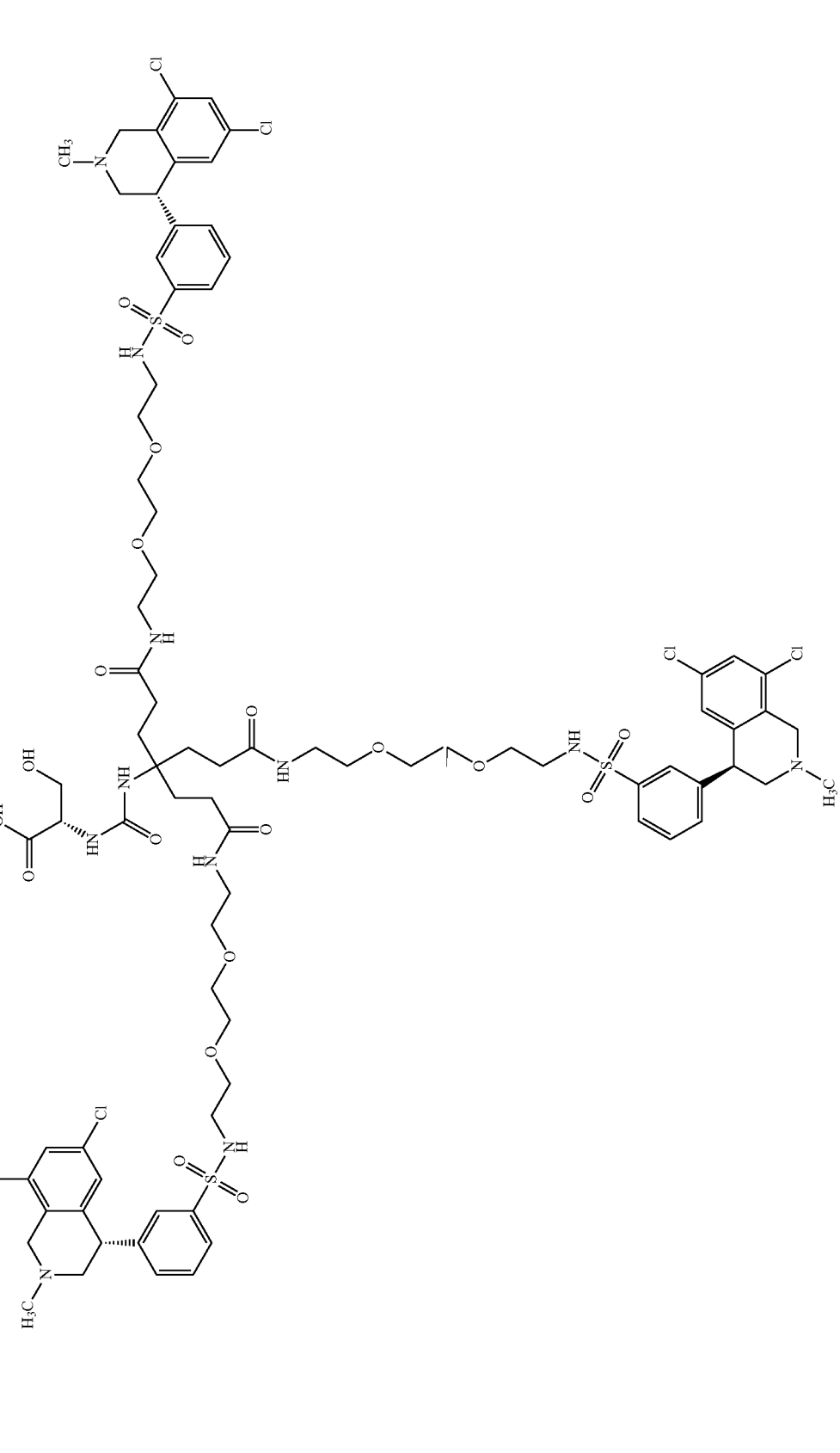 |

TABLE E1-continued
| Cmpd. # | Structure |
|---|---|
| 164 | 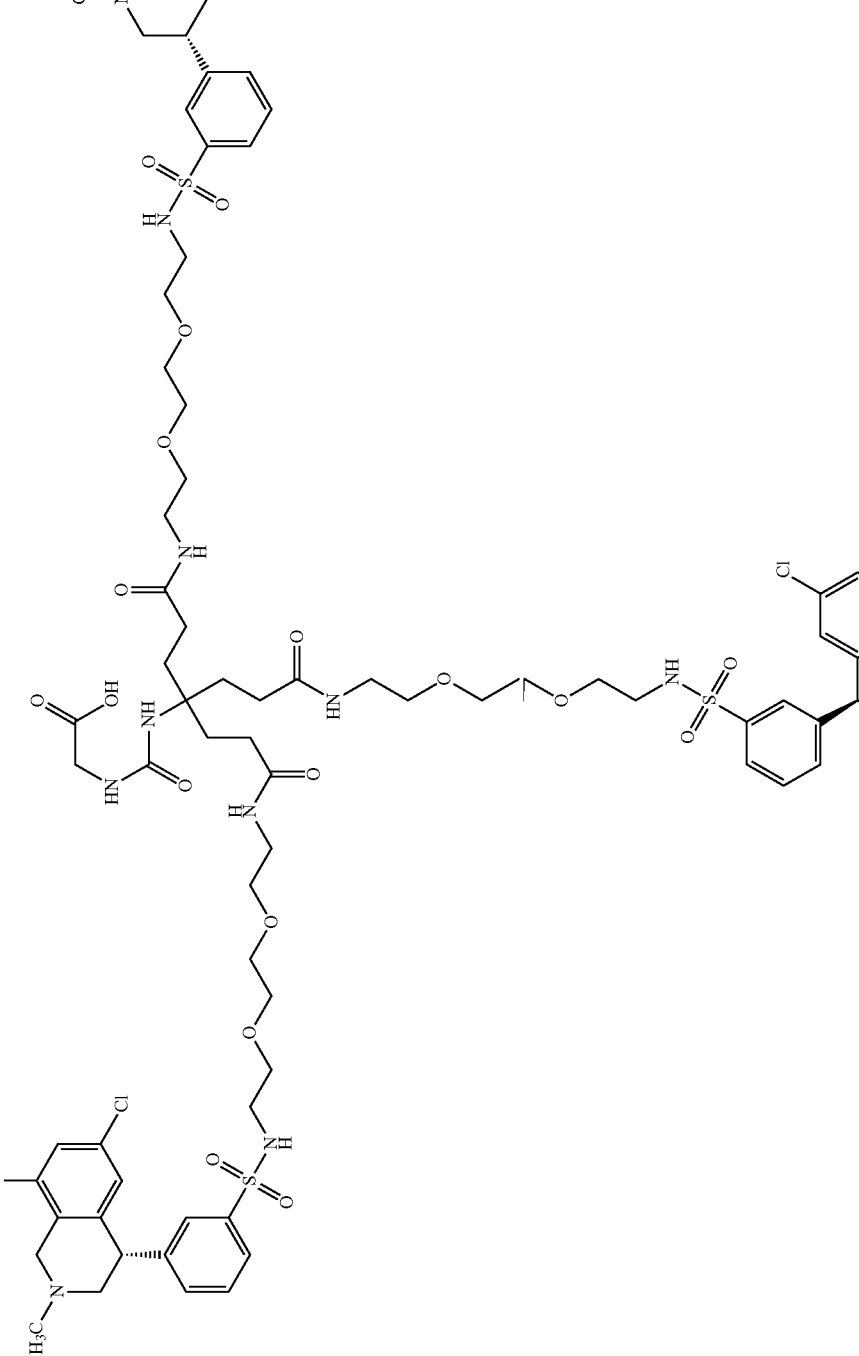 |

TABLE E1-continued
| Cmpd. # | Structure |
|---|---|
| 165 | 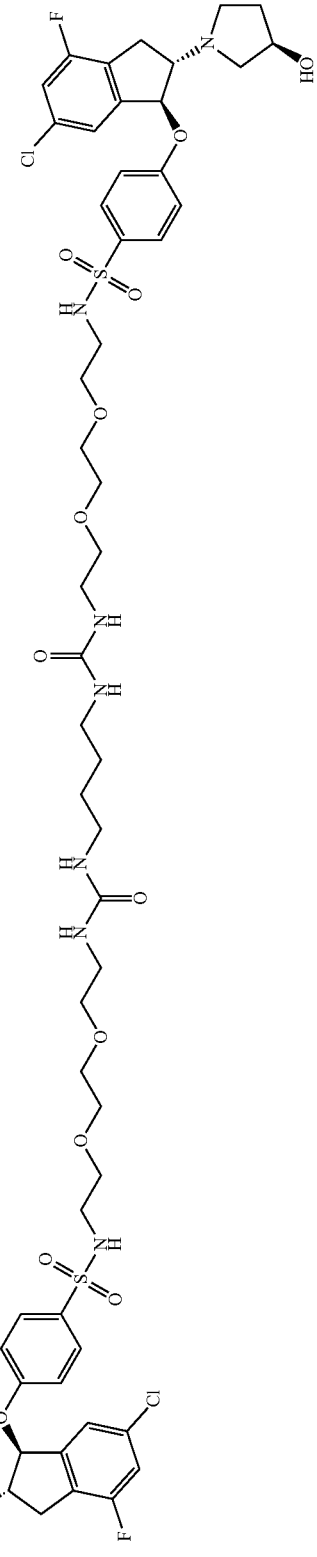 |
| 166 | 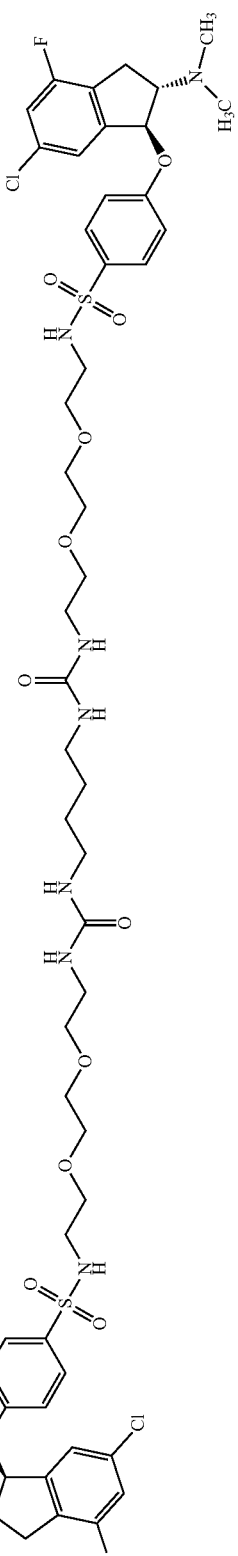 |

TABLE E1-continued
| Cmpd. # | Structure |
|---|---|
| 167 | 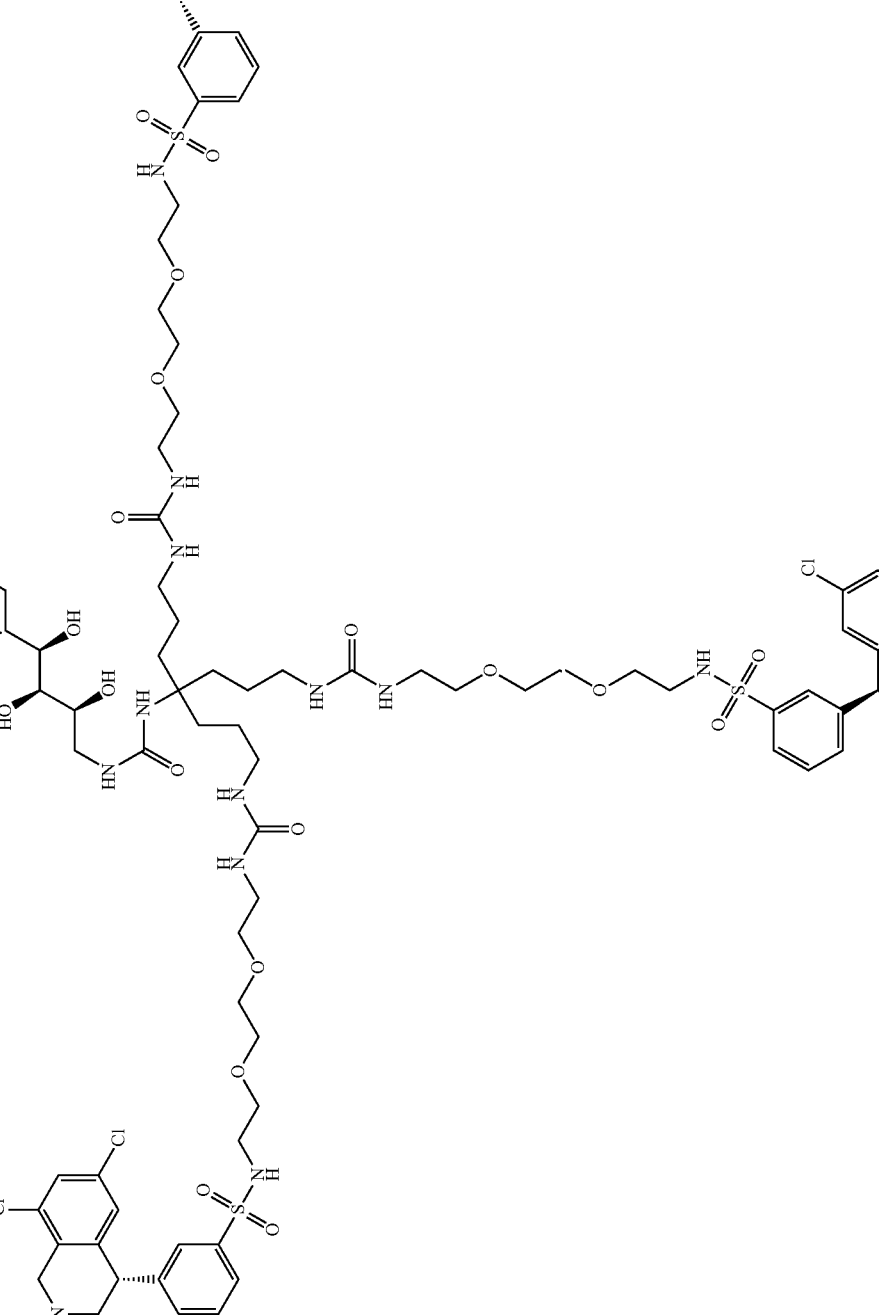 |

TABLE E1-continued
| Cmpd. # | Structure |
|---|---|
| 168 | 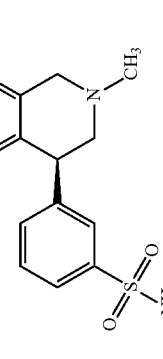 |

TABLE E1-continued
| Cmpd. # | Structure |
|---|---|
| 169 | 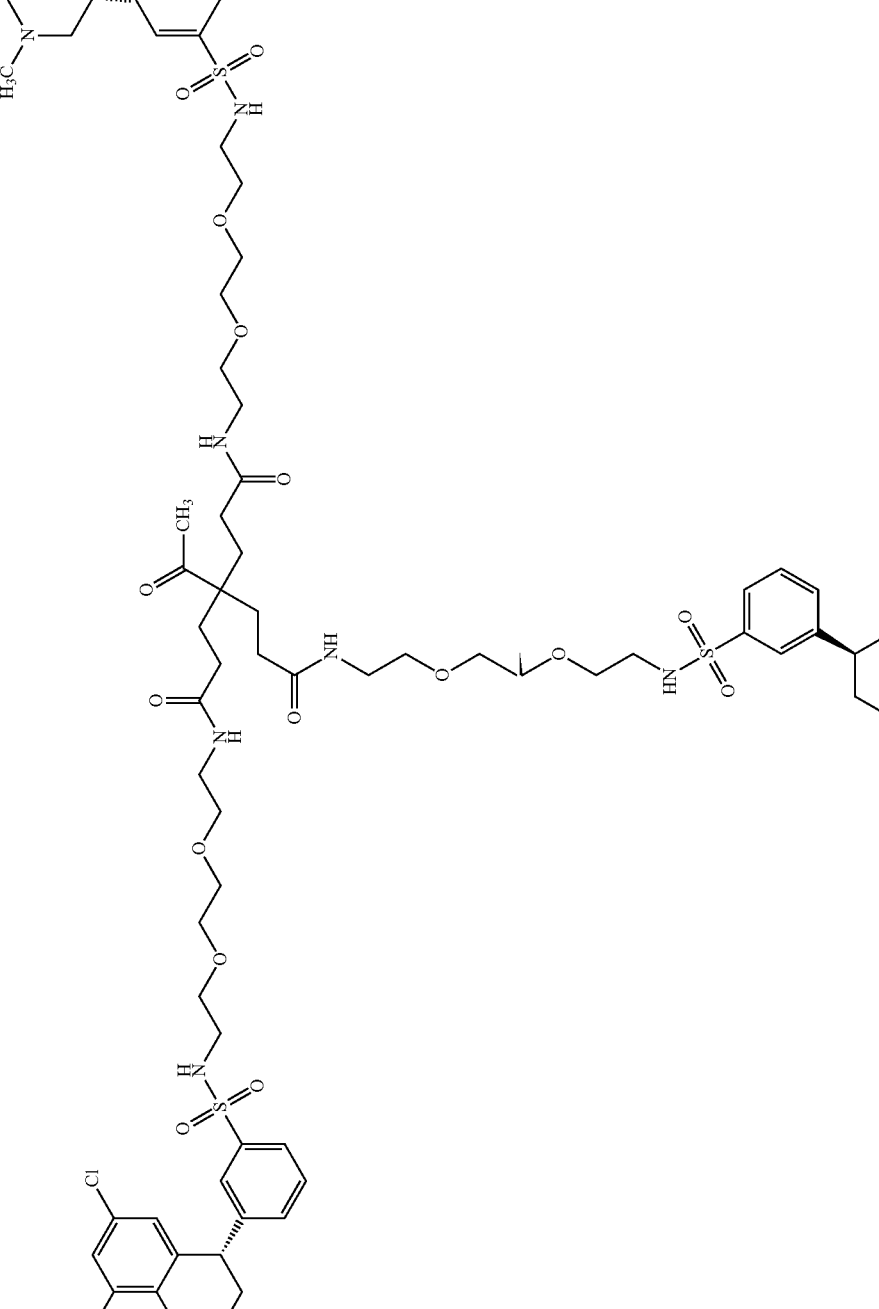 |

TABLE E1-continued
| Cmpd. # | Structure |
|---|---|
| 170 | 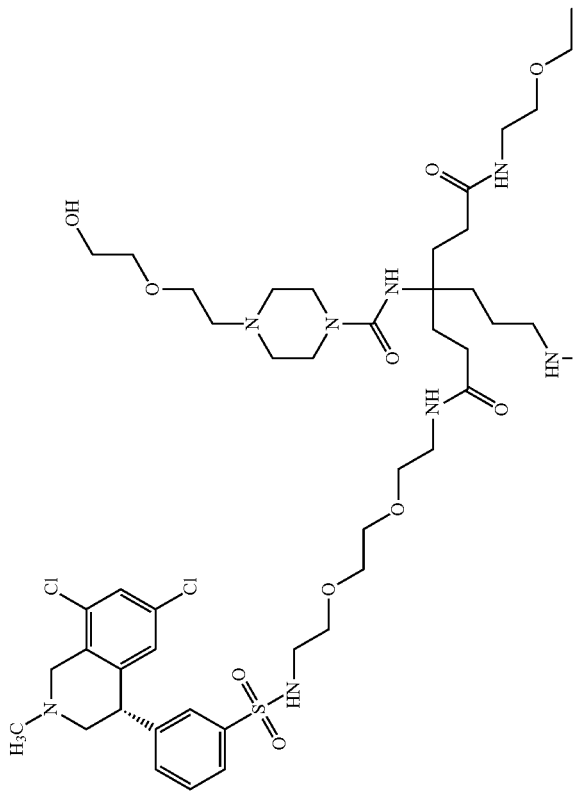 |

TABLE E1-continued
| Cmpd. # | Structure |
|---|---|
| | 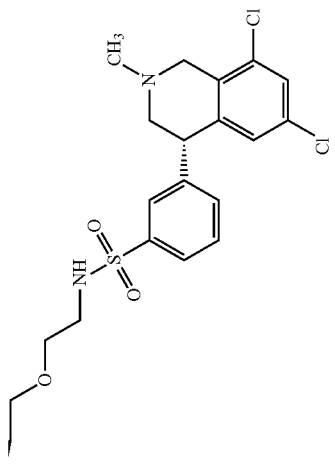 |
| 171 | 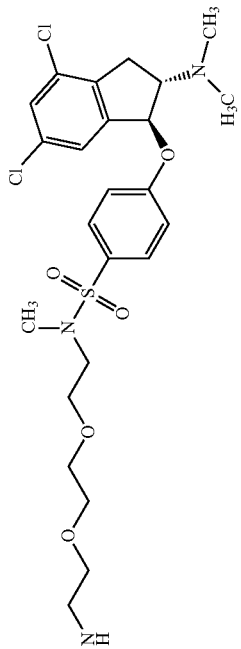 |

TABLE E1-continued
| Cmpd. # | Structure |
|---|---|
| 172 | 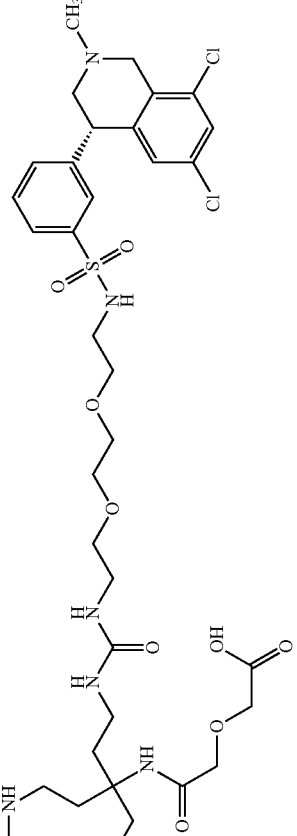 |

TABLE E1-continued
| Cmpd. # | Structure |
|---|---|
| 173 | 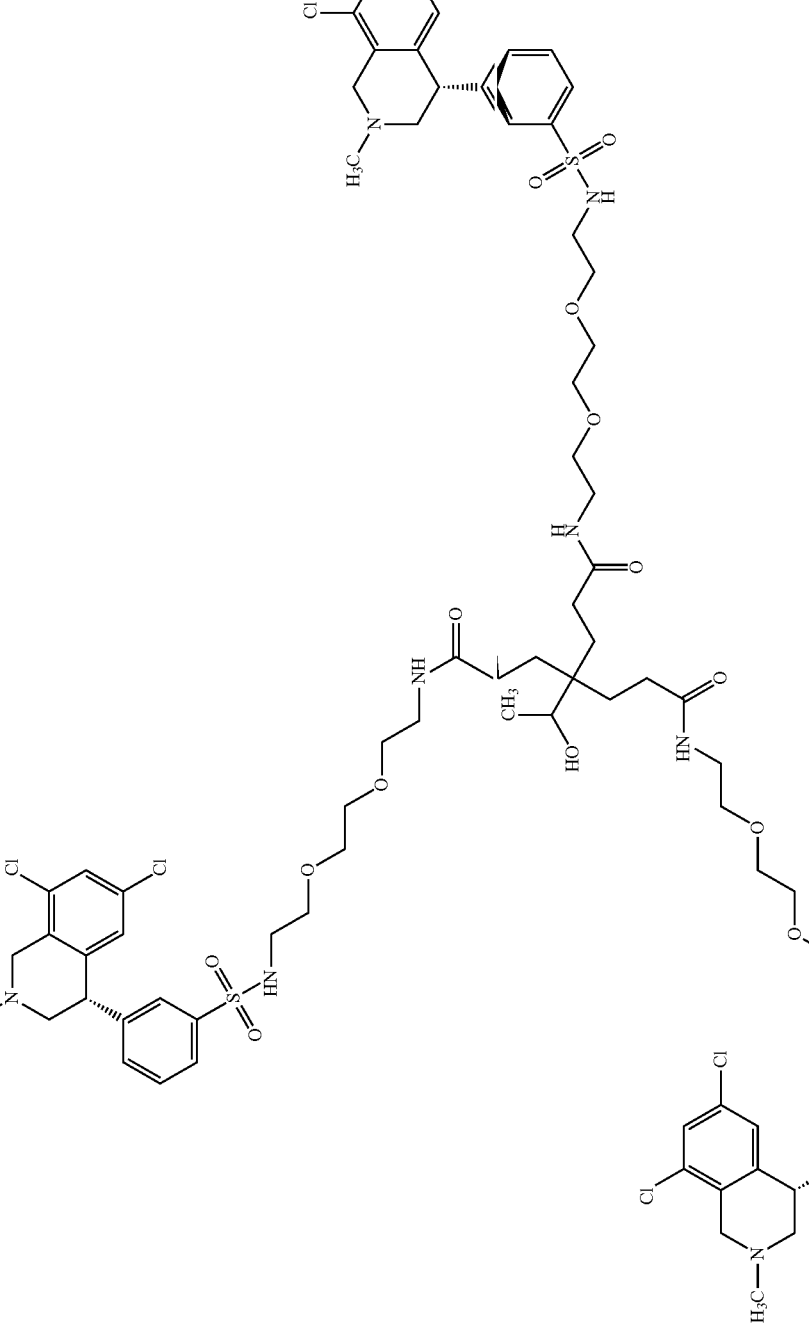 |

TABLE E1-continued

| Cmpd. # | Structure |
|---|---|
| 174 | 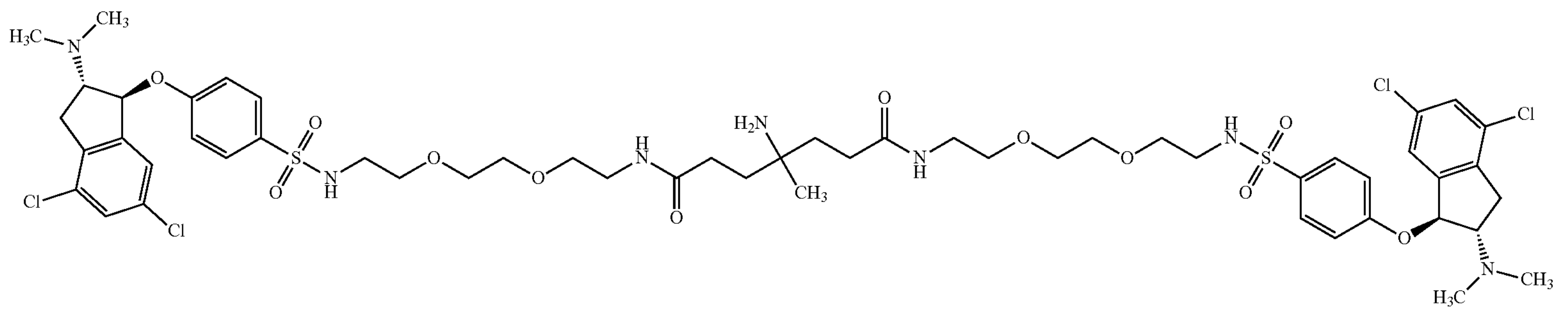 |
| 175 | 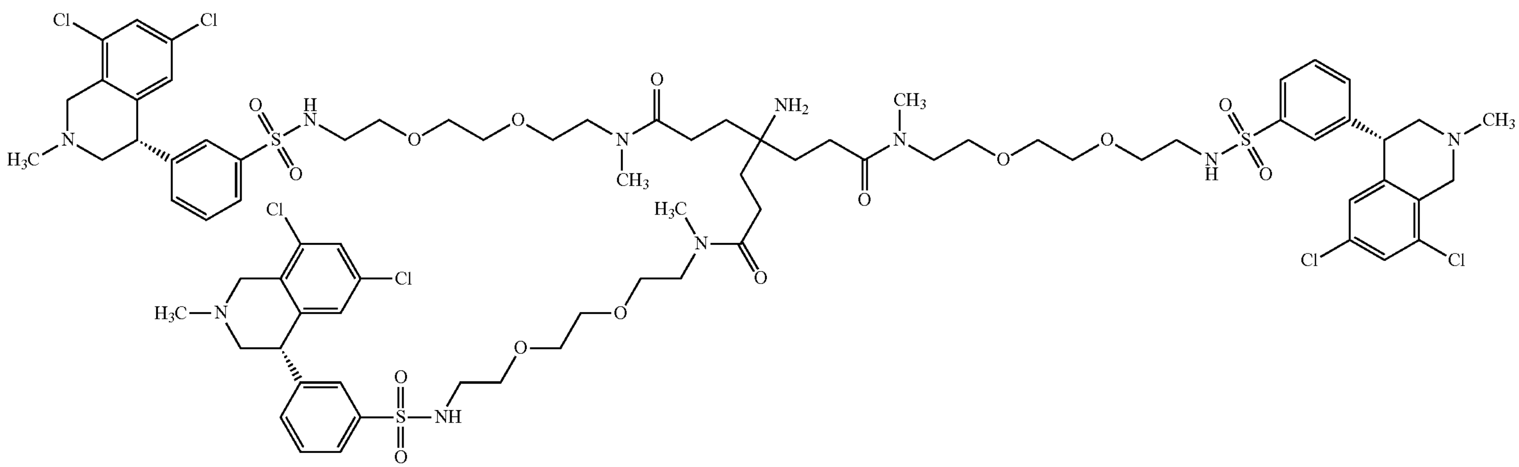 |

TABLE E1-continued
| Cmpd. # | Structure |
|---|---|
| 176 | 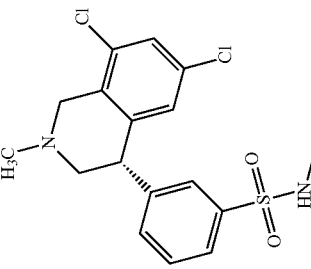 |

TABLE E1-continued
| Cmpd. # | Structure |
|---|---|
| 177 | 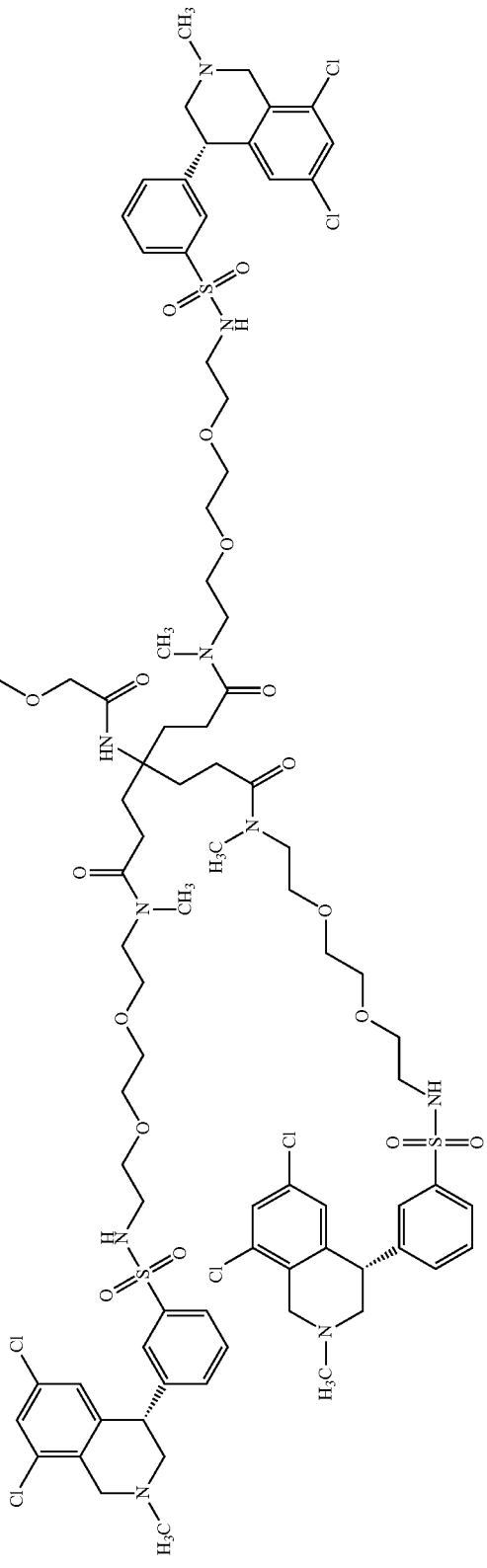 |
| 178 | 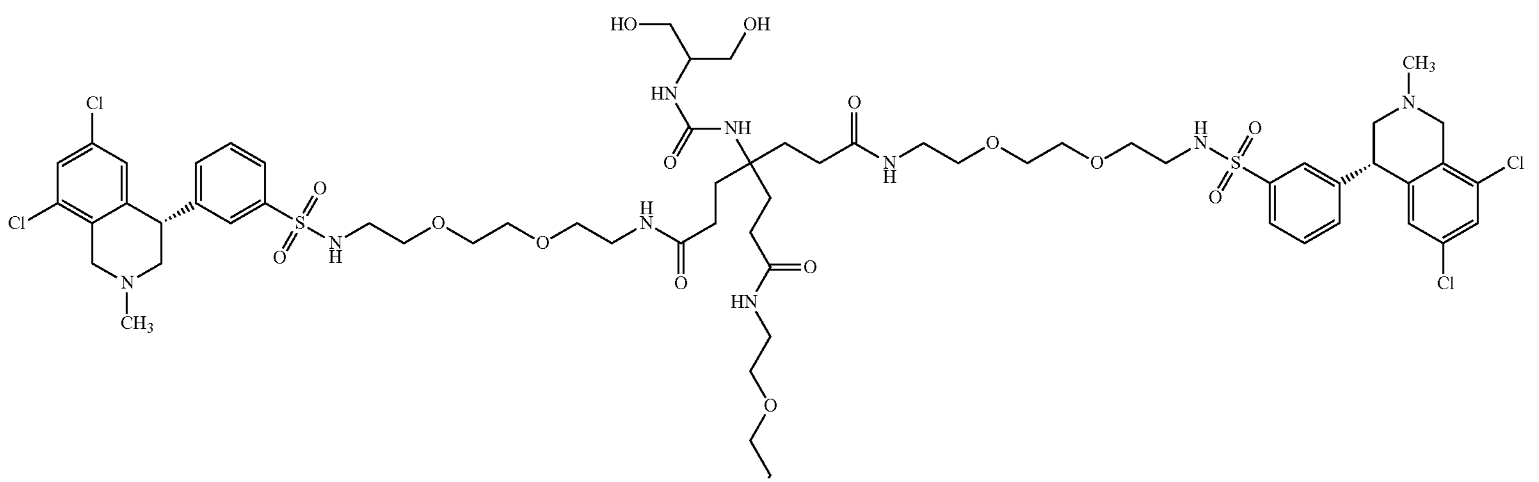 |

TABLE E1-continued
| Cmpd. # | Structure |
|---|---|
| 179 | 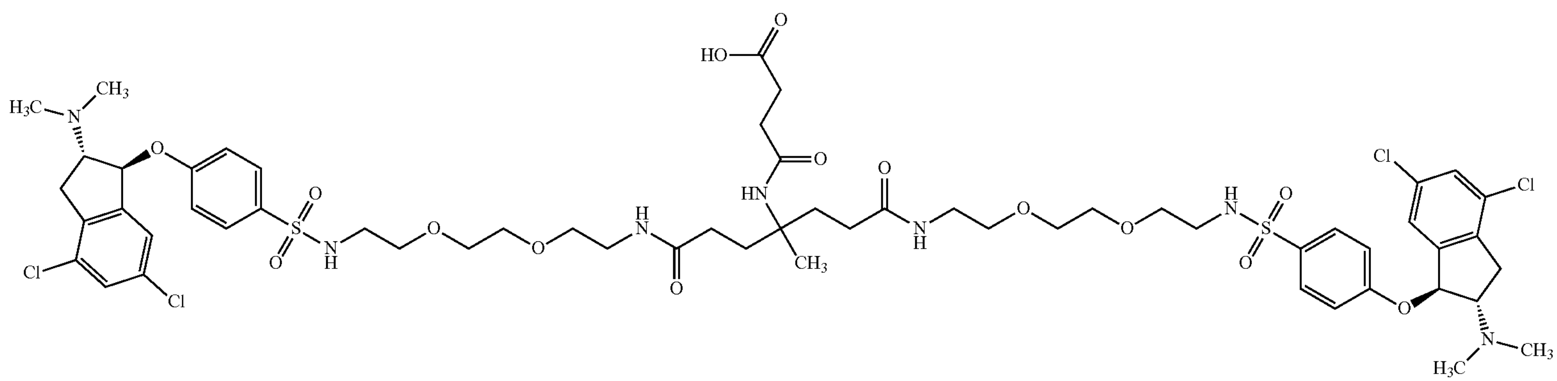 |

TABLE E1-continued
| Cmpd. # | Structure |
|---|---|
| 180 | 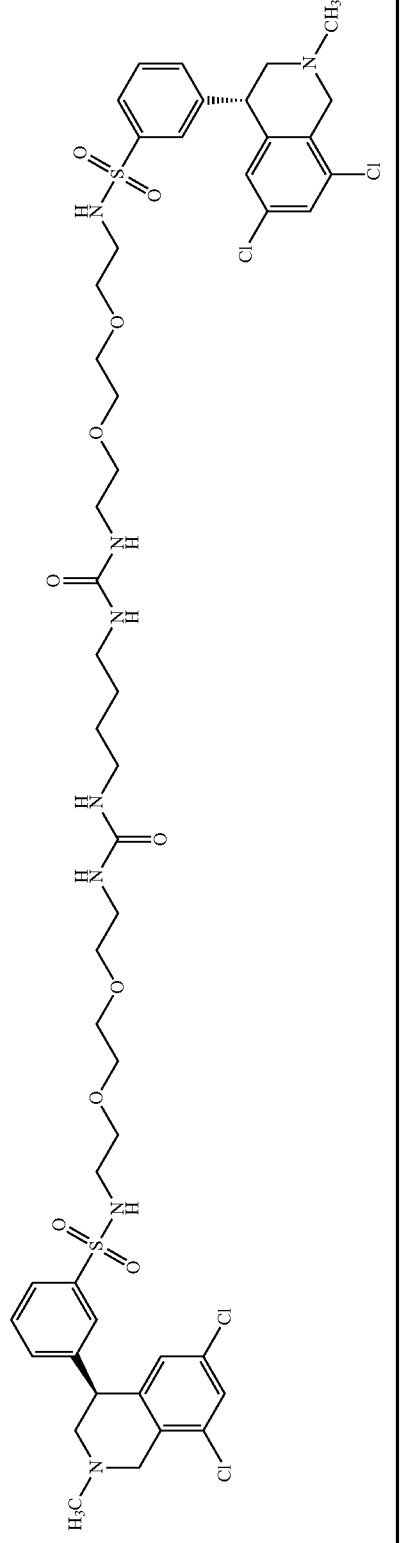 |

Cell-based activity under Prompt Conditions. Rat or human NHE3-mediated $Na^+$-dependent $H^+$ antiport was measured using a modification of the pH sensitive dye method originally reported by Paradiso (*PNAS USA.* 81:7436-7440, 1984). Opossum kidney (OK) cells were obtained from the ATCC and propagated per their instructions. The rat NHE3 gene (GenBank M85300) or the human NHE3 gene (GenBank NM_004174.1) was introduced into OK cells via electroporation, and cells were seeded into 96 well plates and grown overnight. Medium was aspirated from the wells, cells were washed twice with NaCl-HEPES buffer (100 mM NaCl, 50 mM HEPES, 10 mM glucose, 5 mM KCl, 2 mM $CaCl_2$, 1 mM $MgCl_2$, pH 7.4), then incubated for 30 min at room temperature with $NH_4Cl$-HEPES buffer (20 mM $NH_4Cl$, 80 mM NaCl, 50 mM HEPES, 5 mM KCl, 2 mM $CaCl_2$, 1 mM $MgCl_2$, pH 7.4) containing 5 μM bis(acetoxymethyl) 3,3'-(3',6'-bis(acetoxymethoxy)-5-((acetoxymethoxy)carbonyl)-3-oxo-3H-spiro[isobenzofuran-1,9'-xanthene]-2',7'-diyl)dipropanoate (BCECF-AM).

Cells were washed twice with Ammonium free, $Na^+$-free HEPES (100 mM choline, 50 mM HEPES, 10 mM glucose, 5 mM KCl, 2 mM $CaCl_2$, 1 mM $MgCl_2$, pH 7.4) and incubated in the same buffer for 10 minutes at room temperature to lower intracellular pH. NHE3-mediated recovery of neutral intracellular pH was initiated by addition of Na-HEPES buffer containing 0.4 μM ethyl isopropyl amiloride (EIPA, a selective antagonist of NHE-1 activity that does not inhibit NHE3) and 0-30 μM test compound, or a pharmaceutically acceptable salt thereof, and monitoring the pH sensitive changes in BCECF fluorescence ($\lambda_{ex}$ 505 nm, $\lambda_{em}$ 538 nm) normalized to the pH insensitive BCECF fluorescence ($\lambda_{ex}$ 439 nm, $\lambda_{em}$ 538 nm). Initial rates were plotted as the average 2 or more replicates, and $pIC_{50}$ values were estimated using GraphPad Prism. The results are summarized in Table E3 below.

Inhibition of intestinal sodium and phosphate absorption. Urinary sodium concentration and fecal form were measured to assess the ability of selected example compounds to inhibit the absorption of sodium from the intestinal lumen. Eight-week old Sprague-Dawley rats were purchased from Charles River Laboratories (Hollister, Calif.), were housed 2 per cage, and acclimated for at least 3 days before study initiation. Animals were fed Harlan Teklad Global 2018 rodent chow (Indianapolis, Ind.) and water ad libitum throughout the study and maintained in a standard light/dark cycle of 6 AM to 6 PM. On the day of the study, between 4 PM and 5 PM, a group of rats (n=6) were dosed via oral gavage with test compound, or a pharmaceutically acceptable salt thereof, or vehicle (water) at a volume of 10 mL/kg.

After dose administration animals were placed in individual metabolic cages where they were also fed the same chow in meal form and watered ad libitum. At 16 h post-dose, the urine samples were collected and fecal form was assessed by two independent observations. Fecal forms were scored according to a common scale associated with increasing fecal water to the wettest observation in the cage's collection funnel (1, normal pellet; 2, pellet adhering to sides of collection funnel due to moisture; 3, loss of normal pellet shape; 4, complete loss of shape with a blotting pattern; 5, liquid fecal streams evident). A rat's fecal form score (FFS) was determined by averaging both observational scores for all rats within a group (n=6). The vehicle group average was 1.

For urine samples, the volumes were determined gravimetrically and centrifuged at 3,600×g. The supernatants were diluted 100-fold in deionized Milli-Q water then filtered through a 0.2 μm GHP Pall AcroPrep filter plate (Pall Life Sciences, Ann Arbor, Mich.) prior to analysis by ion chromatography. Ten microliters of each filtered extract was injected onto a Dionex ICS-3000 ion chromatograph system (Dionex, Sunnyvale, Calif.). Cations were separated by an isocratic method using 25 mM methanesulfonic acid as the eluent on an IonPac CS12A 2 mm i.d.×250 mm, 8 μm particle size cation exchange column (Dionex). Sodium was quantified using standards prepared from a cation standard mix containing $Li^+$, $Na^+$, $NH_4^+$, $K^+$, $Mg^{2+}$, and $Ca^{2+}$ (Dionex). The mean mass of sodium urinated for every group in the 16 h period was determined with the vehicle group usually urinating approximately 21 mg sodium. The urine Na (uNa) for rats in the test groups were expressed as a percentage of the vehicle mean and the means were compared to that of the vehicle group by utilizing a one-way analysis of variance coupled with a Dunnett's post hoc test. The results are shown in Table E3 below.

| Cmpd # | Prompt Rat NHE3 $pIC_{50}$ | Prompt Human NHE3 $pIC_{50}$ | Dose mg/kg | Urine Na % of control | Urine P % of control | Fecal Form Score average | No. of trials averaged |
|---|---|---|---|---|---|---|---|
| 1 | 6.60 | | 10 | 87% | 52% | 1 | |
| 2 | 6.70 | 6.50 | 10 | 115% | 80% | 1 | |
| 3 | 7.40 | 7.60 | 1 | 41% | 57% | 1 | |
| 4 | 6.90 | 6.80 | 10 | 84% | 106% | 1 | |
| 5 | 6.90 | 7.85 | 10 | 51% | 65% | 1 | |
| | | | 30 | 23% | 105% | 2 | |
| 6 | 8.35 | 8.30 | 1 | 21% | 46% | 2 | |
| 7 | 6.30 | 7.20 | 10 | 76% | 90% | 1 | |
| 8 | 6.90 | 6.40 | 10 | 73% | 101% | 1 | |
| | | | 30 | 31% | 114% | 2 | |
| 9 | 6.50 | 7.10 | 10 | 56% | 77% | 1 | |
| 10 | 6.65 | 7.50 | 10 | 76% | 80% | 1 | |
| 11 | 6.95 | 6.80 | 10 | 60% | 64% | 1 | |
| | | | 30 | 29% | 96% | 2 | |
| 12 | 6.10 | 7.00 | 10 | 82% | 94% | 1 | |
| 13 | 6.70 | 7.40 | 10 | 74% | 56% | 1 | |
| 14 | 7.00 | 7.60 | 10 | 51% | 59% | 1 | |
| 15 | 7.30 | 7.90 | 10 | 77% | 65% | 1 | |
| 16 | 6.70 | 7.80 | 30 | 87% | 123% | 1 | |
| 17 | 7.10 | 6.60 | 30 | 86% | 120% | 1 | |
| 18 | 7.25 | 7.35 | 10 | 74% | 142% | 1 | |
| 18 | 6.90 | 6.90 | 30 | 41% | 109% | 1 | |
| 19 | 7.00 | 7.40 | 10 | 72% | 119% | 1 | |
| 20 | 7.30 | 7.20 | 10 | 86% | 81% | 1 | |
| 21 | 6.10 | 7.00 | 10 | 66% | 101% | 1 | |
| 22 | 7.34 | 6.95 | 1 | 91% | 64% | 1 | |
| | | | 10 | 19% | 40% | 2 | 2 |
| 23 | 6.87 | 8.55 | 10 | 73% | 95% | 1 | 2 |
| 24 | 7.68 | 8.58 | 10 | 100% | 80% | 1 | |
| | | | 30 | 27% | 70% | 3 | |
| 25 | 6.85 | 6.60 | 10 | 87% | 150% | 1 | |
| 26 | 7.50 | 7.70 | 10 | 78% | 77% | 1 | |
| 27 | 7.50 | 8.40 | 10 | 51% | 91% | 1 | 2 |
| 28 | 7.60 | 8.10 | 10 | 83% | 129% | 1 | |
| 29 | 7.50 | 8.10 | 10 | 92% | 102% | 1 | |
| 30 | 7.80 | 8.40 | 10 | 100% | 104% | 1 | |
| 31 | 7.70 | 7.70 | 10 | 96% | 81% | 1 | |
| 32 | 7.30 | 8.40 | 10 | 128% | 122% | 1 | |
| 33 | 7.40 | 7.90 | 10 | 98% | 117% | 1 | |
| 34 | 7.90 | 8.20 | 10 | 76% | 72% | 1 | |
| 35 | 8.00 | 8.30 | 10 | 65% | 57% | 1 | |
| 36 | 7.60 | 8.00 | 10 | 85% | 86% | 1 | |
| 37 | 7.50 | 7.50 | 10 | 63% | 101% | 1 | |
| 38 | 5.50 | 5.60 | 10 | 101% | 120% | 1 | |
| 39 | 7.30 | | 1 | 71% | 166% | 1 | |
| | | | 10 | 68% | 130% | 1 | |
| 40 | <5.00 | <5.00 | 1 | 80% | 149% | 1 | |
| | | | 10 | 90% | 128% | 1 | |
| 41 | 7.90 | 8.20 | 10 | 104% | 133% | 1 | |
| 42 | 7.70 | 8.20 | 10 | 94% | 94% | 1 | |
| 43 | 7.50 | 7.70 | 10 | 70% | 101% | 1 | |
| 44 | 7.70 | 7.90 | 10 | 88% | 102% | 1 | |

| Cmpd # | Prompt Rat NHE3 pIC50 | Prompt Human NHE3 pIC50 | Dose mg/kg | Urine Na % of control | Urine P % of control | Fecal Form Score average | No. of trials averaged |
|---|---|---|---|---|---|---|---|
| 45 | 7.50 | 7.90 | 10 | 97% | 109% | 1 | |
| 46 | 7.80 | 7.90 | 10 | 58% | 112% | 1 | |
| 47 | 7.30 | 7.80 | 10 | 73% | 51% | 1 | |
| 48 | 7.55 | 7.10 | 10 | 68% | 55% | 1 | |
| 49 | 7.65 | 7.40 | 10 | 38% | 77% | 1 | |
| 50 | 7.45 | 7.60 | 10 | 82% | 50% | 1 | |
| 51 | 7.40 | 7.90 | 10 | 79% | 52% | 1 | |
| 52 | 7.35 | 7.40 | 10 | 68% | 71% | 1 | |
| 53 | 7.45 | 7.40 | 10 | 100% | 59% | 1 | |
| 54 | 7.30 | 7.50 | 10 | 75% | 72% | 1 | |
| 55 | 7.70 | 7.90 | 10 | 85% | 45% | 1 | |
| 56 | 6.90 | 7.00 | 10 | 15% | 50% | 2 | |
| 57 | 7.10 | 7.50 | 10 | 25% | 75% | 3 | |
| 58 | 6.30 | 7.30 | 10 | 82% | 68% | 1 | |
| 59 | 6.90 | 7.30 | 10 | 18% | 45% | 2 | |
| 60 | 6.35 | 7.10 | 10 | 67% | 92% | 1 | |
| 61 | 7.00 | 7.80 | 1 | 93% | 96% | 1 | |
| | | | 3 | 50% | 70% | 1 | |
| | | | 10 | 21% | 67% | 3 | |
| 62 | <5.00 | 7.25 | 10 | 121% | 77% | 1 | |
| 63 | 7.20 | 8.00 | 10 | 51% | 95% | 1 | |
| 64 | 7.40 | 8.20 | 10 | 34% | 66% | 1 | |
| 65 | 8.85 | 8.00 | 10 | 93% | 85% | 1 | |
| 66 | 8.35 | 8.35 | 10 | 35% | 30% | 1 | |
| 67 | 8.00 | 8.70 | 10 | 4% | 67% | 2 | |
| 68 | <5.00 | <5.00 | 10 | 70% | 97% | 1 | |
| 69 | 6.60 | 6.70 | 10 | 82% | 78% | 1 | |
| 70 | 6.70 | 7.20 | 10 | 96% | 83% | 1 | |
| 71 | 6.50 | 7.00 | 10 | 80% | 40% | 1 | |
| 72 | 8.30 | 8.25 | 1 | 82% | 99% | 1 | |
| | | | 3 | 74% | 115% | 2 | |
| | | | 10 | 33% | 43% | 1 | |
| 73 | 5.30 | 6.30 | 10 | 74% | 49% | 2 | |
| 74 | 6.30 | 6.80 | 10 | 30% | 44% | 3 | |
| 75 | 6.30 | 6.90 | 10 | 81% | 55% | 1 | |
| 76 | 5.60 | 6.40 | 1 | 58% | 96% | 1 | |
| | | | 3 | 40% | 89% | 2 | |
| | | | 10 | 12% | 61% | 3 | |
| 77 | 6.25 | 7.35 | 1 | 80% | 82% | 2 | |
| | | | 3 | 36% | 79% | 2 | 2 |
| | | | 10 | 17% | 41% | 4 | |
| 78 | 6.00 | 6.50 | 10 | 53% | 39% | 2 | |
| 79 | 6.50 | 7.20 | 1 | 65% | 109% | 1 | |
| | | | 3 | 44% | 81% | 2 | |
| | | | 10 | 17% | 33% | 3 | |
| 80 | 5.50 | 6.93 | 1 | 66% | 70% | 1 | |
| | | | 3 | 55% | 39% | 2 | 2 |
| | | | 10 | 9% | 21% | 3 | |
| 81 | 7.90 | 7.90 | 10 | 11% | 42% | 2 | |
| 82 | 6.80 | 7.10 | 10 | 47% | 69% | 1 | |
| 83 | <5.00 | <5.00 | 10 | 82% | 59% | 1 | |
| 84 | 7.50 | 7.70 | 8 | 7% | 47% | 3 | |
| 85 | 5.80 | 6.10 | 10 | 92% | 85% | 1 | |
| 86 | 5.80 | 5.90 | 10 | 87% | 89% | 1 | |
| 87 | <5.00 | 8.20 | 3 | 54% | 29% | 1 | |
| 88 | 7.07 | 7.93 | 1 | 84% | 77% | 1 | 2 |
| | | | 3 | 22% | 75% | 3 | 3 |
| | | | 10 | 21% | 69% | 5 | |
| 89 | 7.10 | 7.90 | 2.5 | 55% | 50% | 2 | |
| | | | 10 | 49% | 117% | 3 | |
| 90 | 7.20 | 7.85 | 1 | 76% | 65% | 1 | |
| | | | 3 | 30% | 58% | 1 | |
| | | | 10 | 38% | 20% | 5 | |
| 91 | 5.30 | <5.00 | 10 | 77% | 56% | 1 | |
| 92 | <5.00 | | 10 | 62% | 70% | 1 | |
| 93 | <5.00 | | 10 | 78% | 75% | 1 | |
| 94 | <5.00 | 5.60 | 10 | 67% | 66% | 1 | |
| 95 | 6.60 | 7.00 | 10 | 38% | 111% | 2 | |
| 96 | 7.50 | 8.30 | 10 | 33% | 94% | 1 | |
| 97 | 7.60 | 8.50 | 10 | 64% | 78% | 1 | |
| 98 | 8.40 | 8.10 | 10 | 83% | 88% | 1 | |
| 99 | 8.60 | 5.00 | 10 | 41% | 52% | 1 | |
| 100 | 8.10 | 8.30 | 10 | 57% | 68% | 1 | |
| 101 | <5.00 | 8.10 | 10 | 64% | 81% | 1 | |
| 102 | 6.60 | | 10 | 86% | 92% | 1 | |
| 103 | 6.70 | | 10 | 40% | 71% | 1 | |
| 104 | 6.70 | | 10 | 56% | 62% | 2 | |
| 105 | 5.90 | | 3 | 119% | 154% | 1 | |
| 106 | 7.00 | 7.90 | 1 | 98% | 124% | 1 | |
| | | | 3 | 76% | 39% | 2 | |
| | | | 10 | 20% | 64% | 4 | |
| 107 | 6.90 | 8.10 | 1 | 88% | 106% | 1 | |
| | | | 3 | 55% | 66% | 1 | |
| | | | 10 | 28% | 59% | 4 | |
| 108 | 8.40 | | 3 | 13% | 51% | 4 | |
| 109 | 7.40 | 8.10 | 1 | 64% | 65% | 1 | |
| | | | 3 | 52% | 51% | 2 | |
| | | | 10 | 28% | 52% | 4 | |
| 110 | 5.80 | | 3 | 63% | 68% | 1 | |
| 111 | <5.00 | | 10 | 60% | 69% | 2 | |
| 112 | <5.00 | | 10 | 73% | 67% | 1 | |
| 113 | <5.00 | <5.00 | 10 | 64% | 61% | 1 | |
| 114 | <5.00 | <5.00 | 10 | 45% | 100% | 3 | |
| 115 | <5.00 | 8.55 | 10 | 69% | 60% | 1 | |
| 116 | <5.00 | 8.30 | 10 | 84% | 130% | 1 | |
| 117 | 7.50 | 8.20 | 10 | 77% | 98% | 1 | |
| 118 | 7.40 | 8.10 | 10 | 83% | 131% | 1 | |
| 119 | 8.70 | 7.80 | 10 | 43% | 52% | 1 | |
| 120 | 7.80 | | 3 | 71% | 71% | 1 | |
| 121 | <5.00 | | 3 | 92% | 151% | 1 | |
| 122 | 6.20 | 6.80 | 3 | 30% | 87% | 2 | |
| 123 | 7.50 | 7.80 | 1 | 49% | 124% | 1 | 2 |
| | | | 3 | 12% | 88% | 3 | 3 |
| 124 | 7.17 | 7.50 | 1 | 69% | 154% | 1 | |
| | | | 3 | 22% | 61% | 2 | 2 |
| 125 | <5.00 | | 10 | 81% | 278% | 1 | |
| 126 | <5.00 | 6.55 | 10 | 93% | 94% | 1 | |
| 127 | 8.20 | 8.30 | 1 | 55% | 159% | 1 | 2 |
| | | | 3 | 39% | 62% | 1 | 4 |
| | | | 10 | 9% | 53% | 1 | |
| 128 | 7.10 | 8.00 | 1 | 46% | 90% | 1 | 2 |
| | | | 3 | 35% | 58% | 2 | 4 |
| 129 | 5.60 | 6.90 | 3 | 16% | 48% | 2 | |
| 130 | 6.10 | 7.20 | 3 | 18% | 70% | 2 | |
| 131 | 6.10 | 7.20 | 3 | 38% | 68% | 2 | |
| 132 | 6.00 | 7.70 | 3 | 65% | 88% | 1 | |
| 133 | 6.50 | 7.30 | 3 | 23% | 67% | 2 | |
| 134 | 6.50 | 6.50 | 3 | 64% | 72% | 1 | |
| 135 | 7.40 | 8.45 | 1 | 100% | 92% | 1 | |
| | | | 3 | 94% | 44% | 1 | |
| | | | 10 | 58% | 85% | 2 | |
| 136 | <5.00 | 7.70 | 10 | 104% | 93% | 1 | |
| 137 | 7.30 | 7.30 | 1 | 39% | 137% | 1 | |
| | | | 3 | 28% | 139% | 3 | 2 |
| 138 | 7.30 | 7.30 | 3 | 37% | 78% | 2 | |
| 139 | 7.60 | 7.80 | 1 | 80% | 63% | 1 | |
| 140 | 8.90 | 7.70 | 3 | 27% | 45% | 3 | 2 |
| | | | 10 | 110% | 121% | 1 | |
| 141 | 6.90 | 7.40 | 3 | 63% | 24% | 2 | |
| 142 | 8.10 | 7.10 | 3 | 45% | 38% | 2 | |
| 143 | 7.25 | 7.27 | 1 | 68% | 73% | 1 | |
| | | | 3 | 34% | 93% | 3 | 3 |
| 144 | 7.20 | 7.77 | 3 | 32% | 47% | 2 | 2 |
| 145 | 7.60 | 7.70 | 3 | 41% | 51% | 3 | |
| 146 | 7.80 | 8.35 | 3 | 70% | 58% | 2 | |
| 147 | 7.00 | 7.67 | 3 | 40% | 32% | 2 | 3 |
| 148 | 8.40 | 7.80 | 3 | 49% | 146% | 1 | |
| 149 | 8.10 | 8.00 | 1 | 54% | 122% | 1 | |
| | | | 2 | 53% | 69% | 2 | |
| | | | 3 | 46% | 115% | 1 | 2 |
| 150 | 8.60 | 8.00 | 3 | 73% | 74% | 1 | |
| | | | 10 | 12% | 159% | 1 | |
| 151 | 8.30 | 7.50 | 3 | 78% | 52% | 1 | |
| | | | 10 | 42% | 121% | 2 | |
| 152 | <5.00 | 8.70 | 10 | 26% | 74% | 1 | |
| 153 | 6.90 | 7.50 | 3 | 28% | 84% | 3 | |
| 154 | 6.80 | 6.80 | 3 | 112% | 65% | 1 | |
| 155 | 7.70 | 7.90 | 3 | 40% | 44% | 2 | |

-continued

| Cmpd # | Prompt Rat NHE3 pIC$_{50}$ | Prompt Human NHE3 pIC$_{50}$ | Dose mg/kg | Urine Na % of control | Urine P % of control | Fecal Form Score average | No. of trials averaged |
|---|---|---|---|---|---|---|---|
| 156 | 6.70 | 7.20 | 3 | 13% | 67% | 3 | |
| 157 | 7.70 | 7.77 | 3 | 26% | 50% | 3 | 3 |
| 158 | <5.00 | 6.90 | 3 | 32% | 64% | 2 | |
| 159 | 7.20 | 7.30 | 3 | 27% | 55% | 2 | |
| 160 | | 7.70 | 10 | 108% | 77% | 1 | |
| 161 | 9.20 | 7.60 | 3 | 82% | 60% | 2 | |
| 162 | 7.30 | 6.60 | 2 | 130% | 50% | 2 | |
| 163 | 7.90 | 7.60 | 3 | 27% | 48% | 2 | |
| 164 | 7.53 | 8.13 | 3 | 18% | 63% | 3 | 2 |
| 165 | <5.00 | 8.20 | 10 | 104% | 68% | 1 | |
| 166 | <5.00 | 8.40 | 10 | 111% | 43% | 1 | |
| 167 | 5.80 | 8.37 | 3 | 36% | 99% | 2 | |
| 168 | 7.35 | 8.13 | 3 | 56% | 50% | 1 | |
| 169 | 6.50 | 6.20 | 3 | 42% | 64% | 2 | |
| 170 | 7.10 | 7.20 | 3 | 31% | 34% | 2 | |
| 171 | | 8.20 | 10 | 49% | 49% | 1 | |
| 172 | 8.20 | 7.10 | 3 | 26% | 42% | 2 | |
| 173 | 7.60 | 8.10 | 2.5 | 64% | 69% | 2 | |
| 174 | 8.60 | 8.53 | 3 | 37% | 55% | 1 | |
| | | | 10 | 49% | 61% | 1 | |
| 175 | 7.80 | 7.40 | 3 | 102% | 48% | 1 | |
| 176 | 7.50 | 7.40 | 3 | 73% | 92% | 1 | |

-continued

| Cmpd # | Prompt Rat NHE3 pIC$_{50}$ | Prompt Human NHE3 pIC$_{50}$ | Dose mg/kg | Urine Na % of control | Urine P % of control | Fecal Form Score average | No. of trials averaged |
|---|---|---|---|---|---|---|---|
| 177 | 7.70 | 7.80 | 3 | 52% | 45% | 2 | |
| 178 | 7.10 | 7.33 | 3 | 18% | 46% | 3 | |
| 179 | 8.00 | 7.77 | 3 | 40% | 66% | 1 | |
| 180 | 8.03 | 8.30 | 0.03 | 67% | 80% | 1 | |
| | | | 0.1 | 45% | 82% | 1 | |
| | | | 0.3 | 33% | 75% | 3 | |
| | | | 1 | 15% | 69% | 3 | 38 |
| | | | 3 | 53% | 38% | 4 | |

Example 2

Cell-Based Assay of NHE3 Activity Under Prompt and Persistent Conditions

The compounds in Table E4 below, or a pharmaceutically acceptable salt thereof, were tested in a cell-based assay of NHE3 inhibition under prompt conditions (prompt inhibition) and persistent conditions (persistent inhibition). These compounds were also tested in a cell-based assay of NaP2b activity.

TABLE E4

| Cmpd. | Structure |
|---|---|
| Cpd 001 (same as #3 in Table E3) | 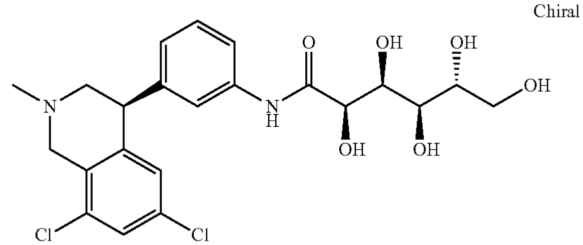 [SMILES: CN1Cc2c(Cl)cc(Cl)cc2[C@H](c2cccc(NC(=O)[C@H](O)[C@@H](O)[C@H](O)[C@H](O)CO)c2)C1] |
| Cpd 002 (same as #180 in Table E3) | 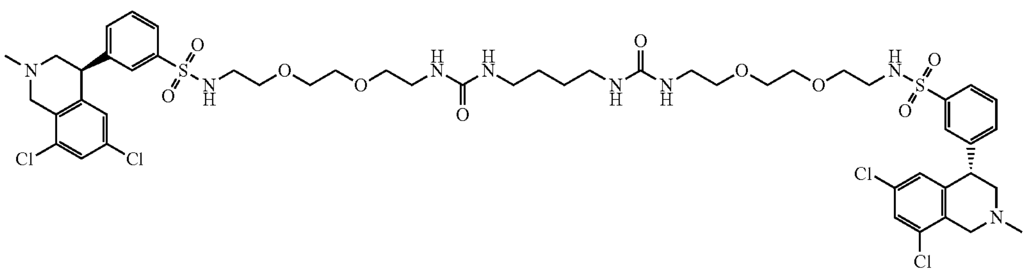 |
| Cpd 003 | 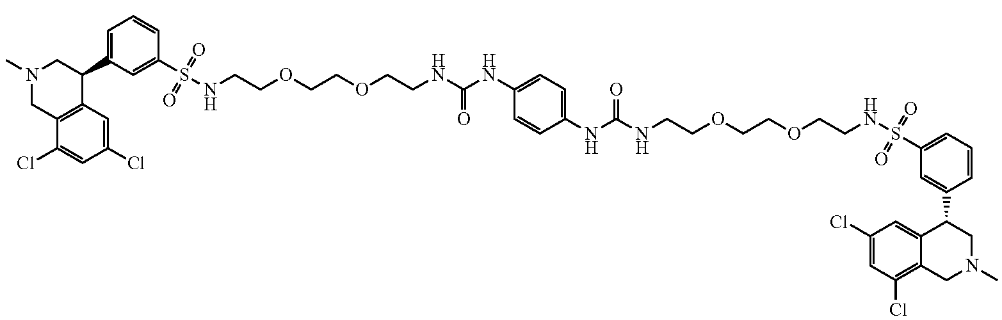 |

TABLE E4-continued

| Cmpd. | Structure |
|---|---|
| Cpd 004 (same as #40 in Table E3) | 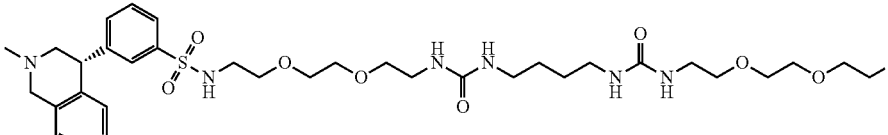 |
| Cpd 005 (same as #39 in Table E3) | 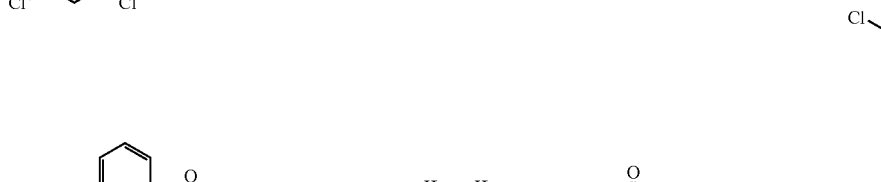 |

Cell-based activity of NHE3 Activity under 'Prompt' Conditions. This assay was performed as described in Example 1 (supra).

Cell-based activity of NHE3 Activity under 'Persistent' Conditions. The ability of compounds to inhibit Rat NHE3-mediated Na$^+$-dependent H$^+$ antiport after application and washout was measured using a modification of the pH sensitive dye method described above. Opossum kidney (OK) cells were obtained from the ATCC and propagated per their instructions. The rat NHE3 gene was introduced into OK cells via electroporation, and cells were seeded into 96 well plates and grown overnight. Medium was aspirated from the wells, cells were washed twice with NaCl-HEPES buffer (100 mM NaCl, 50 mM HEPES, 10 mM glucose, 5 mM KCl, 2 mM CaCl$_2$, 1 mM MgCl$_2$, pH 7.4), then overlayed with NaCl-HEPES buffer containing 0-30 µM test compound.

After a 60 min incubation, the test drug containing buffer was aspirated from the cells, cells were washed twice with NaCl-HEPES buffer without drug, then incubated for 30 min at room temperature with NH$_4$Cl-HEPES buffer (20 mM NH$_4$Cl, 80 mM NaCl, 50 mM HEPES, 5 mM KCl, 2 mM CaCl$_2$, 1 mM MgCl$_2$, pH 7.4) containing 5 uM BCECF-AM. Cells were washed twice with Ammonium free, Natfree HEPES (100 mM choline, 50 mM HEPES, 10 mM glucose, 5 mM KCl, 2 mM CaCl$_2$, 1 mM MgCl$_2$, pH 7.4) and incubated in the same buffer for 10 minutes at room temperature to lower intracellular pH. NHE3-mediated recovery of neutral intracellular pH was initiated (40 min after compound washout) by addition of Na-HEPES buffer containing 0.4 uM ethyl isopropyl amiloride (EIPA, a selective antagonist of NHE-1 activity that does not inhibit NHE3), and monitoring the pH sensitive changes in BCECF fluorescence ($\lambda_{ex}$ 505 nm, $\lambda_{em}$ 538 nm) normalized to the pH insensitive BCECF fluorescence ($\lambda_{ex}$ 439 nm, $\lambda_{em}$ 538 nm). Initial rates were plotted as the average 2 or more replicates, and pIC$_{50}$ values were estimated using GraphPad Prism.

Cell-based assay of NaP2b activity. The rate of phosphate (Pi) uptake into cells was measured using a modification of a literature method (see Mohrmann et al. *Am. J. Phys.* 250(3 pt 1):G323-30, 1986). Briefly, HEK293 cells were transiently transfected with an expression clone encoding either rat or human NaP2b. The next day, transfected cells were treated with a pharmacological agent to minimize endogenous PiT-mediated phosphate transport activity, such that the only remaining sodium-dependent phosphate transport activity is that which was bestowed by introduction of the NaP2b gene. Cells were incubated with radioactive inorganic phosphate in the presence or absence of varying concentrations of test compound. After a short time, cells were washed, harvested, and the amount of hot phosphate taken up in the cells determined by liquid scintillation counting.

HEK293 cells were obtained from the American Type Culture collection and propagated per their instructions. Expression clones for rat and human NaP2b (SLC34A2) were obtained from Open Biosystems (Catalog numbers MRN1768-9510282, and MHS1010-99823026, respectively). There are two putative splice variants of human NaP2b, designated as isoform a and isoform b (NCBI Reference Sequences: NP_006415.2 and NP_001171470.1, respectively). The sequence of the open reading from in MHS1010-99823026 corresponds to isoform b; transfection with this construct was found to confer only very low levels of nonendogenous Pi transport activity. The cDNA was therefore mutated to correspond with isoform a; transfection with this sequence conferred Pi transport significantly over background. Thus, studies of the inhibition of human NaP2b used isoform a exclusively.

Cells were seeded into 96-well plates at 25,000 cells/well and cultured overnight. Lipofectamine 2000 (Invitrogen) was used to introduce the NaP2b cDNA, and the cells were allowed to approach confluence during a second overnight incubation. Medium was aspirated from the cultures, and the cells were washed once with choline uptake buffer (14 mM Tris, 137 mM choline chloride, 5.4 mM KCl, 2.8 mM CaCl2, 1.2 mM MgSO4, 100 uM KH2PO4, 1 mg/mL Bovine Serum Albumin, pH 7.4). Cells were then overlayed with either choline uptake buffer or sodium uptake buffer (14 mM Tris, 137 mM sodium chloride, 5.4 mM KCl, 2.8 mM CaCl2, 1.2 mM MgSO4, 100 uM KH2PO4, PiT-silencing agent, 1 mg/mL Bovine Serum Albumin, pH 7.4) containing 6-9 uCi/mL $^{33}$P orthophosphoric acid (Perkin Elmer) and test compound. Each compound was tested at twelve concentrations ranging from 0.1 nM to 30 uM. Assays were run in duplicate and compounds of interest were tested multiple times. After incubation for 23 minutes at room temperature, assay mixtures were removed, and the cells were washed twice with ice cold stop solution (137 mM sodium chloride, 14 mM Tris, pH 7.4). Cells were lysed by addition of 20 μL 0.1% Tween 80 followed by 100 μL scintillation fluid, and counted using a TopCount (Perkin Elmer). The pIC50 (the negative log of the IC50) values of the test compounds were calculated using GraphPad Prism. Preliminary studies showed that under these conditions, sodium-dependent Pi uptake was linear for at least 30 minutes and tolerated 0.6% (v/v) DMSO without deleterious effects. The results are summarized in Table E5 below.

TABLE E5

| | Rat NHE3 | | Human NHE3 | | |
|---|---|---|---|---|---|
| Compound | pIC$_{50}$ Prompt | pIC$_{50}$ Persistent | pIC$_{50}$ Prompt | pIC$_{50}$ Persistent | pIC$_{50}$ Human Nap2B |
| 001[a] | 7.6 | nd | 7.4 | nd | nd |
| 002[b] | 8 | 8.4 | 8 | 8.2 | <4.5 |
| 003[b] | 8.6 | nd | 8 | 8.1 | nd |
| 004[b] | 7.3 | 5.6 | 7.3 | 5.6 | nd |
| 005[b] | <5.0 | nd | <5.0 | nd | nd |

[a]Compound 001 tested as free base.
[b]Compounds 002, 003, 004 and 005 were tested as the dihydrochloride salt Further experiments were performed to test the compounds under the persistent and prompt conditions described above, and to test their effects on urinary excretion of sodium in rats. The latter was performed by orally dosing the compounds in rats (single dose) and measuring urinary Na excretion (as a % of vehicle). The results are indicated as percentage of urinary sodium (UNa %); low values indicate relatively active compounds. The results are shown in Table E6 below.

TABLE E6

| Compound | pIC$_{50}$ Prompt | pIC$_{50}$ Persistent | UNa (%) |
|---|---|---|---|
| 001[a] | 7.4 | nd | 41 @ 1 mg/kg |
| 002[b] | 8 | 8.2 | 11 @ 1 mg/kg |
| 003[b] | 8 | 8.1 | 22 @ 1 mg/kg |
| 004[b] | 7.3 | 5.6 | 68 @ 10 mg/kg |
| 005[b] | <5.0 | nd | 90 @ 10 mg/kg |

[a]Compound 001 tested as free base.
[b]Compounds 002, 003, 004 and 005 were tested as the dihydrochloride salt These results identified compounds 002 and 003 as persistent inhibitors of NHE3-mediated Na$^+$-dependent H$^+$ antiport, and compound 004 as a non-persistent inhibitor of NHE3-mediated Na$^+$-dependent H$^+$ antiport. Compound 005 was considered inactive.

Example 3

Pharmacodynamic Studies with $^{33}$P Oral Challenge in Normal Function Rats

The compounds identified as Cpds 003, 004, and 005 (from Table E4, as their dihydrochloride salts) were tested for the ability to block intestinal phosphate uptake in rats. Rats were orally challenged with dosing solutions composed of 5 ml/kg (~1.3 ml) of 8 mM Pi with $^{33}$P and +/−10 mg/kg of test compound. Also included were dosing solutions further composed of either (i) 75 mM glucose+4 mM Ca or (ii) 4 mM Ca.

The results are shown in FIGS. 1A-1C. FIG. 1A shows that Cpd 004, a non-persistent NHE3 inhibitor (i.e., with no significant effect on urinary Na and fecal form), was as potent at reducing Pi uptake as a persistent inhibitor such as Cpd 003 (i.e., inducing a significant reduction in UNa, and change in fecal form). Cpd 005 was inactive in this assay. FIGS. 1B-C show that Cpd 003 significantly reduced Pi uptake in the presence of glucose/Ca (1B) and Ca (1C).

Example 4

Effects in a Rat Model of Uremia-Associated Vascular Calcification

Chronic kidney disease (CKD) has multiple pathogenic mechanisms, and advanced CKD is often characterized by disordered mineral metabolism (e.g., hyperphosphatemia, hypercalcemia) and vascular calcification. Studies were thus performed to test the effectiveness of the dihydrochloride salt of Cpd 002 (from Table E4, as the dihydrochloride salt) in a uremic rat model of CKD featuring vascular calcification. This model is characterized by renal insufficiency and regular active Vitamin D$_3$ administration to promote hyperphosphatemia and vascular calcification (see Lopez et al., *J. Am. Soc. Nephrol.* 17:795-804, 2006). The study utilized Sprague-Dawley rats treated as follows: ⅚$^{th}$ nephrectomy by excision; regular calcitriol administration (active vitamin D$_3$) 80 ng/kg i.p. 3/week; and fed a purified 0.9% P diet (inorganic phosphorus).

Figure 2:
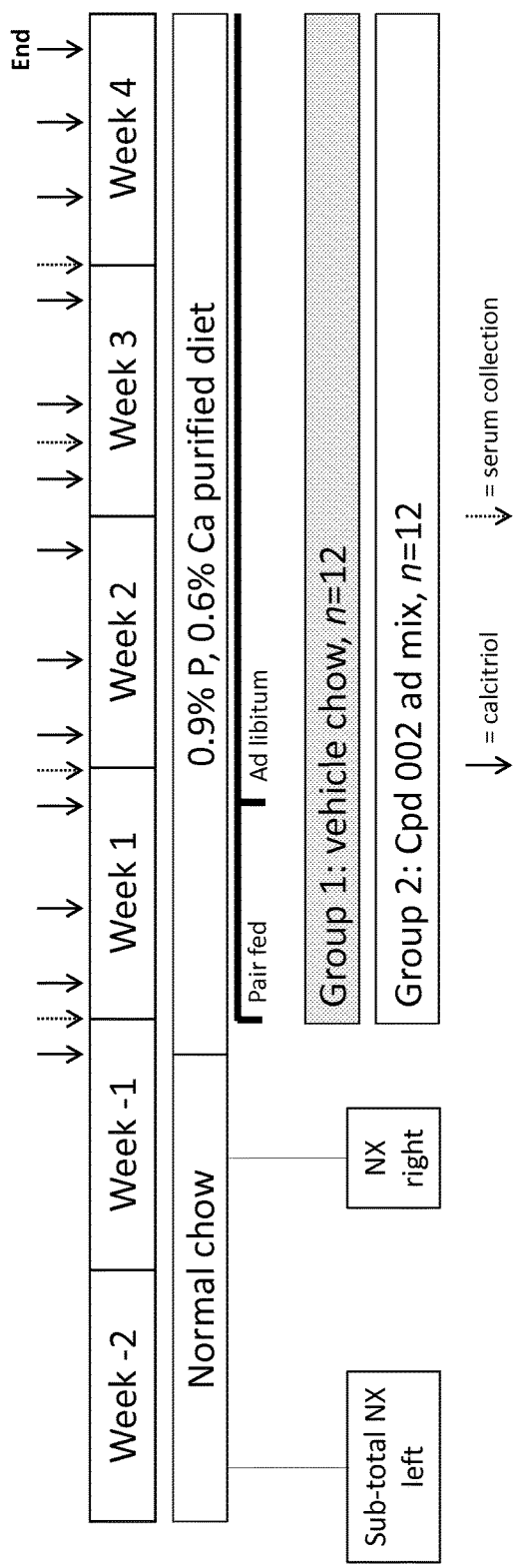
FIG. 2 shows the study design for testing the activity of compounds in a rat model of uremia-associated vascular calcification.
Figure 3:
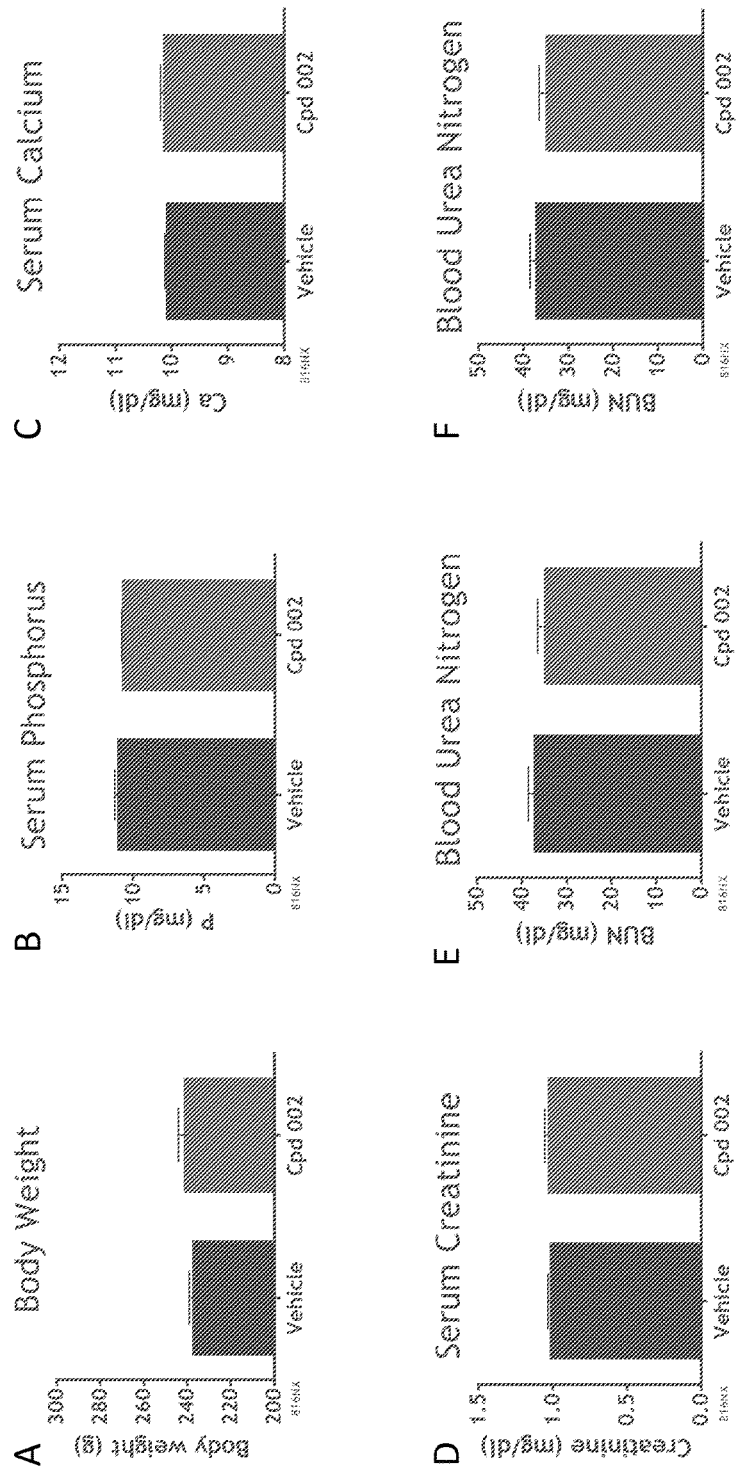
FIGS. 3A-F show the base-line body weight (3A) and serum parameters (serum phosphorus (3B); serum calcium (3C); serum creatinine (3D); blood urea nitrogen (3E-F)) in the rat model of uremia-associated vascular calcification.
Figure 4:
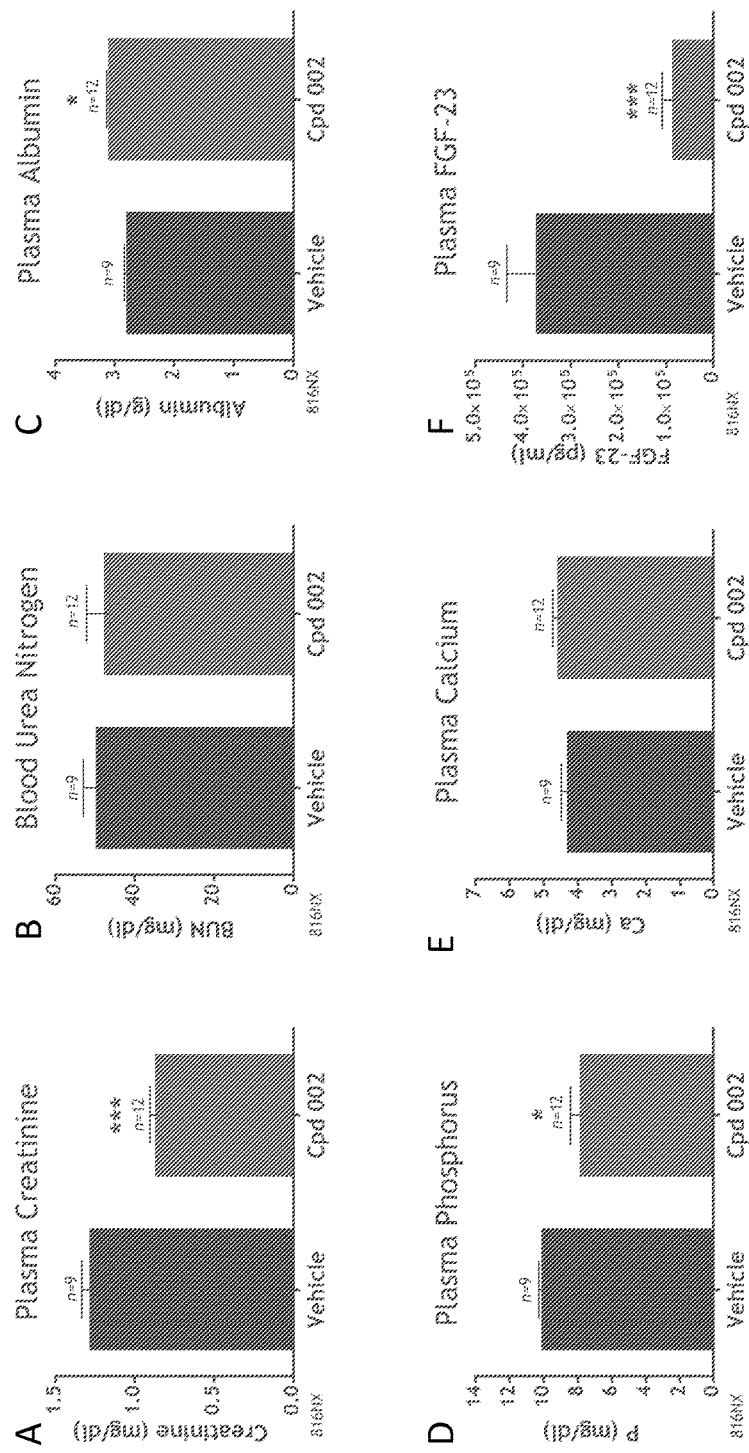
FIGS. 4A-F show the effects of test compound on serum parameters (plasma creatinine (4A); blood urea nitrogen (4B); plasma albumin (4C); plasma phosphorus (4D); plasma calcium (4E); and plasma FGF23 (4F)) in the rat model of uremia-associated vascular calcification. These results show that test compound significant reduced plasma creatinine, plasma phosphorus, and plasma FGF23. Test compound also significantly increased plasma albumin, and a slightly increased plasma calcium.

Rats were stratified into two experimental groups by serum creatinine levels of 0.8 to 1.5 mg/dl and body weight, fed drug-in-chow with powdered vehicle diet or the same diet with Cpd 002 (0.065 mg/g chow) mixed-in, and monitored for weekly body weight and selected serum parameters, daily clinical observations, and endpoint calcification. The study design is illustrated in FIG. 2.

Selected experimental groups were fed vehicle (n=12) or Cpd 002 (n=12) at enrollment (day 0). As shown in FIGS. 3A-F, initial body weights and selected serum parameters such as serum phosphorus, serum calcium, serum creatinine, and blood urea nitrogen were comparable for both groups.

Selected endpoint plasma parameters from day 27 are shown in FIGS. 4A-F. These data show reduced plasma creatinine, reduced plasma phosphorus, and reduced plasma FGF-23.

Figure 5:
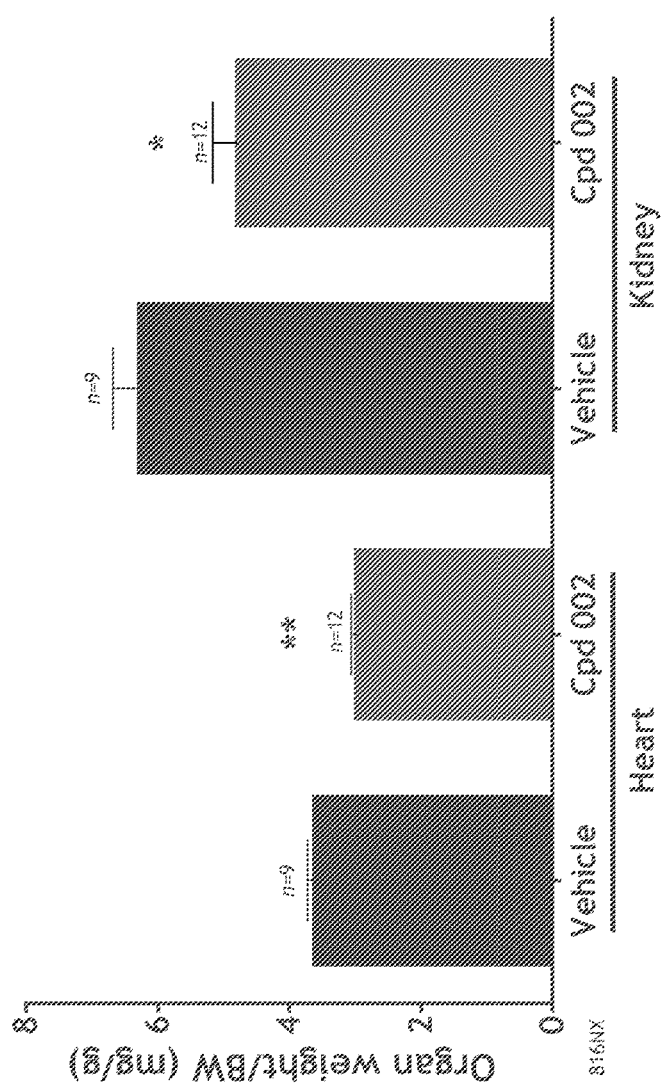
FIG. 5 shows the effects of test compound on the endpoint heart and kidney remnant weights in the rat model of uremia-associated vascular calcification. Administration of test compound significantly reduced the organ weight/body weight values for heart and kidney.

Endpoint heart and kidney remnant weights are shown in FIG. 5. These data show that hypertrophy of the heart and kidney remnants was lessened in Cpd 002 treated rats. Given reduced plasma creatinine, these results suggest that the kidney remnant in Cpd 002 treated rats has more functionality with less mass.

Figure 6:
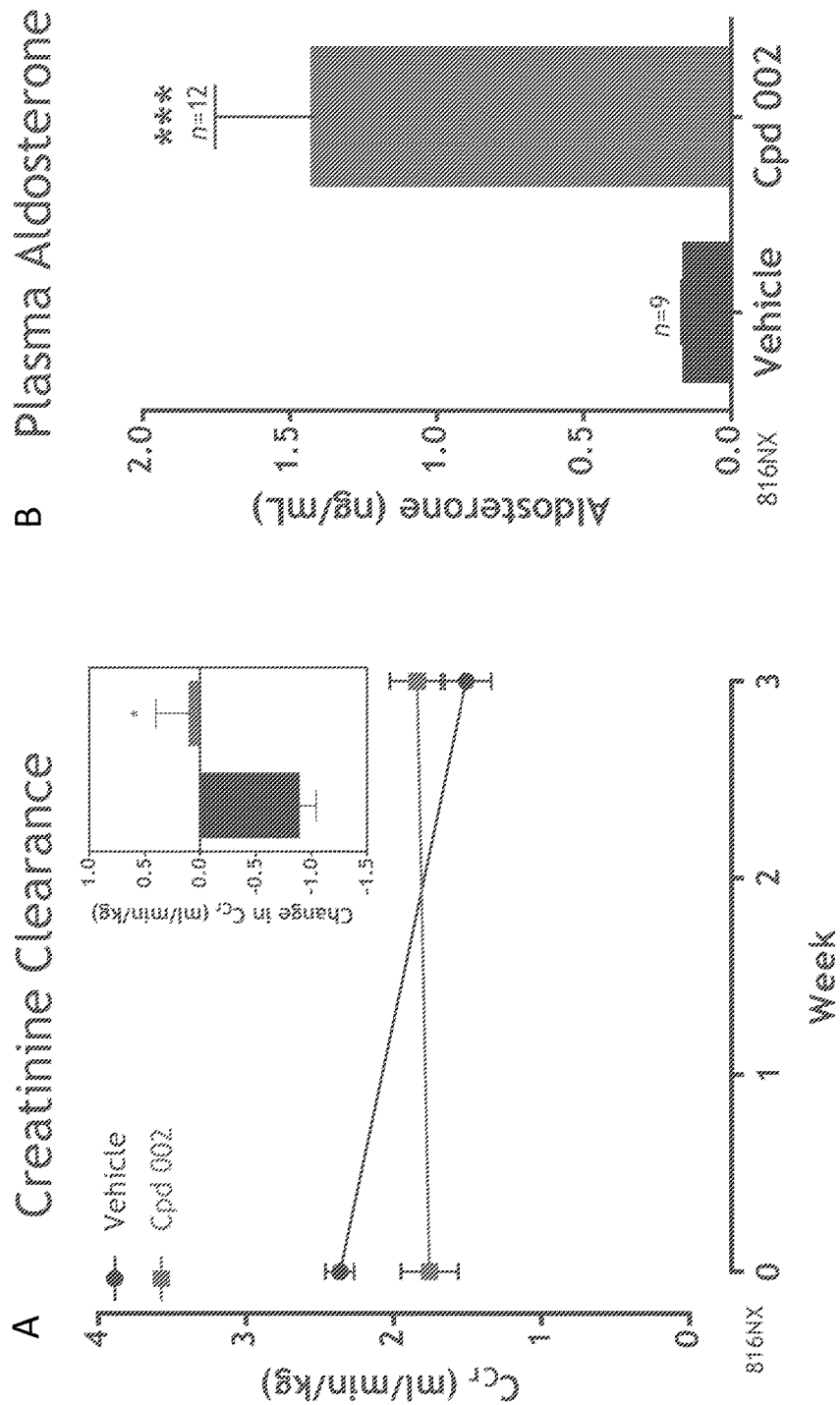
FIGS. 6A-B show the effects of test compound on endpoint creatinine clearance ($C_{Cr}$) and plasma aldosterone levels in the rat model of uremia-associated vascular calcification. Administration of test compound maintained creatinine clearance relative to vehicle-only and also significantly increased plasma aldosterone.

Endpoint creatinine clearance (C$_{Cr}$) and plasma aldosterone levels are shown in FIGS. 6A-B. These results suggest that treatment with Cpd 002 protected against loss of kidney function, and aldosterone increase suggests some volume depletion, which is consistent with lower Na intake.

Figure 7:
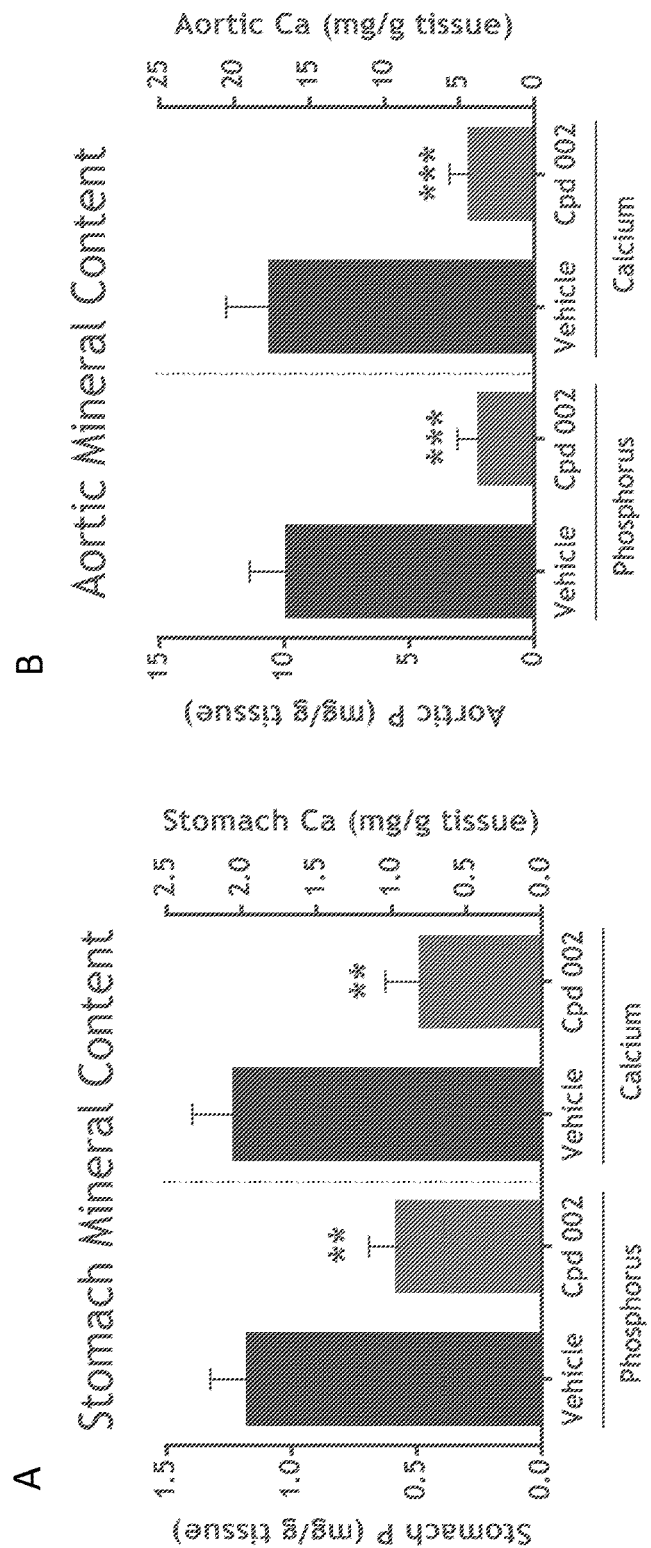
FIGS. 7A-B show the effects of test compound on endpoint vascular and soft tissue calcification in the rat model of uremia-associated vascular calcification. Administration of test compound significantly reduced the stomach and aortic mineral content of phosphorus and calcium.

Endpoint vascular and soft tissue calcification is shown in FIGS. 7A-B. These data shown that treatment with Cpd 002 reduced calcium and phosphorus in the stomach, which is particularly sensitive to calcification, and also reduced vascular calcification as measured by aortic mineral content.

Overall, Cpd 002 was shown to improve kidney function, reduce both heart hypertrophy and renal hypertrophy, exhibit anti-hyperphosphatemic effects, and reduce associated vascular calcification. These effects and decreased moribundity were observed in the treatment group with a trend toward improved mortality outcome. While the benefits from treatment with Cpd 002 can partly result from its effect on fluid overload and hemodynamics, because vascular calcification in this model is highly sensitive to dietary phosphate, the reduction in ectopic calcification points to a reduction in phosphate absorption.

Example 5

Effects in an Adenine-Induced Uremic Rat Model

The effects of Cpd 002 (from Table E4, as the dihydrochloride salt) were tested in an adenine-induced uremic rat model. Rats were fed a diet including 0.75% adenine and 1.2% phosphorus during the nephritis induction phase. The basal diet during the treatment phase was normal chow including 0.3% adenine and 0.6% phosphorus for 2 weeks. The rats were pair-fed the first 5 days (groups 1 and 2 to group 3, 4 days apart), and fed ad libitum afterwards. The treatment groups were as follows: vehicle, n=10; Cpd 002, 2 mg/kg/day drug-in-chow, n=10; and Cpd 002, 5 mg/kg/day drug-in-chow, n=12. Weekly measurements were taken for serum markers and kidney function. The study design is illustrated in FIG. 8A.

Figure 8:
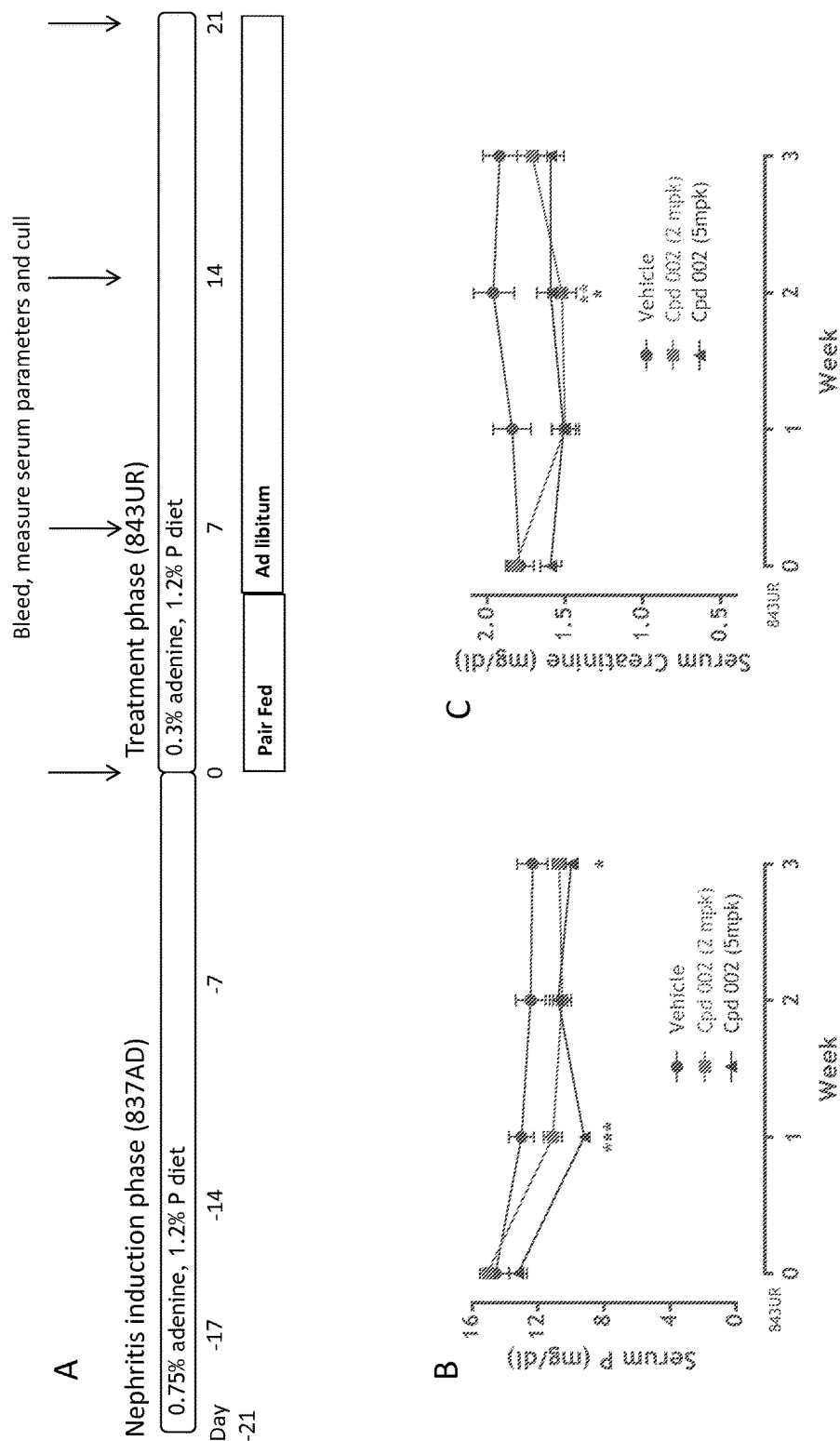
FIG. 8A shows the study design for testing the activity of compounds in an adenine-induced uremic rat model.
FIGS. 8B-C show that test compound significantly reduced serum phosphorus and serum creatinine at early time points in this model of acute renal injury.

As shown in FIGS. 8B-C, Cpd 002 reduced serum phosphorus and serum creatinine at early time points. Here, this adenine-induced model is considered an acute renal injury characterized by a progressive recovery of renal function. Hence, the effects at early time points are significant.

Figure 9:
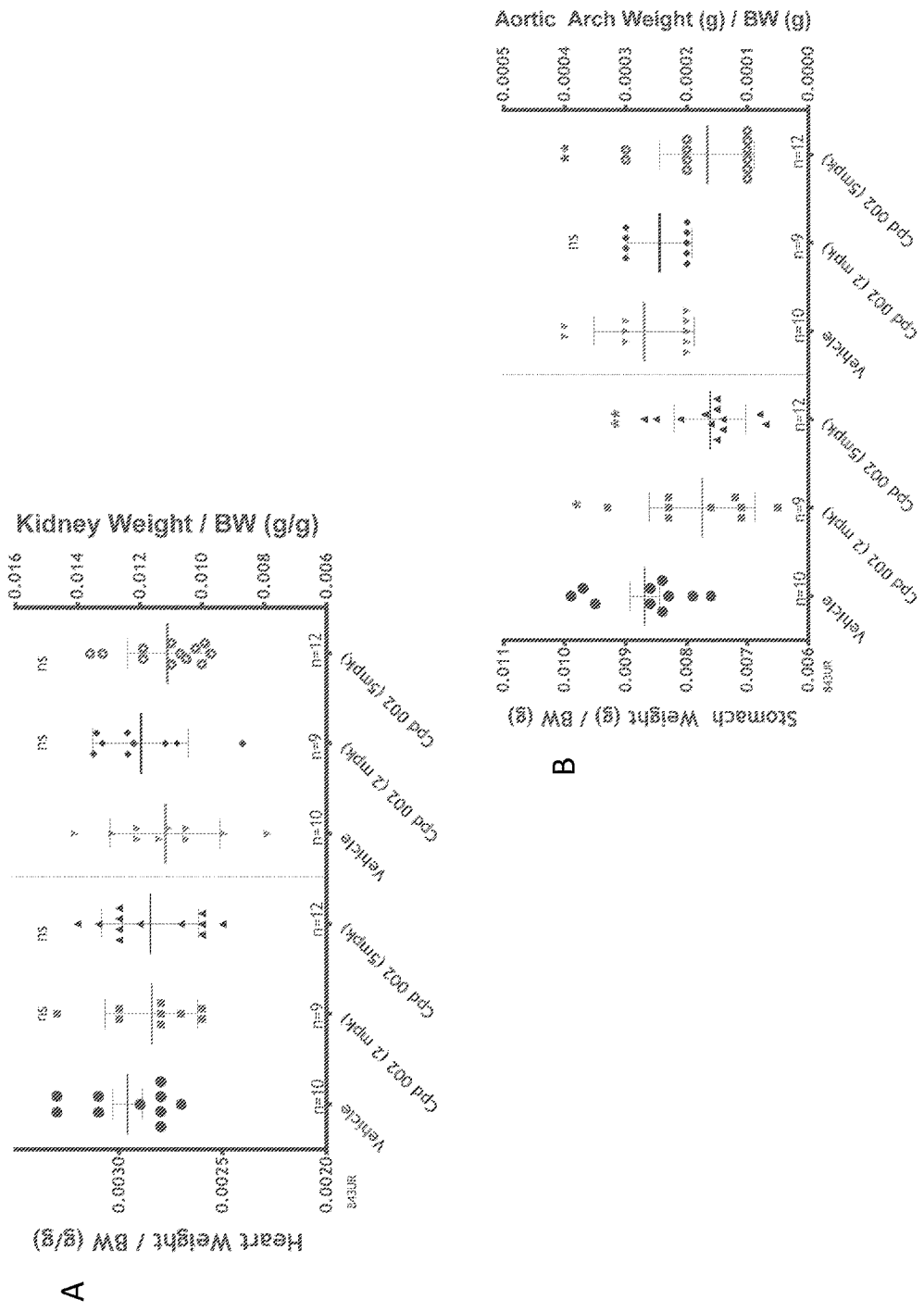
FIGS. 9A-B show the organ weight collection data from week three of the adenine-induced uremic rat model. Administration of test compound showed a tendency to reduce heart and kidney remodeling.
Figure 10:
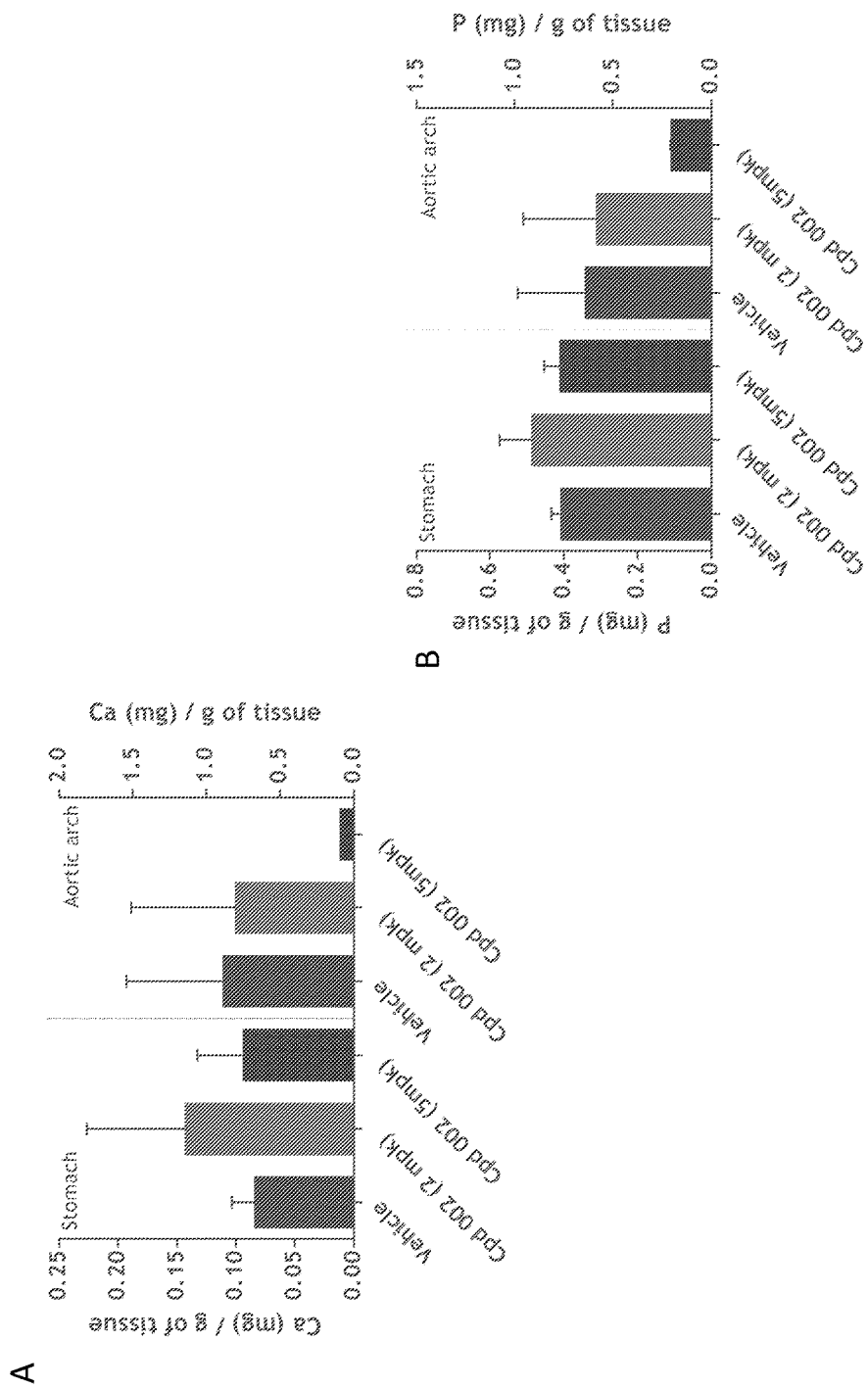
FIGS. 10A-B show the tissue mineralization data from week three of the adenine-induced uremic rat model. Administration of test compound reduced heart and kidney calcification at the highest dose (5 mpk).

Organ weight collection data from week three is shown in FIGS. 9A-B, and tissue mineralization data from week three is shown in FIGS. 10A-B. These data show that treatment with Cpd 002 in this model showed a trend towards lesser heart and kidney remodeling, and a trend towards reduced heart and kidney calcification at the highest dose.

Example 6

Effect on Renal Insufficiency with High Salt Feed in Nephrectomized Rats

Figure 11:
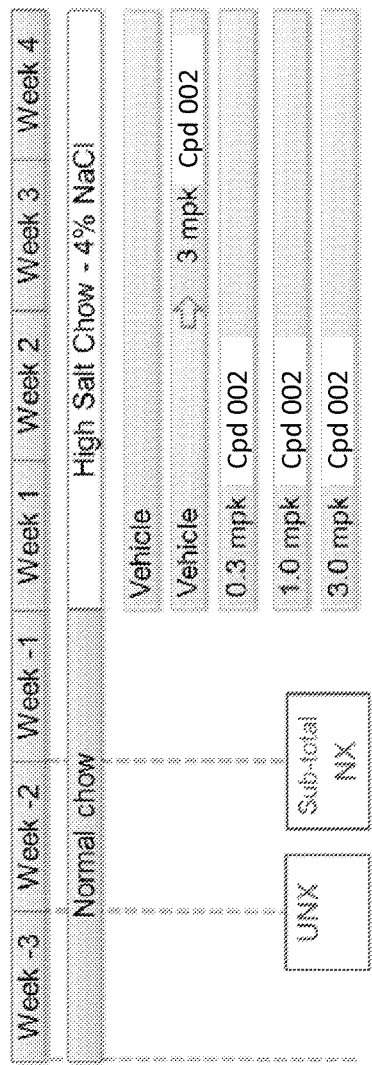
FIG. 11A shows the study design for testing the activity of compounds in dietary salt-induced, partial renal ablation model of chronic kidney disease (CKD).
FIG. 11B shows the effects of test compound on urinary excretion of phosphorus.
Figure 11:
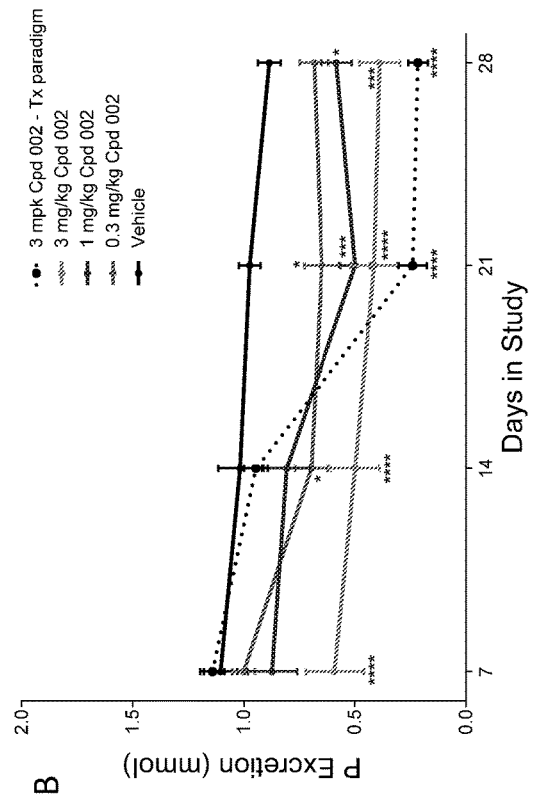

The effects of Cpd 002 (from Table E4, as the dihydrochloride salt) were tested in a dietary salt-induced, partial renal ablation model of CKD. The study design is illustrated in FIG. 11A (12 rats per group). FIG. 11B shows the effects of Cpd 002 on urinary excretion of phosphorus. In this study, Cpd 002 improved blood pressure, fluid overload, albuminuria, and heart and kidney hypertrophy, and also significantly reduced phosphorus urinary excretion. These data suggest an additive contribution for the phosphorus lowering effect of Cpd 002 on improvements in the renal and vascular functions.

Example 7

Effects on Urinary Excretion of Phosphate and Calcium in Rats

The activity of Cpd 002 (from Table E4, as the dihydrochloride salt) was tested for its effects on phosphorus and calcium levels in the urine of rats. Rats were dosed according to the schedule in Table E7.

TABLE E7

| 929uP groups | Dose #1 | Dose #2 10 min later |
|---|---|---|
| 1 | Water | Water |
| 2 | Renvela ® (sevelamer), 48 mg/kg | Water |
| 3 | Water | Cpd 002, 0.1 mg/kg |
| 4 | Water | Cpd 002, 0.3 mg/kg |
| 5 | Water | Cpd 002, 1.0 mg/kg |
| 6 | Water | Cpd 002, 3.0 mg/kg |

Figure 12:
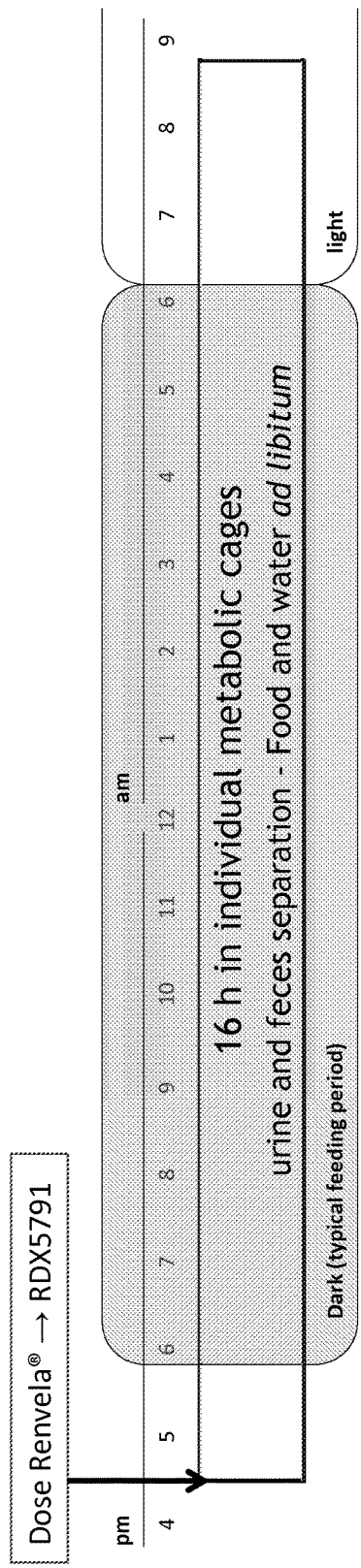
FIG. 12 shows the study design for testing the activity of test compound on urinary excretion of phosphate and calcium in rats.
Figure 13:
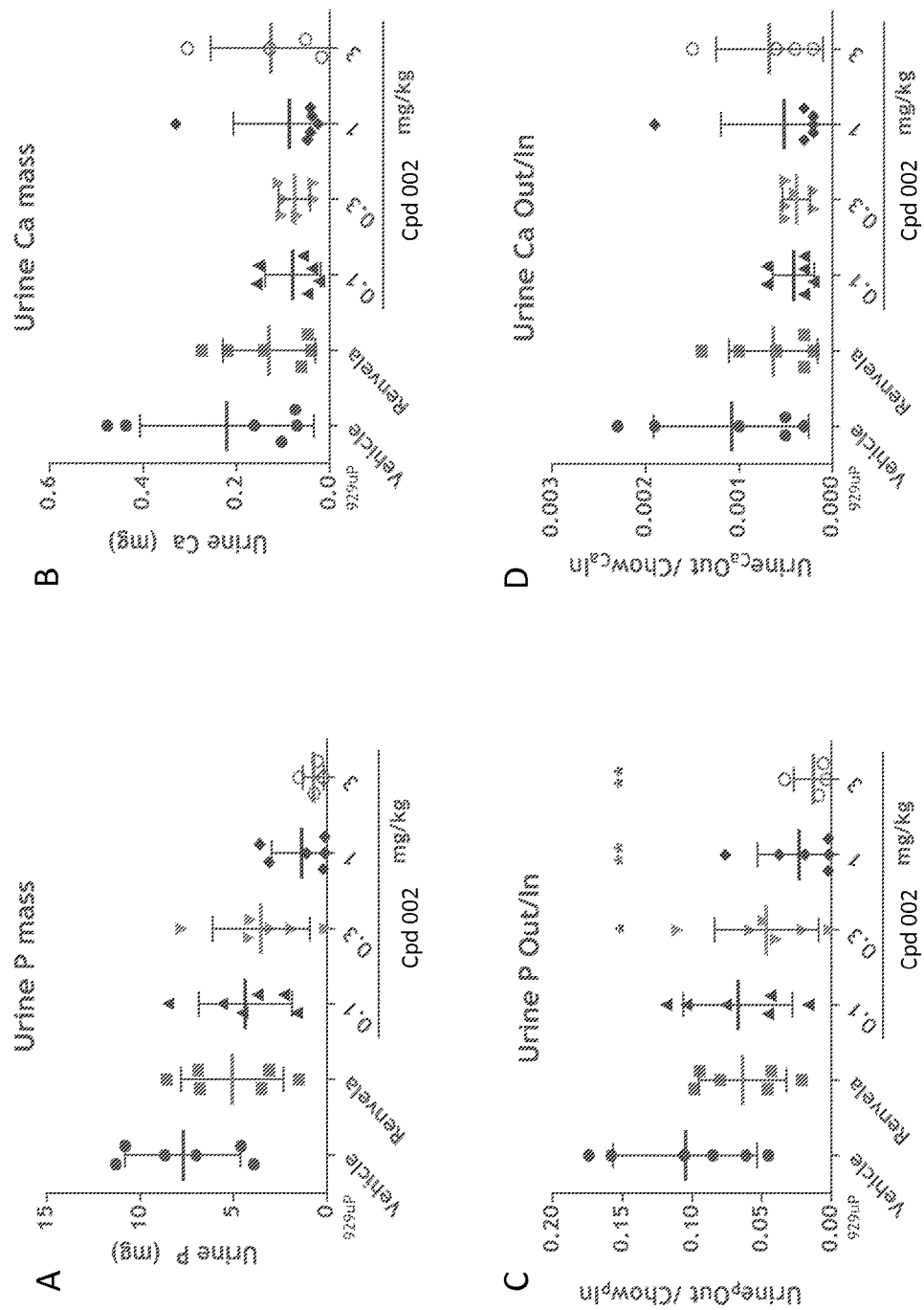
FIGS. 13A-D show that administration of test compound reduced both urine phosphorus mass and urine calcium mass relative to the vehicle-only control. Increasing dosages of test compound also significantly reduced urine phosphorus mass relative to 48 mg/kg Renvela®.

The rats were kept for 16 hours overnight (in the dark, the typical feeding period) in individual metabolic cages, and urine was collected the following morning for analysis of phosphate and calcium levels. The study design is shown in FIG. 12. The results are shown in FIGS. 13A-D. These results show that Cpd 002 reduced both urine phosphorus mass and urine calcium mass relative to the vehicle-only control. Increasing dosages of Cpd 002 also significantly reduced urine phosphorus mass relative to 48 mg/kg Renvela®.

Example 8

Evaluation of Activity in the Reduction of Dietary Phosphorus at Dose 15, 30 and 60 Mg Bid in a 7-Day Repeat Dose Study in Healthy Volunteers A Phase 1, single-center, randomized, double-blind, placebo-controlled study was designed to evaluate the safety, tolerability, and pharmacodynamic activity (PD) on sodium and phosphorus excretion of different dosing regimens of Cpd 002, as the dihydrochloride salt, (see Table E4) in healthy male and female subjects.

Subjects were screened within 3 weeks prior to enrollment and were allocated sequentially to cohorts in their order of completing screening assessments. Each cohort of 15 subjects checked into the clinical pharmacology unit (CPU) on Day-5 before dinner. Subjects were confined to the CPU, Na+-standardized meals (~1500 mg/meal) provided.

In each cohort, 12 subjects were randomized to receive Cpd 002 and 3 subjects to placebo. Subjects received doses of Cpd 002 with approximately 240 mL of non-carbonated water on Days 1 to 7 (just prior to the appropriate meals, depending on twice daily [bid, breakfast, dinner]. Subjects were provided standardized meals within 10 minutes after dosing.

Selection of Study Population—Inclusion Criteria. Subjects were eligible for inclusion in the study if they met all of the following criteria:
1. Healthy man or woman aged 19 to 65 years, inclusive.
2. Body mass index (BMI) between 18 and 29.9 kg/m$^2$, inclusive.
3. No clinically significant abnormalities in medical history, physical examination, or clinical laboratory evaluations at screening.
4. Able to understand and comply with the protocol.
5. Willing and able to sign informed consent.
6. Females were non-pregnant, non-lactating, and either postmenopausal for at least 12 months, as confirmed by follicle-stimulating hormone (FSH) test, surgically sterile (e.g., tubal ligation, hysterectomy, bilateral oophorectomy with appropriate documentation) for at least 90 days, or agreed to use from the time of signing the informed consent until 45 days after end of study 1 of the following forms of contraception: intrauterine device with spermicide, female condom with spermicide, contraceptive sponge with spermicide, diaphragm with spermicide, cervical cap with spermicide, male sexual partner who agrees to use a male condom with spermicide, sterile sexual partner, abstinence, an intravaginal system (e.g., NuvaRing®) with spermicide, or oral, implantable, transdermal, or injectable contraceptives with spermicide.

7. Males were either sterile, abstinent, or agreed to use, from check-in until 45 days from final study visit, 1 of the following approved methods of contraception: a male condom with spermicide; a sterile sexual partner; use by female sexual partner of an intrauterine device with spermicide, a female condom with spermicide, contraceptive sponge with spermicide, an intravaginal system (e.g., NuvaRing), a diaphragm with spermicide, a cervical cap with spermicide, or oral, implantable, transdermal, or injectable contraceptives).

Selection of Study Population—Exclusion Criteria. Subjects were excluded from the study if they met any of the following criteria:

1. Diagnosis or treatment of any clinically symptomatic biochemical or structural abnormality of the gastrointestinal system.
2. Any surgery on the small intestine or colon, excluding appendectomy or cholecystectomy.
3. Clinical evidence of significant cardiovascular, respiratory, renal, hepatic, gastrointestinal, hematologic, metabolic, endocrine, neurologic, psychiatric disease, or any condition that may interfere with the subject successfully completing the trial.
4. Loose stools (BSFS of 6 or 7)≥2 days in the past 7 days.
5. Hepatic dysfunction (alanine aminotransaminase[ALT] or aspartate aminotransaminase [AST])>1.5 times the upper limit of normal [ULN]) or renal impairment (serum creatinine>ULN).
6. Clinically significant laboratory results at screening as determined by the Investigator.
7. Any evidence of or treatment of malignancy, excluding non-melanomatous malignancies of the skin.
8. If, in the opinion of the Investigator, the subject was unable or unwilling to fulfill the requirements of the protocol or had a condition that rendered the results uninterpretable.
9. A diet, which in the opinion of the Investigator, could have impacted the results of the study.
10. Use of diuretic medications; medications that were known to affect stool consistency and/or gastrointestinal motility, including fiber supplements (unless required by study), anti-diarrheals, cathartics, antacids, opiates, narcotics, prokinetic drugs, enemas, antibiotics, probiotic medications or supplements; or salt or electrolyte supplements containing Na+, potassium, chloride, or bicarbonate formulations from CPU check in (Day-5) to CPU check out (Day 9).
11. Use of an investigational agent within 30 days prior to Day-5.
12. Positive virology (active hepatitis B infection [HBsAg], hepatitis C infection [HCV], or human immunodeficiency virus [HIV]), alcohol, or drugs of abuse test during screening,
13. Use of any prescription medication within 7 days before admission to the CPU, or required chronic use of any prescription or non-prescription medication, with the exception of hormonal replacement therapy (HRT) for postmenopausal women and hormonal contraceptives.
14. History of tobacco use, alcohol abuse, illicit drug use, significant mental illness, physical dependence to any opioid, or any history of drug abuse or addiction within 12 months of study enrollment.
15. Had significant blood loss (>450 mL) or had donated 1 or more units of blood or plasma within 8 weeks prior to study entry.

Removal of Subjects from Therapy or Assessment. Subjects were free to discontinue the study at any time, for any reason, and without prejudice to further treatment. The Investigator could have removed a subject if, in the Investigator's judgment, continued participation posed unacceptable risk to the subject or to the integrity of the study data. Subjects who withdrew early could have been replaced, pending discussion with the Sponsor.

Efficacy Evaluation—demographic and other baseline characteristics. All subjects enrolled in the study received study treatment and all had at least 1 post-baseline PD assessment.

An overview of the demographic characteristics of the subjects enrolled in the study overall and by cohort is provided in Table E8 below. Some variability was observed across cohorts (especially in terms of gender and race); however, the baseline characteristics of most cohorts mirrored that of the total population.

No clinically significant abnormal findings were noted for any subject during the physical examination performed at screening.

TABLE E8

Demographic and Baseline Characteristics

| Parameter | Cohort 1<br>30 mg bid<br>(n = 12) | Cohort 3<br>60 mg bid<br>(n = 12) | Cohort 4<br>15 mg bid<br>(n = 12) |
| --- | --- | --- | --- |
| Mean (SD) | 38.8 (16.49) | 37.8 (11.78) | 38.7 (12.91) |
| Median | 31.0 | 33.5 | 36.5 |
| Min, Max | 20, 63 | 22, 61 | 20, 60 |
| Female | 3 (25.0) | 3 (25.0) | 2 (16.7) |
| Male | 9 (75.0) | 9 (75.0) | 10 (83.3) |
| Mean (SD) | 73.7 (11.39) | 79.3 (9.98) | 78.7 (12.99) |
| Median | 71.7 | 75.7 | 79.7 |
| Min, Max | 58, 91 | 67, 103 | 60, 101 |
| Mean (SD) | 24.6 (2.69) | 26.1 (2.46) | 25.7 (2.87) |
| Median | 24.3 | 26.2 | 25.9 |
| Min, Max | 19, 29 | 22, 29 | 20, 30 |
| Asian | 1 (8.3) | 1 (8.3) | 0 |
| Black | 2 (16.7) | 6 (50.0) | 4 (33.3) |
| White | 7 (58.3) | 5 (41.7) | 6 (50.0) |
| Other | 2 (16.7) | 0 | 1 (8.3) |
| Missing | 0 | 0 | 1 (8.3) |

The schedule of events for screening and treatment period is provided in Table E9 below.

TABLE E9

| Procedure | Screening and Baseline Day | | | | | | Double-blind Treatment Period Day | | | | | | | | | Follow-up |
|---|---|---|---|---|---|---|---|---|---|---|---|---|---|---|---|---|
| | -26 to -5 | -5ᵃ | -4 | -3 | -2 | -1 | 1 | 2 | 3 | 4 | 5 | 6 | 7 | 8 | 9ᵃ | 23 ± 2 |
| Informed consent | X | | | | | | | | | | | | | | | |
| Inclusion/exclusion | X | Xᵇ | | | | | | | | | | | | | | |
| Medical history | X | Xᵇ | | | | | | | | | | | | | | |
| Physical examination | X | | | | | | | | | | | | | | X | |
| Vital signs | X | X | X | X | X | X | X | X | X | X | X | X | X | X | X | |
| ECG evaluation | X | | | | | | | | | | | | | | X | |
| Safety laboratory evaluations | X | | X | | | | | | | | | | | | X | |
| Alcohol/drug screen | X | X | | | | | | | | | | | | | | |
| FSH test | X | | | | | | | | | | | | | | | |
| Pregnancy test | X | X | | | | | | | | | | | | | X | |
| Randomization | | | | | | | X | | | | | | | | | |
| Dose administration | | | | | | | X | X | X | X | X | X | X | | | |
| 24-hr urine/stool collection | | | X | X | X | X | X | X | X | X | X | X | X | X | X | |
| Stool form/timing | | | X | X | X | X | X | X | X | X | X | X | X | X | X | |
| Pharmacodynamic laboratory evaluations | | | X | | X | | | X | | | X | | | | X | |
| AE assessment | | | | | | | X | X | X | X | X | X | X | X | X | X |

Study drug. Cpd 002 capsules or corresponding placebo capsules were administered with approximately 240 mL of non-carbonated water at multiples of 15 mg or placebo. Cpd 002 is an amorphous, off-white powder and was supplied as a white, size 0, hydroxypropylmethylcellulose (HPMC) capsule. Each capsule contained 15 mg of Cpd 002. Capsules were packaged in an opaque white high density polyethylene (HDPE) bottle (10/bottle). The drug product was formulated with no excipients.

Placebo was supplied as a white, size 0, HPMC capsule filled with methyl cellulose. Capsules were packaged in an opaque white HDPE bottle (10/bottle).

Method of Assigning Subjects to Treatment Groups. The clinical research organization statistician prepared the randomization scheme in accordance with its standard operating procedures (SOPs) and the randomization plan, which reflected GCP standards.

After obtaining informed consent, subjects were allocated sequentially to cohorts in their order of completing screening assessments.

Within each cohort, a computer generated randomization schedule was used to randomly assign subjects to active Cpd 002 or placebo in a 4:1 ratio.

Once a subject was deemed eligible for randomization, the next available randomization number was assigned sequentially and the subject received the treatment indicated on the randomization schedule. Subjects who withdrew early could be replaced, pending discussion with the Sponsor. Replacement subjects received the same blinded treatment as the original subject.

Selection and Timing of Dose for Each Subject. Subjects were allocated sequentially to cohorts consisting of 15 subjects each in their order of completing screening assessments and received either 002 or placebo based on random assignment. Table E10 provides the actual dosing regimen for each cohort. Because this was an adaptive design protocol, the dosing regimen of each cohort was based on blinded results from previous cohorts.

TABLE E10

Dosing Regimen for Each Cohort

| Cohort No. | Subjectsᵃ | Dose/Administration | Regimen | Total Dose/Day |
|---|---|---|---|---|
| 1 | 15 | 30 mg | bid | 60 mg |
| 3 | 15 | 60 mg | bid | 120 mg |
| 4 | 15 | 15 mg | bid | 30 mg |

ᵃEach cohort consisted of 12 subjects administered CPD002 and 3 subjects administered placebo.

Dosing was administered immediately prior to breakfast and dinner. Subjects were not permitted to eat or drink anything from 8 hours before dosing at breakfast, with the exception of water up to 2 hours prior. Subjects were fed a standardized meal approximately 10 minutes after dosing.

The standardized diet included a Na+ content of approximately 1500 mg for each meal. Dietary phosphorus was not measured nor was it set to a predetermined value. It was expected to range within the typical value, i.e. 750 mg-1250 mg per day.

Subjects did not have salt available to add to meals. Fluid intake was ad libitum (and recorded) except as specified before drug administration. Subjects were to refrain from strenuous physical activity (e.g., contact sports) during study participation.

Blinding. The treatment was administered in a double-blind fashion. Only the site pharmacist responsible for dispensing the product and the bioanalytical laboratory technician responsible for performing the bioanalysis of plasma Cpd 002 had knowledge of the treatments assigned.

The study was not unblinded for the safety reviews between cohorts.

A third party maintained the randomization schedule in a secure location with adequate controls to prevent unauthorized access.

One set of unblinding envelopes (sealed envelopes containing individual subject treatment assignment) was stored at the CPU.

The study was only unblinded once all data from the final cohort was collected and the database was locked.

Prior and Concomitant Therapy. This was a study in healthy subjects. Subjects with prior therapy specified in the exclusion criteria were not eligible for entry into the study.

With the exception of HRT for postmenopausal women and hormonal contraceptives, the use of concomitant medications was prohibited during the study unless needed to treat an AE.

All previous medication (prescription and over-the-counter), vitamin and mineral supplements, and herbs taken by the participant in the past 30 days were recorded in the CRF, including start and stop date, dose and route of administration, frequency and indication. Medications taken for a procedure were also included.

Treatment Compliance. All doses of study drug were given under the supervision of clinic staff, with time and dose administered recorded in the CRF. Clinical staff examined the subject's oral cavity and hands after drug administration to ensure that the capsule(s) was/were swallowed.

Efficacy Variables. The study consisted of a 3-week screening period followed by a 5-day baseline assessment, a 7-day double-blind treatment period with 2 days of follow-up for safety and PD assessments. Fourteen days after the treatment period subjects were contacted by telephone for a safety follow-up.

Subjects were admitted to the CPU 5 days prior to administration of the first dosing of study drug and were confined to the unit for the duration of the treatment period, being released on Day 9.

Safety assessments were performed starting with Day-5 and included physical examination; vital signs; 12-lead ECGs; routine serum chemistry, hematology, and urinalysis; and AE reporting. Pharmacodynamic assessments were performed daily from Day-4 through Day 9 and included urine and stool Na+ excretion, time to first bowel movement, and stool parameters (consistency, weight, and frequency). Pharmacodynamic laboratory assessments (plasma renin, aldosterone, and NT-pro BNP) were collected on Days-4, -1, 3, 6, and 9.

Laboratory Assessments. Blood and urine samples for clinical laboratory tests (hematology, chemistry, urinalysis) were collected during screening (to meet inclusion/exclusion criteria) and at Day-4, and Day 9 after waking and prior to breakfast.

In addition, blood was collected at screening and Day-5 for alcohol/drug screening, FSH test (postmenopausal females only), and pregnancy testing (all females). Virology screening for HBsAg, HCV, and HIV were performed at screening.

Pharmacodynamic Variables. The following PD parameters were monitored as a signal of potential drug activity:
Stool Na+ excretion
Stool Phosphorus excretion Bowel Movements. Study participants were instructed to notify study personnel immediately before they had a bowel movement. Study personnel recorded the time of every bowel movement and assessed the stool parameters (e.g., consistency, weight). Bowel movements that occurred prior to leaving the bathroom were considered 1 bowel movement. All bowel movements were collected, weighed, and stored by the CPU for total Na+ and P analysis; collections were in 24-hour intervals.

Pharmacodynamic Analyses—Stool Sodium and Phosphorus Analytical methods. The human fecal samples were processed with nitric acid to give pre-digested sample ("Pre-digests") prior to laboratory determination of sodium and phosphorus contents. Pre-digest were digested further in nitric acid at 100° C. followed by hydrochloric acid at 100° C. and diluted with deionized water. Yttrium was added to the digestion as internal standard. Calibration standards and quality control samples were digested with the same procedure. Sodium and phosphorus concentrations were determined by an inductively coupled plasma optical emission spectrometric (ICP-OES) method. The light intensity of analyte and yttrium were measured at the SCD (array) detectors. The analyte-to-yttrium intensity ratios were converted to solution concentrations via the instrument software. Total sodium and phosphorus content in each sample was calculated using the sample volumes obtained during the pre-digestion process and the concentrations measured.

Figure 14:
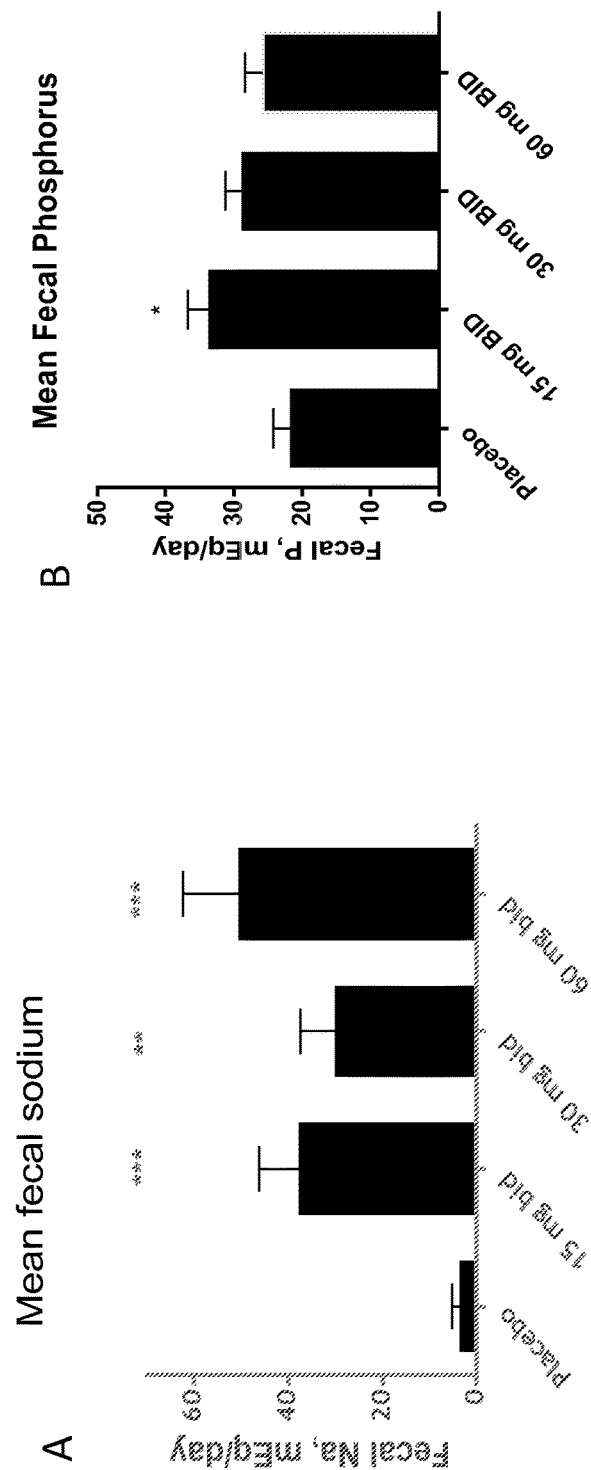
FIGS. 14A-B show the mean average daily fecal excretion of Na (14A; +/−SE) and phosphorus (14B; +/−). Excretion data were averaged over the 7-day treatment period (Day 1 to Day 7) and reported as mEq/day (see Example 8). Statistical analysis was performed by one-way ANOVA; (*); p<0.05, (); p<0.01, (*); p<0.001.

Results. Upon unblinding of the data, pharmacodynamic measurement of fecal and urine P and Na were assigned to the placebo group (3 subjects embedded in each cohort×3 cohorts=9 subjects) and to the 3 treated groups respectively. The data are shown in FIGS. 14A-B. FIG. 14A shows the mean average daily fecal excretion of Na (+/−SE), averaged over the 7-day treatment period (Day 1 to Day 7) and reported as mEq/day. FIG. 14B shows the mean average daily fecal excretion of phosphorus (+/−), averaged over the 7-day treatment period (Day 1 to Day 7) and reported as mEq/day. Statistical analysis was performed by one-way ANOVA; (*); $p<0.05$, (); $p<0.01$, (*); $p<0.001$.

Example 9

Evaluation of Activity in the Reduction of Dietary Phosphorus at Dose 15 Mg Bid in a 7-Day Repeat Dose Crossover Study in Healthy Volunteers A Phase 1, single-center, randomized, 3-way cross-over, open label study was designed to evaluate the pharmacodynamics of Cpd 002 for three different formulations of Cpd 002 administered twice daily PO for 4 days in healthy male and female subjects taking a proton pump inhibitor (omeprazole), utilizing a three-way crossover design. Many potential patients take either PPIs or H2 antagonists for the treatment of gastroesophageal reflux disease (GERD). However, the in vitro dissolution profiles of Cpd 002 formulations can be affected by a high pH, where slower and/or incomplete dissolution is sometimes observed. In order to evaluate the pharmacodynamic activity of the drug in the context of elevated gastric pH, subjects in this study were required to be on omeprazole starting on Day-5 throughout the treatment period.

Subjects were screened within 3 weeks of enrollment. Each subject took Omeprazole 20 mg twice daily beginning on Day-5. Subjects checked in a Clinical Pharmacology Unit (CPU) on Day-2 before dinner. Each subject received a diet standardized for Na+ content while in the CPU. Subjects received one of three formulations of Cpd 002 BID with approximately 240 mL of non-carbonated water on Days 1 to 4, 7 to 10, and 13 to 16 (a different formulation each time). Subjects were fed breakfast and/or dinner within approximately 5 minutes after dosing. There was a two day wash out period between each treatment period.

While confined to the CPU, Na+-standardized meals were provided per CPU procedures. Pharmacodynamic assessment included 24-hour urinary sodium and phosphorus and fecal sodium and phosphorus measurements.

At least 18 healthy male and female subjects were randomized in this study.

Subject Selection Criteria—Inclusion Criteria.
1. Healthy man or woman aged 19 to 65 years, inclusive.
2. Body mass index between 18 and 29.9 kg/m2, inclusive.
3. No clinically significant abnormalities in the medical history, physical examinations, or clinical laboratory evaluations at screening.
4. Able to understand and comply with the protocol.
5. Willing and able to sign informed consent; signed and dated, written informed consent prior to any study specific procedures.
6. Females of child-bearing potential must have a negative pregnancy test at screening and on admission to the unit and must not be lactating.
7. Females of childbearing potential included in the study must use two effective methods of avoiding pregnancy (including oral, transdermal or implanted contraceptives, intrauterine device, female condom with spermicide, diaphragm with spermicide, cervical cap, or use of a condom with spermicide by sexual partner from screening to the follow-up visit.
8. Females of non-child bearing potential, confirmed at screening, must fulfill one of the following criteria:
   a. Post-menopausal defined as amenorrhea for at least 12 months or more; following cessation of all exogenous hormonal treatments and LH and FSH levels in the post-menopausal range; or
   b. Documentation of irreversible surgical sterilization by hysterectomy, bilateral oophorectomy or bilateral salpingectomy but not tubal ligation.
9. Males must be either be sterile, abstinent or agree to use, from check-in until 45 days from final study visit, one of the following approved methods of contraception: a male condom with spermicide; a sterile sexual partner; use by female sexual partner of an IUD with spermicide, a female condom with spermicide, contraceptive sponge with spermicide, an intravaginal system (eg, NuvaRing®), a diaphragm with spermicide, a cervical cap with spermicide, or oral, implantable, transdermal, or injectable contraceptives.
10. For inclusion in the optional genetic research, patients must fulfill all of the inclusion criteria described above and provide informed consent for the genetic sampling and analyses.

Exclusion Criteria. Subjects were excluded from the study if they met any of the following criteria:
1. Diagnosis or treatment of any clinically symptomatic biochemical or structural abnormality of the gastrointestinal (GI) tract.
2. Any surgery on the small intestine or colon, excluding appendectomy or cholecystectomy or any other condition known to interfere with absorption, distribution, metabolism or excretion of drugs.
3. Clinical evidence of significant cardiovascular, respiratory, renal, hepatic, gastrointestinal, hematologic, metabolic, endocrine, neurologic, psychiatric disease, or any condition that may interfere with the subject successfully completing the trial or that would present a safety risk to the subject.
4. History of severe allergy/hypersensitivity or ongoing allergy/hypersensitivity, as judged by the investigator or history of hypersensitivity to drugs with a similar chemical structure or class to CPD002.
5. Loose stools (Bristol Stool Form Score of 6 or 7)>2 days in the past 7 days.
6. Hepatic dysfunction (alanine aminotransaminase [ALT] or aspartate aminotransaminase [AST])>1.5 times the upper limit of normal [ULN]) or renal impairment (serum creatinine>ULN).
7. Clinically significant laboratory results at screening as determined by the investigator.
8. Any evidence of or treatment of malignancy, excluding non-melanomatous malignancies of the skin.
9. If, in the opinion of the investigator the subject is unable or unwilling to fulfill the requirements of the protocol or has a condition, which would render the results uninterpretable.
10. Use of diuretic medications; medications that are known to affect stool consistency and/or GI motility, including fiber supplements (unless required by study), anti-diarrheals, cathartics, antacids, opiates, narcotics, prokinetic drugs, enemas, antibiotics, probiotic medications or supplements; or salt or electrolyte supplements containing sodium, potassium, chloride, or bicarbonate formulations from CPU check in (Day-2) to CPU check out (Day 17).
11. Use of an investigational agent within 30 days prior to Day-2.
12. Positive virology (active hepatitis B infection, hepatitis C infection, or human immunodeficiency virus), alcohol, or drugs of abuse test during screening.
13. Use of any prescription medication within 7 days before admission to the CPU, or required chronic use of any prescription or non-prescription medication, with the exception of hormonal replacement therapy for postmenopausal women and hormonal contraceptives.
14. History of tobacco use, alcohol abuse, illicit drug use, significant mental illness, physical dependence to any opioid, or any history of drug abuse or addiction within 12 months of study enrollment.
15. Have had significant blood loss (>450 mL) or have donated 1 or more units of blood or plasma within 8 weeks prior to study entry.

Study drug. Cpd 002 bis-HCl (e.g., the dihydrochloride salt of Cpd 002) capsules, Cpd 002 bis-HCl tablets and Cpd 002 free base tablets. The Cpd 002 bis-HCl salt is an amorphous, off-white powder. The Cpd 002 free base is a white, crystalline solid. Cpd 002 is presented as either a white size 0 HPMC (hydroxypropylmethylcellulose) capsule or a round, white tablet. The capsules were manufactured at a dosage strength of 15 mg on the basis of the Cpd 002 dihydrochloride formula weight, which is equivalent to 14 mg of the Cpd 002 free base. To ensure comparable dosage strengths across this study, tablets of both the dihydrochloride salt and free base were manufactured at a dosage strength reflecting 14 mg on the basis of the free base. Capsules and tablets were packaged in a white HDPE (high-density polyethylene) bottle. Capsules and tablets of Cpd 002 were stored refrigerated (2 to 8° C.) in the original packaging until use. The components of the tablets are described in Table E11 below.

TABLE E11

| | Free Base | | Dihydrochloride Salt | |
|---|---|---|---|---|
| Component | % Form | Wt/Tablet (mg) | % Form | Wt/Tablet (mg) |
| Cpd 002 | 5.9 | 14.7[a] | 6.4 | 15.9[a] |
| Prosolv HD90 | 86.1 | 215.3 | 85.6 | 214.1 |
| Polyplasdone XL | 5.00 | 12.5 | 5.00 | 12.5 |
| Mg Stearate | 2.00 | 5.0 | 2.00 | 5.0 |
| Cabosil | 1.00 | 2.5 | 1.00 | 2.5 |
| Totals | 100.00 | 250.0 | 100.00 | 250.0 |

[a]Corrected for purity, residual solvents, water content, and inorganic content.

Dose and Route of Administration. Cpd 002 capsules or tablets, 15 mg (14 mg free base equivalents) were administered with approximately 240 mL of non-carbonated water twice daily PO prior to breakfast and dinner for 4 consecutive days per treatment period, with 2 day wash out periods between treatments. Omeprazole 20 mg BID was administered to screened subjects beginning on day-5. All subjects took omeprazole 20 mg twice daily one hour before intake of Cpd 002 each day until their last dose of study drug on Day 16. See Table E12 below.

TABLE E12

| Treatments | Subjects[a] | Dose/Administration[b] | Regimen | Formulation |
|---|---|---|---|---|
| 1 | 18 | 15 mg | BID | Cpd 002 bis-HCl capsule |
| 2 | 18 | 15 mg | BID | Cpd 002 bis-HCl capsule |
| 3 | 18 | 15 mg | BID | Cpd 002 tablet |

[a]All subjects received all three treatments; 6 subjects/treatment period. There was a 2 day wash out between each treatment period.
[b]Doses are in equivalents of CPD002 free base (MW 1145.049).

Once a subject was deemed eligible for randomization, the next available randomization number was assigned sequentially and the subject received the sequence of treatment indicated on the randomization schedule. All doses of study drug were given under the supervision of clinic staff, with time, and dose administered recorded in the case report form (CRF). Clinical staff examined the subject's oral cavity and hands after drug administration to ensure that capsule was swallowed.

Fluid and Food Intake. Subjects participating in the study were given a standardized diet with an approximate sodium content (approximately 1500 mg for each meal). Dietary phosphorus was not measured nor was it set to a predetermined value. It was expected to range within the typical value, i.e. 750 mg-1250 mg per day. Subjects did not have salt or any other sodium containing spices or sauces available to add to meals.

Fluid intake were ad libitum except as specified before drug administration. Daily menus (food and fluid) were similar during each treatment period.

Pharmacodynamic variables. The following parameters were monitored as signal of potential drug activity.
  Urine sodium excretion (daily)
  Fecal sodium excretion (daily)

Bowel movement and urine collection were performed as described earlier (Example 8); the pharmacodynamics activity of the three dosage forms was assessed as follows. A baseline fecal excretion of phosphorus or sodium was established as the average daily fecal excretion of phosphorus or sodium during Day-1 to Day 0, with the exception of one subject for whom the baseline was established during the first washout period, i.e., from Day 6 and Day 7. The daily fecal excretion of phosphorus or sodium upon treatment was measured by averaging fecal phosphorus or sodium excretion over the 4-day treatment period. The same method was used for urine.

Figure 15:
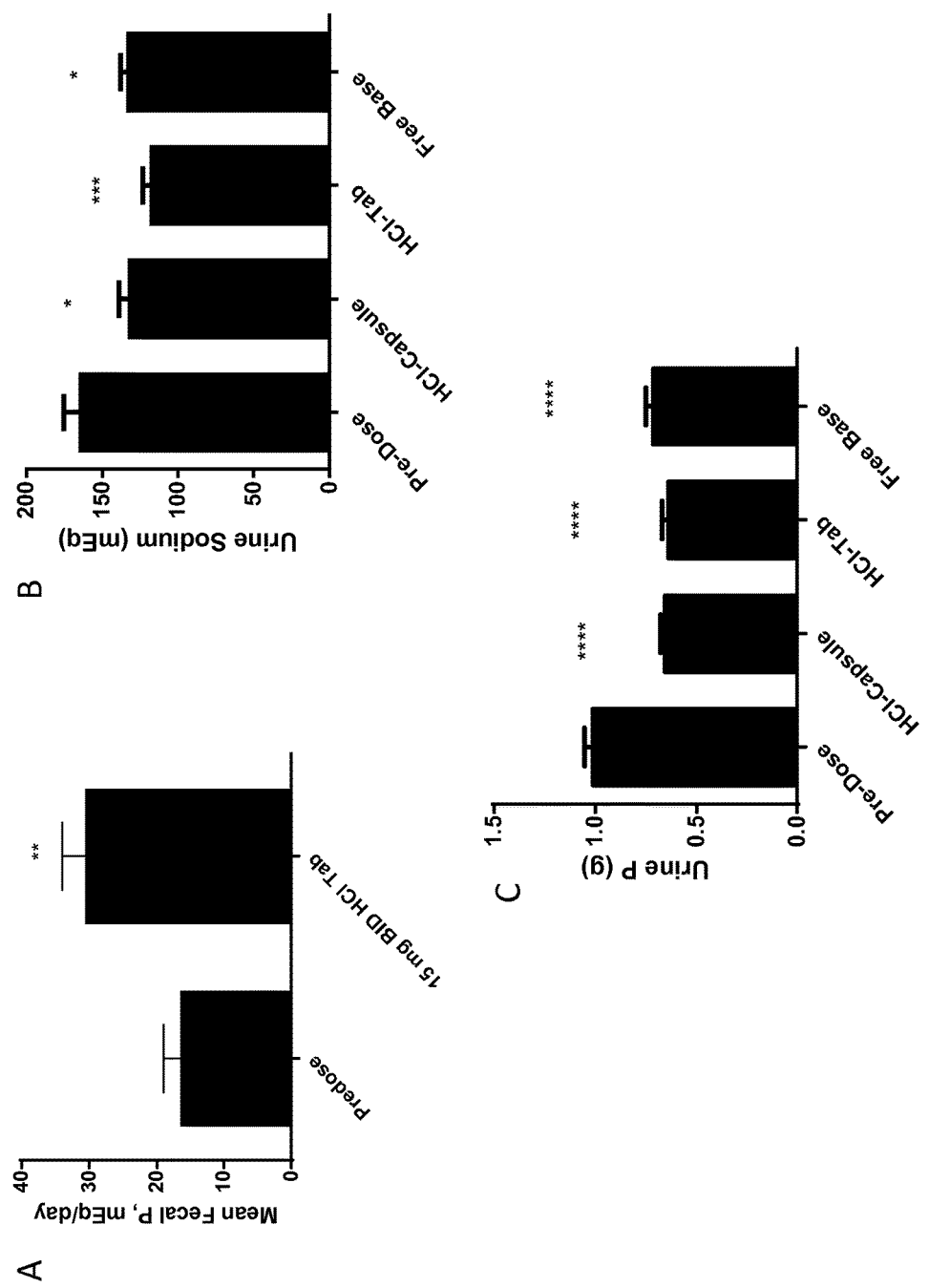
FIGS. 15A-C show the mean average daily fecal excretion of phosphorus (15A; +/−SE) and the mean average daily urinary excretion of sodium (15B; +/−SE) and phosphorus (15C; +/−) (see Example 9). Statistical analysis performed by one-way ANOVA; (*); p<0.05, (); p<0.01, (*); p<0.001.

Results. The results are shown in FIGS. 15A-C. Statistical analysis was performed by one-way ANOVA; (*); $p<0.05$, (); $p<0.01$, (*); $p<0.001$.

FIG. 15A shows the mean average daily excretion of phosphorus (+/−SE). A baseline fecal excretion of phosphorus or sodium was established as the average daily fecal excretion of phosphorus or sodium during Day-1 to Day 0, with the exception of one subject for whom the baseline was established during the first washout period, i.e. from Day 6 and Day 7 (referred to as "Predose"). The daily fecal excretion of phosphorus upon treatment with 15 mg BID HCl tablets was measured by averaging fecal phosphorus or sodium excretion over the 4-day treatment period.

FIG. 15B shows the average daily urinary excretion of sodium (+/−SE). A baseline fecal excretion of sodium was established as the average daily urinary excretion of sodium during Day-1 to Day 0, with the exception of one subject for whom the baseline was established during the first washout period, i.e. from Day 6 and Day 7 (referred to as "Predose"). The daily urinary excretion of sodium upon treatment with the three forms of drug products was measured by averaging urinary sodium excretion over the 4-day treatment period.

FIG. 15C shows the average daily urinary excretion of phosphorus (+/−). A baseline fecal excretion of phosphorus was established as the average daily urinary excretion of phosphorus during Day-1 to Day 0, with the exception of one subject for whom the baseline was established during the first washout period, i.e. from Day 6 and Day 7 (referred to as "Predose"). The daily urinary excretion of phosphorus upon treatment with the three forms of drug products was measured by averaging urinary sodium excretion over the 4-day treatment period.

Example 10

The Effect of Renvela® on the Pharmacodynamics of CP002

A Phase 1, single-center, randomized, open label study was designed to evaluate the effect of Renvela® on the pharmacodynamic activity of CP002, as the dihydrochloride salt (see Table E4) administered twice daily PO for 4 days in healthy male and female subjects.

Subjects were screened within 3 weeks of enrollment. Eighteen subjects checked in to the CPU on Day-2 before dinner. Each subject received a diet standardized for Na+ content while in the CPU. Subjects received 15 mg CP002 BID on Days 1 to 4, and Days 7 to 10. Subjects were fed breakfast and/or dinner within approximately 5 minutes after dosing. During one of the two treatment periods (randomly assigned), subjects received one Renvela® 800 mg tablet with breakfast, lunch and dinner (either Days 1 to 4 or Days 7 to 10). There was a two day wash out period between each treatment period. While confined to the CPU, Na+-standardized meals were provided per CPU procedures. Pharmacodynamic assessment included 24-hour fecal sodium and phosphorus measurements.

The subject selection criteria and description of the study drug were the same as described for Example 9 (supra). The schedule of assessments and procedures is shown in Table E13 below.

TABLE E13

| Study Procedure | Screening<br>-21 to -3 | Run-in | | Treatment Period 1<br>Day | | | | Washout/Run-in | | Treatment Period 2 | | | |
|---|---|---|---|---|---|---|---|---|---|---|---|---|---|
| | | -2 | -1 | 1 | 2 | 3 | 4 | 5 | 6 | 7 | 8 | 9 | 10 |
| Renvela ® administration | | | | X | X | X | X | | | X | X | X | X |
| CP002 administration | | | | X | X | X | X | | | X | X | X | X |
| 24 hour urine/ stool collection | | X | X | X | X | X | X | X | X | X | X | X | X |
| Stool assessment | X | X | X | X | X | X | X | X | X | X | X | X | X |
| PK blood sampling | | | | | | | X | | | | | | X |

Pharmacodynamic variables. A baseline fecal excretion of phosphorus or sodium was established as the average daily fecal excretion of phosphorus or sodium during Day-1 to Day 0. The daily fecal excretion of phosphorus or sodium upon treatment was measured by averaging fecal phosphorus or sodium excretion over the 4-day treatment period. Sodium and phosphorus analytical methods were performed as described in Example 8 (supra).

Figure 16:
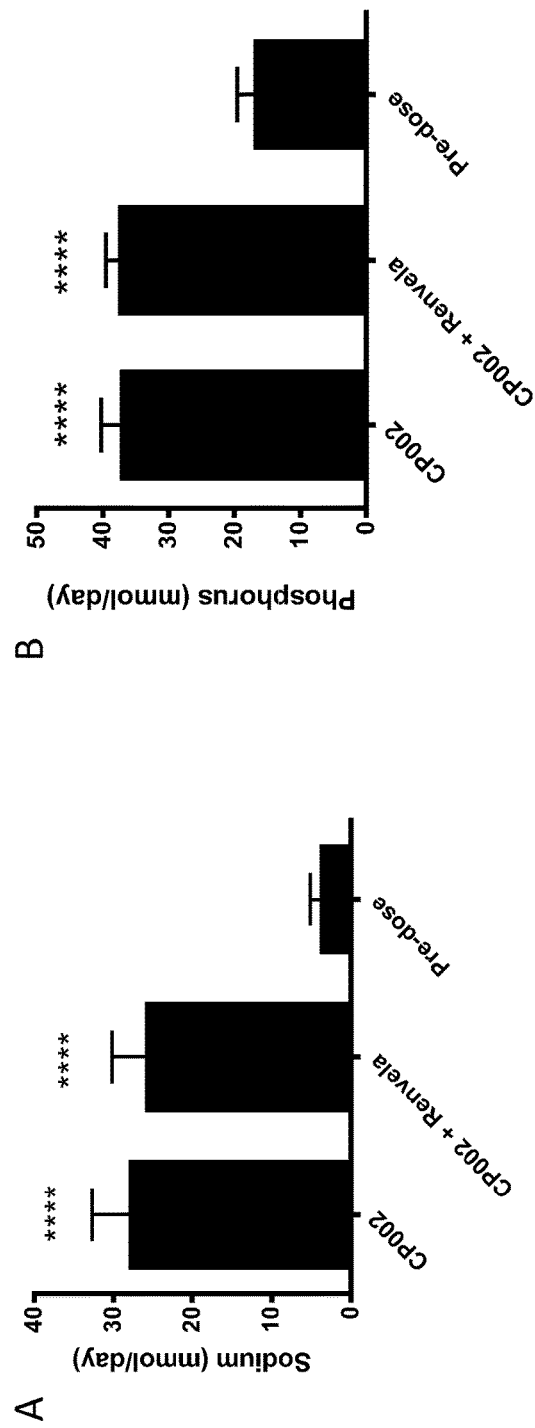
FIGS. 16A-B shown the mean average daily fecal excretion of sodium (16A; +/−SE) and the mean average daily fecal excretion of phoshorus (16B; +/−SE) (see Example 10). Statistical analysis performed by one-way ANOVA followed by Tukey's multiple comparison's test; (*); p<0.05, (); p<0.01, (*); p<0.001. vs. pre-Dose.

Results. The data are shown in FIGS. 16A-B. Statistical analysis performed by one-way ANOVA followed by Tukey's multiple comparison's test; (*); $p<0.05$, (); $p<0.01$, (*); $p<0.001$. vs. pre-Dose.

The mean average daily fecal excretion of sodium (+/−SE) is shown in FIG. 16A. Here, a baseline fecal excretion of sodium was established as the average daily fecal excretion of phosphorus or sodium during Day-1 to Day 0, (referred to as "Predose"). The daily fecal excretion of sodium upon treatment with 15 mg BID bis-HCl tablets was measured by averaging fecal sodium excretion over the 4-day treatment period.

The mean average daily fecal excretion of phoshorus (+/−SE) is shown in FIG. 16B. A baseline fecal excretion of phosphorus was established as the average daily fecal excretion of phosphorus during Day-1 to Day 0, (referred to as "Predose"). The daily fecal excretion of phosphorus upon treatment with 15 mg BID bis-HCl tablets was measured by averaging fecal phosphorus excretion over the 4-day treatment period.

The invention claimed is:

1. A method for inhibiting phosphate uptake in the gastrointestinal tract of a patient in need of phosphate lowering, comprising enterally administering to the patient an effective amount of the compound

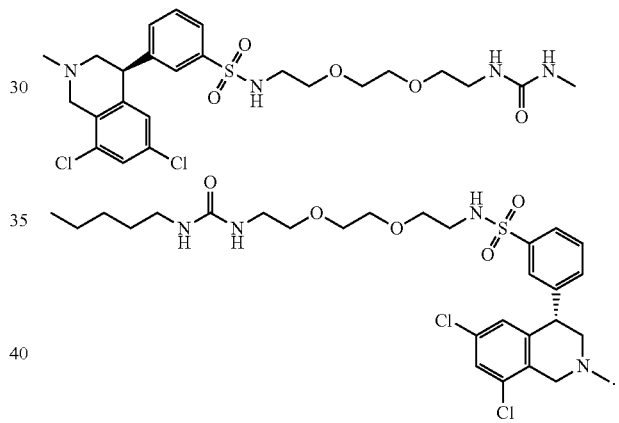

2. The method of claim 1, wherein the pharmaceutically acceptable salt is

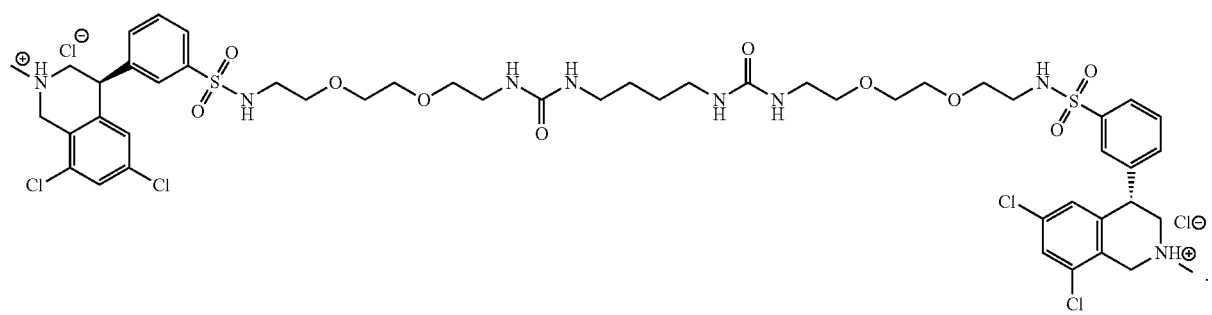

3. A method for treating hyperphosphatemia in a subject in need thereof comprising administering to the subject an effective amount of the compound

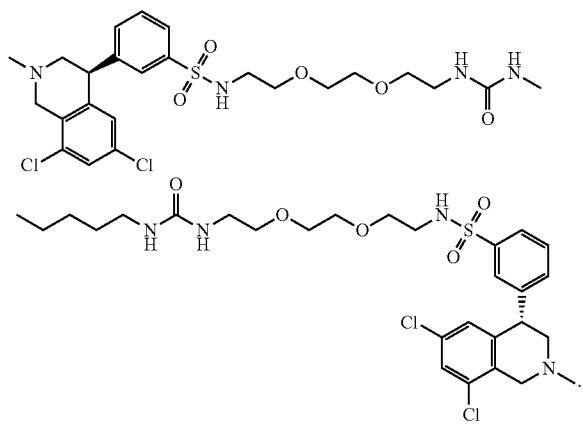

or a pharmaceutically acceptable salt thereof.

4. The method of claim 3, wherein the pharmaceutically acceptable salt is

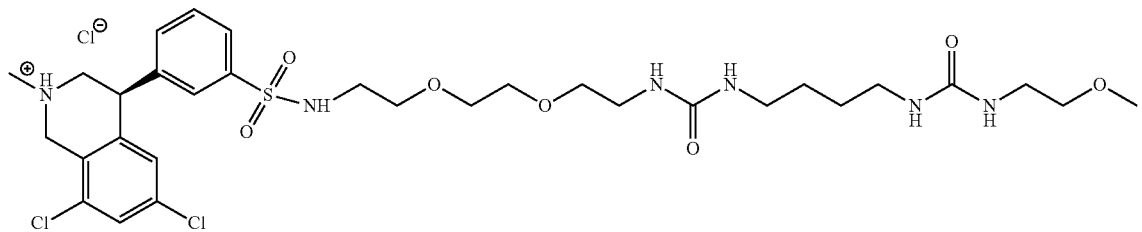

5. The method of claim 1, further comprising administering an additional biologically active agent.

6. The method of claim 5, wherein the additional biologically active agent is a phosphate binder.

7. The method of claim 6, wherein the phosphate binder is selected from the group consisting of sevelamer, sevelamer carbonate, sevelamer hydrochloride, lanthanum carbonate, calcium carbonate, calcium acetate, magnesium carbonate, MCI-196, ferric citrate, magnesium iron hydroxycarbonate, aluminum hydroxide, APS1585, SBR-759, and PA-21.

8. The method of claim 6, wherein the phosphate binder is selected from the group consisting of sevelamer carbonate, lanthanum carbonate, calcium carbonate, calcium acetate, calcium acetate/magnesium carbonate, ferric citrate, magnesium iron hydroxycarbonate, and aluminum hydroxide.

9. The method of claim 6, wherein the phosphate binder is sevelamer, sevelamer carbonate, or sevelamer hydrochloride.

10. The method of claim 3, further comprising administering an additional biologically active agent.

11. The method of claim 10, wherein the additional biologically active agent is a phosphate binder.

12. The method of claim 11, wherein the phosphate binder is selected from the group consisting of sevelamer, sevelamer carbonate, sevelamer hydrochloride, lanthanum carbonate, calcium carbonate, calcium acetate, magnesium carbonate, MCI-196, ferric citrate, magnesium iron hydroxycarbonate, aluminum hydroxide, APS1585, SBR-759, and PA-21.

13. The method of claim 11, wherein the phosphate binder is selected from the group consisting of sevelamer carbonate, lanthanum carbonate, calcium carbonate, calcium acetate, calcium acetate/magnesium carbonate, ferric citrate, magnesium iron hydroxycarbonate, and aluminum hydroxide.

14. The method of claim 11, wherein the phosphate binder is sevelamer, sevelamer carbonate, or sevelamer hydrochloride.

15. The method of claim 3, wherein the hyperphosphatemia is postprandial hyperphosphatemia.

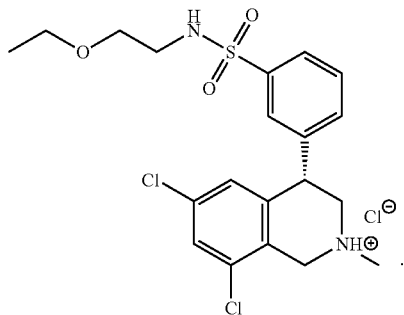

* * * * *

UNITED STATES PATENT AND TRADEMARK OFFICE
CERTIFICATE OF CORRECTION

PATENT NO.         : 10,272,079 B2
APPLICATION NO.    : 14/783983
DATED              : April 30, 2019
INVENTOR(S)        : Christopher Carreras et al.

Page 1 of 1

It is certified that error appears in the above-identified patent and that said Letters Patent is hereby corrected as shown below:

In the Claims

Column 460, Lines 35-45, please delete all of Claim 1 and insert:
-- A method for inhibiting phosphate uptake in the gastrointestinal tract of a patient in need of phosphate lowering, comprising enterally administering to the patient an effective amount of the compound

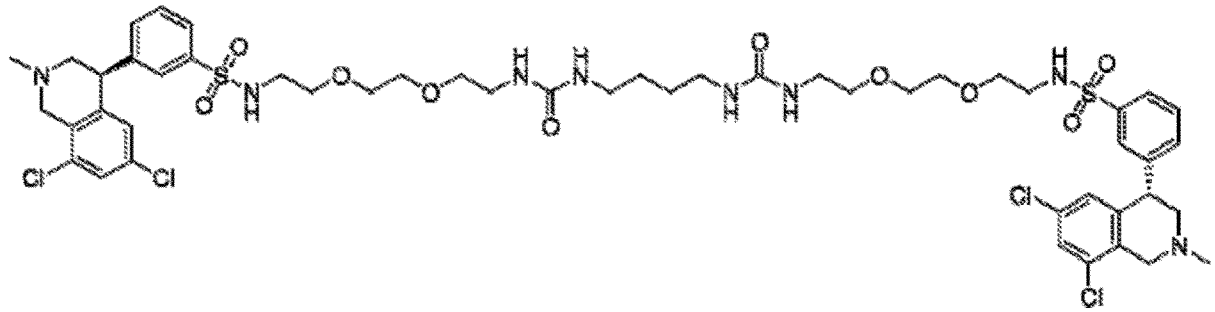

or a pharmaceutically acceptable salt thereof. -- therefor.

Signed and Sealed this
Fifteenth Day of October, 2019

Andrei Iancu
*Director of the United States Patent and Trademark Office*